United States Patent
Hansen

(10) Patent No.: US 9,238,640 B2
(45) Date of Patent: Jan. 19, 2016

(54) ANTI-INFLAMMATORY AGENTS

(75) Inventor: Henrik C. Hansen, Calgary (CA)

(73) Assignee: Resverlogix Corp., Calgary, Alberta (CA)

( * ) Notice: Subject to any disclaimer, the term of this patent is extended or adjusted under 35 U.S.C. 154(b) by 884 days.

(21) Appl. No.: 13/257,082

(22) PCT Filed: Mar. 16, 2010

(86) PCT No.: PCT/IB2010/000826
§ 371 (c)(1),
(2), (4) Date: Nov. 1, 2011

(87) PCT Pub. No.: WO2010/106436
PCT Pub. Date: Sep. 23, 2010

(65) Prior Publication Data
US 2012/0040954 A1 Feb. 16, 2012

Related U.S. Application Data

(60) Provisional application No. 61/161,089, filed on Mar. 18, 2009.

(51) Int. Cl.
| | | |
|---|---|---|
| *A61K 31/54* | (2006.01) |
| *A61K 31/535* | (2006.01) |
| *C07D 401/04* | (2006.01) |
| *A61K 31/517* | (2006.01) |
| *A61K 31/519* | (2006.01) |
| *A61K 31/5377* | (2006.01) |
| *A61K 31/55* | (2006.01) |
| *A61K 31/551* | (2006.01) |
| *C07D 239/91* | (2006.01) |
| *C07D 401/10* | (2006.01) |
| *C07D 401/12* | (2006.01) |
| *C07D 403/04* | (2006.01) |
| *C07D 403/10* | (2006.01) |
| *C07D 403/12* | (2006.01) |
| *C07D 409/10* | (2006.01) |
| *C07D 471/04* | (2006.01) |

(52) U.S. Cl.
CPC ............ *C07D 401/04* (2013.01); *A61K 31/517* (2013.01); *A61K 31/519* (2013.01); *A61K 31/5377* (2013.01); *A61K 31/55* (2013.01); *A61K 31/551* (2013.01); *C07D 239/91* (2013.01); *C07D 401/10* (2013.01); *C07D 401/12* (2013.01); *C07D 403/04* (2013.01); *C07D 403/10* (2013.01); *C07D 403/12* (2013.01); *C07D 409/10* (2013.01); *C07D 471/04* (2013.01)

(58) Field of Classification Search
USPC .................. 514/224.2, 135.2, 235.2
See application file for complete search history.

(56) References Cited

U.S. PATENT DOCUMENTS

| | | | |
|---|---|---|---|
| 2,065,593 | A | 12/1936 | Lubs |
| 2,065,900 | A | 12/1936 | Laska et al. |
| 2,071,329 | A | 2/1937 | Brown |
| 3,251,837 | A | 5/1966 | Holland |
| 3,600,394 | A | 8/1971 | Coyne et al. |
| 3,773,946 | A | 11/1973 | Creger |
| 3,930,024 | A | 12/1975 | Creger |
| 3,965,128 | A | 6/1976 | Fürst et al. |
| 4,613,593 | A | 9/1986 | Yamatsu et al. |
| 4,689,344 | A | 8/1987 | Bar-Tana |
| 4,711,896 | A | 12/1987 | Bar-Tana et al. |
| 4,825,005 | A | 4/1989 | Frey et al. |
| 5,098,903 | A | 3/1992 | Magarian et al. |
| 5,124,337 | A | 6/1992 | Dugar et al. |
| 5,126,351 | A | 6/1992 | Luzzio et al. |
| 5,244,904 | A | 9/1993 | Nagase et al. |
| 5,280,024 | A | 1/1994 | Bolland et al. |
| 5,354,749 | A | 10/1994 | Dressel et al. |
| 5,407,942 | A | 4/1995 | Dressel et al. |
| 5,409,930 | A | 4/1995 | Spada et al. |
| 5,446,071 | A | 8/1995 | Grese |
| 5,474,994 | A | 12/1995 | Leonardi et al. |
| 5,480,883 | A | 1/1996 | Spada et al. |
| 5,539,119 | A | 7/1996 | Nagase et al. |
| 5,576,322 | A | 11/1996 | Takase et al. |
| 5,595,974 | A | 1/1997 | Tomaru |
| 5,693,652 | A | 12/1997 | Takase et al. |
| 5,707,987 | A | 1/1998 | Nakagawa et al. |

(Continued)

FOREIGN PATENT DOCUMENTS

| | | |
|---|---|---|
| AU | 719140 B2 | 7/1998 |
| CA | 2104981 A1 | 3/1994 |

(Continued)

OTHER PUBLICATIONS

Libby et al., Circulations, 2002;105:1135-1143.*
Abdel-Jalil et al., "Synthesis and Antitumor Activity of 2-Aryl-7-fluoro-6-(4-methyl-l-piperazinyl)-4(3*H*)-quinazolinones" *Heterocycles* 65(9):2061-2070 (2005).
Abdul-Rahman et al., "Dinuclear molybdenum complexes derived from diphenols: electrochemical interactions and reduced species" *Polyhedron* 16(24):4353-4362 (1997).
Acton, S. et al., "Identification of Scavenger Receptor SR-BI as a High Density Lipoprotein Receptor" *Science* 271:518-520 (1996).
Asztalos, "High-Density Lipoprotein Metabolism and Progression of Atherosclerosis: New Insights from the HDL Atherosclerosis Treatment Study" *Curr. Opin. Cardiol.* 19:385-391 (2004).

(Continued)

*Primary Examiner* — San-Ming Hui
(74) *Attorney, Agent, or Firm* — Finnegan, Henderson, Farabow, Garrett & Dunner, LLP

(57) ABSTRACT

Disclosed are novel compounds that are useful in regulating the expression of interleukin-6 (IL-6) and/or vascular cell adhesion molecule-1 (VCAM-1), and their use in the treatment and/or prevention of cardiovascular and inflammatory diseases and related disease states, such as, for example, atherosclerosis, asthma, arthritis, cancer, multiple sclerosis, psoriasis, and inflammatory bowel diseases, and autoimmune disease(s). Also, disclosed are compositions comprising the novel compounds, as well as methods for their preparation.

20 Claims, No Drawings

(56) References Cited

U.S. PATENT DOCUMENTS

| | | | |
|---|---|---|---|
| 5,733,913 A | 3/1998 | Blankley et al. | |
| 5,756,344 A | 5/1998 | Onda et al. | |
| 5,756,544 A | 5/1998 | Bisgaier et al. | |
| 5,756,736 A | 5/1998 | Arzeno et al. | |
| 5,756,763 A | 5/1998 | Takeuchi et al. | |
| 5,763,414 A | 6/1998 | Bok et al. | |
| 5,783,577 A | 7/1998 | Houghten et al. | |
| 5,792,461 A | 8/1998 | Bok et al. | |
| 5,792,902 A | 8/1998 | Benoit et al. | |
| 5,798,344 A | 8/1998 | Kuroki et al. | |
| 5,801,180 A | 9/1998 | Takase et al. | |
| 5,817,674 A | 10/1998 | Clemence et al. | |
| 5,854,264 A | 12/1998 | Anthony et al. | |
| 5,877,208 A | 3/1999 | Bok et al. | |
| 5,922,866 A | 7/1999 | Miyata et al. | |
| 5,965,556 A | 10/1999 | Takeuchi et al. | |
| 6,022,901 A | 2/2000 | Goodman | |
| 6,048,903 A | 4/2000 | Toppo | |
| 6,054,435 A | 4/2000 | Or et al. | |
| 6,133,241 A | 10/2000 | Bok et al. | |
| 6,165,984 A | 12/2000 | Bok et al. | |
| 6,168,776 B1 | 1/2001 | Klunk et al. | |
| 6,239,114 B1 | 5/2001 | Guthrie et al. | |
| 6,291,456 B1 | 9/2001 | Stein et al. | |
| 6,303,629 B1 | 10/2001 | Kun | |
| 6,340,759 B1 | 1/2002 | Ueno et al. | |
| 6,414,037 B1 | 7/2002 | Pezzuto et al. | |
| 6,455,577 B2 | 9/2002 | Bok et al. | |
| 6,479,499 B1 | 11/2002 | Kuo et al. | |
| 6,482,479 B1 | 11/2002 | Dübal et al. | |
| 6,512,161 B1 | 1/2003 | Rouy et al. | |
| 6,541,045 B1 | 4/2003 | Charters et al. | |
| 6,541,522 B2 | 4/2003 | Inman et al. | |
| 6,548,548 B2 | 4/2003 | Campbell et al. | |
| 6,613,772 B1 | 9/2003 | Schindler et al. | |
| 6,635,642 B1 | 10/2003 | Jackson et al. | |
| 6,673,780 B2 | 1/2004 | Dasseux et al. | |
| 6,703,422 B2 | 3/2004 | Dasseux et al. | |
| 6,723,319 B1 | 4/2004 | Ito et al. | |
| 7,087,612 B2 | 8/2006 | Rodriguez Sarmiento et al. | |
| 7,173,128 B2 | 2/2007 | Ravichandran et al. | |
| 7,244,776 B2 | 7/2007 | Ravichandran et al. | |
| 7,655,699 B1 | 2/2010 | Boehm et al. | |
| 7,846,915 B2 | 12/2010 | Wong et al. | |
| 8,053,440 B2 | 11/2011 | Hansen | |
| 8,093,273 B2 | 1/2012 | Wong et al. | |
| 8,114,995 B2 | 2/2012 | Hansen et al. | |
| 8,242,130 B2 | 8/2012 | Wong et al. | |
| 8,242,144 B2 | 8/2012 | Wong et al. | |
| 8,410,109 B2 | 4/2013 | Wong et al. | |
| 8,440,196 B1 | 5/2013 | Funakoshi et al. | |
| 8,884,046 B2 | 11/2014 | Lozanov et al. | |
| 8,889,698 B2 | 11/2014 | Hansen | |
| 8,952,021 B2 | 2/2015 | Hansen | |
| 2002/0004608 A1 | 1/2002 | Alig et al. | |
| 2002/0025301 A1 | 2/2002 | Haremza et al. | |
| 2002/0091263 A1 | 7/2002 | Trova | |
| 2003/0064967 A1 | 4/2003 | Luchoomun et al. | |
| 2003/0068526 A1 | 4/2003 | Kamatani et al. | |
| 2003/0072964 A1 | 4/2003 | Kwong et al. | |
| 2003/0171429 A1 | 9/2003 | Chen et al. | |
| 2004/0001834 A1 | 1/2004 | Kim et al. | |
| 2004/0033480 A1 | 2/2004 | Wong | |
| 2004/0058903 A1 | 3/2004 | Takasugi et al. | |
| 2004/0097493 A1 | 5/2004 | Chen et al. | |
| 2004/0198750 A1 | 10/2004 | Green et al. | |
| 2004/0235888 A1 | 11/2004 | Yamamori et al. | |
| 2004/0242615 A1 | 12/2004 | Yamamori et al. | |
| 2004/0248950 A1 | 12/2004 | Ishizuka et al. | |
| 2005/0043300 A1 | 2/2005 | Middleton et al. | |
| 2005/0080021 A1 | 4/2005 | Tucker et al. | |
| 2005/0080024 A1 | 4/2005 | Tucker et al. | |
| 2005/0261319 A1 | 11/2005 | Deuschle et al. | |
| 2006/0116364 A1 | 6/2006 | Hamaoka et al. | |
| 2007/0032430 A1 | 2/2007 | Fogelman et al. | |
| 2007/0099826 A1 | 5/2007 | Wong et al. | |
| 2007/0185160 A1 | 8/2007 | Hattori et al. | |
| 2007/0218155 A1 | 9/2007 | Kuhrts | |
| 2008/0152595 A1 | 6/2008 | Emigh et al. | |
| 2008/0188467 A1* | 8/2008 | Wong et al. | 514/224.2 |
| 2008/0275069 A1 | 11/2008 | Mizutani et al. | |
| 2009/0029987 A1 | 1/2009 | Wong et al. | |
| 2010/0004448 A1* | 1/2010 | Hansen et al. | 544/289 |
| 2010/0093636 A1 | 4/2010 | Schultz et al. | |
| 2011/0201608 A1 | 8/2011 | Hoffmann et al. | |
| 2011/0294807 A1 | 12/2011 | Hansen | |
| 2012/0015905 A1 | 1/2012 | Hansen | |
| 2012/0059002 A1 | 3/2012 | Hansen et al. | |
| 2013/0108672 A1 | 5/2013 | Shenoy | |
| 2014/0107369 A1 | 4/2014 | Lozanov at al, | |
| 2015/0072955 A1 | 3/2015 | Hansen | |

FOREIGN PATENT DOCUMENTS

| | | |
|---|---|---|
| CA | 2345406 A1 | 4/2000 |
| CA | 2676984 A1 | 8/2008 |
| CA | 2815127 A1 | 4/2012 |
| CN | 1067070 C | 6/2001 |
| CN | 1430599 A | 7/2003 |
| DE | 637259 | 10/1936 |
| DE | 652772 | 11/1937 |
| DE | 35 32 279 A1 | 3/1987 |
| DE | 36 01 417 A1 | 7/1987 |
| DE | 42 15 588 A1 | 11/1993 |
| DE | 196 51 099 A1 | 6/1998 |
| DE | 197 56 388 A1 | 6/1999 |
| DE | 199 34 799 A1 | 2/2001 |
| EP | 0 210 342 A2 | 2/1987 |
| EP | 0 182 213 B1 | 9/1990 |
| EP | 0 407 217 A1 | 1/1991 |
| EP | 0 410 834 A1 | 1/1991 |
| EP | 0 258 190 B1 | 11/1991 |
| EP | 0 488 602 A1 | 6/1992 |
| EP | 0 272 455 B1 | 2/1993 |
| EP | 0 375 404 B1 | 2/1994 |
| EP | 0 333 175 B1 | 6/1994 |
| EP | 0 343 499 B1 | 7/1994 |
| EP | 0 409 413 B1 | 8/1994 |
| EP | 0 420 511 B1 | 8/1994 |
| EP | 0 633 022 A2 | 1/1995 |
| EP | 0 569 795 B1 | 4/1995 |
| EP | 0 330 108 B1 | 12/1995 |
| EP | 0 747 051 A2 | 12/1996 |
| EP | 0 564 350 B1 | 5/1997 |
| EP | 0 643 119 B1 | 4/2000 |
| EP | 1 125 908 A1 | 8/2001 |
| EP | 0 498 723 B1 | 9/2001 |
| EP | 0 607 439 B1 | 1/2002 |
| EP | 0 776 893 B1 | 2/2002 |
| EP | 1 195 378 A1 | 4/2002 |
| EP | 1 277 738 A1 | 1/2003 |
| EP | 1 398 032 A1 | 3/2004 |
| EP | 1 418 164 A1 | 5/2004 |
| EP | 1 426 046 A1 | 6/2004 |
| EP | 1 477 481 A1 | 11/2004 |
| EP | 1 637 523 A1 | 3/2006 |
| EP | 1 757 594 A1 | 2/2007 |
| EP | 1 944 301 A1 | 7/2008 |
| EP | 2 005 941 A2 | 12/2008 |
| FR | 803201 | 9/1936 |
| FR | 803619 | 10/1936 |
| FR | 2 244 492 | 4/1975 |
| FR | 2 244 493 | 4/1975 |
| GB | 472489 | 9/1937 |
| GB | 728767 | 4/1955 |
| GB | 1175808 | 12/1969 |
| GB | 1179019 | 1/1970 |
| GB | 2 292 149 A | 2/1996 |
| IE | 902587 A1 | 7/1990 |
| JP | 6-80656 A | 3/1994 |
| JP | 7-41442 A | 2/1995 |
| JP | 7- 61942 A | 3/1995 |
| JP | 7-118241 A | 5/1995 |
| JP | 7-179380 A | 7/1995 |

(56) References Cited

FOREIGN PATENT DOCUMENTS

| | | |
|---|---|---|
| JP | 7-233109 A | 9/1995 |
| JP | 7-247289 A | 9/1995 |
| JP | 10-287678 A | 10/1998 |
| JP | 2004-511502 A | 4/2001 |
| JP | 2001-131151 A | 5/2001 |
| JP | 2001-139550 A | 5/2001 |
| JP | 2001-335476 A | 12/2001 |
| JP | 2002-249483 A | 9/2002 |
| JP | 2004-203751 A | 7/2004 |
| JP | 2004-307440 A | 11/2004 |
| KR | 10-0707532 B1 | 8/2005 |
| NZ | 556545 A | 3/2009 |
| WO | WO 91/18901 A1 | 12/1991 |
| WO | WO 92/09374 A1 | 6/1992 |
| WO | WO 92/18123 A2 | 10/1992 |
| WO | WO 92/20642 A1 | 11/1992 |
| WO | WO 92/21661 A1 | 12/1992 |
| WO | WO 93/07124 A1 | 4/1993 |
| WO | WO 93/08174 A1 | 4/1993 |
| WO | WO 94/14763 A1 | 7/1994 |
| WO | WO 95/03277 A1 | 2/1995 |
| WO | WO 95/23150 A1 | 8/1995 |
| WO | WO 96/15128 A2 | 5/1996 |
| WO | WO 96/31206 A2 | 10/1996 |
| WO | WO 97/10221 A1 | 3/1997 |
| WO | WO 97/15308 A1 | 5/1997 |
| WO | WO 97/28118 A1 | 8/1997 |
| WO | WO 97/28132 A1 | 8/1997 |
| WO | WO 97/28134 A1 | 8/1997 |
| WO | WO 97/29106 A1 | 8/1997 |
| WO | WO 97/48694 A1 | 12/1997 |
| WO | WO 98/11438 A1 | 3/1998 |
| WO | WO 98/26127 A1 | 6/1998 |
| WO | WO 98/30530 A1 | 7/1998 |
| WO | WO 98/50370 A1 | 11/1998 |
| WO | WO 98/51307 A1 | 11/1998 |
| WO | WO 98/51308 A1 | 11/1998 |
| WO | WO 98/55124 A1 | 12/1998 |
| WO | WO 99/00116 A2 | 1/1999 |
| WO | WO 99/11634 A1 | 3/1999 |
| WO | WO 99/18077 A1 | 4/1999 |
| WO | WO 99/29667 A1 | 6/1999 |
| WO | WO 99/47170 A1 | 9/1999 |
| WO | WO 00/10607 A1 | 3/2000 |
| WO | WO 00/17184 A1 | 3/2000 |
| WO | WO 00/23075 A1 | 4/2000 |
| WO | WO 00/35865 A2 | 6/2000 |
| WO | WO 00/44362 A2 | 8/2000 |
| WO | WO 00/55168 A1 | 9/2000 |
| WO | WO 00/64888 A1 | 11/2000 |
| WO | WO 01/00554 A2 | 1/2001 |
| WO | WO 01/60775 A1 | 8/2001 |
| WO | WO 01/82916 A2 | 11/2001 |
| WO | WO 01/83456 A1 | 11/2001 |
| WO | WO 01/90051 A1 | 11/2001 |
| WO | WO 02/32377 A2 | 4/2002 |
| WO | WO 02/44189 A1 | 6/2002 |
| WO | WO 02/074307 A1 | 9/2002 |
| WO | WO 02/087556 A2 | 11/2002 |
| WO | WO 02/096426 A1 | 12/2002 |
| WO | WO 03/007959 A1 | 1/2003 |
| WO | WO 03/016292 A1 | 2/2003 |
| WO | WO 03/018008 A1 | 3/2003 |
| WO | WO 03/040256 A2 | 5/2003 |
| WO | WO 03/040257 A1 | 5/2003 |
| WO | WO 03/070236 A2 | 8/2003 |
| WO | WO 03/099274 A1 | 12/2003 |
| WO | WO 03/106435 A1 | 12/2003 |
| WO | WO 2004/017920 A2 | 3/2004 |
| WO | WO 2004/019933 A1 | 3/2004 |
| WO | WO 2004/032846 A2 | 4/2004 |
| WO | WO 2004/037176 A2 | 5/2004 |
| WO | WO 2004/039795 A2 | 5/2004 |
| WO | WO 2004/047755 A2 | 6/2004 |
| WO | WO 2004/056355 A1 | 7/2004 |
| WO | WO 2004/058717 A1 | 7/2004 |
| WO | WO 2004/065392 A1 | 8/2004 |
| WO | WO 2004/072042 A2 | 8/2004 |
| WO | WO 2004/092196 A2 | 10/2004 |
| WO | WO 2004/094452 A2 | 11/2004 |
| WO | WO 2004/108139 A2 | 12/2004 |
| WO | WO 2004/112710 A2 | 12/2004 |
| WO | WO 2005/042712 A2 | 5/2005 |
| WO | WO 2005/065183 A2 | 7/2005 |
| WO | WO 2005/066162 A1 | 7/2005 |
| WO | WO 2005/075431 A1 | 8/2005 |
| WO | WO 2005/115993 A1 | 12/2005 |
| WO | WO 2006/012577 A2 | 2/2006 |
| WO | WO 2006/071095 A1 | 7/2006 |
| WO | WO 2006/105081 A2 | 10/2006 |
| WO | WO 2007/071055 A1 | 6/2007 |
| WO | WO 2008/092231 A1 | 8/2008 |
| WO | WO 2008/152471 A1 | 12/2008 |
| WO | WO 2010/015520 A1 | 2/2010 |
| WO | WO 2010/100178 A1 | 9/2010 |
| WO | WO 2012/112531 A1 | 8/2012 |
| WO | WO 2015/025226 A2 | 2/2015 |
| WO | WO 2015/025228 A2 | 2/2015 |

OTHER PUBLICATIONS

Baba et al., "Continuous intake of polyphenolic compounds containing cocoa powder reduces LDL oxidative susceptibility and has beneficial effects on plasma HDL-cholesterol concentrations in humans" *Am. J. Clin. Nutr.* 85:709-717 (2007).

Badimon et al., "Role of High Density Lipoproteins in the Regression of Atherosclerosis" *Circulation* 86(Suppl. III):86-94 (1992).

Barrans et al., "Pre-β HDL: Structure and Metabolism" *Biochim, Biophys. Acta* 1300:73-85 (1996).

Barter et al., "Antiinflammatory Properties of HDL" *Circ. Res.* 95:764-772 (2004).

Barter et al., "High Density Lipoproteins and Coronary Heart Disease" *Atherosclerosis* 121:1-12 (1996).

Bayly et al., "Electronic and magnetic metal-metal interactions in dinuclear oxomolybdenum(V) complexes across bis-phenolate bridging ligands with different spacers between the phenolate termini: ligand-centered vs. metal-centered redox activity" *J. Chem. Soc., Dalton Transactions* 9:1401-1414 (2001).

Bertele et al., "Platelet Thromboxane Synthetase Inhibitors with Low Doses of Aspirin: Possible Resolution of the 'Aspirin Dilemma'" *Science* 220:517-519 (1983).

Beugelmans et al., "One-pot Synthesis of 1-Oxo-1,2-Dihydroisoquinolines (Isocarbostyrils) Via $S_{RN}1$ (Ar) Reactions" *Synthesis* 9:729-731 (1981).

Bhilare et al., "Ionic-Liquid-Influenced Expeditious and Stereoselective Synthesis of Olefins" *Synthetic Communications* 37(18):3111-3117 (2007).

Bisagni et al., "A Convenient Way to Dibenzo[c,h]-1,5-Naphthyridines (11-Aza-Benzo[c]phenanthridines)" *Tetrahedron* 52:10427-10440 (1996).

Bisgaier et al., "A Novel Compound that Elevates High Density Lipoprotein and Activates the Peroxisome Proliferator Activated Receptor" *J. Lipid Res.* 39:17-30 (1998).

Boyce et al., "The Acylation and Alkylation of o-Tolunitrile. A New Route to 3-Substituted Isocarbostyrils" *J. Org. Chem.* 31:3807-3809 (1966).

Bradsher et al., "A New Isoquinoline Synthesis Via ORTHO-Substituted Benzylamines" *Tetrahedron Lett.* 31:3149-3150 (1972).

Bradsher et al., "α-Acyl-o-Tolunitriles as Intermediates in the Preparation of 3-Substituted Isoquinolines and 1-Amino-2-benzopyrylium Derivatives" *J. Org. Chem.* 43:3817-3820 (1978).

Buhle et al., "Trivalent Carbon. II. Unsymmetrical Hexaaryldimethylperoxides" *J. Am. Chem. Soc.* 65:584-586 (1943).

Caplus Accession No. 1991:449453, Liu et al. "Synthesis of 2-aryl-9-bromo-4-oxo-4H-pyrano[3,2-c] quinolines" [online]. Retrieved from STN on Jan. 31, 2011. Also published in: *Youji Huaxue* 11(2):191-195 (1991).

Caplus Accession No. 2003:554477, Qin et al., "Synthesis and fungicidal activity of novel diazaflavanones"[online]. Retrieved from STN on Jan. 31, 2011. Also published in: *Nongyaoxue Xuebao* 4(4):28-32 (2002).

(56) References Cited

OTHER PUBLICATIONS

Caplus Accession No. 2004:11346, Hu et al., "Synthesis and fungicidal activity of flavanone derivatives containing isopentenyl group" [online]. Retrieved from STN on Jan. 31, 2011. Also published in: *Yingyong Huaxue* 20(12):1161-1165 (2003).
Caplus Accession No. 2005:46491, Qin et al., "Synthesis and fungicidal activity of 5,7-dihydroxyldiazinflavanones" [online]. Retrieved from STN on Jan. 31, 2011. Also published in: *Huazhong Shifan Daxue Xuebao Zirankexueban*38(3):323-325 (2004).
Chakrabarty et al., "Induction of apoptosis in human cancer cell lines by diospyrin, a plant-derived bisnaphthoquinonoid, and its synthetic derivatives" *Cancer Letters* 188(1-2):85-93 (2002).
Chartier et al., "Synthèse de diazaflavones" *Bull. Soc. Chim. Fr.* 11-12(Pt. 2):1916-1918 (1976).
Cherubini et al., "Role of Antioxidants in Atherosclerosis: Epidemiological and Clinical Update" *Curr. Pharm. Des.* 11:2017-2032 (2005).
Cho et al., "Molecular Modeling of 3-Arylisoquinoline Antitumor Agents Active Against A-549. A Comparative Molecular Field Analysis Study" *Bioorg. Med. Chem.* 10:2953-2961 (2002).
Cho et al., "Synthesis and Antitumor Activity of 3-Arylisoquinoline Derivatives" *Arch. Pharm. Res.* 20:264-268 (1997).
Cho et al., "Synthesis and Biological Evaluation of 3-Arylisoquinolines As Antitumor Agents" *Bioorg. Med. Chem. Lett.* 8:41-46 (1998).
Cho et al., "Synthesis and Comparative Molecular Field Analysis (CoMFA) of Antitumor 3-Arylisoquinoline Derivatives" *Bioorg. Med. Chem.* 6(12):2449-2458 (1998).
Chyu et al., "Differential Effects of Green Tea-Derived Catechin on Developing Versus Established Atherosclerosis in Apolipoprotein E-Null Mice" *Circulation* 109:2448-2453 (2004).
Clarkson et al., "Inhibition of Postmenopausal Atherosclerosis Progression: A Comparison of the Effects of Conjugated Equine Estrogens and Soy Phytoestrogens" *J. Clin. Endocrinol. Metab.* 86(1):41-47 (2001).
Clauson-Kaas et al., "Reactions of 3,4-dihydor-2H-pyrrido[3,2-b]-1,4-oxazines" *Acta Chemica Scandinavica* 25(8):3135-3143 (1971). Retrieved from STN, file HCAPLUS, Accession No. 1972:34186 (Abstract).
Connolly et al., "Synthesis of quinazolinones and quinazolines" *Tetrahedron* 61(43):10153-10202 (2005).
Cooper et al., "Wine polyphenols and promotion of cardiac health" *Nutr. Res. Rev.* 17:111-129 (2004).
Cramer et al., "New Syntheses of Aryl Fluorides and Aryl Fluorosulfonates from Oxyflourides of Sulfur" *J. Org. Chem.* 26:4164-4165 (1961).
Dai et al., "Synthesis of 3,4-Disubstituted Isoquinolines via Palladium-Catalyzed Cross-Coupling of 2-(1-alkynyl)benzaldimines and Organic Halides" *J. Org. Chem.* 68:920-928 (2003).
Dai et al., "Synthesis of 3-Substituted 4-Aroylisoquinolines via Pd-Catalyzed Carbonylative Cyclization of 2-(1-Alkynyl)benzaldimines" *J. Org. Chem.* 67:7042-7047 (2002).
Dansky et al., "High-Density Lipoprotein and Plaque Regression. The Good Cholesterol Gets Even Better" *Circulation* 100:1762-1763 (1999).
Decossin et al., "Subclasses of LpA-I in Coronary Artery Disease: Distribution and Cholesterol Efflux Ability" *Eur. J. Clin. Invest.* 27:299-307 (1997).
Devitt et al., "Synthesis of Heterocyclic-Substituted Chromones and Chalcones" *J. Org. Chem.* 26:4941-4944 (1961).
Edwards et al., "Inhibition of myeloperoxidase release from rat polymorphonuclear leukocytes by a series of azachalcone derivatives" *J. Med. Chem.* 37(25):4357-4362 (1994).
Eiden et al., "1,2-Bisbenzopyranyl-ethene" *Archiv. der Pharmazie* 313(2):120-128 (1980) (German).
Esterbauer et al., "Continuous Monitoring of In Vitro Oxidation of Human Low Density Lipoprotein" *Free Rad. Res. Comms.* 6:67-75 (1989).
Ferreira et al., "Diversity of Structure and Function in Oligomeric Flavanoids" *Tetrahedron* 48:1743-1803 (1992).

Fielding et al., "Molecular Physiology of Reverse Cholesterol Transport" *J. Lipid Res.* 36:211-228 (1995).
Fieser, L.F., "The potentials of some unstable oxidation-reduction systems" *J. Am. Chem. Soc.* 52:4915-4940 (1930).
Fisher Center for Alzheimer'S Research Foundation, "Alzheimer's Disease: 'Good' Cholesterol May Help Keep Alzheimer's at Bay" The Ninth International Conference on Alzheimer's Disease and Related Disorders, Philadelphia, PA, Jul. 22, 2004. Retrieved from the Internet: http://www.alzinfo.org/newsarticle/templates/archivenewstemplate.asp?articleid=156&zoneid=7 on Jul. 28, 2010 (3 pages).
Flammang et al., "2,3-Benzodiazepines: 2-Aminoisoquinolinones From Ring Contraction of 1-oxo-2,3-Benzodiazepines" *C R Acad. Sci. Paris, Series C* 290:361-363 (1980) (French).
Fokialakis et al., "A New Class of Phytoestrogens: Evaluation of the Estrogenic Activity of Deoxybenzoins" *Chem. Biol.* 11:397-406 (2004).
Gaziano et al., "Relation Between Systemic Hypertension and Blood Lipids on the Risk of Myocardial Infarction" *Am. J. Cardiol.* 84(7):768-773 (1999).
Gerritsen et al., "Flavenoids inhibit cytokine-induced endothelial cell adhesion protein gene expression" *Am. J. Pathol.* 147(2):278-292 (1995).
Gidez et al., "Separation and Quantitation of Subclasses of Human Plasma High Density Lipoproteins by a Simple Precipitation Procedure" *J. Lipid Res.* 23:1206-1223 (1982).
Gordon et al., "High Density Lipoprotein As a Protective Factor Against Coronary Heart Disease" *Am. J. Med.* 62(5):707-714 (1977).
Grundy et al., "Definition of Metabolic Syndrome. Report of the National Heart, Lung and Blood Institute/American Heart Association Conference on Scientific Issues Related to Definition" *Circulation* 109:433-438 (2004).
Gugler et al., "Disposition of Quercetin in Man after Single Oral and Intravenous Doses" *Eur. J. Clin. Pharmacol.* 9:229-234 (1975).
Guillory, J.K., "Generation of Polymorphs, Hydrates, Solvates, and Amorphous Solids" Brittain, Harry G. (ed.) *Polymorphism in Pharmaceutical Solids.* vol. 95. Marcel Dekker, Inc., New York; pp. 202-208 (1999).
Hakamata et al., "Differential effects of an acyl-coenzyme A: cholesterol acyltransferase inhibitor on HDL-induced cholesterol efflux from rat macrophage foam cells" *FEBS Letters* 363:29-32 (1995).
Haneke, "*trans*-Resveratrol, [501-36-0], Review of Toxicological Literature" Nat. Inst. Environ. Health Sciences Contract No. N01-ES-65402 (Mar. 2002).
Hazra et al., "New diospyrin derivatives with improved tumour inhibitory activity towards Ehrlich ascites carcinoma" *Medical Science Research* 22(5):351-353 (1994).
Hazra et al., "Synthesis of an antitumor derivative of diospyrin" *IRCS Medical Science* 14(1):35-36 (1986).
Heeg et al., "Plasma Levels of Probucol in Man after Single and Repeated Oral Doses" *La Nouvelle Presse Medicate* 9:2990-2994 (1980).
Hemingway et al., "A gas-liquid chromatographic examination of stilbene derivatives" *J. Chromatog.* 50(3):391-399 (1970).
Hertog et al., "Dietary Antioxidant Flavonoids and Risk of Coronary Heart Disease: the Zutphen Elderly Study" *Lancet* 342:1007-1011 (1993).
Hidaka et al., "Affinity Purification of the Hepatic High-Density Lipoprotein Receptor Identifies Two Acidic Glycoproteins and Enables Further Characterization of Their Binding Properties" *Biochem. J.* 284:161-167 (1992).
Hirano et al., "Genetic Cholesteryl Ester Transfer Protein Deficiency Is Extremely Frequent in the Omagari Area of Japan. Marked Hyperalphalipoproteinemia Caused by CETP Gene Mutation Is Not Associated With Longevity" *Arterioscler Thromb. Vasc. Biol.* 17:1053-1059 (1997).
Hisano et al., "Studies on Organosulfur Compounds. XII. Syntheses and Pharmacological Activities of 2-Heterocyclic Substituted 4(3H)-Quinazolinones" *Chem. Pharm. Bull.* 23(9):1910-1916 (1975).
Huang et al., "Synthesis of Isoquinolines by Palladium-Catalyzed Cyclization, Followed by a Heck Reaction" *Tetrahedron Lett.* 43:3557-3560 (2002).

(56) References Cited

OTHER PUBLICATIONS

Hwang et al., "Syntergistic inhibition of LDL oxidation by phytoestrogens and ascorbic acid" Free Radical *Biology and Medicine* 29(1):79-89 (Jul. 1, 2000).
International Search Report and Written Opinion issued in International Application No. PCT/CA2004/001818; Date of Mailing: Feb. 28, 2005.
International Search Report and Written Opinion issued in International Application No. PCT/CA2007/000146; Date of Mailing: Oct. 29, 2007.
International Search Report and Written Opinion issued in International Application No. PCT/IB2010/000159; Date of Mailing: Aug. 5, 2010.
International Search Report and Written Opinion issued in International Application No. PCT/IB2010/000826; Date of Mailing: Oct. 12, 2010.
International Search Report and Written Opinion issued in International Application No. PCT/US2005/037719; Date of Mailing: Mar. 9, 2007.
International Search Report and Written Opinion issued in International Application No. PCT/US2005/038048; Date of Mailing: Mar. 7, 2007.
International Search Report and Written Opinion issued in International Application No. PCT/US2006/029827; Date of Mailing: Apr. 16, 2007.
International Search Report and Written Opinion issued in International Application No. PCT/US2009/048457; Date of Mailing: Oct. 16, 2009.
International Search Report and Written Opinion issued in International Application No. PCT/US2010/031870; Date of Mailing: Jul. 1, 2010.
Ishibashi et al., "Hypercholesterolemia in Low Density Lipoprotein Receptor Knockout Mice and its Reversal by Adenovirus-Mediated Gene Delivery" *J. Clin. Invest.* 92:883-893 (1993).
Ishibashi et al., "Massive Xanthomatosis and Atherosclerosis in Cholesterol-Fed Low Density Lipoprotein Receptor-Negative Mice" *J. Clin. Invest.* 93:1885-1893 (1994).
Japanese Office Action issued in Japanese Patent Application No. 2008-524272, mailed Jul. 24, 2012, with English translation.
Jayatilake et al., "Kinase Inhibitors From *Polygonum cuspidatum*" *J. Nat. Prod.* 56:1805-1810 (1993).
Jensen et al., "Serum Lipids and Anthropometric Factors Related to the Prevalence of Intermittent Claudication" *Eur. J. Vasc. Endovasc. Surg.* 30:582-587 (2005).
Jeong et al., "Hypocholesterolemic activity of hesperetin derivatives" *Bioorg. Med. Chem. Lett.* 13:2663-2665 (2003).
Jin et al., "Antiplatelet and antithrombotic activities of CP201, a newly synthesized 1,4-naphthoquinone derivative" *Vasc. Pharmacol.* 41(1):35-41 (2004).
Kalusa et al., "An efficient synthesis of 2,3-diaryl (3H)-quinazolin-4-ones via imidoyl chlorides" *Tetrahedron Letters* 49(41):5840-5842 (2008).
Kawamatsu et al., "2-Amino-4-Phenylthiazole Derivatives As Anti-Atherogenic Agents" *Eur. J. Med. Chem.—Chimica Therapeutica* 16(4):355-362 (1981).
Kilbourne et al., "Involvement of Early Growth Response Factor Egr-1 in Apolipoprotein Al Gene Transcription" *J. Biol. Chem.* 270:7004-7010 (1995).
Kim et al., "Hypothetical Drug Binding Receptor Site Analysis Using CoMFA Method for 3-Arylisoquinolines Active Against SK-OV-3 Tumor Cell Line" *Yakhak Hoechi* 46(4):219-225 (2002).
Koudinov et al., "Alzheimer's amyloid beta and lipid metabolism: a missing link?" *FASEB J.* 12:1097-1099 (1998).
Kublak et al., "The preparation of the aza-spirobicyclic system of discorhabdin C via an intramolecular phenolate alkylation" *Tetrahedron Lett.* 31(27):3845-3848 (1990).
Kulkarni, K.R. et al.,"Quantification of $HDL_2$ and $HDL_3$ Cholesterol by the Vertical Auto Profile-II (VAP-II) Methodology" *J. Lipid Res.* 38:2353-2364 (1997).
Kurata et al., "A Candidate High Density Lipoprotein (HDL) Receptor, $HB_2$, with Possible Multiple Functions Shows Sequence Homology with Adhesion Molecules" *J. Atheroscler. Thromb.* 4:112-117 (1998).
Kurowska et al., "Essential Amino Acids in Relation to Hypercholesterolemia Induced in Rabbits by Dietary Casein" *J. Nutr.* 120:831-836 (1990).
Kuzuya et al., "Probucol Prevents Oxidative Injury to Endothelial Cells" *J. Lipid Res.* 32:197-204 (1991).
Laarhoven et al., "Syntheses, infrared spectra and molecular refractions of some sterically hindered *p,p'*-dimethoxystilbenes. Influence of non-planarity in styrene and stilbene derivatives IV" *Recueil des Travaux Chimiques des Pays-Bas* 80:775-791 (1961).
Lagrost et al., "Opposite Effects of Cholesteryl Ester Transfer Protein and Phospholipid Transfer Protein on the Size Distribution of Plasma High Density Lipoproteins" *J. Biol. Chem.* 271:19058-19065 (1996).
Lamon-Fava, "Genistein activates apolipoprotein A-I gene expression in the human hepatoma cell line Hep G2" *J. Nutrition* 130:2489-2492 (2000).
Landshulz et al., "Regulation of Scavenger Receptor, Class B, Type I, a High Density Lipoprotein Receptor, in Liver and Steroidogenic Tissues of the Rat" *J. Clin. Invest.* 98:984-995 (1996).
Letan, "The Relation of Structure to Antioxidant Activity of Quercetin and some of Its Derivatives. I. Primary Activity" *J. Food Sci.* 13(4):518-523 (1966).
Lin et al., "Chemoprevention of Cancer and Cardiovascular Disease by Resveratrol" *Proc. Natl. Sci. Counc. ROC (B)* 23:99-106 (1999).
Lin et al., "Potential bioreductive alkylating agents. 7. Antitumor effects of phenyl-substituted 2-chloromethyl-3-phenyl-1,4-naphthoquinones" *J. Med. Chem.* 19(11):1336-1338 (1976).
Lin et al., "Solvent Effects on Aza-Anionic Cycloaromatization of 2-(2-Substituted-Ethynyl)Benzonitriles" *J. Chinese Chem. Soc.* 48:211-214 (2001).
Lin et al., "The Role of Absorption, Distribution, Metabolism, Excretion and Toxicity in Drug Recovery" *Curr. Top. Med. Chem.* 3:1125-1154 (2003).
Linnell et al. "Isomers of stilbestrol. II." *Q. J. Pharm. Pharmacol.* 15:384-388 (1942).
Lopez et al., "The Synthesis of Substituted 2-Aryl-4(3H)-quinazolinones using $NaHSO_3$/DMA. Steric Effect Upon the Cyclisation-Dehydrogenation Step" *J. Chem. Research (S)*, pp. 258-259 (2000).
Maher et al.,"Lipoprotein (a) and coronary heart disease" *Curr. Opin. Lipidol.* 6:229-235 (1995).
Mahto et al., "Synthesis of 3-Aryl-7-Hydroxy Isochromenes" *Asian J. Chem.* 11(2):431-435 (1999).
Manach et al., "Polyphenols and prevention of cardiovascular diseases" *Curr. Opin. Lipidol.* 16:77-84 (2005).
Marks, F., "Epidermal Growth Control Mechanisms, Hyperplasia, and Tumor Promotion in the Skin" *Cancer Res.* 36:2636-2343 (1976).
Martin et al., "Modified Flavinoids As Strong Photoprotecting UV-Absorbers and Antioxidants" in *Strategies for Safe Food*, Eklund, T. et al.(Eds.), vol. 1, pp. 288-291 (2003).
McKee et al., "Some Basically Substituted Quinazolines" *J. Am. Chem. Soc.* 68(10):1902-1903 (1946).
Meckes et al., "The effects of chrysin and pinostrobin, 2 flavonoids isolated from *Teloxys graveolens* leaves, on isolated guinea-pig ileum" *Phytomedicine* 5(6):459-463 (1998).
Melani et al., "Tricyclic heterocyclic systems: pyrazolo[5',4':4,5]- and pyrazolo-[3',4':4,5]pyrano[2,3-B]pyridine derivatives" *J. Heterocyclic Chem.* 25:1367-1371 (1988).
Middleton et al., "Quercetin inhibits lipopolysaccharide-induced expression of endothelial cell intracellular adhesion molecule-1" *Int. Arch. Allergy Immunol.* 107:435-436 (1995).
Moffett, "Azacoumarins" *J. Org. Chem.* 35(11):3596-3600 (1970).
Mondal et al., "Two-Stage Chemical Oncogenesis in Cultures of C3H/10T1/2 Cells" *Cancer Res.* 36:2254-2260 (1976).
Nigam et al., "Synthesis and Pharmacological Screening of Some New 2-(Phenyl/Chloromethyl)-3-[4 (N, N-Disubstituted Aminocarbonyl) Phenyl]-8-Substituted-4 (3H)-Quinazolones" *Indian Drugs* 27(4):238-243 (1990).

(56) References Cited

OTHER PUBLICATIONS

Nissen et al., "Effect of Recombinant ApoA-I Milano on Coronary Atherosclerosis in Patients with Acute Coronary Syndroms: A Randomized Controlled Trial" *JAMA* 290(17):2292-2300 (2003).
Nourooz-Zadeh, "Ferrous Ion Oxidation in Presence of Xylenol Orange for Detection of Lipid Hydroperoxides in Plasma" *Methods Enzymol.* 300:58-62 (1999).
Ohtomo et al., "Comparative activities of daidzein metabolites, equol and O-desmethylangolensin, on bone mineral density and lipid metabolism in ovariectomixed mice and in osteoclast cell cultures" *Eur. J. Nutr.* 47(5):273-279 (2008).
Ordovas, J.M., "Gene-diet interaction and plasma lipid responses to dietary intervention" *Biochem. Soc. Trans.* 30(2):68-73 (2002).
Parra et al., "A Case-Control Study of Lipoprotein Particles in Two Populations at Contrasting Risk for Coronary Heart Disease" *Atterioscler Thromb.* 12:701-707 (1992).
Patani et al., "Bioisosterism: A Rational Approach in Drug Design" *Chem. Rev.* 96(8):3147-3176 (1996).
Pearson et al., "The *ortho* Bromination of Phenols" *J. Org. Chem.* 32:2358-2360 (1967).
Pettit et al., "Antineoplastic Agents. 465. Structural Modification of Resveratrol: Sodium Resverastatin Phosphate" *J. Med. Chem.* 45:2534-2542 (2002).
Plump et al., "Human apolipoprotein A-I gene expression increases high density lipoprotein and suppresses atherosclerosis in the apolipoprotein E-deficient mouse" *Proc. Natl. Acad. Sci. USA* 91:9607-9611 (1994).
Quinones et al., "The *egr*-1 gene is induced by DNA-damaging agents and non-genotoxic drugs in both normal and neoplastic human cells" *Life Sciences* 72(26):2975-2992 (2003).
Ragione et al., "Antioxidants induce different phenotypes by a distinct modulation of signal transduction" *FEBS Letters* 523:289-294 (2002).
Ragione et al., "p21$^{CIP}$1 Gene Expression Is Modulated by Egr1: A Novel Regulatory Mechanism Involved in the Resveratrol Antiproliferative Effect" *J. Biol. Chem.* 278:23360-23368 (2003).
Rajakumar et al., "TiCl$_4$, Dioxane—A facile and efficient system for de-*O*-benzylation, de-*O*-allylation, and de*O*-xylylation of phenolic ethers" *Synthetic Communications* 33(22):3891-3896 (2003).
Raun et al., "Apolipoprotein A-I possesses an anti-obesity effect associated with increase of energy expenditure and upregulation of UCP1 in brown fat" *J. Cell. Mol. Med.* (2010). "Postprint"; 10.1111/j.1582.4934.2010.01045.x.
Rice-Evans, "Flavonoids and Isoflavones: Absorption, Metabolism, and Bioactivity" *Free Radical Biol. Med.* 36:827-828 (2004).
Richtzenhain, H. "Estrogenic stilbene and diphenylethane derivatives. II." *Chemische Berichte* 82:405-407 (1949) (German).
Rigotti et al., "Regulation by Adrenocorticotropic Hormone of the in Vivo Expression of Scavenger Receptor Class B Type I (SR-BI), a High Density Lipoprotein Receptor, in Steroidogenic Cells of the Murine Adrenal Gland" *J. Biol. Chem.* 271:33545-33549 (1996).
Rimando et al., "Pterostilbene, a New Agonist for the Peroxisome Proliferator-Activated Receptor α-Isoform, Lowers Plasma Lipoproteins and Cholesterol in Hypocholesterolemic Hamsters" *Journal of Agricultural and Food Chemistry* 53(9):3403-3407 (2005).
Rodriguez et al., "Novel Effects of the Acyl-Coenzyme A: Cholesterol Acyltransferase Inhibitor 58-035 on Foam Cell Development in Primary Human Monocyte-Derived Macrophages" *Arterioscler. Thromb. Vasc. Biol.* 19:2199-2206 (1999).
Rose et al., "Oxygen Heterocycles. XIII. From 3-Arylisocoumarins to 3-Arylisoquinolines and 4-Aryl-5*H*-2,3-Benzodiazepines" *J. Chem. Soc. [Section] C: Organic* 17:2205-2208 (1968).
Rubin et al., "Expression of Human Apolipoprotein A-I in Transgenic Mice Results in Reduced Plasma Levels of Murine Apolipoprotein A-I and the Appearance of Two New High Density Lipoprotein Size Subclasses" *Proc. Natl. Acad. Sci. USA* 88:434-438 (1991).
Rubin et al., "Inhibition of Early Atherogenesis in Transgenic Mice by Human Apolipoprotein AI" *Nature* 353:265-267 (1991).

Rubins et al., "Reduction in Stroke with Gemfibrozil in Men with Coronary Heart Disease and Low HDL Cholesterol" *Circulation* 103:2828-2833 (2001).
Sarkhel et al., "3-Arylisocoumarin: Synthesis of 3-(4-Methoxyphenyl)Isocoumarin" *J. Indian Chem. Soc.* 53:915-916 (1976).
Schiess et al., "Thermolytic Ring Opening of Acyloxybenzocyclobutenes: An Efficient Route to 3-Substituted Isoquinolines" *Tetrahedron Lett.* 26:3959-3962 (1985).
Schmutz et al., "Synthese von basisch substituierten Chromonen" *Helv. Chim. Acta* 36:620-626 (1953) (German).
Schork, N.J., "Genetics of Complex Disease. Approaches, Problems, and Solutions" *Am. J. Respir. Crit. Care Med.* 156(4):5103-109 (Oct. 1997).
Schultz et al., "Role of stilbenes in the natural durability of wood: fungicidal structure-activity relationships" *Phytochemistry* 29(5):1501-1507 (1990).
Shah et al., "Effects of Recombinant Apolipoprotein A-I$_{Milano}$ on Aortic Atherosclerosis in Apolipoprotein E-Deficient Mice" *Circulation* 97(8):780-785 (1998).
Shapiro et al., "Micro Assay for 3-Hydroxy-3-Methylglutaryl-CoA Reductase in Rat Liver and L-Cell Fibroblasts" *Biochim. Biophys. Acta* 370:369-377 (1974).
Sharrett et al., "Associations of Lipoprotein Cholesterols, Apolipoproteins A-I and B, and Triglycerides with Carotid Atherosclerosis and Coronary Heart Disease. The Atherosclerosis Risk in Communities (ARIC) Study" *Arterioscler. Thromb.* 14:1098-1104 (1994).
Sieber, R.H., "Reactions of chloroacetaldehyde with aromatic hydrocarbons, phenols, and phenol ethers" *Justus Liebigs Annalen der Chemie* 730:31-46 (1969) (German).
Sliwa et al., "Tautomerie entre structures α-aleoxy-enaminocetone et β-ceto iminoether presentee par les piperidines resultant de la semihydrogenation d'alcoxy-2-acyl-3 pyridines" *J. Heterocyclic Chem.* 16:939-944 (1979) (French).
Slowing et al., "Anti-Inflammatory Activity of Leaf Extracts of *Eugenia jambos* in Rats" *J. Ethnopharmacol.* 43:9-11 (1994).
Smyth et al.,"Non-amine based analogues of lavendustin A as protein-tyrosine kinase inhibitors" *J. Med. Chem.* 36(20):3010-3014 (1993).
Sun et al., "In Vitro Testing of Drug Absorption for Drug 'Developability' Assessment: Forming an Interface Between in Vitro Preclinical Data and Clinical Outcome" *Curr. Opin. Drug Discov. Devel.* 7:75-85 (2004).
Suryadevara et al., "Association of Abnormal Serum Lipids in Elderly Persons with Artherosclerotic Vascular Disease and Demetia, Artroslerotic Vascular Disease Without Demetia, Demetia Without Artherosclerotic Vascular Disease, and No Dementia or Artherosclerotic Vascular Disease" *J. Gerontol. Med. Sci.* 58A(9):859-861 (2003).
Tait et al., "Synthesis and Free Radical Scavenging Activity of 4-(2H-1,2,4-Benzothiadiazine-1,1-dioxide-3-yl)-2,6-bis(1,1-dimethylethyl)phenols" *Tetrahedron* 52(38):12587-12596 (1996).
Talbert, "Current Recommendations for the Treatment of Dyslipidemia" *Pharm. Ther.* 29:104-112 (2004).
Tanne et al., "High-Density Lipoprotein Cholesterol and Risk of Ischemic Stroke Mortaility" *Stroke* 28:83-87 (1997).
Tardif et al., "Probucol and Multivitamins in the Prevention of Restenosis After Coronary Angioplasty" *N. Engl. J. Med.* 337:365-367 (1997).
Theriault et al., "Modulation of hepatic lipoprotein synthesis and secretion by taxifolin, a plant flavonoid," *J. Lipid Res.* 41:1969-1979 (2000).
Toth et al., "Therapeutic Interventions Targeted at the Augmentation of Reserve Cholesterol Transport" *Curr. Opin. Cardiol.* 19:374-379 (2004).
Tovar et al., "Pyrylium Salts via Electrophilic Cyclization: Applications for Novel 3-Arylisoquinoline Syntheses" *J. Org. Chem.* 64:6499-6504 (1999).
Tudan, "Selective Inhibition of Protein Kinase C, Mitogen-Activated Protein Kinase, and Neutrophil Activation in Response to Calcium Pyrophosphate Dihydrate Crystals, Formyl-Methionyl-Leucyl-

(56) References Cited

OTHER PUBLICATIONS

Phenylalanine, and Phorbol Ester by O-(Chloroacetyl-carbamoyl) Fumagillol (AGM-01470; TNP-470)" *Biochem. Pharmacol.* 58:1869-1880 (1999).
Utermann, "The Mysteries of Lipoprotein(a)" *Science* 246:904-910 (1989).
Van Der Goot et al., "The Growth-Inhibitory Action of Some 1-Aminoisoquinolines and Related Compounds on Mycoplasma Gallisepticum" *Eur. J. Med. Chem.* 10:603-606 (1975).
Varin et al., "Enzymatic Assay for Flavonoid Sulfotransferase" *Anal. Biochem.* 161:176-180 (1987).
Vippagunta et al., "Crystalline solids" *Adv. Drug Delivery Rev.* 48:3-26 (2001).
Walle, "Absorption and Metabolism of Flavonoids" *Free Radical Biol. Med.* 36(7):829-837 (2004).
Webster Ninth New Collegiate Dictionary, Definition of 'Prevent', 1 page (2000).
Wei et al., "Total Cholesterol and High Density Lipoprotein Cholesterol as Important Predictors of Erectile Dysfunction" *Am. J. Epidemiol.* 140(10):930-937 (1994).
Welsh et al., "Dyslipidemia in Diabetic Patients" *Prospectives in Cardiology*, Aug. 2002, pp. 40-48.
Wölle et al., "Selective inhibition of tumor necrosis factor-induced vascular cell adhesion molecule-1 gene expression by a novel flavonoid: lack of effect on transcription factor NF-kappa-B" *Arterioscler. Thromb. Vasc. Biol.* 16(12):1501-1508 (1996).
Wurm, "1,4-Naphthoquinones, XXI: 2-(3,5 Di-*tert*-butyl-4-hydroxyphenyl)-1,4-naphtoquinones as 5-lipozxygenase inhibitors" *Archiv. der Pharmazie* 324(8):491-495 (1991).
Wurm et al., "1,4-Naphthoquinones, XXVI: Phenyl-1,4-naphthoquinone derivatives with the hydroxylation patterns of bioflavonoids" *Pharmazie* 52(10):739-743 (1997) (German).
Yamakoshi et al., "Isoflavone aglycone-rich extract without soy protein attenuates atherosclerosis development in cholesterol-fed rabbits" *Journal of Nutrition* 130(8):1887-1893 (2000).
Yardley et al., "In vitro activity of diospyrin and derivatives against *Leishmania donovani, Trypanosome cruzi* and *Trypanosoma brucei brucei*" *Phytotherapy Research* 10(7):559-562 (1996).
Yoshioka et al., "Semiempirical Investigation of Stilbene-Linked Diradicals and Magnetic Study of Their Bis(*N-tert*-butylnitroxide) Variants" *J. Org. Chem.* 59(15):4272-4280 (1994).
Office Action in U.S. Appl. No. 11/255,103: Restriction Requirement, mailed Mar. 26, 2008.
Office Action in U.S. Appl. No. 11/255,103, mailed Sep. 24, 2008.
Office Action in U.S. Appl. No. 11/255,103 mailed Aug. 31, 2009.
Office Action in U.S. Appl. No. 11/255,103, mailed Mar. 31, 2010.
Office Action in U.S. Appl. No. 11/255,103, mailed Nov. 10, 2010.
Office Action in U.S. Appl. No. 11/255,103: Notice of Allowance, mailed Jun. 7, 2011.
Office Action in U.S. Appl. No. 11/255,103: Notice of Allowance, mailed Sep. 15, 2011.
Office Action in U.S. Appl. No. 11/670,238: Restriction Requirement, mailed Mar. 31, 2010.
Office Action in U.S. Appl. No. 11/670,238: Restriction Requirement, mailed Jul. 20, 2010.
Office Action in U.S. Appl. No. 11/670,238, mailed Oct. 7, 2010.
Office Action in U.S. Appl. No. 11/670,238, mailed Apr. 19, 2011.
Office Action in U.S. Appl. No. 11/670,238, mailed Jun. 22, 2011.
Office Action in U.S. Appl. No. 11/670,238: Notice of Allowance, mailed Aug. 3, 2011.
Office Action in U.S. Appl. No. 11/670,238: Notice of Allowance, mailed Sep. 16, 2011.
Office Action in U.S. Appl. No. 11/990,162: Restriction Requirement, mailed Jul. 10, 2009.
Office Action in U.S. Appl. No. 11/990,162, mailed Oct. 14, 2009.
Office Action in U.S. Appl. No. 11/990,162, mailed Apr. 1, 2010.
Office Action in U.S. Appl. No. 11/990,162, mailed Dec. 28, 2010.
Office Action in U.S. Appl. No. 11/990,162, mailed Sep. 26, 2011.
Office Action in U.S. Appl. No. 11/990,162, mailed Mar. 19, 2012.
Office Action in U.S. Appl. No. 12/369,296, mailed Nov. 10, 2011.
Office Action in U.S. Appl. No. 12/369,296, mailed Mar. 13, 2012.
Office Action in U.S. Appl. No. 12/369,296: Notice of Allowance, mailed Apr. 12, 2012.
Office Action in U.S. Appl. No. 12/490,877, mailed Sep. 15, 2011.
Office Action in U.S. Appl. No. 12/490,877: Notice of Allowance, mailed Nov. 25, 2011.
Andersson, "Pharmacology of apolipoprotein A-I" *Curr. Opin. Lipidol.* 8:225-228 (1997).
Badimon et al. "Regression of Atherosclerotic Lesions by High Density Lipoprotein Plasma Fraction in the Cholesterol-fed Rabbit" *J. Clin. Invest.* 85: 1234-1241 (1990).
International Search Report and Written Opinion issued in International Application No. PCT/IB2012/002721; Date of Mailing: Mar. 14, 2013.
Miyazaki, et al. "Intravenous Injection of Rabbit Apolipoprotein A-I Inhibits the Progression of Atherosclerosis in Cholesterol-Fed Rabbits" *Arterioscler, Thromb, Vasc Biol.* 15: 1882-1888 (1995).
Nicholls et al., "Efficacy and Safety of a Novel Oral Inducer of Apolipoprotein A-I Synthesis in Statin-Treated Patients with Stable Coronary Artery Disease" *J. Am. Coll. Cardiol.* 57(9):1111-1119 (2011).
Tall "Plasma High Density Lipoproteins" *J. Clin, Invest.* 86: 379-384 (1990).
Baron et al., "The pathogenesis of adoptive murine autoimmune diabetes requires an interaction between $\alpha$4-integrins and vascular cell adhesion molecule-1" *J. Clin. Invest.*, 93:1700-1708 (1994).
Bauer and Hermann, "Interleukin-6 in clinical medicine" *Ann. Hematol.*, 62:203-210 (1991).
Berliner et al., "Atherosclerosis: Basic Mechanisms. Oxidation, Inflammation and Genetics" *Circulation*, 91:2488-2496 (1995).
Burkly et al., "Protection against adoptive transfer of autoimmune diabetes mediated through very late antigen-4 integrin" *Diabetes*, 43:529-534 (1994).
Cahlin et al., "Experimental Cancer Cachexia: The Role of Host-derived Cytokines Interleukin (IL)-6, IL-12, Interferon-$\gamma$, and Tumor Necrosis Factor $\alpha$ Evaluated in Gene Knockout, Tumor-bearing Mice on C57 Bl Background and Eicosanoid-dependent Cachexia" *Cancer Res.*, 60:5488-5493 (2000).
Campbell et al, "Essential role for interferon-$\gamma$ and interleukin-6 in autoimmune insulin-dependent diabetes in NOD/Wehi mice" *J. Clin. Invest.*, 87(2):739-742 (1991).
Campbell et al., "Neurologic disease induced in transgenic mice by cerebral overexpression of interleukin 6" *Proc. Natl. Acad. Sci. USA*, 90(21):10061-10065 (1993).
Chung et al., "Characterization of the Role of IL-6 in the Progression of Prostate Cancer" *The Prostate*, 38(3):199-207 (1999).
Emilie et al., "Administration of an anti-interleukin-6 monoclonal antibody to patients with acquired immunodeficiency syndrome and lymphoma: effect on lymphoma growth and on B clinical symptoms" *Blood*, 84:2472-2479 (1994).
Fisher et al., "Increased post-traumatic survival of neurons in IL-6-knockout mice on a background of EAE susceptibiity" *J. Neuroimmunol.*, 119:1-9 (2001).
Folkman and Shing, "Angiogenesis" *J. Biol. Chem.*, 267(16):10931-10934 (1992).
Frei et al., "Interieukin-6 is elevated in plasma in multiple sclerosis" *J. Neuroimmunol.*, 31:147-153 (1991).
Gabay, "Interleukin-6 and chronic inflammation" *Arthritis Research & Therapy*, 8(Suppl 2):S3 (2006).
Grau, "Implications of cytokines in immunopathology: experimental and clinical data" *Eur. Cytokine Netw.*, 1(4):203-210 (1990).
Hirano et al., "Excessive production of interleukin 6/B cell stimulatory factor-2 in rheumatoid arthritis" *Eur. J. Immunol.* 18(11):1797-1801 (1988).
Hirano et al., "Biological and clinical aspects of interleukin 6" *Immunol. Today*, 11:443-449 (1990).
International Search Report and Written Opinion issued in International Application No. PCT/IB2013/003031; Date of Mailing: May 28, 2014.
Ishihara and Hirano, "IL-6 in autoimmune disease and chronic inflammatory proliferative disease" *Cytokine Growth Factor Rev.*, 13(4-5):357-368 (2002).

(56) References Cited

OTHER PUBLICATIONS

Jafri et al., "Baseline and on-treatment high-density lipoprotein cholesterol and the risk of cancer in randomized controlled trials of lipid-altering therapy" *J. Am. Coll. Cardiol.*, 55:2846-2854 (2010).
Jilka et al., "Increased osteoclast development after estrogen loss: mediation by interleukin-6" *Science*, 257(5066):88-91 (1992).
Kishimoto and Hirano., "Molecular regulation of B lymphocyte response" *Ann. Rev. Immunol.*, 6:485-512 (1988).
Kishimoto, "The biology of interleukin-6" *Blood*, 74:1-10 (1989).
Klein et al., "Murine anti-interleukin-6 monoclonal antibody therapy for a patient with plasma cell leukemia" *Blood*, 78:1198-1204 (1991).
Koch et al, "Angiogenesis mediated by soluble forms of E-selectin and vascular cell adhesion molecule-1" *Nature*, 376:517-519 (1995).
Koch et al., "Immunolocalization of endothelial and leukocyte adhesion molecules in human rheumatoid and osteoarthritic synovial tissues" *Lab. Invest.*, 64:313-322 (1991).
Landi et al., "HDL-cholesterol and physical performance: results from the ageing and longevity study in the sirente geographic area (ilSIRENTE Study)" *Age and Ageing*, 36(5):514-520 (2007).
McGrowder et al., "The role of high density lipoproteins in reducing the risk of vascular diseases, neurogenerative disorders, and cancer" *Cholesterol*, 2011, Article 496925, 9 pages.
Mitchell et al., "Bromination of 4,6-dimethoxyindoles" *Tetrahedron*, 68(39):8163-8171 (2012).
Morales-Ducret et al., "$\alpha_4/\beta_1$ integrin (VLA-4) ligands in arthritis. Vascular cell adhesion molecule-1 expression in synovium and on fibroblast-like synoviocytes" *J. Immunol.*, 149:1424-1431 (1992).
Musselman et al., "Higher than normal plasma interleukin-6 concentrations in cancer patients with repression: preliminary findings" *Am. J. Psychiatry*, 158:1252-1257 (2001).
Ohkawara et al., "In situ expression of the cell adhesion molecules in bronchial tissues from asthmatics with air flow limitation: in vivo evidence of VCAM-1/VLA-4 interaction in selective eosinophil infiltration" *Am. J. Respir. Cell Mol. Biol.*, 12:4-12 (1995).
Orosz et al., "Role of the endothelial adhesion molecule VCAM in murine cardiac allograft rejection" *Immunol. Lett.*, 32(1):7-12 (1992).
Pilewski et al., "Cell adhesion molecules in asthma: homing, activation, and airway remodeling" *Am. J. Respir. Cell Mol. Biol.*, 12:1-3 (1995).
Quintanilla et al.; "Interleukin-6 induces Alzheimer-type phosphorylation of tau protein by deregulating the cdk5/p35 pathway" *Exp. Cell Res.*, 295:245-257 (2004).
Rabb et al., "The role of the leukocyte adhesion molecules VLA-4, LFA-1, and Mac-1 in allergic airway responses in the rat" *Am. J. Respir. Care Med.*, 149:1186-1191 (1994).
Reitz et al., "Association of higher levels of high-density lipoprotein cholesterol in elderly individuals and lower risk of late-onset Alzheimer Disease" *Arch Neurol.*, 67(12):1491-1497 (2010).
Roodman et al., "Interleukin 6. A potential autocrine/paracrine factor in Paget's disease of bone" *J. Clin. Invest.*, 89:46-52 (1992).
Rossi et al., "Optimizing the use of anti-interleukin-6 monoclonal antibody with dexamethasone and 140 mg/m$^2$ of melphalan in multiple myeloma: results of a pilot study including biological aspects" *Bone Marrow Transplantation*, 36:771-779 (2005).
Rubins et al., For the Veterans Affairs High-Density Lipoprotein Cholesterol Intervention Trial Study Group, "Gemfibrozil for the secondary prevention of coronary heart disease in men with low levels of high-density lipoprotein cholestrol" *N. Engl. J. Med.*, 341:410-418 (1999).
Schultz et al., "Protein composition determines the anti-atherogenic properties of HDL in transgenic mice" *Nature*, 365:762-764 (1993).
Sehgal, "Interleukin 6 in infection and cancer" *Exp. Biol. Med.*, 195:183-191 (1990).
Singh-Manoux et al., "Low HDL cholesterol is a risk factor for deficit and decline in memory in midlife: the Whitehall II Study" *Atherosclerosis, Thrombosis and Vascular Biology*, 28(8):1556-1562 (2008).
Stampfer, "Cardiovascular disease and Alzheimer's disease: common links" *J Intern Med*, 260(3):211-223 (2006).
Taga et al., "Receptors for B cell stimulatory factor 2. Quantitation, specificity, distribution, and regulation of their expression" *J. Exp. Med.*, 166:967-981 (1987).
Trikha et al., "Targeted anti-interleukin-6 monoclonal antibody therapy for cancer: a review of the rationale and clinical evidence" *Clin. Cancer Res.*, 9:4653-4665 (2003).
Wijdenes et al., "Human recombinant dimeric IL-6 binds to its receptor as detected by anti-IL-6 monoclonal antibodies" *Mol. Immunol.*, 28:1183-1192 (1991).
Yang et al., "Inhibition of insulitis and prevention of diabetes in nonobese diabetic mice by blocking L-selectin and very late antigen 4 adhesion receptors" *Proc. Natl. Acad. Sci. USA*, 90:10494-10498 (1993).
Adamis, "Is diabetic retinopathy an inflammatory disease?" *Br. J. Ophthamol.* 86:363-365 (2002).
Atreya and Neurath, "Involvement of IL-6 in the Pathogenesis of Inflammatory Bowel Disease and Colon Cancer" *Clin. Rev. Allergy Immunol.*, 28;187-195 (2005).
Avicele® PH-301, Product Specification Bulletin, FMC Corporation [online]; downloaded from http://www.signetchem.com/downloads/datasheets/Fmc-biopolymer/Avicel-Ph-301-Specifications.pdf, on May 13, 2015.
Benson et al., "Topical steroid treatment of allergic rhinitis decreases nasal fluid $T_H2$ cytokines, eosinophils, eosinophil cationic protein, and IgE but has no significant effect on IFN-$\gamma$, IL-1$\beta$, TNF-$\alpha$, or neutrophils" *J. Allergy Clin. Immunol.* 106:307-312 (2000).
Bindu et al., "Friend Turns Foe: Transformation of Anti-Inflammatory HDL to Proinflammatory HDL during Acute-Phase Response" *Cholesterol*; 2011: Article ID 274629 [online] doi:10.1155/2011/274629, 7 p, (2011).
Booth and Bishop, "TGF-$\beta$, IL-6, IL-17 and CTGF direct multiple pathologies of chronic cardiac allograft rejection" *Immunotherapy*, 2(4):511-520 (2010). Author manuscript, NIH Public Access, May 1, 2011.
Borgatti et al., "Induction by TNF-$\alpha$ of IL-6 and IL-8 in Cystic Fibrosis Bronchial IB3-1 Epithelial Cells Encapsulated in Alginate Microbeads," *J. Biomed. Biotechnol.* 2010: Article ID 907964, doi: 10.1155/2010/907964, 11 pages (2010).
Choudhary and Ahlawat, "Interleukin-6 and C-Reactive Protein in Pathogenesis of Diabetic Nephropathy" *Iran J. Kidney Dis.*, 2:72-79 (2008).
Colotta et al., "Cancer-related inflammation, the seventh hallmark of cancer: links to genetic instability" *Carcinogenesis*, 30(7):1073-1081 (2009).
Córdoba-Lanús et al., "Association of *IL-6* Gene Polymorphisms and COPD in a Spanish Population" *Respiratory Medicine*, 102:1805-1811 (2008).
Exner et al., "Interleukin-6 Promoter Genotype and Restenosis after Femoropopliteal Balloon Angioplasty: Initial Observations" *Radiology* 231:839-844 (2004).
Fattori et al., "Development of Progressive Kidney Damage and Myeloma Kidney in Interleukin-6 Transgenic Mice" *Blood*, 83(9):2570-2579 (1994).
Grossman et al., "Interleukin 6 is expressed in high levels in psoriatic skin and stimulates proliferation of cultured human keratinocytes" *Proc. Natl. Acad. Sci. USA* 86:6367-6371 (1989).
Hoekzema et al., "Analysis of Interleukin-6 in Endotoxin-Induced Uveitis" *Invest. Ophthalmol. Vis. Sci.* 32(1):38-95 (1991).
International Search Report and Written Opinion issued in International Application No. PCT/IB2014/002546; Date of Mailing: Mar. 13, 2015.
International Search Report and Written Opinion issued in International Application No. PCT/IB2015/002560; Date of Mailing: Mar. 19, 2015.
Leszczynska and Mesquida, "IL-6 Receptor Antagonist: Tocilizumab" in *Advances in the Treatment of Noninfectious Uveitis with Biologics: Anti-TNF and Beyond.* Marina Mesquida (Ed.), OMICS Group eBooks, Foster City, CA, 2014; 9 pages [online]. www.esciencecentral.org/ebooks.
Molnár and Balázs, "High Circulating IL-6 Level in Graves' Ophthalmopathy," *Autoimmunity* 25:91-96 (1997).

(56) References Cited

OTHER PUBLICATIONS

Nakagiri et al., "Immunology Mini-review: The Basics of TH17 and Interleukin-6 in Transplantation" *Transplantation Proceedings*, 44:1035-1040 (2012).

Neurath and Finotto, "IL-6 signaling in autoimmunity, chronic inflammation and inflammation-associated cancer," *Cytokine & Growth Factor Reviews* 22:33-89 (2011).

Rose-John and Schooltink, "Cytokines Are a Therapeutic Target for the Prevention of Inflammation-Induced Cancers" *Recent Results in Cancer Research* 174:57-66 (2007).

Rose-John et al., "The IL-6/sIL-6R complex as a novel target for therapeutic approaches" *Expert Opin. Ther. Targets* 11(5):613-624 (2007).

"RVX 208" R&D Insight Profile in *Drugs* 11(2):207-213 (2011).

Saito et al., "Topical Antigen Provocation Increases the Number of Immunoreactive IL-4-, IL-5 and IL-6-Positive Cells in the Nasal Mucosa of Patients with Perennial Allergic Rhinitis," *Int. Arch. Allergy Immunol.* 114:81-85 (1997).

Scheller et al., "Interleukin-6 Trans-Signalling in Chronic Inflammation and Cancer" *Scand. J. Immunol.*, 63:321-329 (2006).

Scheller et al., "The pro- and anti-inflammatory properties of the cytokine interleukin-6" *Biochim. Biophys. Acta*, 1813:878-888 (2011).

Shoji et al., "Concentration of Soluble Interleukin-6 Receptors in Tears of Allergic Conjunctival Disease in Patients" *Jpn J. Ophthalmol.* 51:332-337 (2007).

Tackey et al., "Rationale for interleukin-6 blockade in systemic lupus" *Lupus* 13(5):339-343 (2004). Author manuscript, NIH Public Access, Oct. 11, 2007.

Toshitani et al., "Increased Interleukin 6 Production by T Cells Derived from Patients with Atopic Dermatitis," *J. Invest. Dermatol.* 100:299-304 (1993).

Turner et al., "Interleukin-6 Levels in the Conjunctival Epithelium of Patients with Dry Eye Disease Treated with Cyclosporine Ophthalmic Emulsion" *Cornea* 19(4):492-496 (2000).

Tuttle, "Linking Metabolism and Immunology: Diabetic Nephropathy Is an Inflammatory Disease" *J. Am. Soc. Nephrol.* 16:1537-1538 (2005).

Perez-Villa et al., "Elevated Levels of Serum Interleukin-6 are Associated With Low Grade Cellular Rejection in Patients With Heart Transplantation" *Transplant. Proc.* 38:3012-3015 (2006).

Stelmasiak et al., "Interleukin-6 concentration in serum and cerebrospinal fluid in multiple sclerosis patients" *Med. Sci. Monit.* 6(6):1104-1108 (2000).

Van Lenten et al., "Multiple indications for anti-inlammatory peptides" *Curr. Opin. Investig. Drugs* 9(11):1157-1162 (Nov. 2008).

* cited by examiner

ANTI-INFLAMMATORY AGENTS

This application is a national stage entry under 35 U.S.C. §371 of PCT/IB2010/000826, filed Mar. 16, 2010, which claims the benefit of U.S. Provisional Application No. 61/161,089, filed Mar. 18, 2009, the disclosure of which is incorporated herein by reference in its entirety.

The present invention relates to novel compounds that are useful in regulating the expression of interleukin-6 (IL-6) and/or vascular cell adhesion molecule-1 (VCAM-1), and their use in the treatment and/or prevention of cardiovascular and inflammatory diseases and related disease states, such as, for example, atherosclerosis, asthma, arthritis, cancer, multiple sclerosis, psoriasis, and inflammatory bowel diseases, and autoimmune disease(s). The invention also includes pharmaceutical compositions comprising the novel compounds, as well as methods for their preparation.

Coronary heart disease (CHD) remains a leading cause of death in industrialized nations. A primary cause of CHD is atherosclerosis, a disease characterized by the deposition of lipids in the arterial vessel wall, resulting in a narrowing of the vessel passages and, ultimately leading to hardening of the vascular system.

It is generally accepted that atherosclerosis can begin with local injury to the arterial endothelium, followed by proliferation of arterial smooth muscle cells from the medial layer to the intimal layer, along with the deposition of lipids and the accumulation of foam cells in the lesion. As the atherosclerotic plaque develops, it progressively occludes more of the affected blood vessel and can eventually lead to ischemia or infarction. Thus, there is a continued effort to develop treatments to inhibit or prevent the progression of atherosclerosis in patients in need thereof.

Cardiovascular disease has been linked to several causative factors, including hypercholesterolemia, hyperlipidemia, and the expression of vascular cell adhesion molecule-1 (VCAM-1) in vascular endothelial cells. VCAM-1 promotes the adhesion of lymphocytes, monocytes, eosinophils, and basophils. Certain melanoma cells can use VCAM-1 to adhere to the endothelium, and VCAM-1 may participate in monocyte recruitment to atherosclerotic sites. As a result, VCAM-1 is of interest as a drug target.

The VCAM-1 gene is a member of the immunoglobulin (Ig) superfamily and encodes a cell-surface sialoglycoprotein expressed by cytokine-activated endothelial cells. This type-1 membrane protein mediates leukocyte-endothelial cell adhesion and signal transduction, and may play a role in the development of arterosclerosis and rheumatoid arthritis. VCAM-1, also known as CD106, has several roles in the immune system. The VCAM-1 protein contains six or seven immunoglobulin domains, and is expressed in both large and small vessels only after endothelial cells are stimulated by cytokines.

Adhesion of leukocytes to the endothelium represents a fundamental, early event in many inflammatory conditions, including atherosclerosis, autoimmune disorders, and bacterial and viral infections. Leukocyte recruitment to the endothelium begins when inducible adhesion molecule receptors on the surface of endothelial cells interact with their counter-receptors on immune cells. Vascular endothelial cells determine which type(s) of leukocyte(s) (e.g., monocytes, lymphocytes, neutrophils) are recruited, by selectively expressing specific adhesion molecules, such as VCAM-1, intracellular adhesion molecule-1 (ICAM-1), and E-selectin.

In the early stage of the atherosclerotic lesion, there is localized endothelial expression of VCAM-1 and selective recruitment of mononuclear leukocytes that express the integrin counter-receptor VLA-4. Because of the selective expression of VLA-4 on monocytes and lymphocytes, but not neutrophils, VCAM-1 is important in mediating the selective adhesion of mononuclear leukocytes. Subsequent conversion of leucocytes to foamy macrophages results in the synthesis of a wide variety of inflammatory cytokines, growth factors, and chemoattractants that help expand leukocyte and platelet recruitment, smooth muscle cell proliferation, endothelial cell activation, and the extracellular matrix synthesis characteristic of maturing atherosclerotic plaques.

VCAM-1 is also a mediator in inflammatory diseases. For example, it is known that the expression of VCAM-1 and ICAM-1 are increased in asthmatics (Pilewski et al. (1995) *Am. J. Respir. Cell Mol. Biol.* 12, 1-3; Ohkawara et al. (1995) *Am J. Respir. Cell Mol. Biol.* 12, 4-12). Further examples of non-cardiovascular inflammatory diseases mediated by VCAM-1 include rheumatoid and osteoarthritis, asthma, dermatitis, and multiple sclerosis. Blocking the integrin receptors for VCAM-1 and ICAM-1 (VLA-4 and LFA-1, respectively) suppresses both early- and late-phase responses in an ovalbumin-sensitized rat model of allergic airway responses (Rabb et al. (1994) *Am. J. Respir. Care Med.* 149, 1186-1191). There is also increased expression of endothelial adhesion molecules, including VCAM-1, in the microvasculature of rheumatoid synovium (Koch et al. (1991) Lab. Invest. 64, 313-322; Morales-Ducret et al. (1992) *Immunol.* 149, 1421-31).

Neutralizing antibodies directed against VCAM-1 or its counter receptor, VLA-4, can delay the onset of diabetes in a mouse model (NOD mice), which spontaneously develop the disease (Yang et al. (1993) *Proc. Natl. Acad. Sci. USA* 90, 10494-10498; Burkly et al. (1994) *Diabetes* 43, 523-534; Baron et al. (1994) *J. Clin. Invest.* 93, 1700-1708). Monoclonal antibodies to VCAM-1 can also have beneficial effects in animal models of allograft rejection, suggesting that inhibitors of VCAM-1 expression may also have utility in preventing transplant rejection (Oroez et al. (1992) *Immunol. Lett.* 32, 7-12).

VCAM-1 is expressed by cells in both a membrane-bound and soluble form. The soluble form has been shown to induce chemotaxis of vascular endothelial cells in vitro and to stimulate an angiogenic response in rat cornea (Koch et al. (1995) *Nature* 376, 517-519). Inhibitors of the expression of soluble VCAM-1 have potential therapeutic value in treating diseases with an angiogenic component, including tumor growth and metastasis (Folkman & Shing (1992) *Biol. Chem.* 10931-10934).

Because cardiovascular and inflammatory diseases are currently a leading cause of death and disability in the developed world, there is a strong need to identify new methods and pharmaceutical agents for its treatment. Thus, there is a need to identify and manipulate synthetic compounds that can affect the expression of mediators of the inflammatory process, such as, for example, VCAM-1.

Interleukin-6 (IL-6) is a 22-27-kDa secreted glycoprotein that exhibits growth stimulatory and pro-inflammatory activities. IL-6 has also been called interferon-β2 (IFN-β2), IL-1-inducible 26-kDa protein, hepatocyte-stimulating factor, cytotoxic T-cell differentiation factor, and B-cell stimulatory factor (Trikha et al. (2003) *Clin. Cancer Res.* 9, 4653-4665). IL-6 was originally identified in monocytes/macrophages, fibroblasts, and endothelial cells.

IL-6 is secreted by various cell types and exerts its activities by binding to a high-affinity receptor complex, consisting of two membrane glycoproteins, an 80-kDa component receptor that binds IL-6 with low affinity (IL-6R) and a signal-transducing component of 130 kDa (also known as gp130) that does not bind IL-6 itself, but is required for high-affinity binding of IL-6 by the complex. The IL-6R can be cleaved by a transmembrane metalloproteinase to yield a soluble IL-6R.

IL-6 levels are rapidly elevated in the circulation in numerous infectious, inflammatory, autoimmune diseases, and in some cancers, in association with increased synthesis of other cytokines, stimulated by infection, trauma, and immunological challenge. (Trikha et al. (2003) *Clin. Cancer Res.* 9, 4653-4665). IL-6 has been implicated in various diseases and disorders, including multiple myeloma (Rossi et al. (2005) *Bone Marrow Transplantation* 36, 771-779), lymphomas (Emilie et al. (1994) *Blood* 84, 2472-2479), neurological disorders, such as neurodegeneration, astrocytosis, and cerebral angiogenesis (Campbell et al. (1993) *Proc. Natl. Acad. Sci. USA* 90, 10061-10065), autoimmune disorders (e.g., rheumatoid arthritis), inflammatory diseases, Alzheimer's disease, myocardial infarction, Paget's disease, osteoporosis, solid tumors, prostate and bladder cancers (Trikha et al. (2003) *Clin. Cancer Res.* 9, 4653-4665), septic shock, transplants, acute infections of the central nervous system, cardiac myxoma (Wijdenes et al. (1991) *Mol. Immunol.* 28, 1183-1192), tumor-induced cachexia (Cahlin et al. (2000) *Cancer Res.* 60, 5488-5489), cancer-associated depression, and cerebral edema secondary to brain tumors (Musselman et al. (2001) *Am. J. Psychiatry* 158, 1252-1257). Inflammation and IL-6 are now specifically thought to be linked to heart attacks (Taubesi (2002) *Science* 296, 242).

Generally, it is known that IL-6 is abnormally produced in some inflammatory, autoimmune, and neoplasmic diseases. It has been proposed that abnormal production of IL-6 is an aspect of the mechanisms of these diseases (Hirano et al. (1990) *Immunol. Today,* 11, 443-449; Sehgal (1990) *Proc. Soc. Exp. Biol. Med.* 195, 183-191; Grau (1990) *Eur. Cytokine Net* 1, 203-210; Bauer et al. (1991) *Ann. Hematol.* 62, 203-210; Campbell et al. (1991) *J. Clin. Invest.* 7, 739-742; Roodman et al. (1992) *J. Clin. Invest.* 89, 46-52). In particular, it is known that IL-6 is associated with neuropathological processes, and its level in blood is increased in diseases invading the central nervous system. It has been found that IL-6 increases the level of tau epitope, by stimulating the dementia-associated phosphorylation of the tau protein in neuronal cells (Quintanilla et al. (2004) *Exp. Cell Res.* 295, 245-257). Mice lacking IL-6 have enhanced resistance to glutamate toxicity and increased viability of neuronal cells (Fisher et al. (2001) *J. Neuroimmunol.* 119, 1-9). It has also been found that IL-6 amplifies a calcium influx signal for the neurotransmitter N-methyl-D-aspartate (NMDA), through voltage-sensitive calcium channels, which provides some evidence that the increased IL-6 level may play a role in inducing pathological changes in central nervous system diseases (Qiu et al. (1998) 18, 10445-10456). It has also been reported that the abnormal expression of IL-6 is a pathogenic mechanism in other diseases, including cardiac myxoma, uterine cancer (Kishimoto et al. (1988) *Ann. Rev. Immunol.* 6, 485), multiple myeloma, histiocytomas (Taga et al. (1987) *J. Exp. Med.* 166, 967), plasmacytoma, hematological diseases, including plasma cell dyscrasias, leukemia, and lymphoma (Kishimoto (1989) *Blood* 74, 1; Taga et al. (1987) *J. Exp. Med.* 166, 967; Klein et al. (1991) *Blood* 78, 1198-1204), proliferative glomerulonephritis, activated multiclonal B-cell (types I-IV) allergic diseases, rheumatoid arthritis (Hirano et al. (1988) *Eur. J. Immunol.* 18, 1797), diabetes (Campbell et al. (1991) *J. Clin. Invest.* 87, 739-742), multiple sclerosis, Systemic Lupus Erythematosus, septic shock, bacterial infections, viral infections, osteoporosis (Roodman et al. (1992) *J. Clin. Invest.* 89, 46-52; Jilka et al. (1992) *Science* 257, 88-91), chronic immunodeficiency syndrome and autoimmune immunodeficiency syndromes, including AIDS (*Med. Immunol.* (1988) 15, 195-201), and inflammatory diseases, including inflammatory bowel diseases (such as Crohn's disease and ulcerative colitis) (WO99/47170). It is known that IL-6 is associated with some central nervous system diseases (Frei et al. (1991) *J. Neuroimmunol.* 31, 147).

Interleukin-6 is secreted by many advanced cancers, such as hormone-independent prostate cancer, and is believed to be a growth factor for such cancers. Additionally, the secretion of IL-6 by cancer cells is believed to cause cachexia, the wasting syndrome characteristic of advanced cancers. Thus, reducing the level of IL-6 would be useful in treating such cancers. IL-6 also plays a key role in B cell development. Autoimmune diseases with a significant antibody component, such as rheumatoid arthritis, could be treated by decreasing IL-6 levels. Disorders involving B cell proliferation, such as multiple myeloma and B cell lymphoma, could also be treated by reducing IL-6 activity. Additionally, IL-6 plays an important role in bone remodeling by promoting bone resorption. Reducing IL-6 activity would have the effect of reducing bone resorption and could be used to treat osteoporosis.

Accordingly, there have been various attempts to reduce the levels of IL-6, which are believed to be associated with the pathogenic mechanisms of these various diseases and conditions. A steroid formulation has been used for suppressing the cytokines in the art, but such medicines may causes severe side-effects, such as peptic ulcers, if administered for an extended period.

Anti-IL-6 antibodies have been shown to be effective in treating several diseases and disorders. For example, anti-IL-6 monoclonal antibodies have been shown to block the proliferation of myeloma cells both in vivo and in vitro (Rossi et al. (2005) *Bone Marrow Transplantation* 36, 771-779). Administration of anti-IL-6 antibodies to chronic rheumatoid arthritis patients was found to alleviate the symptoms of the disease (Wendling et al. (1993) *J. Rheumatol.* 20, 259-262). Anti-IL-6 antibodies have also been shown to be effective in treating AIDS-associated lymphoma (Emilie et al. (1994) *Blood* 84, 2472-2479), and metastatic renal cell carcinoma (Blay et al. (1997) *Int. J. Cancer* 72, 424-430). Clinical results involving the administration of anti-IL-6 antibodies to treat various other diseases and disorders are summarized in Trikha et al. (2003) *Clin. Cancer Res.* 9, 4653-4665.

Thus, the present invention provides non-naturally occurring compounds that are useful for regulating the expression of interleukin-6 (IL-6) and vascular cell adhesion molecule-1 (VCAM-1), as well as the use of such compounds for the treatment and prevention of cardiovascular and inflammatory diseases, such as, for example, atherosclerosis, asthma, arthritis, cancer, multiple sclerosis, psoriasis, inflammatory bowel diseases, and autoimmune disease(s).

Without wishing to be bound to theory, it is believed that the compounds of the invention act by inhibiting expression of IL-6 and/or VCAM-1 in the subject receiving the compound. However, regardless of the mechanism of action, administration of one or more compounds of the present invention will reduce the levels of IL-6 and/or VCAM-1 in the subject and as a result treat or reduce the incidence of cardiovascular and/or inflammatory diseases.

One aspect of the invention provides a method for inhibiting the expression of, or reducing IL-6 and/or VCAM-1 in a subject comprising administering to the subject in need thereof, a therapeutically effective amount of at least one compound of Formula I:

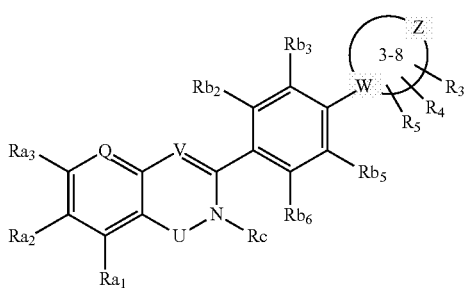

(I)

or a stereoisomer, tautomer, pharmaceutically acceptable salt, or hydrate thereof, wherein:

Q and V are independently selected from CH and nitrogen;

U is selected from C=O, C=S, $SO_2$, S=O, $SR_1$, $CR_1R_2$, $CR_1OR_2$, $CR_1SR_2$;

$R_1$ and $R_2$ are independently selected from hydrogen and $C_1$-$C_6$ alkyl;

Rc is selected from hydrogen, $C_1$-$C_6$ alkyl, and $C_3$-$C_6$ cycloalkyl;

$Ra_1$, $Ra_2$, and $Ra_3$ are independently selected from hydrogen, $C_1$-$C_6$ alkyl, $C_1$-$C_6$ alkenyl, $C_1$-$C_6$ alkynyl, $C_1$-$C_6$ alkoxy, halogen, amino, amide, hydroxyl, heterocycle, and $C_3$-$C_6$ cycloalkyl, wherein $Ra_1$ and $Ra_2$ and/or $Ra_2$ and $Ra_3$ may be connected to form a cycloalkyl or a heterocycle;

$Rb_2$ and $Rb_6$ are independently selected from hydrogen, halogen, $C_1$-$C_6$ alkyl, $C_1$-$C_6$ alkenyl, $C_3$-$C_6$ cycloalkyl, hydroxyl, and amino;

$Rb_3$ and $Rb_5$ are independently selected from hydrogen, halogen, $C_1$-$C_6$ alkyl, $C_1$-$C_6$ alkoxy, $C_3$-$C_6$ cycloalkyl, hydroxyl, and amino, wherein $Rb_2$ and $Rb_3$ and/or $Rb_5$ and $Rb_6$ may be connected to form a cycloalkyl or a heterocycle;

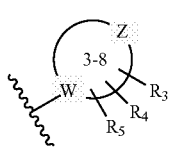

represents a 3-8 membered ring system wherein:

W is selected from carbon and nitrogen;

Z is selected from $CR_6R_7$, $NR_8$, oxygen, sulfur, —S(O)—, and —$SO_2$—;

said ring system being optionally fused to another ring selected from cycloakyl, heterocycle, and phenyl, and wherein said ring system is selected from, for example, rings having the structures

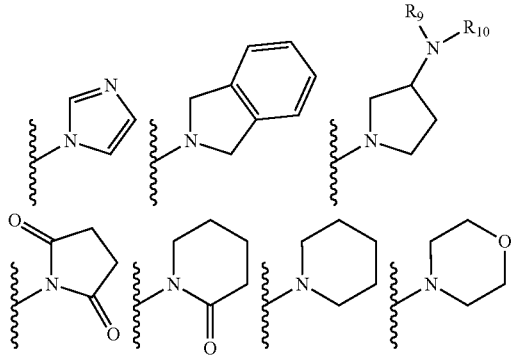

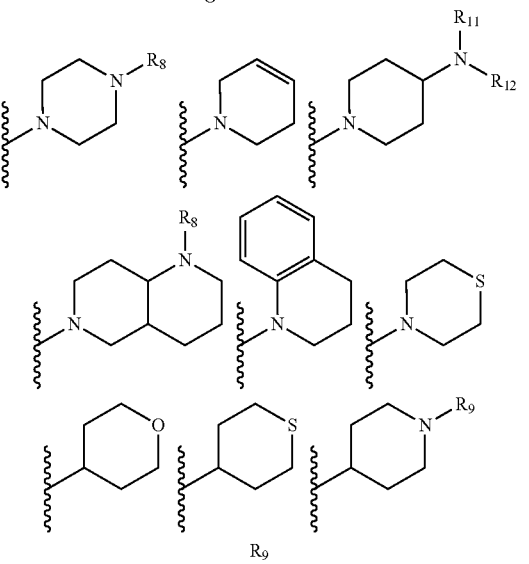

$R_3$, $R_4$, and $R_5$ are independently selected from hydrogen, $C_1$-$C_6$ alkyl, $C_1$-$C_6$ alkenyl, $C_1$-$C_6$ alkynyl, $C_1$-$C_6$ alkoxy, $C_3$-$C_6$ cycloalkyl, aryl, aryloxy, hydroxyl, amino, amide, oxo, —CN, and sulfonamide;

$R_6$ and $R_7$ are independently selected from hydrogen, $C_1$-$C_6$ alkyl, $C_1$-$C_6$ alkenyl, $C_1$-$C_6$ alkynyl, $C_3$-$C_6$ cycloalkyl, aryl, halogen, hydroxyl, —CN, amino, sulfonyl, acyl, and amido;

$R_8$ is selected from hydrogen, $C_1$-$C_6$ alkyl, $C_1$-$C_6$ alkenyl, $C_1$-$C_6$ alkynyl, acyl, and $C_3$-$C_6$ cycloalkyl; and $R_9$, $R_{10}$, $R_{11}$, and $R_{12}$ are independently selected from hydrogen, $C_1$-$C_6$ alkyl, $C_1$-$C_6$ alkenyl, $C_1$-$C_6$ alkynyl, $C_3$-$C_6$ cycloalkyl, aryl, heterocycle, hydroxyl, sulfonyl, and acyl, provided that if Q=CH, then at least one of $Ra_1$, $Ra_2$, and $Ra_3$ is not hydrogen;

if Z=NAc, then only one of $Ra_1$, $Ra_2$, or $Ra_3$ is hydrogen, and $Ra_1$ is not —OCH$_2$CH$_2$OMe; and if $Ra_1$ and $Ra_3$ are both OMe, then $R_8$ is not —C(O)CH$_2$OH.

In certain embodiments, the method for inhibiting the expression of, or reducing IL-6 and/or VCAM-1 in a subject, comprises administering a therapeutically effective amount of at least one compound of Formula II:

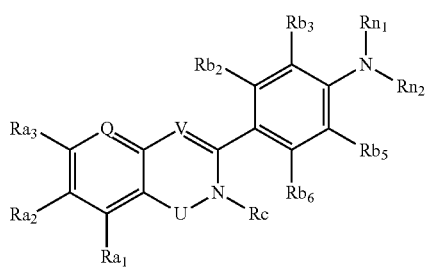

(II)

or a stereoisomer, tautomer, pharmaceutically acceptable salt, or hydrate thereof, wherein:

Q and V are independently selected from CH and nitrogen;

U is selected from C=O, C=S, SO$_2$, S=O, SR$_1$, CR$_1$R$_2$, CR$_1$OR$_2$, and CR$_1$SR$_2$;

$R_1$ and $R_2$ are independently selected from hydrogen and $C_1$-$C_6$ alkyl;

Rc is selected from hydrogen, $C_1$-$C_6$ alkyl, and $C_3$-$C_6$ cycloalkyl;

$Ra_1$, $Ra_2$, and $Ra_3$ are independently selected from hydrogen, $C_1$-$C_6$ alkyl, $C_1$-$C_6$ alkenyl, $C_1$-$C_6$ alkynyl, $C_1$-$C_6$ alkoxy, $C_3$-$C_6$ cycloalkyl, halogen, amino, amide, hydroxyl, cycloalkyl, and heterocycle, wherein $Ra_1$ and $Ra_2$ and/or $Ra_2$ and $Ra_3$ may be connected to form a cycloalkyl or a heterocycle;

$Rb_2$ and $Rb_6$ are independently selected from hydrogen, halogen, $C_1$-$C_6$ alkyl, $C_1$-$C_6$ alkenyl, $C_3$-$C_6$ cycloalkyl, hydroxyl, and amino;

$Rb_3$ and $Rb_5$ are independently selected from hydrogen, halogen, $C_1$-$C_6$ alkyl, $C_1$-$C_6$ alkoxy, $C_3$-$C_6$ cycloalkyl, hydroxyl, and amino, wherein $Rb_2$ and $Rb_3$ and/or $Rb_5$ and $Rb_6$ may be connected to form a cycloalkyl or a heterocycle;

$Rn_1$ is selected from hydrogen, $C_1$-$C_6$ alkyl, and $C_3$-$C_6$ cycloalkyl; and $Rn_2$ is selected from $C_1$-$C_6$ alkyl, $C_3$-$C_6$ cycloalkyl, heterocycle, aryl, alkenyl, sulfonyl, and acyl, wherein $Rn_1$ and/or $Rn_2$ may be connected with $Rb_3$ and/or $Rb_5$ to form a 5- or 6-membered heterocyclic ring, provided that at least one of $Ra_1$, $Ra_2$, and $Ra_3$ are not hydrogen; and $Rn_1$ and $Rn_2$ are not both methyl or ethyl.

In other embodiments, the method for inhibiting the expression of, or reducing IL-6 and/or VCAM-1 in a subject, comprises administering a therapeutically effective amount of at least one compound of Formula III:

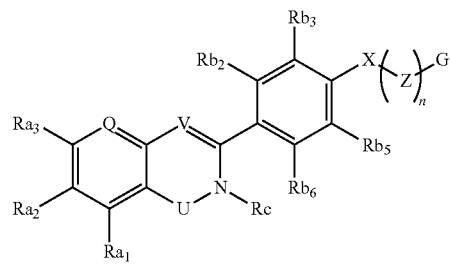

(III)

or a stereoisomer, tautomer, pharmaceutically acceptable salt, or hydrate thereof, wherein:

Q is selected from CR$_{12}$ and nitrogen;

V is selected from CH and nitrogen;

U is selected from C=O, C=S, SO$_2$, S=O, SR$_1$, CR$_1$R$_2$, CR$_1$OR$_2$, CR$_1$SR$_2$;

X is selected from oxygen, sulfur, SR$_1$, nitrogen, NR$_6$R$_7$, and CR$_6$R$_7$, Z is selected from unsubstituted $C_1$-$C_6$ alkyl and $C_1$-$C_6$ alkyl substituted with one or more groups selected from $C_1$-$C_3$ alkyl, $C_1$-$C_3$ alkoxy, cyclopropyl, hydroxyl, amino, and halogen;

n is selected from 0, 1, 2, 3, 4, or 5;

G is selected from heterocycle, cycloalkyl, and aryl;

$R_1$ and $R_2$ are independently selected from hydrogen, and $C_1$-$C_6$ alkyl;

$R_6$, $R_7$, and $R_{12}$ are independently selected from hydrogen, $C_1$-$C_6$ alkyl, $C_3$-$C_6$ cycloalkyl, heterocycle, $C_1$-$C_6$ alkoxy, and halogen;

Rc is selected from hydrogen, $C_1$-$C_6$ alkyl, and $C_3$-$C_6$ cycloalkyl;

$Ra_1$, $Ra_2$, and $Ra_3$ are independently selected from hydrogen, $C_1$-$C_6$ alkyl, $C_1$-$C_6$ alkenyl, $C_1$-$C_6$ alkynyl, $C_1$-$C_6$ alkoxy, $C_3$-$C_6$ cycloalkyl, halogen, amino, amide, hydroxyl, and heterocycle, wherein $Ra_1$ and $Ra_2$ and/or $Ra_2$ and $Ra_3$ may be connected to form a cycloalkyl or a heterocycle;

$Rb_2$ and $Rb_6$ are independently selected from hydrogen, halogen, $C_1$-$C_6$ alkyl, $C_3$-$C_6$ cycloalkyl, $C_1$-$C_6$ alkenyl, hydroxyl, and amino; and $Rb_3$ and $Rb_5$ are independently selected from hydrogen, halogen, $C_1$-$C_6$ alkyl, $C_3$-$C_6$ cycloalkyl, $C_1$-$C_6$ alkoxy, hydroxyl, and amino, wherein $Rb_2$ and $Rb_3$ and/or $Rb_5$ and $Rb_6$ may be connected to form a cycloalkyl or a heterocycle;

provided that if $Ra_1$ and $Ra_3$ are OMe, and Q=CH, then

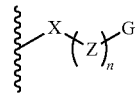

is not

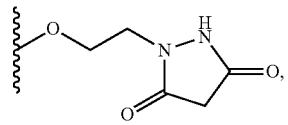

-continued

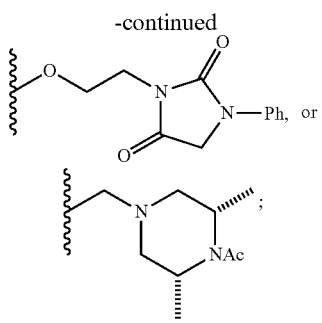

at least one of $Ra_1$, $Ra_2$, and $Ra_3$ is not hydrogen; and
if $Ra_2$ or $Ra_3$ is chloro, then $Ra_1$ is not hydrogen.

In some embodiments, the method for inhibiting the expression of, or reducing IL-6 and/or VCAM-1 in a subject, comprises administering a therapeutically effective amount of at least one compound of Formula IV:

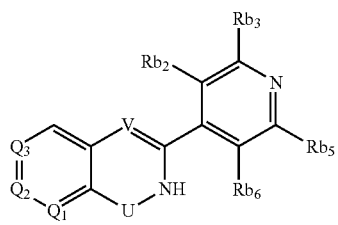

or a stereoisomer, tautomer, pharmaceutically acceptable salt, or hydrate thereof, wherein:
$Q_1$ is selected from nitrogen and C—$Ra_1$;
$Q_2$ is selected from nitrogen and C—$Ra_2$;
$Q_3$ is selected from nitrogen and C—$Ra_3$;
V is selected from CH and nitrogen;
U is selected from C=O, C=S, $SO_2$, S=O, $SR_1$, $CR_1R_2$, $CR_1OR_2$, $CR_1SR_2$;
$R_1$ and $R_2$ are independently selected from hydrogen and $C_1$-$C_6$ alkyl;
$Ra_2$, and $Ra_3$ are independently selected from hydrogen, $C_1$-$C_6$ alkyl, $C_1$-$C_6$ alkenyl, $C_1$-$C_6$ alkynyl, $C_1$-$C_6$ alkoxy, $C_3$-$C_6$ cycloalkyl, amino, amide, and heterocycle, wherein $Ra_1$ and $Ra_2$ and/or $Ra_2$ and $Ra_3$ may be connected to form a cycloalkyl or a heterocycle;
$Rb_2$ and $Rb_6$ are independently selected from hydrogen, halogen, $C_1$-$C_6$ alkyl, $C_3$-$C_6$ cycloalkyl, $C_1$-$C_6$ alkenyl, hydroxyl, and amino; and
$Rb_3$ and $Rb_5$ are independently selected from hydrogen, methyl, ethyl, $C_3$-$C_6$ cycloalkyl, $C_1$-$C_3$ alkoxy, and amino, wherein
$Rb_2$ and $Rb_3$ and/or $Rb_5$ and $Rb_6$ may be connected to form a cycloalkyl or a heterocycle,
provided that
if $Ra_3$ is alkoxy, then $Ra_1$ is not hydrogen;
if $Ra_2$ is

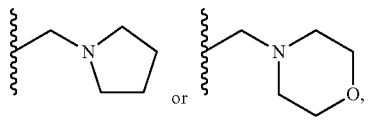

then $Rb_3$ is not hydrogen; and
if $Rb_2$, $Rb_5$, and $Rb_6$ are hydrogen, then $Rb_3$ is not —$CH_2OH$.

In a further embodiment, the method for inhibiting the expression of, or reducing IL-6 and/or VCAM-1 in a subject, comprises administering a therapeutically effective amount of at least one compound of Formula V:

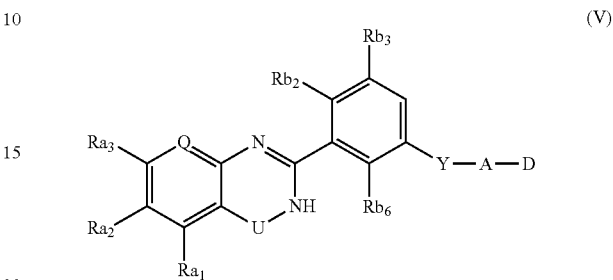

or a stereoisomer, tautomer, pharmaceutically acceptable salt, or hydrate thereof, wherein:
Q is selected from $CR_6$ and nitrogen;
U is selected from C=O, C=S, $SO_2$, S=O, $SR_1$, $CR_1R_2$, $CR_1OR_2$, $CR_1SR_2$;
Y is selected from oxygen, nitrogen, sulfur, $NR_6$, $CR_6R_7$;
A is $C_1$-$C_4$ alkyl, wherein the alkyl chain may be connected to Y, D, $Rb_3$ and/or $R_{b5}$ to form a cycloalkyl or heterocycle;
D may be absent or present, and if present is selected from —$OR_1$, —$NR_1R_2$,
$R_1$ and $R_2$ are independently selected from hydrogen, $C_1$-$C_6$ alkyl, $C_3$-$C_6$ cycloalkyl, sulfonamide, carboxamide, acyl, and nitrile, wherein $R_1$ and $R_2$ may be connected to form a cycloalkyl or a heterocycle;
$R_6$ and $R_7$ are independently selected from hydrogen, $C_1$-$C_6$ alkyl, $C_3$-$C_6$ cycloalkyl, $C_1$-$C_6$ alkoxy, hydroxyl, and halogen;
$Ra_1$, $Ra_2$, and $Ra_3$ are independently selected from hydrogen, $C_1$-$C_6$ alkyl, $C_1$-$C_6$ alkenyl, $C_1$-$C_6$ alkynyl, $C_1$-$C_6$ alkoxy, $C_3$-$C_6$ cycloalkyl, halogen, amino, amide, hydroxyl, and heterocycle, wherein $Ra_1$ and $Ra_2$ and/or $Ra_2$ and $Ra_3$ may be connected to form a cycloalkyl or a heterocycle;
$Rb_2$ and $Rb_6$ are independently selected from hydrogen, halogen, $C_1$-$C_6$ alkyl, and $C_3$-$C_6$ cycloalkyl; and
$Rb_3$ is selected from hydrogen, halogen, $C_1$-$C_6$ alkyl, $C_3$-$C_6$ cycloalkyl, $C_1$-$C_6$ alkoxy, hydroxyl, and amino, wherein
$Rb_2$ and $Rb_3$ and/or $Rb_6$ and $Rb_6$ may be connected to form a cycloalkyl or a heterocycle,
provided that
at least one of $Ra_1$, $Ra_2$, and $Ra_3$ is not hydrogen; and
if $Ra_1$ and $Ra_3$ are both hydrogen, and Y=nitrogen, then $Ra_2$ is not hydrogen, —OAc, or —OMe.

The invention also provides pharmaceutical compositions comprising one or more compounds of the invention, (i.e., compounds of Formula I, Formula II, Formula III, Formula IV, and Formula V, and stereoisomers, tautomers, pharmaceutically acceptable salts, and hydrates of compounds of Formula I, II, III, IV, and V) together with at least one pharmaceutically acceptable carrier, adjuvant, and/or excipient. In addition, methods of preparing compounds of Formula I, Formula II, Formula III, Formula IV, and Formula V, and stereoisomers, tautomers, and pharmaceutically acceptable salts and hydrates thereof are encompassed by the invention.

The invention further provides methods of treatment and/or prevention of cardiovascular and inflammatory diseases and related disease states by administering to a subject in need thereof, a therapeutically effective amount of one or more compounds of Formula I, Formula II, Formula III, Formula IV, Formula V, or tautomers, stereoisomers, pharmaceutically acceptable salts, or hydrates of compounds of Formula I, Formula II, Formula III, Formula IV, and Formula V. The invention also includes methods of regulating the expression of interleukin-6 (IL-6) and vascular cell adhesion molecule-1 (VCAM-1) in a subject, such as a human, comprising administering a therapeutically effective amount of any of the compounds of the invention described herein or a pharmaceutically acceptable composition comprising one or more compounds of the invention.

DEFINITIONS

As used in the present specification, the following words, phrases and symbols are generally intended to have the meanings as set forth below, except to the extent that the context in which they are used indicates otherwise. The following abbreviations and terms have the indicated meanings throughout:

As used herein, "cardiovascular disease" refers to diseases, disorders and conditions of the heart and circulatory system that are mediated by VCAM-1 and/or IL-6. Exemplary cardiovascular diseases, including cholesterol- or lipid-related disorders, include, but are not limited to, acute coronary syndrome, angina, arteriosclerosis, atherosclerosis, carotid atherosclerosis, cerebrovascular disease, cerebral infarction, congestive heart failure, congenital heart disease, coronary heart disease, coronary artery disease, coronary plaque stabilization, dyslipidemias, dyslipoproteinemias, endothelium dysfunctions, familial hypercholesterolemia, familial combined hyperlipidemia, hypoalphalipoproteinemia, hypertriglyceridemia, hyperbetalipoproteinemia, hypercholesterolemia, hypertension, hyperlipidemia, intermittent claudication, ischemia, ischemia reperfusion injury, ischemic heart diseases, cardiac ischemia, metabolic syndrome, multi-infarct dementia, myocardial infarction, obesity, peripheral vascular disease, reperfusion injury, restenosis, renal artery atherosclerosis, rheumatic heart disease, stroke, thrombotic disorder, transitory ischemic attacks, and lipoprotein abnormalities associated with Alzheimer's disease, obesity, diabetes mellitus, syndrome X, impotence, multiple sclerosis, Parkinson's diseases and an inflammatory diseases.

As used herein, "inflammatory diseases" includes refers to diseases, disorders and conditions, that are mediated by VCAM-1 and/or IL-6. Exemplary inflammatory diseases, include, but are not limited to, arthritis, asthma, dermatitis, psoriasis, cystic fibrosis, post transplantation late and chronic solid organ rejection, multiple sclerosis, systemic lupus erythematosus, inflammatory bowel diseases, autoimmune diabetes, diabetic retinopathy, diabetic nephropathy, diabetic vasculopathy, ocular inflammation, uveitis, rhinitis, ischemia-reperfusion injury, post-angioplasty restenosis, chronic obstructive pulmonary disease (COPD), glomerulonephritis, Graves disease, gastrointestinal allergies, conjunctivitis, atherosclerosis, coronary artery disease, angina, and small artery disease.

"Subject" refers to an animal, such as a mammal, that has been or will be the object of treatment, observation, or experiment. The methods described herein may be useful for both human therapy and veterinary applications. In one embodiment, the subject is a human.

As used herein, "treatment" or "treating" refers to an amelioration of a disease or disorder, or at least one discernible symptom thereof. In another embodiment, "treatment" or "treating" refers to an amelioration of at least one measurable physical parameter, not necessarily discernible by the patient. In yet another embodiment, "treatment" or "treating" refers to inhibiting the progression of a disease or disorder, either physically, e.g., stabilization of a discernible symptom, physiologically, e.g., stabilization of a physical parameter, or both. In yet another embodiment, "treatment" or "treating" refers to delaying the onset of a disease or disorder. For example, treating a cholesterol disorder may comprise decreasing blood cholesterol levels.

As used herein, "prevention" or "preventing" refers to a reduction of the risk of acquiring a given disease or disorder.

A dash ("-") that is not between two letters or symbols is used to indicate a point of attachment for a substituent. For example, —$CONH_2$ is attached through the carbon atom.

By "optional" or "optionally" is meant that the subsequently described event or circumstance may or may not occur, and that the description includes instances where the event or circumstance occurs and instances in which is does not. For example, "optionally substituted aryl" encompasses both "aryl" and "substituted aryl" as defined below. It will be understood by those skilled in the art, with respect to any group containing one or more substituents, that such groups are not intended to introduce any substitution or substitution patterns that are sterically impractical, synthetically non-feasible and/or inherently unstable.

As used herein, the term "hydrate" refers to a crystal form with either a stoichiometric or non-stoichiometric amount of water is incorporated into the crystal structure.

The term "acyl" term as used herein refers to a carbonyl radical attached to an alkyl, alkenyl, alkynyl, cycloalkyl, heterocycyl, aryl, or heteroaryl. Exemplary acyl groups include, but are not limited to, acetyl, formyl, propionyl, benzoyl, and the like.

The term "aldehyde" or "formyl" as used herein refers to —CHO.

The term "alkenyl" as used herein refers to an unsaturated straight or branched hydrocarbon having at least one carbon-carbon double bond, such as a straight or branched group of 2-22, 2-8, or 2-6 carbon atoms, referred to herein as ($C_2$-$C_{22}$)alkenyl, ($C_2$-$C_8$)alkenyl, and ($C_2$-$C_6$)alkenyl, respectively. Exemplary alkenyl groups include, but are not limited to, vinyl, allyl, butenyl, pentenyl, hexenyl, butadienyl, pentadienyl, hexadienyl, 2-ethylhexenyl, 2-propyl-2-butenyl, and 4-(2-methyl-3-butene)-pentenyl.

The term "alkoxy" as used herein refers to an alkyl group attached to an oxygen (—O-alkyl-). "Alkoxy" groups also include an alkenyl group attached to an oxygen ("alkenyloxy") or an alkynyl group attached to an oxygen ("alkynyloxy") groups. Exemplary alkoxy groups include, but are not limited to, groups with an alkyl, alkenyl or alkynyl group of 1-22, 1-8, or 1-6 carbon atoms, referred to herein as ($C_1$-$C_{22}$)alkoxy, ($C_1$-$C_8$)alkoxy, and ($C_1$-$C_6$)alkoxy, respectively. Exemplary alkoxy groups include, but are not limited to methoxy and ethoxy.

The term "alkyl" as used herein refers to a saturated straight or branched hydrocarbon, such as a straight or branched group of 1-22, 1-8, or 1-6 carbon atoms, referred to herein as ($C_1$-$C_{22}$)alkyl, ($C_1$-$C_8$)alkyl, and ($C_1$-$C_6$)alkyl, respectively. Exemplary alkyl groups include, but are not limited to, methyl, ethyl, propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, butyl, isobutyl, t-butyl, pentyl, isopentyl, neopentyl, hexyl, heptyl, and octyl.

The term "alkynyl" as used herein refers to an unsaturated straight or branched hydrocarbon having at least one carbon-carbon triple bond, such as a straight or branched group of 2-22, 2-8, or 2-6 carbon atoms, referred to herein as ($C_2$-$C_{22}$) alkynyl, ($C_2$-$C_8$)alkynyl, and ($C_2$-$C_6$)alkynyl, respectively. Exemplary alkynyl groups include, but are not limited to, ethynyl, propynyl, butynyl, pentynyl, hexynyl, methylpropynyl, 4-methyl-1-butynyl, 4-propyl-2-pentynyl, and 4-butyl-2-hexynyl.

The term "amide" as used herein refers to the form —$NR_aC(O)(R_b)$— or —$C(O)NR_bR_c$, wherein $R_a$, $R_b$ and $R_c$ are each independently selected from alkyl, alkenyl, alkynyl, aryl, arylalkyl, cycloalkyl, haloalkyl, heteroaryl, heterocyclyl, and hydrogen. The amide can be attached to another group through the carbon, the nitrogen, $R_b$, or $R_c$. The amide also may be cyclic, for example $R_b$ and $R_c$, may be joined to form a 3- to 12-membered ring, such as a 3- to 10-membered ring or a 5- or 6-membered ring. The term "amide" encompasses groups such as sulfonamide, urea, ureido, carbamate, carbamic acid, and cyclic versions thereof. The term "amide" also encompasses an amide group attached to a carboxy group, e.g., -amide-COOH or salts such as -amide-COONa, an amino group attached to a carboxy group (e.g., -amino-COON or salts such as -amino-COONa).

The term "amine" or "amino" as used herein refers to the form —$NR_dR_e$ or —$N(R_d)R_e$—, where $R_d$ and $R_e$ are independently selected from alkyl, alkenyl, alkynyl, aryl, arylalkyl, carbamate, cycloalkyl, haloalkyl, heteroaryl, heterocyclyl, and hydrogen. The amino can be attached to the parent molecular group through the nitrogen. The amino also may be cyclic, for example any two of $R_d$ and $R_e$ may be joined together or with the N to form a 3- to 12-membered ring (e.g., morpholino or piperidinyl). The term amino also includes the corresponding quaternary ammonium salt of any amino group. Exemplary amino groups include alkylamino groups, wherein at least one of $R_d$ or $R_e$ is an alkyl group.

The term "aryl" as used herein refers to a mono-, bi-, or other multi-carbocyclic, aromatic ring system. The aryl group can optionally be fused to one or more rings selected from aryls, cycloalkyls, and heterocyclyls. The aryl groups of this invention can be substituted with groups selected from alkoxy, aryloxy, alkyl, alkenyl, alkynyl, amide, amino, aryl, arylalkyl, carbamate, carboxy, cyano, cycloalkyl, ester, ether, formyl, halogen, haloalkyl, heteroaryl, heterocyclyl, hydroxyl, ketone, nitro, phosphate, sulfide, sulfinyl, sulfonyl, sulfonic acid, sulfonamide, and thioketone. Exemplary aryl groups include, but are not limited to, phenyl, tolyl, anthracenyl, fluorenyl, indenyl, azulenyl, and naphthyl, as well as benzo-fused carbocyclic moieties such as 5,6,7,8-tetrahydronaphthyl. Exemplary aryl groups also include, but are not limited to a monocyclic aromatic ring system, wherein the ring comprises 6 carbon atoms, referred to herein as "($C_6$)aryl."

The term "arylalkyl" as used herein refers to an alkyl group having at least one aryl substituent (e.g., -aryl-alkyl-). Exemplary arylalkyl groups include, but are not limited to, arylalkyls having a monocyclic aromatic ring system, wherein the ring comprises 6 carbon atoms, referred to herein as "($C_6$)arylalkyl."

The term "aryloxy" as used herein refers to an aryl group attached to an oxygen atom. Exemplary aryloxy groups include, but are not limited to, aryloxys having a monocyclic aromatic ring system, wherein the ring comprises 6 carbon atoms, referred to herein as "($C_6$)aryloxy."

The term "arylthio" as used herein refers to an aryl group attached to an sulfur atom. Exemplary arylthio groups include, but are not limited to, arylthios having a monocyclic aromatic ring system, wherein the ring comprises 6 carbon atoms, referred to herein as "($C_6$)arylthio."

The term "arylsulfonyl" as used herein refers to an aryl group attached to a sulfonyl group, e.g., —$S(O)_2$-aryl-. Exemplary arylsulfonyl groups include, but are not limited to, arylsulfonyls having a monocyclic aromatic ring system, wherein the ring comprises 6 carbon atoms, referred to herein as "($C_6$)arylsulfonyl."

The term "benzyl" as used herein refers to the group —$CH_2$-phenyl.

The term "bicyclic aryl" as used herein refers to an aryl group fused to another aromatic or non-aromatic carbocyclic or heterocyclic ring. Exemplary bicyclic aryl groups include, but are not limited to, naphthyl or partly reduced forms thereof, such as di-, tetra-, or hexahydronaphthyl.

The term "bicyclic heteroaryl" as used herein refers to a heteroaryl group fused to another aromatic or non-aromatic carbocylic or heterocyclic ring. Exemplary bicyclic heteroaryls include, but are not limited to 5,6- or 6,6-fused systems, wherein one or both rings contain heteroatoms. The term "bicyclic heteroaryl" also encompasses reduced or partly reduced forms of fused aromatic system wherein one or both rings contain ring heteroatoms. The ring system may contain up to three heteroatoms, independently selected from oxygen, nitrogen, and sulfur. The bicyclic system may be optionally substituted with one or more groups selected from alkoxy, aryloxy, alkyl, alkenyl, alkynyl, amide, amino, aryl, arylalkyl, carbamate, carboxy, cyano, cycloalkyl, ester, ether, formyl, halogen, haloalkyl, heteroaryl, heterocyclyl, hydroxyl, ketone, nitro, phosphate, sulfide, sulfinyl, sulfonyl, sulfonic acid, sulfonamide, and thioketone. Exemplary bicyclic heteroaryl's include, but are not limited to, quinazolinyl, benzothiophenyl, benzoxazolyl, benzimidazolyl, benzothiazolyl, benzofuranyl, indolyl, quinolinyl, isoquinolinyl, phthalazinyl, benzotriazolyl, benzopyridinyl, and benzofuranyl.

The term "carbamate" as used herein refers to the form —$R_gOC(O)N(R_h)$—, —$R_gOC(O)N(R_h)R_i$—, or —$OC(O)NR_hR_i$, wherein $R_g$, $R_h$ and $R_i$ are each independently selected from alkyl, alkenyl, alkynyl, aryl, arylalkyl, cycloalkyl, haloalkyl, heteroaryl, heterocyclyl, and hydrogen. Exemplary carbamates include, but are not limited to, arylcarbamates or heteroaryl carbamates (e.g., wherein at least one of $R_g$, $R_h$ and $R_i$ are independently selected from aryl or heteroaryl, such as pyridine, pyridazine, pyrimidine, and pyrazine).

The term "carbonyl" as used herein refers to —$C(O)$—.

The term "carboxy" as used herein refers to —COOH or its corresponding carboxylate salts (e.g., —COONa). The term carboxy also includes "carboxycarbonyl," e.g. a carboxy group attached to a carbonyl group, e.g., —$C(O)$—COOH or salts, such as —$C(O)$—COONa.

The term "cyano" as used herein refers to —CN.

The term "cycloalkoxy" as used herein refers to a cycloalkyl group attached to an oxygen.

The term "cycloalkyl" as used herein refers to a saturated or unsaturated cyclic, bicyclic, or bridged bicyclic hydrocarbon group of 3-12 carbons, or 3-8 carbons, referred to herein as "($C_3$-$C_8$)cycloalkyl," derived from a cycloalkane. Exemplary cycloalkyl groups include, but are not limited to, cyclohexanes, cyclohexenes, cyclopentanes, and cyclopentenes. Cycloalkyl groups may be substituted with alkoxy, aryloxy, alkyl, alkenyl, alkynyl, amide, amino, aryl, arylalkyl, carbamate, carboxy, cyano, cycloalkyl, ester, ether, formyl, halogen, haloalkyl, heteroaryl, heterocyclyl, hydroxyl, ketone, nitro, phosphate, sulfide, sulfinyl, sulfonyl, sulfonic acid, sulfonamide and thioketone. Cycloalkyl groups can be fused to other cycloalkyl saturated or unsaturated, aryl, or heterocyclyl groups.

The term "dicarboxylic acid" as used herein refers to a group containing at least two carboxylic acid groups such as saturated and unsaturated hydrocarbon dicarboxylic acids and salts thereof. Exemplary dicarboxylic acids include alkyl dicarboxylic acids. Dicarboxylic acids may be substituted with alkoxy, aryloxy, alkyl, alkenyl, alkynyl, amide, amino, aryl, arylalkyl, carbamate, carboxy, cyano, cycloalkyl, ester, ether, formyl, halogen, haloalkyl, heteroaryl, heterocyclyl, hydrogen, hydroxyl, ketone, nitro, phosphate, sulfide, sulfinyl, sulfonyl, sulfonic acid, sulfonamide and thioketone. Dicarboxylic acids include, but are not limited to succinic acid, glutaric acid, adipic acid, suberic acid, sebacic acid, azelaic acid, maleic acid, phthalic acid, aspartic acid, glutamic acid, malonic acid, fumaric acid, (+)/(−)-malic acid, (+)/(−) tartaric acid, isophthalic acid, and terephthalic acid. Dicarboxylic acids further include carboxylic acid derivatives thereof, such as anhydrides, imides, hydrazides (for example, succinic anhydride and succinimide).

The term "ester" refers to the structure —C(O)O—, —C(O)O—$R_j$—, —$R_k$C(O)O—$R_j$—, or —$R_k$C(O)O—, where O is not bound to hydrogen, and $R_j$ and $R_k$ can independently be selected from alkoxy, aryloxy, alkyl, alkenyl, alkynyl, amide, amino, aryl, arylalkyl, cycloalkyl, ether, haloalkyl, heteroaryl, and heterocyclyl. $R_k$ can be a hydrogen, but $R_j$ cannot be hydrogen. The ester may be cyclic, for example the carbon atom and $R_j$, the oxygen atom and $R_k$, or $R_j$ and $R_k$ may be joined to form a 3- to 12-membered ring. Exemplary esters include, but are not limited to, alkyl esters wherein at least one of $R_j$ or $R_k$ is alkyl, such as —O—C(O)-alkyl, —C(O)—O-alkyl-, and -alkyl-C(O)—O-alkyl-. Exemplary esters also include aryl or heteroaryl esters, e.g. wherein at least one of $R_j$ or $R_k$ is a heteroaryl group such as pyridine, pyridazine, pyrimidine and pyrazine, such as a nicotinate ester. Exemplary esters also include reverse esters having the structure —$R_k$C(O)O—, where the oxygen is bound to the parent molecule. Exemplary reverse esters include succinate, D-argininate, L-argininate, L-lysinate and D-lysinate. Esters also include carboxylic acid anhydrides and acid halides.

The term "ether" refers to the structure —$R_l$O—$R_m$—, where $R_l$ and $R_m$ can independently be alkyl, alkenyl, alkynyl, aryl, cycloalkyl, heterocyclyl, and ether. The ether can be attached to the parent molecular group through $R_l$ or $R_m$. Exemplary ethers include, but are not limited to, alkoxyalkyl and alkoxyaryl groups. Ethers also includes polyethers, e.g., where one or both of $R_l$ and $R_m$ are ethers.

The terms "halo" or "halogen" or "Hal" as used herein refer to F, Cl, Br, or I.

The term "haloalkyl" as used herein refers to an alkyl group substituted with one or more halogen atoms. "Haloalkyls" also encompass alkenyl or alkynyl groups substituted with one or more halogen atoms.

The term "heteroaryl" as used herein refers to a mono-, bi-, or multi-cyclic, aromatic ring system containing one or more heteroatoms, for example 1-3 heteroatoms, such as nitrogen, oxygen, and sulfur. Heteroaryls can be substituted with one or more substituents including alkoxy, aryloxy, alkyl, alkenyl, alkynyl, amide, amino, aryl, arylalkyl, carbamate, carboxy, cyano, cycloalkyl, ester, ether, formyl, halogen, haloalkyl, heteroaryl, heterocyclyl, hydroxyl, ketone, nitro, phosphate, sulfide, sulfinyl, sulfonyl, sulfonic acid, sulfonamide and thioketone. Heteroaryls can also be fused to non-aromatic rings. Illustrative examples of heteroaryl groups include, but are not limited to, pyridinyl, pyridazinyl, pyrimidyl, pyrazyl, triazinyl, pyrrolyl, pyrazolyl, imidazolyl, (1,2,3)- and (1,2,4)-triazolyl, pyrazinyl, pyrimidinyl, tetrazolyl, furyl, thienyl, isoxazolyl, thiazolyl, furyl, phenyl, isoxazolyl, and oxazolyl. Exemplary heteroaryl groups include, but are not limited to, a monocyclic aromatic ring, wherein the ring comprises 2-5 carbon atoms and 1-3 heteroatoms, referred to herein as "($C_2$-$C_5$)heteroaryl."

The terms "heterocycle," "heterocyclyl," or "heterocyclic" as used herein refer to a saturated or unsaturated 3-, 4-, 5-, 6-, or 7-membered ring containing one, two, or three heteroatoms independently selected from nitrogen, oxygen, and sulfur. Heterocycles can be aromatic (heteroaryls) or non-aromatic. Heterocycles can be substituted with one or more substituents including alkoxy, aryloxy, alkyl, alkenyl, alkynyl, amide, amino, aryl, arylalkyl, carbamate, carboxy, cyano, cycloalkyl, ester, ether, formyl, halogen, haloalkyl, heteroaryl, heterocyclyl, hydroxyl, ketone, nitro, phosphate, sulfide, sulfinyl, sulfonyl, sulfonic acid, sulfonamide, and thioketone. Heterocycles also include bicyclic, tricyclic, and tetracyclic groups in which any of the above heterocyclic rings is fused to one or two rings independently selected from aryl, cycloalkyl, and heterocycle. Exemplary heterocycles include acridinyl, benzimidazolyl, benzofuryl, benzothiazolyl, benzothienyl, benzoxazolyl, biotinyl, cinnolinyl, dihydrofuryl, dihydroindolyl, dihydropyranyl, dihydrothienyl, dithiazolyl, furyl, homopiperidinyl, imidazolidinyl, imidazolinyl, imidazolyl, indolyl, isoquinolyl, isothiazolidinyl, isothiazolyl, isoxazolidinyl, isoxazolyl, morpholinyl, oxadiazolyl, oxazolidinyl, oxazolyl, piperazinyl, piperidinyl, pyranyl, pyrazolidinyl, pyrazinyl, pyrazolyl, pyrazolinyl, pyridazinyl, pyridyl, pyrimidinyl, pyrimidyl, pyrrolidinyl, pyrrolidin-2-onyl, pyrrolinyl, pyrrolyl, quinolinyl, quinoxaloyl, tetrahydrofuryl, tetrahydroisoquinolyl, tetrahydropyranyl, tetrahydroquinolyl, tetrazolyl, thiadiazolyl, thiazolidinyl, thiazolyl, thienyl, thiomorpholinyl, thiopyranyl, and triazolyl.

The terms "hydroxy" and "hydroxyl" as used herein refers to —OH.

The term "hydroxyalkyl" as used herein refers to a hydroxy attached to an alkyl group.

The term "hydroxyaryl" as used herein refers to a hydroxy attached to an aryl group.

The term "ketone" as used herein refers to the structure —C(O)—$R_n$ (such as acetyl, —C(O)$CH_3$ or —$R_n$—C(O)—$R_o$—. The ketone can be attached to another group through $R_n$ or $R_o$. $R_n$ or $R_o$ can be alkyl, alkenyl, alkynyl, cycloalkyl, heterocyclyl, or aryl, or $R_n$ and $R_o$ can be joined to form a 3- to 12-membered ring.

The term "monoester" as used herein refers to an analogue of a dicarboxylic acid wherein one of the carboxylic acids is functionalized as an ester and the other carboxylic acid is a free carboxylic acid or salt of a carboxylic acid. Examples of monoesters include, but are not limited to, to monoesters of succinic acid, glutaric acid, adipic acid, suberic acid, sebacic acid, azelaic acid, oxalic, and maleic acid.

The term "nitro" as used herein refers to —$NO_2$.

The term "perfluoroalkoxy" as used herein refers to an alkoxy group in which all of the hydrogen atoms have been replaced by fluorine atoms.

The term "perfluoroalkyl" as used herein refers to an alkyl group in which all of the hydrogen atoms have been replaced by fluorine atoms. Exemplary perfluoroalkyl groups include, but are not limited to, $C_1$-$C_5$ perfluoroalkyl, such as trifluoromethyl.

The term "perfluorocycloalkyl" as used herein refers to a cycloalkyl group in which all of the hydrogen atoms have been replaced by fluorine atoms.

The term "phenyl" as used herein refers to a 6-membered carbocyclic aromatic ring. The phenyl group can also be fused to a cyclohexane or cyclopentane ring. Phenyl can be substituted with one or more substituents including alkoxy, aryloxy, alkyl, alkenyl, alkynyl, amide, amino, aryl, arylalkyl, carbamate, carboxy, cyano, cycloalkyl, ester, ether, formyl, halogen, haloalkyl, heteroaryl, heterocyclyl, hydroxyl, ketone, nitro, phosphate, sulfide, sulfinyl, sulfonyl, sulfonic acid, sulfonamide, and thioketone.

The term "phosphate" as used herein refers to the structure —OP(O)O$_2$—, —R$_x$OP(O)O$_2$—, —OP(O)O$_2$R$_y$—, or —R$_x$OP(O)O$_2$R$_y$—, wherein R$_x$ and R$_y$ can be alkyl, alkenyl, alkynyl, aryl, cycloalkyl, heterocyclyl, and hydrogen.

The term "sulfide" as used herein refers to the structure —R$_z$S—, where R$_z$ can be alkyl, alkenyl, alkynyl, aryl, arylalkyl, cycloalkyl, haloalkyl, heteroaryl, heterocyclyl. The sulfide may be cyclic, forming a 3 to 12-membered ring. The term "alkylsulfide" as used herein refers to an alkyl group attached to a sulfur atom.

The term "sulfinyl" as used herein refers to the structure —S(O)O—, —R$_p$S(O)O—, —R$_p$S(O)OR$_q$—, or —S(O)OR$_q$—, wherein R$_p$ and R$_q$ can be alkyl, alkenyl, aryl, arylalkyl, cycloalkyl, haloalkyl, heteroaryl, heterocyclyl, and hydroxyl. Exemplary sulfinyl groups include, but are not limited to, alkylsulfinyls wherein at least one of R$_p$ or R$_q$ is alkyl, alkenyl, or alkynyl.

The term "sulfonamide" as used herein refers to the structure —(R$_r$)—N—S(O)$_2$—R$_s$— or —R$_t$(R$_r$)—N—S(O)$_2$—R$_s$, where R$_t$, R$_r$, and R$_s$ can be, for example, hydrogen, alkyl, alkenyl, alkynyl, aryl, cycloalkyl, and heterocyclyl. Exemplary sulfonamides include alkylsulfonamides (e.g., where R$_s$ is alkyl), arylsulfonamides (e.g., where R$_s$ is aryl), cycloalkyl sulfonamides (e.g., where R$_s$ is cycloalkyl), and heterocyclyl sulfonamides (e.g., where R$_s$ is heterocyclyl).

The term "sulfonate" as used herein refers to –OSO$_3$—. Sulfonate includes salts such as —OSO$_3$Na, —OSO$_3$K and the acid —OSO$_3$H.

The term "sulfonic acid" refers to —SO$_3$H— and its corresponding salts (e.g., —SO$_3$K— and —SO$_3$Na—).

The term "sulfonyl" as used herein refers to the structure R$_u$SO$_2$—, where R$_u$ can be alkyl, alkenyl, alkynyl, aryl, cycloalkyl, and heterocyclyl (e.g., alkylsulfonyl). The term "alkylsulfonyl" as used herein refers to an alkyl group attached to a sulfonyl group. "Alkylsulfonyl" groups can optionally contain alkenyl or alkynyl groups.

The term "thioketone" refers to the structure —R$_v$—C(S)—R$_w$—. The ketone can be attached to another group through R$_v$ or R$_w$. R$_v$ or R$_w$ can be alkyl, alkenyl, alkynyl, cycloalkyl, heterocyclyl, or aryl, or R$_v$ and R$_w$ can be joined to form a 3- to 12-membered ring.

"Alkyl" groups can be substituted with or interrupted by or branched with at least one group selected from alkoxy, aryloxy, alkyl, alkenyl, alkynyl, amide, amino, aryl, arylalkyl, carbamate, carboxy, cyano, cycloalkyl, ester, ether, formyl, halogen, haloalkyl, ketone, heteroaryl, heterocyclyl, hydroxyl, nitro, phosphate, sulfide, sulfinyl, sulfonyl, sulfonic acid, sulfonamide, thioketone, ureido, and N. The substituents may be branched to form a substituted or unsubstituted heterocycle or cycloalkyl.

"Alkenyl," "alkynyl", "alkoxy", "amino" and "amide" groups can be substituted with or interrupted by or branched with at least one group selected from alkoxy, aryloxy, alkyl, alkenyl, alkynyl, amide, amino, aryl, arylalkyl, carbamate, carbonyl, carboxy, cyano, cycloalkyl, ester, ether, formyl, halogen, haloalkyl, heteroaryl, heterocyclyl, hydroxyl, ketone, nitro, phosphate, sulfide, sulfinyl, sulfonyl, sulfonic acid, sulfonamide, thioketone, ureido, and N. The substituents may be branched to form a substituted or unsubstituted heterocycle or cycloalkyl.

As used herein, a "suitable substituent" refers to a group that does not nullify the synthetic or pharmaceutical utility of the compounds of the invention or the intermediates useful for preparing them. Examples of suitable substituents include, but are not limited to: $C_{1-22}$, $C_{1-8}$, and $C_{1-6}$ alkyl, alkenyl or alkynyl; $C_{1-6}$ aryl, $C_{2-5}$ heteroaryl; $C_{3-7}$ cycloalkyl; $C_{1-22}$, $C_{1-8}$, and $C_{1-6}$ alkoxy; $C_6$ aryloxy; —CN; —OH; oxo; halo, carboxy; amino, such as —NH($C_{1-22}$, $C_{1-8}$, or $C_{1-6}$ alkyl), —N($C_{1-22}$, $C_{1-8}$, and $C_{1-6}$ alkyl)$_2$, —NH(($C_6$)aryl), or —N(($C_6$)aryl)$_2$; formyl; ketones, such as —CO($C_{1-22}$, $C_{1-8}$, and $C_{1-6}$ alkyl), —CO(($C_6$ aryl) esters, such as —CO$_2$($C_{1-22}$, $C_{1-8}$, and $C_{1-6}$ alkyl) and —CO$_2$ ($C_6$ aryl). One of skill in art can readily choose a suitable substituent based on the stability and pharmacological and synthetic activity of the compound of the invention.

As used herein, "inhibiting" refers to blocking, suppressing, or in any other way, reducing the expression of IL-6 mRNA and/or VCAM-1 mRNA, and/or the level of protein.

As used herein, "reducing" refers to reducing the overall levels of IL-6 and/or VCAM-1, e.g., by inhibiting the expression of, eliminating, and/or modifying IL-6 mRNA and/or VCAM-1 mRNA, and/or the level of protein.

The term "pharmaceutically acceptable carrier" as used herein refers to any and all solvents, dispersion media, coatings, isotonic and absorption delaying agents, and the like, that are compatible with pharmaceutical administration. The use of such media and agents for pharmaceutically active substances is well known in the art. The compositions may also contain other active compounds providing supplemental, additional, or enhanced therapeutic functions.

The term "pharmaceutically acceptable composition" as used herein refers to a composition comprising at least one compound as disclosed herein formulated together with one or more pharmaceutically acceptable carriers.

The term "pharmaceutically acceptable prodrugs" as used herein represents those prodrugs of the compounds of the present invention that are, within the scope of sound medical judgment, suitable for use in contact with the tissues of humans and lower animals without undue toxicity, irritation, allergic response, commensurate with a reasonable benefit/risk ratio, and effective for their intended use, as well as the zwitterionic forms, where possible, of the compounds of the invention. A discussion is provided in Higuchi et al., "Prodrugs as Novel Delivery Systems," *ACS Symposium Series*, Vol. 14, and in Roche, E. B., ed. *Bioreversible Carriers in Drug Design*, American Pharmaceutical Association and Pergamon Press, 1987, both of which are incorporated herein by reference.

The term "pharmaceutically acceptable salt(s)" refers to salts of acidic or basic groups that may be present in compounds used in the present compositions. Compounds included in the present compositions that are basic in nature are capable of forming a wide variety of salts with various inorganic and organic acids. The acids that may be used to prepare pharmaceutically acceptable acid addition salts of such basic compounds are those that form non-toxic acid addition salts, i.e., salts containing pharmacologically acceptable anions, including but not limited to sulfate, citrate, matate, acetate, oxalate, chloride, bromide, iodide, nitrate, sulfate, bisulfate, phosphate, acid phosphate, isonicotinate, acetate, lactate, salicylate, citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate (i.e., 1,1'-methylene-bis-(2-hydroxy-3-naphthoate)) salts. Compounds included in the present compositions that include an amino moiety may form pharmaceutically acceptable salts with various amino acids, in addition to the acids mentioned above. Compounds included in the present compositions, that are acidic in nature are capable of forming base salts with various pharmacologically acceptable cations. Examples of such salts include alkali metal or alkaline earth metal salts and, particularly, calcium, magnesium, sodium, lithium, zinc, potassium, and iron salts.

The compounds of the disclosure may contain one or more chiral centers and/or double bonds and, therefore, exist as stereoisomers, such as geometric isomers, enantiomers or diastereomers. The term "stereoisomers" when used herein consist of all geometric isomers, enantiomers or diastereomers. These compounds may be designated by the symbols "R" or "S," depending on the configuration of substituents around the stereogenic carbon atom. The present invention encompasses various stereoisomers of these compounds and mixtures thereof. Stereoisomers include enantiomers and diastereomers. Mixtures of enantiomers or diastereomers may be designated "(±)" in nomenclature, but the skilled artisan will recognize that a structure may contain an implicit chiral center.

Individual stereoisomers of compounds of the present invention can be prepared synthetically from commercially available starting materials that contain asymmetric or stereogenic centers, or by preparation of racemic mixtures followed by resolution methods well known to those of ordinary skill in the art. These methods of resolution include, but are not limited to (1) attachment of a mixture of enantiomers to a chiral auxiliary, separation of the resulting mixture of diastereomers by recrystallization or chromatography and liberation of the optically pure product from the auxiliary, (2) salt formation employing an optically active resolving agent, or (3) direct separation of the mixture of optical enantiomers on chiral chromatographic columns. Stereoisomeric mixtures can also be resolved into their component stereoisomers by well known methods, including, but not limited to chiral-phase gas chromatography, chiral-phase high performance liquid chromatography, crystallizing the compound as a chiral salt complex, and/or crystallizing the compound in a chiral solvent. Stereoisomers can also be obtained from stereomerically-pure intermediates, reagents, and catalysts by well known asymmetric synthetic methods.

Geometric isomers can also exist in the compounds of the present invention. The present invention encompasses the various geometric isomers and mixtures thereof resulting from the arrangement of substituents around a carbon-carbon double bond or arrangement of substituents around a carbocyclic ring. Substituents around a carbon-carbon double bond are designated as being in the "Z" or "E" configuration wherein the terms "Z" and "E" are used in accordance with IUPAC standards. Unless otherwise specified, structures depicting double bonds encompass both the E and Z isomers.

Substituents around a carbon-carbon double bond alternatively can be referred to as "cis" or "trans," where "cis" represents substituents on the same side of the double bond and "trans" represents substituents on opposite sides of the double bond. The arrangements of substituents around a carbocyclic ring are designated as "cis" or "trans." The term "cis" represents substituents on the same side of the plane of the ring and the term "trans" represents substituents on opposite sides of the plane of the ring. Mixtures of compounds wherein the substituents are disposed on both the same and opposite sides of plane of the ring are designated "cis/trans."

The compounds disclosed herein may exist as tautomers and both tautomeric forms are intended to be encompassed by the scope of the invention, even though only one tautomeric structure is depicted. For example, any claim to compound A below is understood to include tautomeric structure B, and vice versa, as well as mixtures thereof.

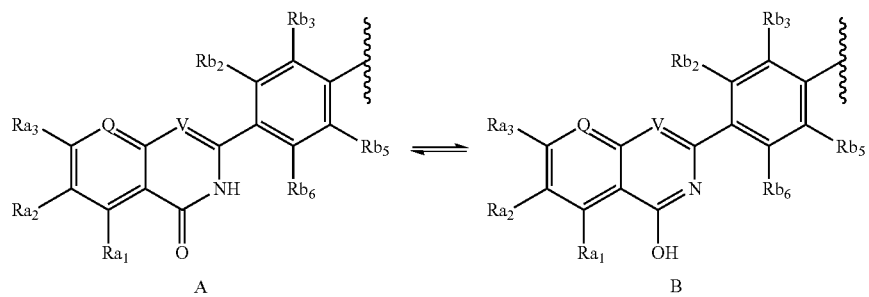

EXEMPLARY EMBODIMENTS

Formula I Methods and Compounds

In certain embodiments, the method for inhibiting the expression of, or reducing IL-6 and/or VCAM-1 in a subject, comprises administering a therapeutically effective amount of at least one compound of Formula I:

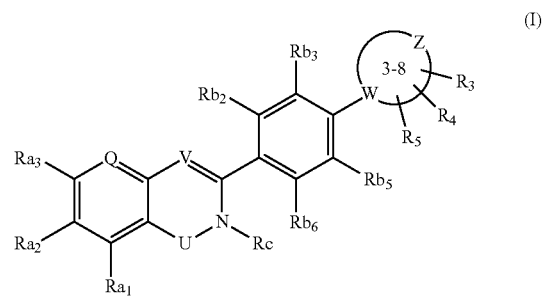

(I)

or a stereoisomer, tautomer, pharmaceutically acceptable salt, or hydrate thereof, wherein:

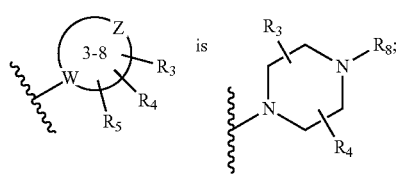

$R_3$ and $R_4$ are independently selected from hydrogen, $C_1$-$C_6$ alkyl, $C_1$-$C_6$ alkenyl, $C_1$-$C_6$ alkynyl, $C_1$-$C_6$ alkoxy, $C_3$-$C_6$ cycloalkyl, aryloxy, aryl, hydroxyl, amino, amide, oxo, —CN, and sulfonamide; and $R_8$ is selected from hydrogen, $C_1$-$C_6$ alkyl, $C_1$-$C_6$ alkenyl, acyl, and $C_1$-$C_6$ alkynyl.

In some embodiments, the method for inhibiting the expression of, or reducing IL-6 and/or VCAM-1 in a subject, comprises administering a therapeutically effective amount of at least one compound of Formula I, wherein:

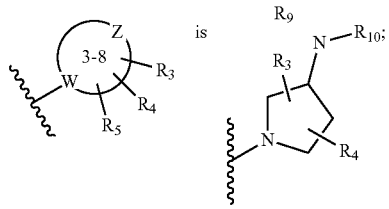

$R_3$ and $R_4$ are independently selected from hydrogen, $C_1$-$C_6$ alkyl, $C_1$-$C_6$ alkenyl, $C_1$-$C_6$ alkynyl, $C_1$-$C_6$ alkoxy, $C_3$-$C_6$ cycloalkyl, aryloxy, aryl, hydroxyl, amino, amide, oxo, —CN, and sulfonamide; and $R_9$ and $R_{10}$ are independently selected from hydrogen, $C_1$-$C_6$ alkyl, $C_1$-$C_6$ alkenyl, $C_1$-$C_6$ alkynyl, $C_3$-$C_6$ cycloalkyl, aryl, heterocycle, sulfonyl, carbamate, carboxamide, and acyl.

In some embodiments, the method for inhibiting the expression of, or reducing IL-6 and/or VCAM-1 in a subject, comprises administering a therapeutically effective amount of at least one compound of Formula I, wherein:

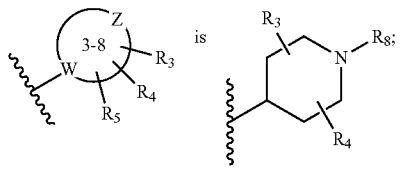

$R_3$ and $R_4$ are independently selected from hydrogen, $C_1$-$C_6$ alkyl, $C_1$-$C_6$ alkenyl, $C_1$-$C_6$ alkynyl, $C_1$-$C_6$ alkoxy, $C_3$-$C_6$ cycloalkyl, aryloxy, aryl, hydroxyl, amino, amido, oxo, —CN, and sulfonamide; and $R_8$ is selected from hydrogen, $C_1$-$C_6$ alkyl, $C_1$-$C_6$ alkenyl, $C_1$-$C_6$ alkynyl, acyl, and $C_3$-$C_6$ cycloalkyl.

In some embodiments, the method for inhibiting the expression of, or reducing IL-6 and/or VCAM-1 in a subject, comprises administering a therapeutically effective amount of at least one compound of Formula I, wherein:

U is C=O;

Rc is hydrogen;

Ra$_2$ is hydrogen;

Ra$_1$ and Ra$_3$ are independently selected from $C_1$-$C_6$ alkoxy, hydrogen, and halogen;

Rb$_2$, Rb$_3$, Rb$_5$, and Rb$_6$ are each hydrogen;

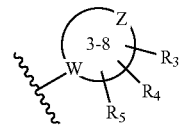

is selected from

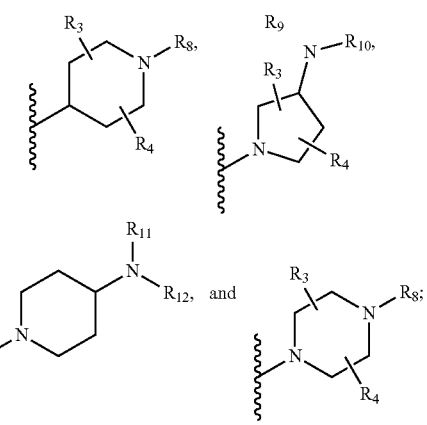

$R_3$ and $R_4$ are independently selected from hydrogen and $C_1$-$C_6$ alkyl;

$R_8$ is selected from $C_1$-$C_6$ alkyl and hydrogen; and $R_9$, $R_{10}$, $R_{11}$, and $R_{12}$ are independently selected from $C_1$-$C_6$ alkyl, hydrogen, acyl, and sulfonyl.

In some embodiments, the method for inhibiting the expression of, or reducing –6 and/or VCAM-1 in a subject, comprises administering a therapeutically effective amount of at least one compound of Formula I, wherein:

U is C=O;

Rc is hydrogen;

Ra$_2$ is hydrogen;

Ra$_1$ and Ra$_3$ are independently selected from methoxy, hydrogen, and halogen;

Rb$_2$, Rb$_3$, Rb$_5$, and Rb$_6$ are each hydrogen;

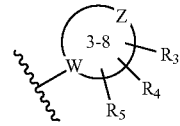

is selected from

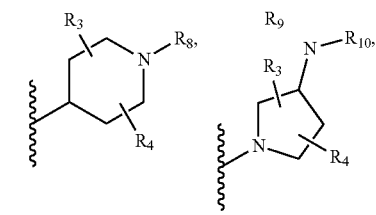

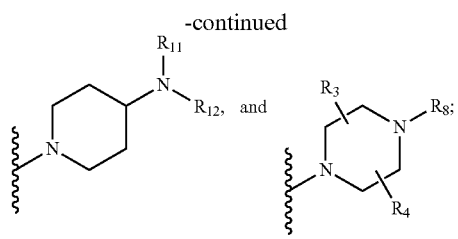

R₃ and R₄ are independently selected from hydrogen and methyl;

R₈ is selected from hydrogen, hydroxyethyl, butyl, acetyl, isopropyl, 4-hexanoyl, 4-isobutyryl, benzoyl, 4-fluorobenzoyl, 4-picolinoyl, 4-nicotinoyl, 4-isonicotinoyl, thiophene-2-carbonyl, 5-chloro-1-methyl-1H-pyrazole-4-carbonyl, 3,3,3-trifluoropropanoyl, 2,5-dichlorothiophene-3-carbonyl, cyclopropanecarbonyl, 4-fluorobenzyl, benzyl, 2,2,2-trifluoroethyl, tertbutoxycarbonyl, and formyl;

R₉ and R₁₀ are independently selected from hydrogen, methyl, cyclopropylmethyl, and acetyl; and R₁₁ and R₁₂ are independently selected from hydrogen, acetyl, methanesulfonyl, dimethylaminocarbonyl, benzoyl, benzyl, ethyl, and isopropyl.

In certain embodiments, the method for inhibiting the expression of, or reducing IL-6 and/or VCAM-1 in a subject, comprises administering a therapeutically effective amount of at least one compound of Formula I selected from:

5,7-dimethoxy-2-(4-morpholinophenyl)quinazolin-4(3H)-one;
2-(4-((3R,5S)-4-acetyl-3,5-dimethylpiperazin-1-yl)phenyl)-5,7-dimethoxypyrido[2,3-d]pyrimidin-4(3H)-one;
2-(4-(4-hydroxypiperidin-1-yl)phenyl)-5,7-dimethoxypyrido[2,3-d]pyrimidin-4(3H)-one;
2-(4-((3R,5S)-4-acetyl-3,5-dimethylpiperazin-1-yl)phenyl)-5-methoxy-7-(2-methoxyethoxy)quinazolin-4(3H)-one;
2-(4-(4-isopropylpiperazin-1-yl)phenyl)-5,7-dimethoxyquinazolin-4(3H)-one;
2-(4-(4-acetylpiperazin-1-yl)phenyl)-5,7-dimethoxyquinazolin-4(3H)-one;
5,7-dimethoxy-2-(4-(piperazin-1-yl)phenyl)quinazolin-4(3H)-one;
N-(1-(4-(5,7-dimethoxy-4-oxo-3,4-dihydroquinazolin-2-yl)phenyl)piperidin-4-yl)acetamide;
N-(1-(4-(5,7-dimethoxy-4-oxo-3,4-dihydroquinazolin-2-yl)phenyl)piperidin-4-yl)methanesulfonamide;
3-(1-(4-(5,7-dimethoxy-4-oxo-3,4-dihydroquinazolin-2-yl)phenyl)piperidin-4-yl)-1,1-dimethylurea;
2-(4-(4-hexanoylpiperazin-1-yl)phenyl)-5,7-dimethoxyquinazolin-4(3H)-one;
2-(4-(4-isobutyrylpiperazin-1-yl)phenyl)-5,7-dimethoxyquinazolin-4(3H)-one;
2-(4-(4-benzoylpiperazin-1-yl)phenyl)-5,7-dimethoxyquinazolin-4(3H)-one;
2-(4-(4-(4-fluorobenzoyl)piperazin-1-yl)phenyl)-5,7-dimethoxyquinazolin-4(3H)-one;
N-(1-(4-(5,7-dimethoxy-4-oxo-3,4-dihydroquinazolin-2-yl)phenyl)piperidin-4-yl)benzamide;
5,7-dimethoxy-2-(4-(4-picolinoylpiperazin-1-yl)phenyl)quinazolin-4(3H)-one;
5,7-dimethoxy-2-(4-(4-nicotinoylpiperazin-1-yl)phenyl)quinazolin-4(3H)-one;
2-(4-(4-isonicotinoylpiperazin-1-yl)phenyl)-5,7-dimethoxyquinazolin-4(3H)-one;
5,7-dimethoxy-2-(4-(4-(thiophene-2-carbonyl)piperazin-1-yl)phenyl)quinazolin-4(3H)-one;
2-(4-(4-(5-chloro-1-methyl-1H-pyrazole-4-carbonyl)piperazin-1-yl)phenyl)-5,7-dimethoxyquinazolin-4(3H)-one;
5,7-dimethoxy-2-(4-(4-(3,3,3-trifluoropropanoyl)piperazin-1-yl)phenyl)quinazolin-4(3H)-one;
2-(4-(4-(2,5-dichlorothiophene-3-carbonyl)piperazin-1-yl)phenyl)-5,7-dimethoxyquinazolin-4(3H)-one;
2-(4-(4-(cyclopropanecarbonyl)piperazin-1-yl)phenyl)-5,7-dimethoxyquinazolin-4(3H)-one;
2-(4-(4-(4-fluorobenzyl)piperazin-1-yl)phenyl)-5,7-dimethoxyquinazolin-4(3H)-one;
2-(4-(4-benzylpiperazin-1-yl)phenyl)-5,7-dimethoxyquinazolin-4(3H)-one;
2-(4-(4-(2,2,2-trifluoroethyl)piperazin-1-yl)phenyl)quinazolin-4(3H)-one;
2-(4-(4-butylpiperazin-1-yl)phenyl)-5,7-dimethoxyquinazolin-4(3H)-one;
2-(4-(4-acetyl-1,4-diazepan-1-yl)phenyl)-5,7-dimethoxyquinazolin-4(3H)-one;
2-(4-(1,4-diazepan-1-yl)phenyl)-5,7-dimethoxyquinazolin-4(3H)-one;
5,7-dimethoxy-2-(4-(4-methyl-1,4-diazepan-1-yl)phenyl)quinazolin-4(3H)-one;
N-(1-(4-(5,7-dimethoxy-4-oxo-3,4-dihydroquinazolin-2-yl)phenyl)piperidin-4-yl)-N-ethylacetamide;
2-(4-((3R,5S)-4-acetyl-3,5-dimethylpiperazin-1-yl)phenyl)-5,7-dimethoxyquinazolin-4(3H)-one;
2-(4-((3R,5S)-3,5-dimethylpiperazin-1-yl)phenyl)-5,7-dimethoxyquinazolin-4(3H)-one;
2-(4-(4-acetyl-3-methylpiperazin-1-yl)phenyl)-5,7-dimethoxyquinazolin-4(3H)-one;
N-(1-(4-(5,7-dimethoxy-4-oxo-3,4-dihydroquinazolin-2-yl)phenyl)pyrrolidin-3-yl)acetamide;
2-(4-(4-isopropylpiperazin-1-yl)phenyl)-8-methoxyquinazolin-4(3H)-one;
2-(4-(4-(2-hydroxyethyl)piperazin-1-yl)phenyl)-5,7-dimethoxyquinazolin-4(3H)-one;
N-(1-(4-(5,7-dimethoxy-4-oxo-3,4-dihydroquinazolin-2-yl)phenyl)piperidin-4-yl)-N-isopropylacetamide;
5-chloro-2-(4-(4-isopropylpiperazin-1-yl)phenyl)quinazolin-4(3H)-one;
2-(4-((3R,5S)-4-isopropyl-3,5-dimethylpiperazin-1-yl)phenyl)-5,7-dimethoxyquinazolin-4(3H)-one;
5,7-dimethoxy-2-(4-(piperidin-4-yl)phenyl)quinazolin-4(3H)-one;
5,7-dimethoxy-2-(4-(3-(methylamino)pyrrolidin-1-yl)phenyl)quinazolin-4(3H)-one;
tert-butyl 4-(4-(5,7-dimethoxy-4-oxo-3,4-dihydroquinazolin-2-yl)phenyl)piperidine-1-carboxylate;
N-(1-(4-(5,7-dimethoxy-4-oxo-3,4-dihydroquinazolin-2-yl)phenyl)pyrrolidin-3-yl)-N-methylacetamide;
2-(4-(4-(isopropylamino)piperidin-1-yl)phenyl)-5,7-dimethoxyquinazolin-4(3H)-one;
2-(4-(1-acetylpiperidin-4-yl)phenyl)-5,7-dimethoxyquinazolin-4(3H)-one;
5,7-dimethoxy-2-(4-(3-methylpiperazin-1-yl)phenyl)quinazolin-4(3H)-one;
N-benzyl-N-(1-(5-(5,7-dimethoxy-4-oxo-3,4-dihydroquinazolin-2-yl)pyridin-2-yl)piperidin-4-yl)acetamide;
2-(6-(4-(benzylamino)piperidin-1-yl)pyridin-3-yl)-5,7-dimethoxyquinazolin-4(3H)-one;
4-(4-(5,7-dimethoxy-4-oxo-3,4-dihydroquinazolin-2-yl)phenyl)piperazine-1-carbaldehyde;
2-(4-(2-(1-acetylazetidin-3-yl)ethoxy)-3,5-dimethylphenyl)-5,7-dimethoxyquinazolin-4(3H)-one;
2-(4-(3-(cyclopropylmethylamino)pyrrolidin-1-yl)phenyl)-5,7-dimethoxyquinazolin-4(3H)-one; and 5,7-dimethoxy-2-(4-(4-oxopiperidin-1-yl)phenyl)pyrido[2,3-d]pyrimidin-4(3H)-one, or a stereoisomer, tautomer, pharmaceutically acceptable salt, or hydrate thereof.

Another aspect of the invention provides compounds of Formula I:

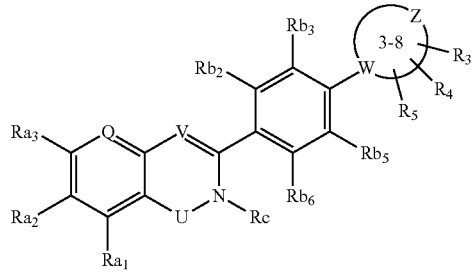

(I)

and stereoisomers, tautomers, pharmaceutically acceptable salts, and hydrates thereof,
wherein:
 Q and V are independently selected from CH and nitrogen;
 U is selected from C=O and $SO_2$;
 W is selected from carbon and nitrogen;
 Rc is selected from hydrogen, $C_1$-$C_6$ alkyl, and $C_3$-$C_6$ cycloalkyl;
 $Ra_1$, $Ra_2$, and $Ra_3$ are independently selected from hydrogen, $C_1$-$C_6$ alkyl, $C_1$-$C_6$ alkenyl, $C_1$-$C_6$ alkynyl, $C_1$-$C_6$ alkoxy, halogen, amino, amide, hydroxyl, heterocycle, and $C_3$-$C_6$ cycloalkyl, wherein $Ra_1$ and $Ra_2$ and/or $Ra_2$ and $Ra_3$ may be connected to form a cycloalkyl or a heterocycle;
 $Rb_2$ and $Rb_6$ are independently selected from hydrogen, halogen, $C_1$-$C_6$ alkyl, $C_1$-$C_6$ alkenyl, $C_3$-$C_6$ cycloalkyl, hydroxyl, and amino;
 $Rb_3$ and $Rb_5$ are independently selected from hydrogen, halogen, $C_1$-$C_6$ alkyl, $C_1$-$C_6$ alkoxy, $C_3$-$C_6$ cycloalkyl, hydroxyl, and amino, wherein $Rb_2$ and $Rb_3$ and/or $Rb_5$ and $Rb_6$ may be connected to form a cycloalkyl or a heterocycle;

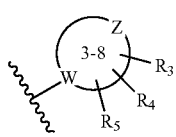

represents a 3-8 membered ring system wherein:
 W is selected from carbon and nitrogen;
 Z is selected from $CR_6R_7$, $NR_8$, oxygen, sulfur, —S(O)—, and —$SO_2$—; said ring system being optionally fused to another ring selected from cycloakyl, heterocycle, and phenyl, and wherein said ring system is selected from, for example, rings having the structures

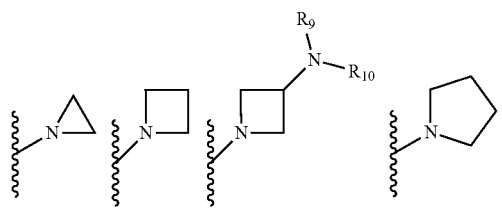

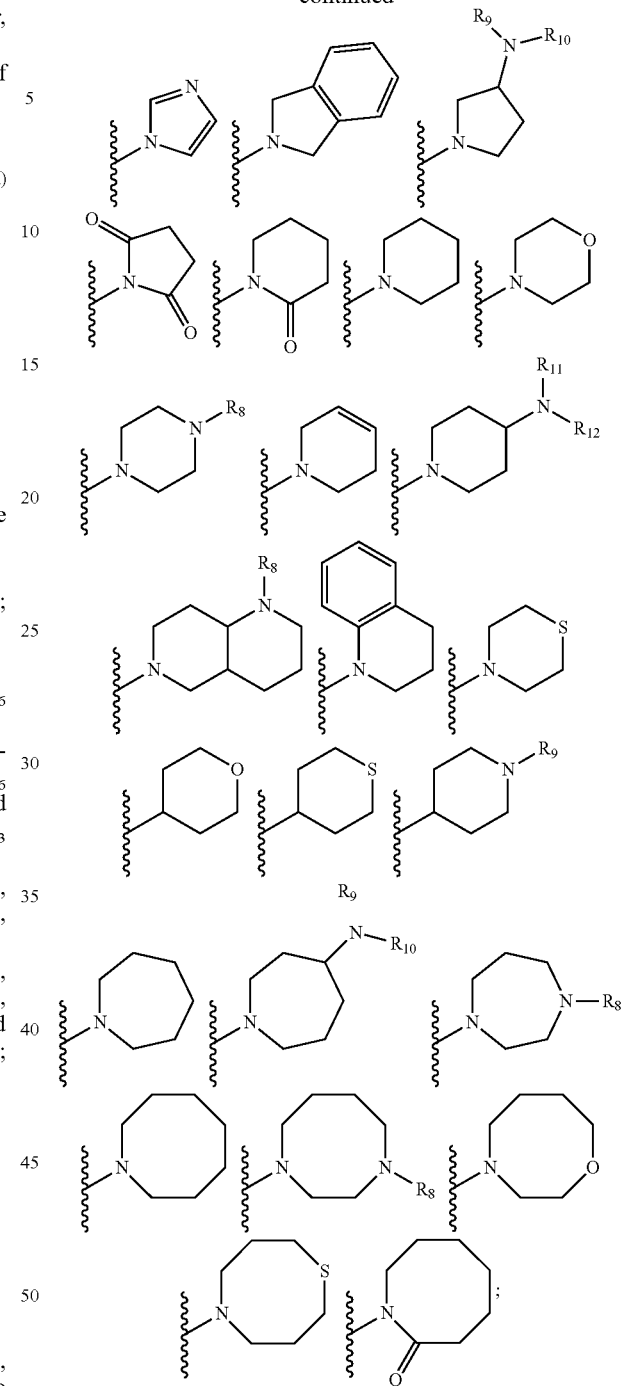

$R_3$, $R_4$, and $R_5$ are independently selected from hydrogen, $C_1$-$C_6$ alkyl, $C_1$-$C_6$ alkenyl, $C_1$-$C_6$ alkynyl, $C_1$-$C_6$ alkoxy, $C_3$-$C_6$ cycloalkyl, aryl, aryloxy, hydroxyl, amino, amide, oxo, —CN, and sulfonamide;
 $R_6$, and $R_7$ are independently selected from hydrogen, $C_1$-$C_6$ alkyl, $C_1$-$C_6$ alkenyl, $C_1$-$C_6$ alkynyl, $C_3$-$C_6$ cycloalkyl, aryl, halogen, hydroxyl, acyl, and —CN;
 $R_8$ is selected from hydrogen, $C_1$-$C_6$ alkyl, $C_1$-$C_6$ alkenyl, $C_1$-$C_6$ alkynyl, $C_3$-$C_6$ cycloalkyl and acyl; and
 $R_9$, $R_{10}$, $R_{11}$, and $R_{12}$ are independently selected from hydrogen, $C_1$-$C_6$ alkyl, $C_1$-$C_6$ alkenyl, $C_1$-$C_6$ alkynyl, $C_3$-$C_6$ cycloalkyl, aryl, hydroxyl, sulfonyl, and acyl, provided that
if Q=CH, then at least one of $Ra_1$, $Ra_2$, and $Ra_3$ is not hydrogen; if Z=NAc, then only one of $Ra_1$, $Ra_2$, and $Ra_3$ is hydrogen, and $Ra_1$ is not —$OCH_2CH_2OMe$;

if $Ra_1$ and $Ra_3$ are both OMe, than $R_8$ is not —C(O)$CH_2OH$; and further provided that the compound of Formula I is not 5,7-dimethoxy-2-(4-morpholinophenyl)quinazolin-4(3H)-one, 5,7-dimethoxy-2-(4-(4-methylpiperazin-1-yl)phenyl) quinazolin-4(3H)-one, or 2-(4-(1-cyclopentylpiperidin-4-yl) phenyl)-3-methylquinazolin-4(3H)-one.

Some embodiments provide compounds of Formula I, and stereoisomers, tautomers, pharmaceutically acceptable salts, and hydrates thereof,
wherein:

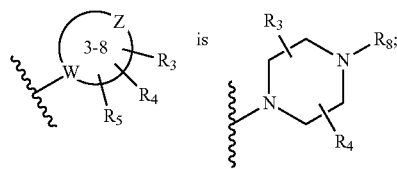

$R_3$ and $R_4$ are independently selected from hydrogen, $C_1$-$C_6$ alkyl, $C_1$-$C_6$ alkenyl, $C_1$-$C_6$ alkynyl, $C_1$-$C_6$ alkoxy, $C_3$-$C_6$ cycloalkyl, aryloxy, aryl, hydroxyl, amino, amide, oxo, —CN, and sulfonamide; and $R_8$ is selected from hydrogen, $C_1$-$C_6$ alkyl, $C_1$-$C_6$ alkenyl, $C_1$-$C_6$ alkynyl, acyl, and $C_3$-$C_6$ cycloalkyl.

Other embodiments provide compounds of Formula I, and stereoisomers, tautomers, pharmaceutically acceptable salts, and hydrates thereof,
wherein:

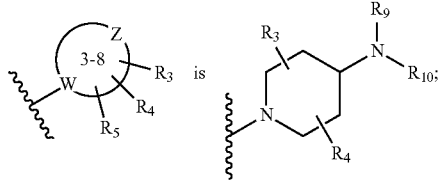

$R_3$ and $R_4$ are independently selected from hydrogen, $C_1$-$C_6$ alkyl, $C_1$-$C_6$ alkenyl, $C_1$-$C_6$ alkynyl, $C_1$-$C_6$ alkoxy, $C_3$-$C_6$ cycloalkyl, aryloxy, aryl, hydroxyl, amino, amide, oxo, —CN, and sulfonamide; and $R_9$ and $R_{10}$ are independently selected from hydrogen, $C_1$-$C_6$ alkyl, $C_1$-$C_6$ alkenyl, $C_1$-$C_6$ alkynyl, $C_3$-$C_6$ cycloalkyl, aryl, heterocycle, sulfonyl, carbamate, carboxamide, and acyl.

Still other embodiments provide compounds of Formula I, and stereoisomers, tautomers, pharmaceutically acceptable salts, and hydrates thereof,
wherein:

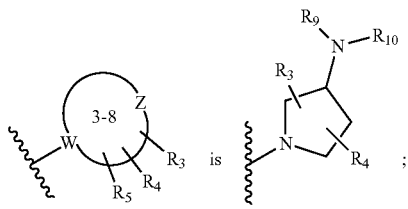

$R_3$ and $R_4$ are independently selected from hydrogen, $C_1$-$C_6$ alkyl, $C_1$-$C_6$ alkenyl, $C_1$-$C_6$ alkynyl, $C_1$-$C_6$ alkoxy, $C_3$-$C_6$ cycloalkyl, aryloxy, aryl, hydroxyl, amino, amide, oxo, —CN, and sulfonamide; and $R_9$ and $R_{10}$ are independently selected from hydrogen, $C_1$-$C_6$ alkyl, $C_1$-$C_6$ alkenyl, $C_1$-$C_6$ alkynyl, $C_3$-$C_6$ cycloalkyl, aryl, heterocycle, sulfonyl, carboxamide, carbamate, and acyl.

Certain embodiments provide compounds of Formula I, and stereoisomers, tautomers, pharmaceutically acceptable salts, and hydrates thereof,
wherein:

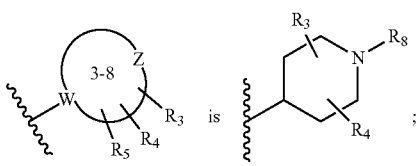

$R_3$ and $R_4$ are independently selected from hydrogen, $C_1$-$C_6$ alkyl, $C_1$-$C_6$ alkenyl, $C_1$-$C_6$ alkynyl, $C_1$-$C_6$ alkoxy, $C_3$-$C_6$ cycloalkyl, aryloxy, aryl, hydroxyl, amino, amide, oxo, —CN, and sulfonamide; and $R_8$ is selected from hydrogen, $C_1$-$C_6$ alkyl, $C_1$-$C_6$ alkenyl, $C_1$-$C_6$ alkynyl, acyl, and $C_3$-$C_6$ cycloalkyl.

Some embodiments provide compounds of Formula I, and stereoisomers, tautomers, pharmaceutically acceptable salts, and hydrates thereof,
wherein:
U is C=O
Rc is hydrogen;
$Ra_2$ is hydrogen;
$Ra_1$ and $Ra_3$ are independently selected from $C_1$-$C_6$ alkoxy, hydrogen, and halogen;
$Rb_2$, $Rb_3$, $Rb_5$, and $Rb_6$ are each hydrogen;

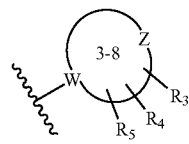

is selected from

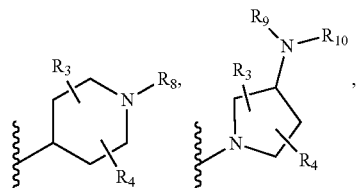

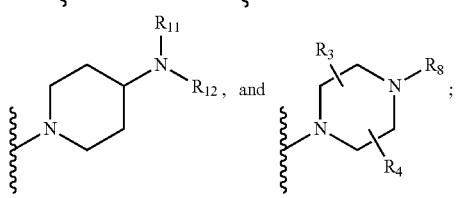

R$_3$ and R$_4$ are independently selected from hydrogen and C$_1$-C$_6$ alkyl;

R$_8$ is selected from C$_1$-C$_6$ alkyl, and hydrogen; and

R$_9$, R$_{10}$, R$_{11}$, and R$_{12}$ are independently selected from C$_1$-C$_6$ alkyl, hydrogen, and sulfonyl.

Other embodiments provide compounds of Formula I, and stereoisomers, tautomers, pharmaceutically acceptable salts, and hydrates thereof,
wherein:
U is C=O
Rc is hydrogen;
Ra$_2$ is hydrogen;
Ra$_1$ and Ra$_3$ are independently selected from methoxy, hydrogen, and halogen;
Rb$_2$, Rb$_3$, Rb$_5$, and Rb$_6$ are each hydrogen;

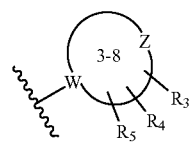

is selected from

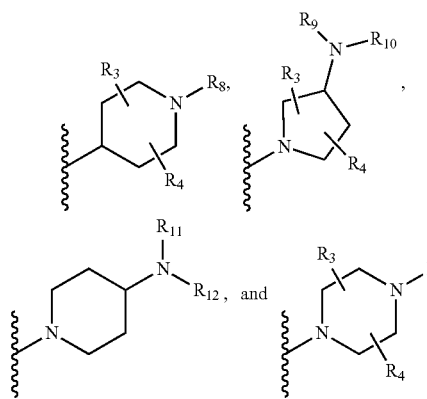

R$_3$ and R$_4$ are independently selected from hydrogen and methyl;

R$_8$ is selected from hydrogen, hydroxyethyl, butyl, acetyl, isopropyl, 4-hexanoyl, 4-isobutyryl, benzoyl, 4-fluorobenzoyl, 4-picolinoyl, 4-nicotinoyl, 4-isonicotinoyl, thiophene-2-carbonyl, 5-chloro-1-methyl-1H-pyrazole-4-carbonyl, 3,3,3-trifluoropropanoyl, 2,5-dichlorothiophene-3-carbonyl, cyclopropanecarbonyl, 4-fluorobenzyl, benzyl, 2,2,2-trifluoroethyl, tertbutoxycarbonyl, and formyl;

R$_9$ and R$_{10}$ are independently selected from hydrogen, methyl, cyclopropylmethyl, and acetyl; and R$_{11}$ and R$_{12}$ are independently selected from hydrogen, acetyl, methanesulfonyl, dimethylaminocarbonyl, benzoyl, benzyl, ethyl, and isopropyl.

In one embodiment, compounds of Formula I are selected from:

2-(4-((3R,5S)-4-acetyl-3,5-dimethylpiperazin-1-yl)phenyl)-5,7-dimethoxypyrido[2,3-d]pyrimidin-4(3H)-one;

2-(4-(4-hydroxypiperidin-1-yl)phenyl)-5,7-dimethoxypyrido[2,3-d]pyrimidin-4(3H)-one;

2-(4-((3R,5S)-4-acetyl-3,5-dimethylpiperazin-1-yl)phenyl)-5-methoxy-7-(2-methoxyethoxy)quinazolin-4(3H)-one;

2-(4-(4-isopropylpiperazin-1-yl)phenyl)-5,7-dimethoxyquinazolin-4(3H)-one;

2-(4-(4-acetylpiperazin-1-yl)phenyl)-5,7-dimethoxyquinazolin-4(3H)-one;

5,7-dimethoxy-2-(4-(piperazin-1-yl)phenyl)quinazolin-4(3H)-one;

N-(1-(4-(5,7-dimethoxy-4-oxo-3,4-dihydroquinazolin-2-yl)phenyl)piperidin-4-yl)acetamide;

N-(1-(4-(5,7-dimethoxy-4-oxo-3,4-dihydroquinazolin-2-yl)phenyl)piperidin-4-yl)methanesulfonamide 3-(1-(4-(5,7-dimethoxy-4-oxo-3,4-dihydroquinazolin-2-yl)phenyl)piperidin-4-yl)-1,1-dimethylurea;

2-(4-(4-hexanoylpiperazin-1-yl)phenyl)-5,7-dimethoxyquinazolin-4(3H)-one;

2-(4-(4-isobutyrylpiperazin-1-yl)phenyl)-5,7-dimethoxyquinazolin-4(3H)-one;

2-(4-(4-benzoylpiperazin-1-yl)phenyl)-5,7-dimethoxyquinazolin-4(3H)-one;

2-(4-(4-(4-fluorobenzoyl)piperazin-1-yl)phenyl)-5,7-dimethoxyquinazolin-4(3H)-one;

N-(1-(4-(5,7-dimethoxy-4-oxo-3,4-dihydroquinazolin-2-yl)phenyl)piperidin-4-yl)benzamide;

5,7-dimethoxy-2-(4-(4-picolinoylpiperazin-1-yl)phenyl)quinazolin-4(3H)-one;

5,7-dimethoxy-2-(4-(4-nicotinoylpiperazin-1-yl)phenyl)quinazolin-4(3H)-one;

2-(4-(4-isonicotinoylpiperazin-1-yl)phenyl)-5,7-dimethoxyquinazolin-4(3H)-one;

5,7-dimethoxy-2-(4-(4-(thiophene-2-carbonyl)piperazin-1-yl)phenyl)quinazolin-4(3H)-one;

2-(4-(4-(5-chloro-1-methyl-1H-pyrazole-4-carbonyl)piperazin-1-yl)phenyl)-5,7-dimethoxyquinazolin-4(3H)-one;

5,7-dimethoxy-2-(4-(4-(3,3,3-trifluoropropanoyl)piperazin-1-yl)phenyl)quinazolin-4(3H)-one;

2-(4-(4-(2,5-dichlorothiophene-3-carbonyl)piperazin-1-yl)phenyl)-5,7-dimethoxyquinazolin-4(3H)-one;

2-(4-(4-(cyclopropanecarbonyl)piperazin-1-yl)phenyl)-5,7-dimethoxyquinazolin-4(3H)-one;

2-(4-(4-(4-fluorobenzyl)piperazin-1-yl)phenyl)-5,7-dimethoxyquinazolin-4(3H)-one;

2-(4-(4-benzylpiperazin-1-yl)phenyl)-5,7-dimethoxyquinazolin-4(3H)-one;

2-(4-(4-(2,2,2-trifluoroethyl)piperazin-1-yl)phenyl)quinazolin-4(3H)-one;

2-(4-(4-butylpiperazin-1-yl)phenyl)-5,7-dimethoxyquinazolin-4(3H)-one;

2-(4-(4-acetyl-1,4-diazepan-1-yl)phenyl)-5,7-dimethoxyquinazolin-4(3H)-one;

2-(4-(1,4-diazepan-1-yl)phenyl)-5,7-dimethoxyquinazolin-4(3H)-one;

5,7-dimethoxy-2-(4-(4-methyl-1,4-diazepan-1-yl)phenyl)quinazolin-4(3H)-one;

N-(1-(4-(5,7-dimethoxy-4-oxo-3,4-dihydroquinazolin-2-yl)phenyl)piperidin-4-yl)-N-ethylacetamide;

2-(4-((3R,5S)-4-acetyl-3,5-dimethylpiperazin-1-yl)phenyl)-5,7-dimethoxyquinazolin-4(3H)-one;

2-(4-((3R,5S)-3,5-dimethylpiperazin-1-yl)phenyl)-5,7-dimethoxyquinazolin-4(3H)-one;

2-(4-(4-acetyl-3-methylpiperazin-1-yl)phenyl)-5,7-dimethoxyquinazolin-4(3H)-one;

N-(1-(4-(5,7-dimethoxy-4-oxo-3,4-dihydroquinazolin-2-yl)phenyl)pyrrolidin-3-yl)acetamide;

2-(4-(4-isopropylpiperazin-1-yl)phenyl)-8-methoxyquinazolin-4(3H)-one;

2-(4-(4-(2-hydroxyethyl)piperazin-1-yl)phenyl)-5,7-dimethoxyquinazolin-4(3H)-one;

N-(1-(4-(5,7-dimethoxy-4-oxo-3,4-dihydroquinazolin-2-yl)phenyl)piperidin-4-yl)-N-isopropylacetamide;

5-chloro-2-(4-(4-isopropylpiperazin-1-yl)phenyl)quinazolin-4(3H)-one;
2-(4-((3R,5S)-4-isopropyl-3,5-dimethylpiperazin-1-yl)phenyl)-5,7-dimethoxyquinazolin-4(3H)-one;
5,7-dimethoxy-2-(4-(piperidin-4-yl)phenyl)quinazolin-4(3H)-one;
5,7-dimethoxy-2-(4-(3-(methylamino)pyrrolidin-1-yl)phenyl)quinazolin-4(3H)-one;
tert-butyl 4-(4-(5,7-dimethoxy-4-oxo-3,4-dihydroquinazolin-2-yl)phenyl)piperidine-1-carboxylate;
N-(1-(4-(5,7-dimethoxy-4-oxo-3,4-dihydroquinazolin-2-yl)phenyl)pyrrolidin-3-yl)-N-methylacetamide;
2-(4-(4-(isopropylamino)piperidin-1-yl)phenyl)-5,7-dimethoxyquinazolin-4(3H)-one;
2-(4-(1-acetylpiperidin-4-yl)phenyl)-5,7-dimethoxyquinazolin-4(3H)-one;
5,7-dimethoxy-2-(4-(3-methylpiperazin-1-yl)phenyl)quinazolin-4(3H)-one;
N-benzyl-N-(1-(5-(5,7-dimethoxy-4-oxo-3,4-dihydroquinazolin-2-yl)pyridin-2-yl)piperidin-4-yl)acetamide;
2-(6-(4-(benzylamino)piperidin-1-yl)pyridin-3-yl)-5,7-dimethoxyquinazolin-4(3H)-one;
4-(5,7-dimethoxy-4-oxo-3,4-dihydroquinazolin-2-yl)phenyl)piperazine-1-carbaldehyde;
2-(4-(2-(1-acetylazetidin-3-yl)ethoxy)-3,5-dimethylphenyl)-5,7-dimethoxyquinazolin-4(3H)-one;
2-(4-(3-(cyclopropylmethylamino)pyrrolidin-1-yl)phenyl)-5,7-dimethoxyquinazolin-4(3H)-one; and
5,7-dimethoxy-2-(4-(4-oxopiperidin-1-yl)phenyl)pyrido[2,3-d]pyrimidin-4(3H)-one, and tautomers, stereoisomers, pharmaceutically acceptable salts, and hydrates thereof.

Formula II Methods and Compounds

In certain embodiments, the method for inhibiting the expression of, or reducing IL-6 and/or VCAM-1 in a subject, comprises administering a therapeutically effective amount of at least one compound of Formula II:

(II)

or a stereoisomer, tautomer, pharmaceutically acceptable salt, or hydrate thereof,
wherein:
Q is CH;
V is N;
U is C=O;
Rc is hydrogen;
$Ra_2$ is hydrogen;
$Ra_1$ and $Ra_3$ are each $C_1$-$C_6$ alkyl;
$Rb_2$, $Rb_3$, and $Rb_6$ are each hydrogen;
$Rn_1$ is hydrogen;
$Rn_2$ is selected from sulfonyl, heterocycle, and aryl; and
$Rb_5$ is selected from hydrogen or may be connected with $Rn_2$ to form a heterocycle.

In some embodiments, the method for inhibiting the expression of, or reducing IL-6 and/or VCAM-1 in a subject, comprises administering a therapeutically effective amount of at least one compound of Formula II, wherein:
Q is CH;
V is N;
U is C=O;
Rc is hydrogen;
$Ra_2$ is hydrogen;
$Ra_1$ and $Ra_3$ are each methoxy;
$Rb_2$, $Rb_3$, and $Rb_6$ are each hydrogen;
$Rn_1$ is hydrogen;
$Rn_2$ is selected from methanesulfonyl, pyridin-4-yl, 4-methylphenyl, and pyridin-3-yl; and
$Rb_5$ is selected from hydrogen or may be connected with $Rn_2$ to form a heterocycle selected from (2-hydroxymethyl)-1H-pyrrol-5-yl, (2-hydroxyethyl)-1H-pyrrol-5-yl, 2-(pyrrolidin-1-yl-ylmethyl)-1H-pyrrol-5-yl, 3-(hydroxymethyl)-1H-pyrazol-5-yl, 2-(pyrrolidin-1-yl-ylethyl)-1H-pyrrol-5-yl, and 2-((dimethylamino)methyl)-1H-pyrrol-5-yl.

In certain embodiments, the method for inhibiting the expression of, or reducing IL-6 and/or VCAM-1 in a subject, comprises administering a therapeutically effective amount of at least one compound of Formula II selected from:
2-(4-(dimethylamino)naphthalen-1-yl)-6,7-dimethoxyquinazolin-4(3H)-one;
2-(4-(bis(2-hydroxyethyl)amino)phenyl)-5,7-dimethoxypyrido[2,3-d]pyrimidin-4(3H)-one;
2-(2-(hydroxymethyl)-1H-indol-5-yl)-5,7-dimethoxyquinazolin-4(3H)-one;
2-(2-(2-hydroxyethyl)-1H-indol-5-yl)-5,7-dimethoxyquinazolin-4(3H)-one;
5,7-dimethoxy-2-(2-(pyrrolidin-1-ylmethyl)-1H-indol-5-yl)quinazolin-4(3H)-one;
2-(3-(hydroxymethyl)-1H-indazol-5-yl)-5,7-dimethoxyquinazolin-4(3H)-one;
5,7-dimethoxy-2-(2-(2-(pyrrolidin-1-yl)ethyl)-1H-indol-5-yl)quinazolin-4(3H)-one;
2-(2-((dimethylamino)methyl)-1H-indol-5-yl)-5,7-dimethoxyquinazolin-4(3H)-one;
N-(4-(5,7-dimethoxy-4-oxo-3,4-dihydroquinazolin-2-yl)phenyl)methanesulfonamide;
5,7-dimethoxy-2-(4-(pyridin-4-ylamino)phenyl)quinazolin-4(3H)-one;
5,7-dimethoxy-2-(4-(p-tolylamino)phenyl)quinazolin-4(3H)-one; and
5,7-dimethoxy-2-(4-(pyridin-3-ylamino)phenyl)quinazolin-4(3H)-one, or a stereoisomer, tautomer, pharmaceutically acceptable salt, or hydrate thereof.

Another aspect of the invention provides compounds of Formula II:

(II)

and stereoisomers, tautomers, pharmaceutically acceptable salts, and hydrates thereof, wherein:
Q and V are independently selected from CH and nitrogen;
U is selected from C=O and S=O;
$R_1$ and $R_2$ are independently selected from hydrogen, and $C_1$-$C_6$ alkyl;
Rc is selected from hydrogen, $C_1$-$C_6$ alkyl, and $C_3$-$C_6$ cycloalkyl;
$Ra_1$, $Ra_2$, and $Ra_3$ are independently selected from hydrogen, $C_1$-$C_6$ alkyl, $C_1$-$C_6$ alkenyl, $C_1$-$C_6$ alkynyl, $C_1$-$C_6$ alkoxy, $C_3$-$C_6$ cycloalkyl, halogen, amino, amide, hydroxyl, and heterocycle, wherein $Ra_1$ and $Ra_2$ and/or $Ra_2$ and $Ra_3$ may be connected to form a cycloalkyl or a heterocycle;
$Rb_2$ and $Rb_6$ are independently selected from hydrogen, halogen, $C_1$-$C_6$ alkyl, $C_1$-$C_6$ alkenyl, $C_3$-$C_6$ cycloalkyl, hydroxyl, and amino;
$Rb_3$ and $Rb_5$ are independently selected from hydrogen, halogen, $C_1$-$C_6$ alkyl, $C_1$-$C_6$ alkoxy, $C_3$-$C_6$ cycloalkyl, hydroxyl, and amino, wherein
$Rb_2$ and $Rb_3$ and/or $Rb_5$ and/or $Rb_6$ may be connected to form a cycloalkyl or a heterocycle;
$Rn_1$ is selected from hydrogen, $C_1$-$C_6$ alkyl, and $C_3$-$C_6$ cycloalkyl; and
$Rn_2$ is selected from $C_1$-$C_6$ alkyl, $C_3$-$C_6$ cycloalkyl, heterocycle, aryl, alkenyl, acyl, and sulfonyl, wherein $Rn_1$ and/or $Rn_2$ may be connected with $Rb_3$ and/or $Rb_5$ to form a 5- or 6-membered heterocyclic ring,
provided that
at least one of $Ra_1$, $Ra_2$, and $Ra_3$ is not hydrogen; and
$Rn_1$ and $Rn_2$ are not both hydrogen, methyl, ethyl, or —$CH_2CH_2OH$.

Another embodiment provides compounds of Formula II, and stereoisomers, tautomers, pharmaceutically acceptable salts, and hydrates thereof,
wherein:
Q is CH;
V is N;
U is C=O;
Rc is hydrogen;
$Ra_2$ is hydrogen;
$Ra_1$ and $Ra_3$ are each $C_1$-$C_6$ alkyl;
$Rb_2$, $Rb_3$, and $Rb_6$ are each hydrogen;
$Rn_1$ is hydrogen;
$Rn_2$ is selected from sulfonyl, heterocycle, and aryl; and
$Rb_5$ is selected from hydrogen or may be connected with $Rn_2$ to form a heterocycle.

Another embodiment provides compounds of Formula II, and stereoisomers, tautomers, pharmaceutically acceptable salts, and hydrates thereof,
wherein:
Q is CH;
V is N;
U is C=O;
Rc is hydrogen;
$Ra_2$ is hydrogen;
$Ra_1$ and $Ra_3$ are each methoxy;
$Rb_2$, $Rb_3$, and $Rb_6$ are each hydrogen;
$Rn_1$ is hydrogen;
$Rn_2$ is selected from methanesulfonyl, pyridin-4-yl, 4-methylphenyl, and pyridin-3-yl; and
$Rb_5$ is selected from hydrogen or may be connected with $Rn_2$ to form a heterocycle selected from (2-hydroxymethyl)-1H-pyrrol-5-yl, (2-hydroxyethyl)-1H-pyrrol-5-yl, 2-(pyrrolidin-1-yl-ylmethyl)-1H-pyrrol-5-yl, 3-(hydroxymethyl)-1H-pyrazol-5-yl, 2-(pyrrolidin-1-yl-ylethyl)-1H-pyrrol-5-yl, and 2-((dimethylamino)methyl)-1H-pyrrol-5-yl.

In one embodiment, compounds of Formula II are selected from:
2-(2-(hydroxymethyl)-1H-indol-5-yl)-5,7-dimethoxyquinazolin-4(3H)-one;
2-(2-(2-hydroxyethyl)-1H-indol-5-yl)-5,7-dimethoxyquinazolin-4(3H)-one;
5,7-dimethoxy-2-(2-(pyrrolidin-1-ylmethyl)-1H-indol-5-yl)quinazolin-4(3H)-one;
2-(3-(hydroxymethyl)-1H-indazol-5-yl)-5,7-dimethoxyquinazolin-4(3H)-one;
5,7-dimethoxy-2-(2-(2-(pyrrolidin-1-yl)ethyl)-1H-indol-5-yl)quinazolin-4(3H)-one;
2-(2-((dimethylamino)methyl)-1H-indol-5-yl)-5,7-dimethoxyquinazolin-4(3H)-one;
N-(4-(5,7-dimethoxy-4-oxo-3,4-dihydroquinazolin-2-yl)phenyl)methanesulfonamide;
5,7-dimethoxy-2-(4-(pyridin-4-ylamino)phenyl)quinazolin-4(3H)-one;
5,7-dimethoxy-2-(4-(p-tolylamino)phenyl)quinazolin-4(3H)-one; and
5,7-dimethoxy-2-(4-(pyridin-3-ylamino)phenyl)quinazolin-4(3H)-one, and tautomers, stereoisomers, pharmaceutically acceptable salts, and hydrates thereof.

Formula III Methods and Compounds

In certain embodiments, the method for inhibiting the expression of, or reducing IL-6 and/or VCAM-1 in a subject, comprises administering a therapeutically effective amount of at least one compound of Formula III:

(III)

or a stereoisomer, tautomer, pharmaceutically acceptable salt, or hydrate thereof,
wherein:
U is C=O;
Q is selected from $CR_{12}$ and nitrogen;
V is selected from nitrogen;
Z is selected from unsubstituted $C_1$-$C_6$ alkyl;
$R_{12}$ is selected from $C_1$-$C_6$ alkoxy and halogen;
Rc is selected from hydrogen and $C_1$-$C_6$ alkyl;
$Ra_2$ is selected from hydrogen and $C_1$-$C_6$ alkoxy;
$Ra_1$ and $Ra_3$ are independently selected from hydrogen, $C_1$-$C_6$ alkyl, $C_1$-$C_6$ alkoxy, halogen, and heterocycle;
$Rb_2$ and $Rb_6$ are both hydrogen;
$Rb_3$ and $Rb_5$ are independently selected from hydrogen and $C_1$-$C_6$ alkyl;
X is selected from oxygen and $CH_2$;
n is selected from 0, 1, 2, 3, or 4; and
G is selected from heterocycle, cycloalkyl, and aryl.

In other embodiments, U is C=O in compounds of Formula III that may be used to inhibit the expression of, or reduce IL-6 and/or VCAM-1 in a subject, wherein:
Q is selected from $CR_{12}$ and nitrogen;
V is selected from nitrogen;
$R_{12}$ is selected from methoxy and chlorine;
Rc is selected from hydrogen and (pyrrolidin-1-yl)propyl;

Ra₂ is selected from hydrogen and methoxy;
Ra₁ and Ra₃ are independently selected from hydrogen, methyl, chlorine, fluorine, methoxy, isopropoxy, and pyrrolidin-1-yl;
Rb₂ and Rb₆ are both hydrogen;
Rb₃ and Rb₅ are independently selected from hydrogen and methyl;

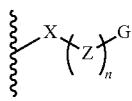

is selected from (N,N-dimethylpiperidine-1-carboxamide)-4-oxy, 1-acetylpiperidin-4-yloxy, 2-(isoindolin-2-yl)ethoxy, 2-(pyrrolidin-1-yl)ethoxy, 3-(pyrrolidin-1-yl)propoxy, 4-(pyrrolidin-1-yl)butoxy, (4-acetylpiperazin-1-yl)ethoxy, (1H-imidazol-1-yl)ethoxy, (4-methylpiperazin-1-yl)ethoxy, (piperidin-1-yl)ethoxy, (1-isopropylimidazolidine-2,4-dione)-3-ethoxy, (5-phenylimidazolidine-2,4-dione)-3-ethoxy, (imidazolidine-2,4-dione)-3-methyl, (2-azepan-1-yl)ethoxy, (2-azetidin-1-yl)ethoxy, N-(azetidin-3-yl)acetamide-1-ethoxy, (isoindoline-1,3-dione)-2-ethoxy, (5-oxopyrrolidin-2-yl)methoxy, (4-isopropylpiperazin-1-yl)methyl, N-isopropyl-N-(piperidin-4-methyl)acetamide-1-methyl, (4-(isopropylamino)piperidin-1-yl)methyl, (pyrrolidine-2,5-dione)ethoxy, and (1H-tetrazol-5-yl)methyl.

In certain embodiments, the method for inhibiting the expression of, or reducing IL-6 and/or VCAM-1 in a subject, comprises administering a therapeutically effective amount of at least one compound of Formula III selected from:
3-(3,5-dimethyl-4-(2-morpholinoethoxy)phenyl)-6,8-dimethoxyisoquinolin-1(2H)-one;
2-(3,5-dimethyl-4-(2-morpholinoethoxy)phenyl)-5,7-dimethoxyquinazolin-4(3H)-one;
3-(3,5-dimethyl-4-(2-(4-methylpiperazin-1-yl)ethoxy)phenyl)-6,8-dimethoxyisoquinolin-1(2H)-one;
2-(3,5-dimethyl-4-(2-morpholinoethoxy)phenyl)quinazolin-4(3H)-one;
7-(3,5-dimethyl-4-(2-morpholinoethoxy)phenyl)-2,4-dimethoxy-1,6-naphthyridin-5(6H)-one;
5,7-dimethoxy-2-(4-((4-methylpiperazin-1-yl)methyl)phenyl)quinazolin-4(3H)-one;
5,7-dimethoxy-2-(4-(morpholinomethyl)phenyl)quinazolin-4(3H)-one;
2-(4-((4-ethylpiperazin-1-yl)methyl)phenyl)-5,7-dimethoxyquinazolin-4(3H)-one;
2-(3,5-dimethyl-4-(2-(pyrrolidin-1-yl)ethoxy)phenyl)-5,7-dimethoxyquinazolin-4(3H)-one;
4-(4-(5,7-dimethoxy-4-oxo-3,4-dihydroquinazolin-2-yl)phenoxy)-N,N-dimethylpiperidine-1-carboxamide;
2-(4-(1-acetylpiperidin-4-yloxy)phenyl)-5,7-dimethoxyquinazolin-4(3H)-one;
2-(4-(2-(isoindolin-2-yl)ethoxy)-3,5-dimethylphenyl)-5,7-dimethoxyquinazolin-4(3H)-one;
2-(3,5-dimethyl-4-(2-(pyrrolidin-1-yl)ethoxy)phenyl)-5-methoxyquinazolin-4(3H)-one;
5,7-dichloro-2-(3,5-dimethyl-4-(2-(pyrrolidin-1-yl)ethoxy)phenyl)quinazolin-4(3H)-one;
2-(3,5-dimethyl-4-(3-(pyrrolidin-1-yl)propoxy)phenyl)-5,7-dimethoxy-3-(3-(pyrrolidin-1-yl)propyl)quinazolin-4(3H)-one;
2-(4-(2-(4-acetylpiperazin-1-yl)ethoxy)-3,5-dimethylphenyl)-5,7-dimethoxyquinazolin-4(3H)-one;
2-(4-(2-(1H-imidazol-1-yl)ethoxy)-3,5-dimethylphenyl)-5,7-dimethoxyquinazolin-4(3H)-one;
2-(3,5-dimethyl-4-(2-(pyrrolidin-1-yl)ethoxy)phenyl)-7-methoxyquinazolin-4(3H)-one;
2-(3,5-dimethyl-4-(2-(4-methylpiperazin-1-yl)ethoxy)phenyl)-5,7-dimethoxyquinazolin-4(3H)-one;
2-(3,5-dimethyl-4-(2-(piperidin-1-yl)ethoxy)phenyl)-5,7-dimethoxyquinazolin-4(3H)-one;
5,7-dimethoxy-2-(3-methyl-4-(2-(pyrrolidin-1-yl)ethoxy)phenyl)quinazolin-4(3H)-one;
3-(2-(4-(5,7-dimethoxy-4-oxo-3,4-dihydroquinazolin-2-yl)-2,6-dimethylphenoxy)ethyl)-1-isopropylimidazolidine-2,4-dione;
2-(3,5-dimethyl-4-(3-(pyrrolidin-1-yl)propoxy)phenyl)-5,7-dimethoxyquinazolin-4(3H)-one;
5,7-dimethoxy-2-(4-(2-(pyrrolidin-1-yl)ethoxy)phenyl)quinazolin-4(3H)-one;
2-(3,5-dimethyl-4-(3-(pyrrolidin-1-yl)propyl)phenyl)-5,7-dimethoxyquinazolin-4(3H)-one;
2-(3,5-dimethyl-4-(4-(pyrrolidin-1-yl)butoxy)phenyl)-5,7-dimethoxyquinazolin-4(3H)-one;
2-(3,5-dimethyl-4-(2-(pyrrolidin-1-yl)ethoxy)phenyl)-8-methoxyquinazolin-4(3H)-one;
3-(2-(4-(5,7-dimethoxy-4-oxo-3,4-dihydroquinazolin-2-yl)-2,6-dimethylphenoxy)ethyl)-5-phenylimidazolidine-2,4-dione;
3-(4-(5,7-dimethoxy-4-oxo-3,4-dihydroquinazolin-2-yl)benzyl)imidazolidine-2,4-dione;
2-(3,5-dimethyl-4-(2-(pyrrolidin-1-yl)ethoxy)phenyl)-6-methoxyquinazolin-4(3H)-one;
2-(3,5-dimethyl-4-(2-(pyrrolidin-1-yl)ethoxy)phenyl)-5,7-dimethoxypyrido[2,3-d]pyrimidin-4(3H)-one;
2-(3,5-dimethyl-4-(2-(pyrrolidin-1-yl)ethoxy)phenyl)-7-fluoro-5-(pyrrolidin-1-yl)quinazolin-4(3H)-one;
5-chloro-2-(3,5-dimethyl-4-(2-(pyrrolidin-1-yl)ethoxy)phenyl)quinazolin-4(3H)-one;
2-(4-(2-(azepan-1-yl)ethoxy)-3,5-dimethylphenyl)-5,7-dimethoxyquinazolin-4(3H)-one;
2-(3,5-dimethyl-4-(2-(pyrrolidin-1-yl)ethoxy)phenyl)-5,7-difluoroquinazolin-4(3H)-one;
2-(4-(2-(azetidin-1-yl)ethoxy)-3,5-dimethylphenyl)-5,7-dimethoxyquinazolin-4(3H)-one;
N-(1-(2-(4-(5,7-dimethoxy-4-oxo-3,4-dihydroquinazolin-2-yl)-2,6-dimethylphenoxy)ethyl)azetidin-3-yl)acetamide;
2-(3,5-dimethyl-4-(2-(pyrrolidin-1-yl)ethoxy)phenyl)-5,7-diisopropoxyquinazolin-4(3H)-one;
8-chloro-2-(3,5-dimethyl-4-(2-(pyrrolidin-1-yl)ethoxy)phenyl)quinazolin-4(3H)-one;
2-(3,5-dimethyl-4-(2-(pyrrolidin-1-yl)ethoxy)phenyl)-5,7-dimethylquinazolin-4(3H)-one;
2-(2-(4-(6,8-dimethoxy-1-oxo-1,2-dihydroisoquinolin-3-yl)-2,6-dimethylphenoxy)ethyl)isoindoline-1,3-dione;
2-(3,5-dimethyl-4-(2-(pyrrolidin-1-yl)ethoxy)phenyl)-5,7-diisopropoxypyrido[2,3-d]pyrimidin-4(3H)-one;
2-(2-(4-(5,7-dimethoxy-4-oxo-3,4-dihydroquinazolin-2-yl)-2,6-dimethylphenoxy)ethyl)isoindoline-1,3-dione;
(S)-2-(3,5-dimethyl-4-((5-oxopyrrolidin-2-yl)methoxy)phenyl)-5,7-dimethoxyquinazolin-4(3H)-one;
2-(4-((4-isopropylpiperazin-1-yl)methyl)phenyl)-5,7-dimethoxyquinazolin-4(3H)-one;
N-(1-(4-(5,7-dimethoxy-4-oxo-3,4-dihydroquinazolin-2-yl)benzyl)piperidin-4-yl)-N-isopropylacetamide;
2-(4-((4-(isopropylamino)piperidin-1-yl)methyl)phenyl)-5,7-dimethoxyquinazolin-4(3H)-one;
2-(4-((1H-tetrazol-5-yl)methyl)phenyl)-5,7-dimethoxyquinazolin-4(3H)-one; and 1-(2-(4-(5,7-dimethoxy-4-oxo-3,4-dihydroquinazolin-2-yl)-2,6-dimethylphenoxy)ethyl)pyrrolidine-2,5-dione, or a stereoisomer, tautomer, pharmaceutically acceptable salt, or hydrate thereof.

Another aspect of the invention provides compounds of Formula III:

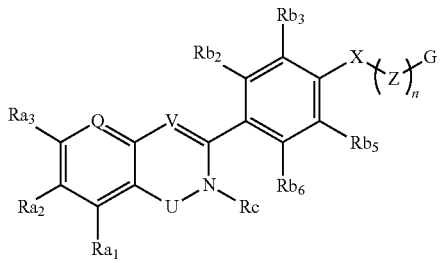

(III)

and stereoisomers, tautomers, pharmaceutically acceptable salts, and hydrates thereof,
wherein:

Q is selected from $CR_{12}$ and nitrogen;
V is selected from CH and nitrogen;
U is selected from C=O, S=O, and $SO_2$;
Z is selected from unsubstituted $C_1$-$C_6$ alkyl and $C_1$-$C_6$ alkyl substituted with one or more groups selected from $C_1$-$C_3$ alkyl, $C_1$-$C_3$ alkoxy, cyclopropyl, hydroxyl, amino, and halogen;
X is selected from oxygen, nitrogen, sulfur, $NR_6R_7$, and $CR_6R_7$;
n is selected from 0, 1, 2, 3, 4, or 5;
G is selected from heterocycle, cycloalkyl, and aryl;
$R_6$, $R_7$, and $R_{12}$ are independently selected from hydrogen, $C_1$-$C_6$ alkyl, $C_3$-$C_6$ cycloalkyl, $C_1$-$C_6$ alkoxy, and halogen;
Rc is selected from hydrogen, $C_1$-$C_6$ alkyl, and $C_3$-$C_6$ cycloalkyl;
$Ra_1$, $Ra_2$, and $Ra_3$ are independently selected from hydrogen, $C_1$-$C_6$ alkyl, $C_1$-$C_6$ alkenyl, $C_1$-$C_6$ alkynyl, $C_1$-$C_6$ alkoxy, $C_3$-$C_6$ cycloalkyl, halogen, amino, amide, hydroxyl, and heterocycle, wherein $Ra_1$ and $Ra_2$ and/or $Ra_2$ and $Ra_3$ may be connected to form a cycloalkyl or a heterocycle;
$Rb_2$ and $Rb_6$ are independently selected from hydrogen, halogen, $C_1$-$C_6$ alkyl, $C_3$-$C_6$ cycloalkyl, $C_1$-$C_6$ alkenyl, hydroxyl, and amino; and
$Rb_3$ and $Rb_5$ are independently selected from hydrogen, halogen, $C_1$-$C_6$ alkyl, $C_3$-$C_6$ cycloalkyl, $C_1$-$C_6$ alkoxy, hydroxyl, and amino, wherein
$Rb_2$ and $Rb_3$ and/or $Rb_5$ and $Rb_6$ may be connected to form a cycloalkyl or a heterocycle;
provided that
if X=oxygen and n is 3, then Rc is hydrogen;
at least one of $Ra_1$, $Ra_2$, and $Ra_3$ is not hydrogen;
if $Ra_2$ or $Ra_3$ is chloro, then $Ra_1$ is not hydrogen;
if $Ra_1$ and $Ra_3$ are OMe, and Q=CH, then

is not

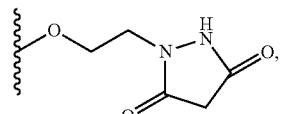

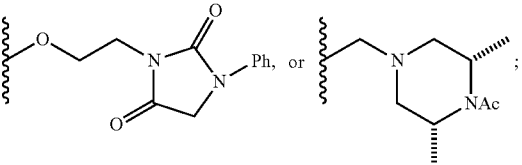

if $Ra_1$ and $Ra_3$ are OMe and $Ra_2$ is hydrogen, then

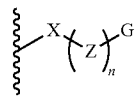

is not

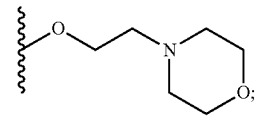 [SMILES: *OCCN1CCOCC1]

and further provided that the compound of Formula III is not 2-(3,5-dimethyl-4-(2-(pyrrolidin-1-yl)ethoxy)phenyl)-5,7-dimethoxyquinazolin-4(3H)-one, 2-(2-(4-(5,7-dimethoxy-4-oxo-3,4-dihydroquinazolin-2-yl)-2,6-dimethylphenoxy)ethyl)isoindoline-1,3-dione, 3-(3,5-dimethyl-4-(2-(4-methylpiperazin-1-yl)ethoxy)phenyl)-6,8-dimethoxyisoquinolin-1(2H)-one, 2-(4-((4-ethylpiperazin-1-yl)methyl)phenyl)-5,7-dimethoxyquinazolin-4(3H)-one, 5,7-dimethoxy-2-(4-((4-methylpiperazin-1-yl)methyl)phenyl)quinazolin-4(3H)-one, or 5,7-dimethoxy-2-(4-(morpholinomethyl)phenyl)quinazolin-4(3H)-one.

Some embodiments provide compounds of Formula III, and stereoisomers, tautomers, pharmaceutically acceptable salts, and hydrates thereof,
wherein:
Q is selected from $CR_{12}$ and nitrogen;
V is selected from nitrogen;
$R_{12}$ is selected from $C_1$-$C_6$ alkoxy, and halogen;
Rc is selected from hydrogen and $C_1$-$C_6$ alkyl;
$Ra_2$ is selected from hydrogen and $C_1$-$C_6$ alkoxy;
$Ra_1$ and $Ra_3$ are independently selected from hydrogen, $C_1$-$C_6$ alkyl, $C_1$-$C_6$ alkoxy, halogen, and heterocycle;
$Rb_2$ and $Rb_6$ are both hydrogen;
$Rb_3$ and $Rb_5$ are independently selected from hydrogen and $C_1$-$C_6$ alkyl;
X is selected from oxygen and $CH_2$;
n is selected from 0, 1, 2, 3, or 4; and
G is selected from heterocycle, cycloalkyl, and aryl.

Some embodiments provide compounds of Formula III, and stereoisomers, tautomers, pharmaceutically acceptable salts, and hydrates thereof,
wherein:
Q is selected from $CR_{12}$ and nitrogen;
V is selected from nitrogen;
$R_{12}$ is selected from methoxy and chlorine;
Rc is selected from hydrogen and (pyrrolidin-1-yl)propyl;
$Ra_2$ is selected from hydrogen and methoxy;

Ra₁ and Ra₃ are independently selected from hydrogen, methyl, chlorine, fluorine, methoxy, isopropoxy, and pyrrolidin-1-yl;

Rb₂ and Rb₆ are both hydrogen;

Rb₃ and Rb₅ are independently selected from hydrogen and methyl; and

is selected from (N,N-dimethylpiperidine-1-carboxamide)-4-oxy, 1-acetylpiperidin-4-yloxy, 2-(isoindolin-2-yl)ethoxy, 2-(pyrrolidin-1-yl)ethoxy, 3-(pyrrolidin-1-yl)propoxy, 4-(pyrrolidin-1-yl)butoxy, (4-acetylpiperazin-1-yl)ethoxy, (1H-imidazol-1-yl)ethoxy, (4-methylpiperazin-1-yl)ethoxy, (piperidin-1-yl)ethoxy, (1-isopropylimidazolidine-2,4-dione)-3-ethoxy, (5-phenylimidazolidine-2,4-dione)-3-ethoxy, (imidazolidine-2,4-dione)-3-methyl, (2-azepan-1-yl)ethoxy, (2-azetidin-1-yl)ethoxy, N-(azetidin-3-yl)acetamide-1-ethoxy, (isoindoline-1,3-dione)-2-ethoxy, (5-oxopyrrolidin-2-yl)methoxy, (4-isopropylpiperazin-1-yl)methyl, N-isopropyl-N-(piperidin-4-methyl)acetamide-1-methyl, (4-(isopropylamino)piperidin-1-yl)methyl, (pyrrolidine-2,5-dione)ethoxy, and (1H-tetrazol-5-yl)methyl.

In one embodiment, compounds of Formula III are selected from:
4-(4-(5,7-dimethoxy-4-oxo-3,4-dihydroquinazolin-2-yl)phenoxy)-N,N-dimethylpiperidine-1-carboxamide;
2-(4-(1-acetylpiperidin-4-yloxy)phenyl)-5,7-dimethoxyquinazolin-4(3H)-one;
2-(4-(2-(isoindolin-2-yl)ethoxy)-3,5-dimethylphenyl)-5,7-dimethoxyquinazolin-4(3H)-one;
2-(3,5-dimethyl-4-(2-(pyrrolidin-1-yl)ethoxy)phenyl)-5-methoxyquinazolin-4(3H)-one;
5,7-dichloro-2-(3,5-dimethyl-4-(2-(pyrrolidin-1-yl)ethoxy)phenyl)quinazolin-4(3H)-one;
2-(3,5-dimethyl-4-(3-(pyrrolidin-1-yl)propoxy)phenyl)-5,7-dimethoxy-3-(3-(pyrrolidin-1-yl)propyl)quinazolin-4(3H)-one;
2-(4-(2-(4-acetylpiperazin-1-yl)ethoxy)-3,5-dimethylphenyl)-5,7-dimethoxyquinazolin-4(3H)-one;
2-(4-(2-(1H-imidazol-1-yl)ethoxy)-3,5-dimethylphenyl)-5,7-dimethoxyquinazolin-4(3H)-one;
2-(3,5-dimethyl-4-(2-(pyrrolidin-1-yl)ethoxy)phenyl)-7-methoxyquinazolin-4(3H)-one;
2-(3,5-dimethyl-4-(2-(4-methylpiperazin-1-yl)ethoxy)phenyl)-5,7-dimethoxyquinazolin-4(3H)-one;
2-(3,5-dimethyl-4-(2-(piperidin-1-yl)ethoxy)phenyl)-5,7-dimethoxyquinazolin-4(3H)-one;
5,7-dimethoxy-2-(3-methyl-4-(2-(pyrrolidin-1-yl)ethoxy)phenyl)quinazolin-4(3H)-one;
3-(2-(4-(5,7-dimethoxy-4-oxo-3,4-dihydroquinazolin-2-yl)-2,6-dimethylphenoxy)ethyl)-1-isopropylimidazolidine-2,4-dione;
2-(3,5-dimethyl-4-(3-(pyrrolidin-1-yl)propoxy)phenyl)-5,7-dimethoxyquinazolin-4(3H)-one;
5,7-dimethoxy-2-(4-(2-(pyrrolidin-1-yl)ethoxy)phenyl)quinazolin-4(3H)-one;
2-(3,5-dimethyl-4-(3-(pyrrolidin-1-yl)propyl)phenyl)-5,7-dimethoxyquinazolin-4(3H)-one;
2-(3,5-dimethyl-4-(4-(pyrrolidin-1-yl)butoxy)phenyl)-5,7-dimethoxyquinazolin-4(3H)-one;
2-(3,5-dimethyl-4-(2-(pyrrolidin-1-yl)ethoxy)phenyl)-8-methoxyquinazolin-4(3H)-one;
3-(2-(4-(5,7-dimethoxy-4-oxo-3,4-dihydroquinazolin-2-yl)-2,6-dimethylphenoxy)ethyl)-5-phenylimidazolidine-2,4-dione;
3-(4-(5,7-dimethoxy-4-oxo-3,4-dihydroquinazolin-2-yl)benzyl)imidazolidine-2,4-dione;
2-(3,5-dimethyl-4-(2-(pyrrolidin-1-yl)ethoxy)phenyl)-6-methoxyquinazolin-4(3H)-one;
2-(3,5-dimethyl-4-(2-(pyrrolidin-1-yl)ethoxy)phenyl)-5,7-dimethoxypyrido[2,3-d]pyrimidin-4(3H)-one;
2-(3,5-dimethyl-4-(2-(pyrrolidin-1-yl)ethoxy)phenyl)-7-fluoro-5-(pyrrolidin-1-yl)quinazolin-4(3H)-one;
5-chloro-2-(3,5-dimethyl-4-(2-(pyrrolidin-1-yl)ethoxy)phenyl)quinazolin-4(3H)-one;
2-(4-(2-(azepan-1-yl)ethoxy)-3,5-dimethylphenyl)-5,7-dimethoxyquinazolin-4(3H)-one;
2-(3,5-dimethyl-4-(2-(pyrrolidin-1-yl)ethoxy)phenyl)-5,7-difluoroquinazolin-4(3H)-one;
2-(4-(2-(azetidin-1-yl)ethoxy)-3,5-dimethylphenyl)-5,7-dimethoxyquinazolin-4(3H)-one;
N-(1-(2-(4-(5,7-dimethoxy-4-oxo-3,4-dihydroquinazolin-2-yl)-2,6-dimethylphenoxy)ethyl)azetidin-3-yl)acetamide;
2-(3,5-dimethyl-4-(2-(pyrrolidin-1-yl)ethoxy)phenyl)-5,7-diisopropoxyquinazolin-4(3H)-one,
8-chloro-2-(3,5-dimethyl-4-(2-(pyrrolidin-1-yl)ethoxy)phenyl)quinazolin-4(3H)-one;
2-(3,5-dimethyl-4-(2-(pyrrolidin-1-yl)ethoxy)phenyl)-5,7-dimethylquinazolin-4(3H)-one;
2-(2-(4-(6,8-dimethoxy-1-oxo-1,2-dihydroisoquinolin-3-yl)-2,6-dimethylphenoxy)ethyl)isoindoline-1,3-dione;
2-(3,5-dimethyl-4-(2-(pyrrolidin-1-yl)ethoxy)phenyl)-5,7-diisopropoxypyrido[2,3-d]pyrimidin-4(3H)-one;
(S)-2-(3,5-dimethyl-4-((5-oxopyrrolidin-2-yl)methoxy)phenyl)-5,7-dimethoxyquinazolin-4(3H)-one;
2-(4-((4-isopropylpiperazin-1-yl)methyl)phenyl)-5,7-dimethoxyquinazolin-4(3H)-one;
N-(1-(4-(5,7-dimethoxy-4-oxo-3,4-dihydroquinazolin-2-yl)benzyl)piperidin-4-yl)-N-isopropylacetamide;
2-(4-((4-(isopropylamino)piperidin-1-yl)methyl)phenyl)-5,7-dimethoxyquinazolin-4(3H)-one;
2-(4-((1H-tetrazol-5-yl)methyl)phenyl)-5,7-dimethoxyquinazolin-4(3H)-one; and
1-(2-(4-(5,7-dimethoxy-4-oxo-3,4-dihydroquinazolin-2-yl)-2,6-dimethylphenoxy)ethyl)pyrrolidine-2,5-dione, and tautomers, stereoisomers, pharmaceutically acceptable salts, and hydrates thereof.

Formula IV Methods and Compounds

In certain embodiments, the method for inhibiting the expression of, or reducing IL-6 and/or VCAM-1 in a subject, comprises administering a therapeutically effective amount of at least one compound of Formula IV:

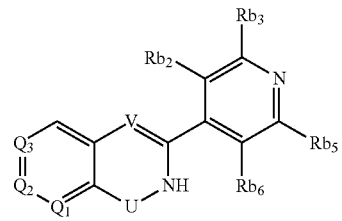

(IV)

or a stereoisomer, tautomer, pharmaceutically acceptable salt, or hydrate thereof, wherein:
U is C=O;
V is nitrogen;
$Rb_2$ and $Rb_6$ are both hydrogen;
$Rb_3$ and $Rb_5$ are independently selected from $C_1$-$C_6$ alkyl and hydrogen;
$Q_2$ is selected from $C_1$-$C_6$ alkyl and hydrogen; and
$Q_1$ and $Q_3$ are independently selected from hydrogen and $C_1$-$C_6$ alkoxy.

In some embodiments, U is C=O in compounds of Formula IV that may be used to inhibit the expression of, or reduce IL-6 and/or VCAM-1 in a subject, wherein
V is nitrogen;
$Rb_2$ and $Rb_6$ are both hydrogen;
$Rb_3$ and $Rb_5$ are independently selected from methyl and hydrogen;
$Q_2$ is selected from hydrogen, (4-methylpiperazin-1-yl)methyl, morpholinoethyl, morpholinomethyl, and (pyrrolidin-1-yl)ethyl; and
$Q_1$ and $Q_3$ are independently selected from hydrogen, benzyloxyethoxy, methoxy, methoxyethoxy, (pyrrolidin-1-yl)ethoxy, phenoxyethoxy, and isopropoxyethoxy.

In one embodiment, the method for inhibiting the expression of, or reducing IL-6 and/or VCAM-1 in a subject, comprises administering a therapeutically effective amount of at least one compound of Formula IV selected from:
7-(2-(benzyloxy)ethoxy)-5-methoxy-2-(pyridin-4-yl)quinazolin-4(3H)-one;
2-(2,6-dimethylpyridin-4-yl)-5,7-dimethoxyquinazolin-4(3H)-one;
2-(2,6-dimethylpyridin-4-yl)-5-methoxy-7-(2-methoxyethoxy)quinazolin-4(3H)-one,
2-(2,6-dimethylpyridin-4-yl)-5,7-bis(2-methoxyethoxy)quinazolin-4(3H)-one;
2-(2,6-dimethylpyridin-4-yl)-7-methoxy-5-(2-(pyrrolidin-1-yl)ethoxy)quinazolin-4(3H)-one;
2-(2,6-dimethylpyridin-4-yl)-6-((4-methylpiperazin-1-yl)methyl)quinazolin-4(3H)-one;
2-(2,6-dimethylpyridin-4-yl)-5-methoxy-7-(2-phenoxyethoxy)quinazolin-4(3H)-one;
2-(2,6-dimethylpyridin-4-yl)-7-methoxy-5-(2-phenoxyethoxy)quinazolin-4(3H)-one;
2-(2,6-dimethylpyridin-4-yl)-7-methoxy-5-(2-methoxyethoxy)quinazolin-4(3H)-one;
2-(2,6-dimethylpyridin-4-yl)-5-methoxy-7-(2-(pyrrolidin-1-yl)ethoxy)quinazolin-4(3H)-one;
2-(2,6-dimethylpyridin-4-yl)-7-(2-isopropoxyethoxy)-5-methoxyquinazolin-4(3H)-one;
2-(2,6-dimethylpyridin-4-yl)-5,7-bis(2-isopropoxyethoxy)quinazolin-4(3H)-one;
7-(2-(benzyloxy)ethoxy)-2-(2,6-dimethylpyridin-4-yl)-5-methoxyquinazolin-4(3H)-one;
2-(2,6-dimethylpyridin-4-yl)-6-(2-morpholinoethyl)quinazolin-4(3H)-one;
2-(2-methylpyridin-4-yl)-6-(morpholinomethyl)quinazolin-4(3H)-one;
5-methoxy-7-(2-methoxyethoxy)-2-(2-methylpyridin-4-yl)quinazolin-4(3H)-one;
2-(2,6-dimethylpyridin-4-yl)-6-(2-(pyrrolidin-1-yl)ethyl)quinazolin-4(3H)-one;
2-(2,6-dimethylpyridin-4-yl)-5-(2-isopropoxyethoxy)-7-methoxyquinazolin-4(3H)-one; and
2-(2,6-dimethylpyridin-4-yl)-7-(2-methoxyethoxy)-5-(2-(pyrrolidin-1-yl)ethoxy)quinazolin-4(3H)-one, or a stereoisomer, tautomer, pharmaceutically acceptable salt, or hydrate thereof.

Another aspect of the invention provides compounds of Formula IV:

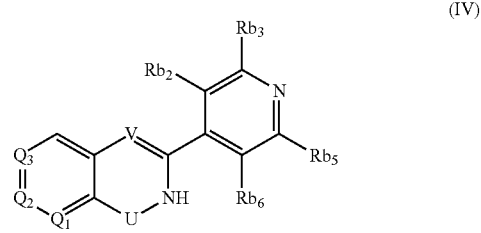

(IV)

and stereoisomers, tautomers, pharmaceutically acceptable salts, and hydrates thereof,
wherein:
$Q_1$ is selected from nitrogen and C—$Ra_1$;
$Q_2$ is selected from nitrogen and C—$Ra_2$;
$Q_3$ is selected from nitrogen and C—$Ra_3$;
V is selected from CH and nitrogen;
U is selected from C=O and S=O;
$Ra_1$, $Ra_2$, and $Ra_3$ are independently selected from hydrogen, $C_1$-$C_6$ alkyl, $C_1$-$C_6$ alkenyl, $C_1$-$C_6$ alkynyl, $C_1$-$C_6$ alkoxy, $C_3$-$C_6$ cycloalkyl, amino, amide, and heterocycle, wherein $Ra_1$ and $Ra_2$ and/or $Ra_2$ and $Ra_3$ may be connected to form a cycloalkyl or a heterocycle;
$Rb_2$ and $Rb_6$ are independently selected from hydrogen, halogen, $C_1$-$C_6$ alkyl, $C_3$-$C_6$ cycloalkyl, $C_1$-$C_6$ alkenyl, hydroxyl, and amino; and
$Rb_3$ and $Rb_5$ are independently selected from hydrogen, methyl, ethyl, $C_3$-$C_6$ cycloalkyl, $C_1$-$C_3$ alkoxy, and amino, wherein
$Rb_2$ and $Rb_3$ and/or $Rb_5$ and $Rb_6$ may be connected to form a cycloalkyl or a heterocycle,
provided that
at least one of $Ra_1$, $Ra_2$, and $Ra_3$ is hydrogen;
if $Ra_3$ is alkoxy, then $Ra_1$ is not hydrogen;
if $Ra_2$ is

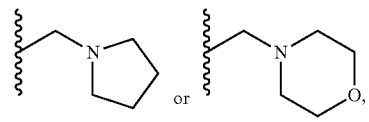

then $Rb_3$ is not hydrogen;
if $Rb_2$, $Rb_5$, and $Rb_6$ are hydrogen, then $Rb_3$ is not —$CH_2OH$; and
one of $Rb_3$ and $Rb_5$ is not hydrogen.

Other embodiments provide compounds of Formula IV, and stereoisomers, tautomers, pharmaceutically acceptable salts, and hydrates thereof, wherein:
U is C=O;
V is nitrogen;
$Rb_2$ and $Rb_6$ are both hydrogen;
$Rb_3$ and $Rb_5$ are independently selected from $C_1$-$C_6$ alkyl and hydrogen;
$Q_2$ is selected from $C_1$-$C_6$ alkyl and hydrogen; and
$Q_1$ and $Q_3$ are independently selected from hydrogen and $C_1$-$C_6$ alkoxy.

Another embodiment provides compounds of Formula IV, and stereoisomers, tautomers, pharmaceutically acceptable salts, and hydrates thereof, wherein:

U is C=O;
V is nitrogen;
$Rb_2$ and $Rb_6$ are both hydrogen;
$Rb_3$ and $Rb_5$ are independently selected from methyl and hydrogen;
$Q_2$ is selected from hydrogen, (4-methylpiperazin-1-yl) methyl, morpholinoethyl, morpholinomethyl, and (pyrrolidin-1-yl)ethyl; and
$Q_1$ and $Q_3$ are independently selected from hydrogen, benzyloxyethoxy, methoxy, methoxyethoxy, (pyrrolidin-1-yl) ethoxy, phenoxyethoxy, and isopropoxyethoxy.

In one embodiment, compounds of Formula IV are selected from:

7-(2-(benzyloxy)ethoxy)-5-methoxy-2-(pyridin-4-yl) quinazolin-4(3H)-one, 2-(2,6-dimethylpyridin-4-yl)-5,7-dimethoxyquinazolin-4 (3H)-one;

2-(2,6-dimethylpyridin-4-yl)-5-methoxy-7-(2-methoxyethoxy)quinazolin-4(3H)-one;

2-(2,6-dimethylpyridin-4-yl)-5,7-bis(2-methoxyethoxy) quinazolin-4(3H)-one;

2-(2,6-dimethylpyridin-4-yl)-7-methoxy-5-(2-(pyrrolidin-1-yl)ethoxy)quinazolin-4(3H)-one;

2-(2,6-dimethylpyridin-4-yl)-6-((4-methylpiperazin-1-yl) methyl)quinazolin-4(3H)-one;

2-(2,6-dimethylpyridin-4-yl)-5-methoxy-7-(2-phenoxyethoxy)quinazolin-4(3H)-one;

2-(2,6-dimethylpyridin-4-yl)-7-methoxy-5-(2-phenoxyethoxy)quinazolin-4(3H)-one;

2-(2,6-dimethylpyridin-4-yl)-7-methoxy-5-(2-methoxyethoxy)quinazolin-4(3H)-one;

2-(2,6-dimethylpyridin-4-yl)-5-methoxy-7-(2-(pyrrolidin-1-yl)ethoxy)quinazolin-4(3H)-one;

2-(2,6-dimethylpyridin-4-yl)-7-(2-isopropoxyethoxy)-5-methoxyquinazolin-4(3H)-one;

2-(2,6-dimethylpyridin-4-yl)-5,7-bis(2-isopropoxyethoxy) quinazolin-4(3H)-one;

7-(2-(benzyloxy)ethoxy)-2-(2,6-dimethylpyridin-4-yl)-5-methoxyquinazolin-4(3H)-one;

2-(2,6-dimethylpyridin-4-yl)-6-(2-morpholinoethyl) quinazolin-4(3H)-one;

2-(2-methylpyridin-4-yl)-6-(morpholinomethyl)quinazolin-4(3H)-one;

5-methoxy-7-(2-methoxyethoxy)-2-(2-methylpyridin-4-yl) quinazolin-4(3H)-one;

2-(2,6-dimethylpyridin-4-yl)-6-(2-(pyrrolidin-1-yl)ethyl) quinazolin-4(3H)-one;

2-(2,6-dimethylpyridin-4-yl)-5-(2-isopropoxyethoxy)-7-methoxyquinazolin-4(3H)-one; and 2-(2,6-dimethylpyridin-4-yl)-7-(2-methoxyethoxy)-5-(2-(pyrrolidin-1-yl)ethoxy)quinazolin-4(3H)-one, and tautomers, stereoisomers, pharmaceutically acceptable salts, and hydrates thereof.

Formula V Methods and Compounds

In certain embodiments, the method for inhibiting the expression of, or reducing IL-6 and/or VCAM-1 in a subject, comprises administering a therapeutically effective amount of at least one compound of Formula V:

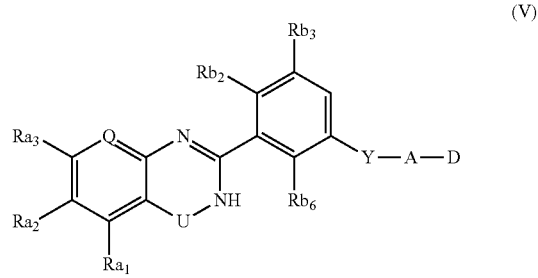

or a stereoisomer, tautomer, pharmaceutically acceptable salt, or hydrate thereof,
wherein:
U is C=O;
$Ra_2$ is selected from hydrogen and amino;
$Ra_1$ and $Ra_3$ are independently selected from hydrogen and $C_1$-$C_6$ alkoxy;
Q is CH;
$Rb_3$ is selected from hydrogen, $C_1$-$C_6$ alkyl, and $C_1$-$C_6$ alkoxy;
$Rb_2$ and $Rb_6$ are both hydrogen;
Y is selected from oxygen;
A is $C_1$-$C_4$ alkyl;
D may be absent or present, and if present is selected from hydroxy, heterocycle, and $NR_1R_2$; and
$R_1$ and $R_2$ are independently selected from hydrogen and $C_1$-$C_6$ alkyl.

In some embodiments, the method for inhibiting the expression of, or reducing IL-6 and/or VCAM-1 in a subject, comprises administering a therapeutically effective amount of at least one compound of Formula V, wherein:
U is C=O;
$Ra_2$ is selected from hydrogen and amino;
$Ra_1$ and $Ra_3$ are independently selected from hydrogen and $C_1$-$C_6$ alkoxy;
Q is CH;
$Rb_3$ is selected from hydrogen, methyl, and methoxy;
$Rb_2$ and $Rb_6$ are both hydrogen;
Y is selected from oxygen;
A is selected from methyl and ethyl;
D may be absent or present, and if present is selected from hydroxy, pyrrolidin-1-yl, and $NR_1R_2$; and
$R_1$ and $R_2$ are independently selected from hydrogen and acetyl.

In one embodiment, the method for inhibiting the expression of, or reducing IL-6 and/or VCAM-1 in a subject, comprises administering a therapeutically effective amount of at least one compound of Formula V selected from:

2-(3,5-dimethoxyphenyl)-5,7-dimethoxyquinazolin-4(3H)-one;

2-(3-(2-hydroxyethoxy)phenyl)-5,7-dimethoxyquinazolin-4 (3H)-one;

2-(3-(2-hydroxyethoxy)-5-methylphenyl)-5,7-dimethoxyquinazolin-4(3H)-one;

5,7-dimethoxy-2-(3-methoxy-5-(2-(pyrrolidin-1-yl)ethoxy) phenyl)quinazolin-4(3H)-one;

N-(2-(3-(5,7-dimethoxy-4-oxo-3,4-dihydroquinazolin-2-yl)-5-methoxyphenoxy)ethyl)acetamide;

2-(3,5-dimethoxyphenyl)-6-(pyridin-4-ylamino)quinazolin-4(3H)-one; and 5,7-dimethoxy-2-(3-methoxyphenyl)quinazolin-4(3H)-one, or a stereoisomer, tautomer, pharmaceutically acceptable salt, or hydrate thereof.

Another aspect of the invention provides compounds of Formula V:

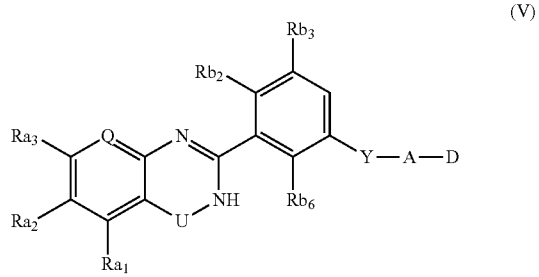

(V)

and stereoisomers, tautomers, pharmaceutically acceptable salts, and hydrates thereof,
wherein:
Q is selected from $CR_6$ and nitrogen;
U is selected from C=O and $SO_2$,
Y is selected from oxygen, nitrogen, sulfur, $NR_6$, $CR_6R_7$;
A is $C_1$-$C_4$ alkyl, wherein the alkyl chain may be connected to Y, D, $R_{b3}$ and/or $R_{b5}$ to form a cycloalkyl or heterocycle;
D may be absent or present, and if present is selected from —$OR_1$, —$NR_1R_2$;
$R_1$ and $R_2$ are independently selected from hydrogen, $C_1$-$C_6$ alkyl, $C_3$-$C_6$ cycloalkyl, sulfonamide, carboxamide, acyl, and nitrile, wherein $R_1$ and $R_2$ may be connected to form a cycloalkyl or a heterocycle;
$R_6$ and $R_7$ are independently selected from hydrogen, $C_1$-$C_6$ alkyl, $C_3$-$C_6$ cycloalkyl, $C_1$-$C_6$ alkoxy, hydroxyl, and halogen;
$Ra_1$, $Ra_2$, and $Ra_3$ are independently selected from hydrogen, $C_1$-$C_6$ alkyl, $C_1$-$C_6$ alkenyl, $C_1$-$C_6$ alkynyl, $C_1$-$C_6$ alkoxy, $C_3$-$C_6$ cycloalkyl, halogen, amino, amide, hydroxyl, and heterocycle, wherein $Ra_1$ and $Ra_2$ and/or $Ra_2$ and $Ra_3$ may be connected to form a cycloalkyl or a heterocycle;
$Rb_2$ and $Rb_6$ are independently selected from hydrogen, halogen, $C_1$-$C_6$ alkyl, and $C_3$-$C_6$ cycloalkyl; and
$Rb_3$ is selected from hydrogen, halogen, $C_1$-$C_6$ alkyl, $C_3$-$C_6$ cycloalkyl, $C_1$-$C_6$ alkoxy, hydroxyl, and amino, wherein
$Rb_2$ and $Rb_3$ and/or $Rb_5$ and $Rb_6$ may be connected to form a cycloalkyl or a heterocycle,
provided that
at least one of $Ra_1$, $Ra_2$, and $Ra_3$ is not hydrogen;
if $Ra_1$ and $Ra_3$ are both hydrogen, and Y=nitrogen, then $Ra_2$ is not hydrogen, —OAc, or —OMe; and further provided that the compound of Formula V is not 2-(3,5-dimethoxyphenyl)-5,7-dimethoxyquinazolin-4(3H)-one or 2-(3,5-dimethylphenyl)-5,7-dimethoxyquinazolin-4(3H)-one.

Some embodiments provide compounds of Formula V and stereoisomers, tautomers, pharmaceutically acceptable salts, and hydrates thereof, wherein:
U is C=O;
$Ra_2$ is selected from hydrogen and amino;
$Ra_1$ and $Ra_3$ are independently selected from hydrogen and $C_1$-$C_6$ alkoxy;
Q is CH;
$Rb_3$ is selected from hydrogen, $C_1$-$C_6$ alkyl, and $C_1$-$C_6$ alkoxy;
$Rb_2$ and $Rb_6$ are both hydrogen;
Y is selected from oxygen;
A is $C_1$-$C_4$ alkyl;
D may be absent or present, and if present is selected from hydroxy, heterocycle, and $NR_1R_2$; and
$R_1$ and $R_2$ are independently selected from hydrogen and $C_1$-$C_6$ alkyl.

Some embodiments provide compounds of Formula V and stereoisomers, tautomers, pharmaceutically acceptable salts, and hydrates thereof, wherein:
U is C=O;
$Ra_2$ is selected from hydrogen and amino;
$Ra_1$ and $Ra_3$ are independently selected from hydrogen and $C_1$-$C_6$ alkoxy;
Q is CH;
$Rb_3$ is selected from hydrogen, methyl, and methoxy;
$Rb_2$ and $Rb_6$ are both hydrogen;
Y is selected from oxygen;
A is selected from methyl and ethyl;
D may be absent or present, and if present is selected from hydroxy, pyrrolidin-1-yl, and $NR_1R_2$; and
$R_1$ and $R_2$ are independently selected from hydrogen and acetyl.

In one embodiment, compounds of Formula V are selected from:
2-(3-(2-hydroxyethoxy)phenyl)-5,7-dimethoxyquinazolin-4(3H)-one;
2-(3-(2-hydroxyethoxy)-5-methylphenyl)-5,7-dimethoxyquinazolin-4(3H)-one;
5,7-dimethoxy-2-(3-methoxy-5-(2-(pyrrolidin-1-yl)ethoxy)phenyl)quinazolin-4(3H)-one;
N-(2-(3-(5,7-dimethoxy-4-oxo-3,4-dihydroquinazolin-2-yl)-5-methoxyphenoxy)ethyl)acetamide;
2-(3,5-dimethoxyphenyl)-6-(pyridin-4-ylamino)quinazolin-4(3H)-one; and
5,7-dimethoxy-2-(3-methoxyphenyl)quinazolin-4(3H)-one, and tautomers, stereoisomers, pharmaceutically acceptable salts, and hydrates thereof.

Pharmaceutical Compositions

Pharmaceutical compositions of the invention comprise at least one compound of Formula I, II, III, IV, V, or tautomer, stereoisomer, pharmaceutically acceptable salt or hydrate thereof formulated together with one or more pharmaceutically acceptable carriers. These formulations include those suitable for oral, rectal, topical, buccal and parenteral (e.g., subcutaneous, intramuscular, intradermal, or intravenous) administration. The most suitable form of administration in any given case will depend on the degree and severity of the condition being treated and on the nature of the particular compound being used.

Formulations suitable for oral administration may be presented in discrete units, such as capsules, cachets, lozenges, or tablets, each containing a predetermined amount of a compound of the invention as powder or granules; as a solution or a suspension in an aqueous or non-aqueous liquid; or as an oil-in-water or water-in-oil emulsion. As indicated, such formulations may be prepared by any suitable method of pharmacy which includes the step of bringing into association at least one compound of the invention as the active compound and a carrier or excipient (which may constitute one or more accessory ingredients). The carrier must be acceptable in the sense of being compatible with the other ingredients of the formulation and must not be deleterious to the recipient. The carrier may be a solid or a liquid, or both, and may be formulated with at least one compound described herein as the active compound in a unit-dose formulation, for example, a tablet, which may contain from about 0.05% to about 95% by weight of the at least one active compound. Other pharmacologically active substances may also be present including other compounds. The formulations of the invention may be prepared by any of the well known techniques of pharmacy consisting essentially of admixing the components.

For solid compositions, conventional nontoxic solid carriers include, for example, pharmaceutical grades of mannitol, lactose, starch, magnesium stearate, sodium saccharin, talc, cellulose, glucose, sucrose, magnesium carbonate, and the like. Liquid pharmacologically administrable compositions can, for example, be prepared by, for example, dissolving or dispersing, at least one active compound of the invention as described herein and optional pharmaceutical adjuvants in an excipient, such as, for example, water, saline, aqueous dextrose, glycerol, ethanol, and the like, to thereby form a solution or suspension. In general, suitable formulations may be prepared by uniformly and intimately admixing the at least one active compound of the invention with a liquid or finely divided solid carrier, or both, and then, if necessary, shaping the product. For example, a tablet may be prepared by compressing or molding a powder or granules of at least one compound of the invention, which may be optionally combined with one or more accessory ingredients. Compressed tablets may be prepared by compressing, in a suitable machine, at least one compound of the invention in a free-flowing form, such as a powder or granules, which may be optionally mixed with a binder, lubricant, inert diluent and/or surface active/dispersing agent(s). Molded tablets may be made by molding, in a suitable machine, where the powdered form of at least one compound of the invention is moistened with an inert liquid diluent.

Formulations suitable for buccal (sub-lingual) administration include lozenges comprising at least one compound of the invention in a flavored base, usually sucrose and acacia or tragacanth, and pastilles comprising the at least one compound in an inert base such as gelatin and glycerin or sucrose and acacia.

Formulations of the invention suitable for parenteral administration comprise sterile aqueous preparations of at least one compound of Formula I, II, III, IV, V, or tautomers, stereoisomers, pharmaceutically acceptable salts, and hydrates thereof, which are approximately isotonic with the blood of the intended recipient. These preparations are administered intravenously, although administration may also be effected by means of subcutaneous, intramuscular, or intradermal injection. Such preparations may conveniently be prepared by admixing at least one compound described herein with water and rendering the resulting solution sterile and isotonic with the blood. Injectable compositions according to the invention may contain from about 0.1 to about 5% w/w of the active compound.

Formulations suitable for rectal administration are presented as unit-dose suppositories. These may be prepared by admixing at least one compound as described herein with one or more conventional solid carriers, for example, cocoa butter, and then shaping the resulting mixture.

Formulations suitable for topical application to the skin may take the form of an ointment, cream, lotion, paste, gel, spray, aerosol, or oil. Carriers and excipients which may be used include Vaseline, lanoline, polyethylene glycols, alcohols, and combinations of two or more thereof. The active compound (i.e., at least one compound of Formula I, II, III, IV, V, or tautomers, stereoisomers, pharmaceutically acceptable salts, and hydrates thereof) is generally present at a concentration of from about 0.1% to about 15% w/w of the composition, for example, from about 0.5 to about 2%.

The amount of active compound administered may be dependent on the subject being treated, the subject's weight, the manner of administration and the judgment of the prescribing physician. For example, a dosing schedule may involve the daily or semi-daily administration of the encapsulated compound at a perceived dosage of about 1 µg to about 1000 mg. In another embodiment, intermittent administration, such as on a monthly or yearly basis, of a dose of the encapsulated compound may be employed. Encapsulation facilitates access to the site of action and allows the administration of the active ingredients simultaneously, in theory producing a synergistic effect. In accordance with standard dosing regimens, physicians will readily determine optimum dosages and will be able to readily modify administration to achieve such dosages.

A therapeutically effective amount of a compound or composition disclosed herein can be measured by the therapeutic effectiveness of the compound. The dosages, however, may be varied depending upon the requirements of the patient, the severity of the condition being treated, and the compound being used. In one embodiment, the therapeutically effective amount of a disclosed compound is sufficient to establish a maximal plasma concentration. Preliminary doses as, for example, determined according to animal tests, and the scaling of dosages for human administration is performed according to art-accepted practices.

Toxicity and therapeutic efficacy can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compositions that exhibit large therapeutic indices are preferable.

Data obtained from the cell culture assays or animal studies can be used in formulating a range of dosage for use in humans. Therapeutically effective dosages achieved in one animal model may be converted for use in another animal, including humans, using conversion factors known in the art (see, e.g., Freireich et al., *Cancer Chemother. Reports* 50(4): 219-244 (1966) and Table 1 for Equivalent Surface Area Dosage Factors).

TABLE 1

Equivalent Surface Area Dosage Factors

| From: | To: | | | | |
| --- | --- | --- | --- | --- | --- |
| | Mouse (20 g) | Rat (150 g) | Monkey (3.5 kg) | Dog (8 kg) | Human (60 kg) |
| Mouse | 1 | 1/2 | 1/4 | 1/6 | 1/12 |
| Rat | 2 | 1 | 1/2 | 1/4 | 1/7 |
| Monkey | 4 | 2 | 1 | 3/5 | 1/3 |
| Dog | 6 | 4 | 3/5 | 1 | 1/2 |
| Human | 12 | 7 | 3 | 2 | 1 |

The dosage of such compounds lies preferably within a range of circulating concentrations that include the $ED_{50}$ with little or no toxicity. The dosage may vary within this range depending upon the dosage form employed and the route of administration utilized. Generally, a therapeutically effective amount may vary with the subject's age, condition, and gender, as well as the severity of the medical condition in the subject. The dosage may be determined by a physician and adjusted, as necessary, to suit observed effects of the treatment.

In one embodiment, a compound of Formula I, II, III, IV, V or a tautomer, stereoisomer, pharmaceutically acceptable salt or hydrate thereof, is administered in combination with another therapeutic agent. The other therapeutic agent can provide additive or synergistic value relative to the administration of a compound of the invention alone. The therapeutic agent can be, for example, a statin; a PPAR agonist, e.g., a thiazolidinedione or fibrate; a niacin, a RVX, FXR or LXR agonist; a bile-acid reuptake inhibitor; a cholesterol absorption inhibitor; a cholesterol synthesis inhibitor; a cholesteryl ester transfer protein (CETP), an ion-exchange resin; an antioxidant; an inhibitor of AcylCoA cholesterol acyltransferase (ACAT inhibitor); a tyrophostine; a sulfonylurea-based drug; a biguanide; an alpha-glucosidase inhibitor; an apolipoprotein E regulator; a HMG-CoA reductase inhibitor, a microsomal triglyceride transfer protein; an LDL-lowing drug; an HDL-raising drug; an HDL enhancer; a regulator of the apolipoprotein A-IV and/or apolipoprotein genes; or any cardiovascular drug.

In another embodiment, a compound of Formula I, II, III, IV, V or a tautomer, stereoisomer, pharmaceutically acceptable salt or hydrate thereof, is administered in combination with one or more anti-inflammatory agents. Anti-inflammatory agents can include immunosuppressants, TNF inhibitors, corticosteroids, non-steroidal anti-inflammatory drugs (NSAIDs), disease-modifying anti-rheumatic drugs (DMARDS), and the like. Exemplary anti-inflammatory agents include, for example, prednisone; methylprednisolone (Medrol®), triamcinolone, methotrexate (Rheumatrex®, Trexall®), hydroxychloroquine (Plaquenil®), sulfasalazine (Azulfidine®), leflunomide (Arava®), etanercept (Enbrel®), infliximab (Remicade®), adalimumab (Humira®), rituximab (Rituxan®), abatacept (Orencia®), interleukin-1, anakinra (Kineret™) ibuprofen, ketoprofen, fenoprofen, naproxen, aspirin, acetaminophen, indomethacin, sulindac, meloxicam, piroxicam, tenoxicam, lornoxicam, ketorolac, etodolac, mefenamic acid, meclofenamic acid, flufenamic acid, tolfenamic acid, diclofenac, oxaprozin, apazone, nimesulide, nabumetone, tenidap, etanercept, tolmetin, phenylbutazone, oxyphenbutazone, diflunisal, salsalate, olsalazine or sulfasalazine.

Therapeutic Methods

In one embodiment, a method of treating or preventing cardiovascular and inflammatory diseases and related disease states, characterized by altered expression of markers of inflammation such as IL-6 and/or VCAM-1 proliferation, comprises administering to a subject (e.g., a mammal, such as e.g., a human) a therapeutically effective amount of at least one compound of the invention, i.e., a compound of Formula I, II, III, IV, V, or a tautomer, stereoisomer, pharmaceutically acceptable salt or hydrate thereof. In another embodiment, at least one compound of the invention may be administered as a pharmaceutically acceptable composition, comprising one or more compounds of the invention and a pharmaceutically acceptable carrier.

In one embodiment, the inflammatory diseases and related disease states are those where inhibition of IL-6 and/or VCAM-1 proliferation is desirable.

In some embodiments, the methods of the invention comprise administering at least one compound of the invention to a subject, such as a human, as a preventative measure against cardiovascular and inflammatory diseases and related disease states, such as, for example, atherosclerosis, asthma, arthritis, cancer, multiple sclerosis, psoriasis, and inflammatory bowel diseases, and autoimmune disease(s).

In one embodiment, at least one compound of the invention is administered as a preventative measure to a subject, such as a human, having a genetic predisposition to cardiovascular and inflammatory diseases and related disease states, such as, for example, familial hypercholesterolemia, familial combined hyperlipidemia, atherosclerosis, a dyslipidemia, a dyslipoproteinemia, arthritis, cancer, multiple sclerosis, or Alzheimer's disease.

In another embodiment, at least one compound of the present invention is administered as a preventative measure to a subject, such as a human, having a non-genetic predisposition to a disease including a cardiovascular disease or an inflammatory disorder. Examples of such non-genetic predispositions include cardiac bypass surgery and PTCA (which can lead to restenosis), an accelerated form of atherosclerosis, diabetes in women, (which can lead to polycystic ovarian disease), and cardiovascular disease (which can lead to impotence). Accordingly, compositions of the invention may be used for the prevention of one disease or disorder and concurrently treating another (e.g., prevention of polycystic ovarian disease while treating diabetes; prevention of impotence while treating a cardiovascular disease).

Angioplasty and open heart surgery, such as coronary bypass surgery, may be required to treat cardiovascular diseases, such as atherosclerosis. These surgical procedures entail using invasive surgical devices and/or implants, and are associated with a high risk of restenosis and thrombosis. Accordingly, the compounds of the invention may be used as coatings on surgical devices (e.g., catheters) and implants (e.g., stents) to reduce the risk of restenosis and thrombosis associated with invasive procedures used in the treatment of cardiovascular diseases.

In another embodiment, the compounds of the invention may be used for the prevention of one disease or disorder while concurrently treating another (e.g., prevention of polycystic ovarian disease while treating diabetes; prevention of impotence while treating a cardiovascular disease).

EXAMPLES

The invention is further illustrated by the following non-limiting examples, wherein the following abbreviations have the following meanings. If an abbreviation is not defined, it has its generally accepted meaning.

AcOH=acetic acid
BINAP=2,2'-bis(diphenylphosphino)-1,1'-binaphthyl
Boc=N-tert-butoxycarbonyl
TBDMS=tert-butyldimethylsilyl
dba=dibenzylidene acetone
DCM=dichloromethane
DMAP=dimethylaminopyridine
DMF=dimethylformamide
DMSO=dimethylsulfoxide
EDCl=1-ethyl-3-(3'-dimethylaminopropyl)carbodiimide
EtOH=ethanol
EtOAc=ethyl acetate
IBX=1,2-benziodexol-3(1H)-one-1-hydroxy-1-oxide
MeOH=methanol
HOBt=N-hydroxybenzotriazole
THF=tetrahydrofuran
TEA=triethylamine
p-TSA=p-toluenesulfonic acid
TBAF=tetrabutylammonium fluoride
DMA=N,N-dimethylacetamide
DIBAL-H=diisobutylaluminum hydride
TPAP=tetrapropylammonium perruthenate
NMO=N-methylmorpholine N-oxide
DDQ=2,3-dicyano-5,6-dichloro-parabenzoquinone
DME=1,2-dimethoxyethane
TFA=trifluoroacetic acid
DPPF=1,1'-bis(diphenylphosphino)ferrocene
Pd(OAc)$_2$=palladium(II) acetate
Pd(PPh$_3$)$_4$=tetrakis(triphenylphosphine)palladium(0)

Example 1

Preparation of 2-(4-(4-(2-hydroxyethyl)piperazin-1-yl)phenyl)-5,7-dimethoxyquinazolin-4(3H)-one (2)

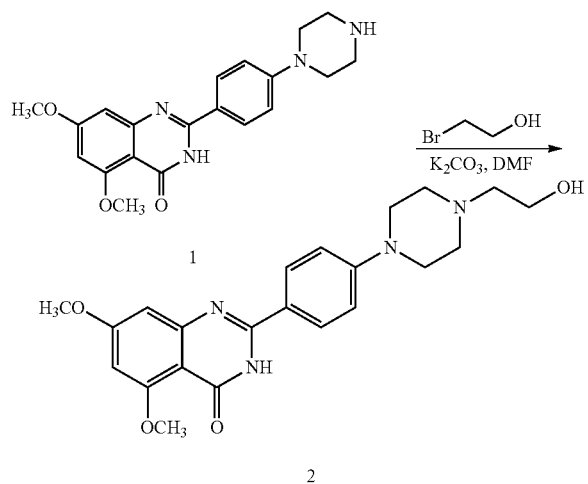

To a solution of 5,7-dimethoxy-2-(4-(piperazin-1-yl)phenyl)quinazolin-4(3H)-one (1) (0.68 mmol) in DMF (8 mL) was added potassium carbonate (0.68 mmol) and 2-bromoethanol (0.68 mmol). The resulting solution was stirred at room temperature overnight. Then, the mixture was diluted with water, extracted with EtOAc, washed with brine, dried over anhydrous $Na_2SO_4$, filtered, and concentrated in vacuo to afford 2. The material was purified by flash chromatography on silica gel, eluting with 50% to 100% of 92:7:1 $CHCl_3$/MeOH/concentrated $NH_4OH$ in $CH_2Cl_2$. The product was further purified by reverse-phase chromatography, eluting with 10% to 90% $CH_3CN$ in $H_2O$, to afford the title compound (0.025 g, 9%). $^1H$ NMR (300 MHz, DMSO-$d_6$): δ 11.45 (s, 1H), 8.08 (d, J=8.9 Hz, 2H), 7.00 (d, J=9.1 Hz, 2H), 6.68 (s, 1H), 6.46 (s, 1H), 4.30-4.55 (m, 1H), 3.88 (s, 3H), 3.83 (s, 3H), 3.43-3.67 (m, 2H), 3.10-3.43 (m, 7H), 2.77-3.04 (m, 1H), 2.31-2.64 (m, 2H). ESI MS m/z 411 $[M+H]^+$.

Example 2

Preparation of 2-(4-(4-butylpiperazin-1-yl)phenyl)-5,7-dimethoxyquinazolin-4(3H)-one (7)

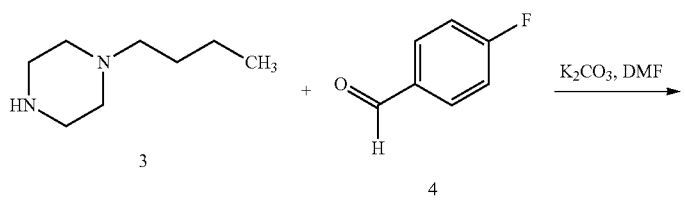

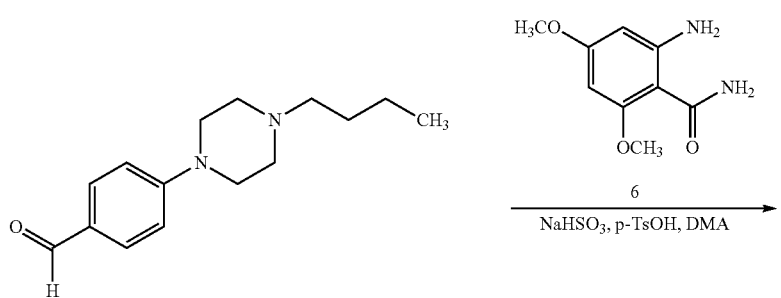

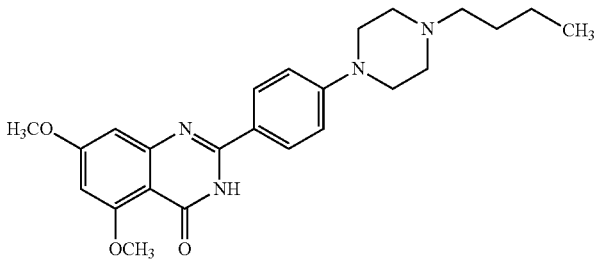

To a solution of 1-(N-butyl)-piperazine (3) (7.03 mmol) in DMF (8 mL) was added 4-fluorobenzaldehyde (4) (8.43 mmol) and potassium carbonate (8.43 mmol). The resulting solution was heated to 120° C. for 5 hours and diluted with water. The solution was extracted with EtOAc, washed with water, brine, dried over anhydrous $Na_2SO_4$, filtered, and concentrated in vacuo. The material was purified by flash chromatography on silica gel to afford 4-(4-butylpiperazin-1-yl)benzaldehyde (5).

To a solution of 2-amino-4,6-dimethoxybenzamide (6) (1.19 mmol) in DMA (10 mL) was added 4-(4-butylpiperazin-1-yl)benzaldehyde (5) (1.09 mmol), $NaHSO_3$ (1.30 mmol), and p-TsOH (0.10 mmol). The resulting solution was heated to 155° C. for 4 hours and cooled to room temperature. The solution was diluted with water, extracted with EtOAc, washed with brine, dried over anhydrous $Na_2SO_4$, filtered, and concentrated in vacuo. The material was purified by flash chromatography on silica gel eluting with 10% to 50% of 92:7:1 $CHCl_3$/MeOH/concentrated $NH_4OH$ in $CH_2Cl_2$, to afford the compound 7 (0.06 g, 13%). $^1$H NMR (300 MHz, DMSO-$d_6$): δ 11.76 (s, 1H), 8.09 (d, J=8.9 Hz, 2H), 7.00 (d, J=9.0 Hz, 2H), 6.68 (s, 1H), 6.47 (s, 1H), 3.88 (s, 3H), 3.83 (s, 3H), 3.17-3.42 (m, 4H), 2.39-2.58 (m, 4H), 2.23-2.37 (m, 2H), 1.37-1.56 (m, 2H), 1.26-1.37 (m, 2H), 0.84-0.94 (m, 3H). APCI MS m/z 423 $[M+H]^+$.

Example 3

Preparation of 2-(4-(1-acetylpiperidin-4-yl)phenyl)-5,7-dimethoxyquinazolin-4(3H)-one (13)

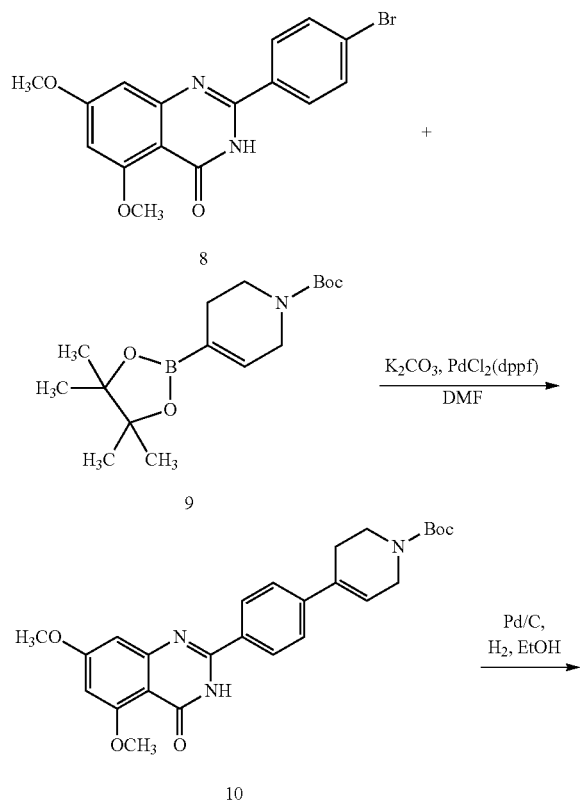

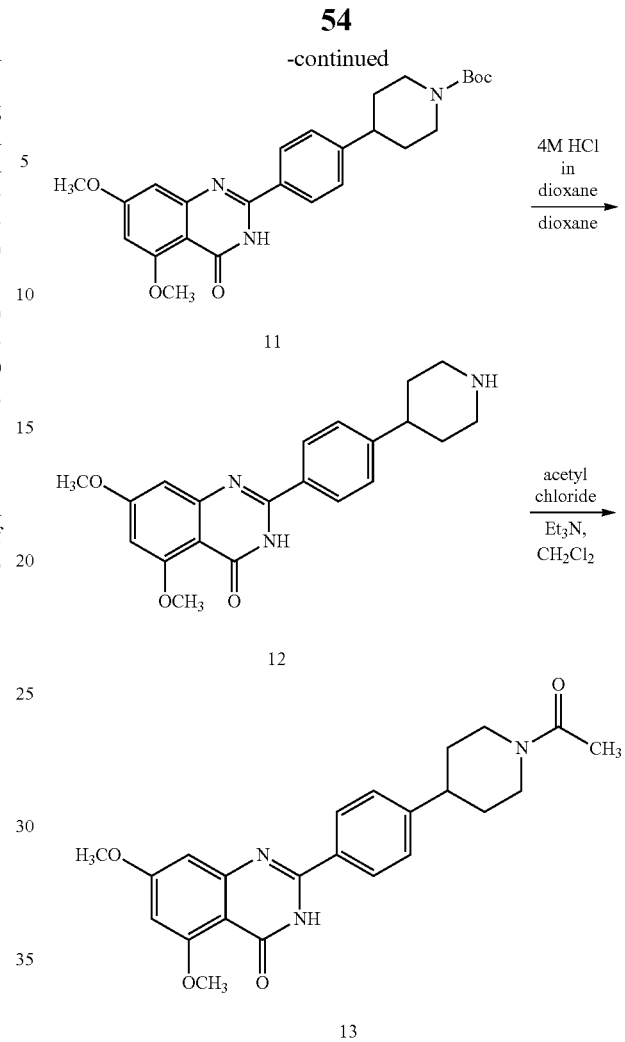

A solution of 2-(4-bromophenyl)-5,7-dimethoxyquinazolin-4(3H)-one (8) (3.23 mmol), $K_2CO_3$ (9.69 mmol), $PdCl_2$(dppf) (0.32 mmol) and tert-butyl 4-(4,4,5,5-tetramethyl-1,3,2-dioxaborolan-2-yl)-5,6-dihydropyridine-1(2H)-carboxylate (9) (3.23 mmol) in DMF (50 mL) was heated to 110° C. overnight. The resulting solution was concentrated in vacuo and the material was purified by flash chromatography on silica gel to give tert-butyl 4-(4-(5,7-dimethoxy-4-oxo-3,4-dihydroquinazolin-2-yl)phenyl)-5,6-dihydropyridine-1(2H)-carboxylate (10).

A solution of tert-butyl 4-(4-(5,7-dimethoxy-4-oxo-3,4-dihydroquinazolin-2-yl)phenyl)-5,6-dihydropyridine-1(2H)-carboxylate (10) (0.34 mmol) in EtOH (10 mL) and HOAc (5 mL) was purged with nitrogen and 10% Pd/C (0.016 g) was added. The mixture was stirred under 1 atmosphere of hydrogen overnight. Then, the solution was filtered through Celite, with MeOH washings, and the filtrate was concentrated in vacuo. The material was purified by flash chromatography on silica gel to afford tert-butyl 4-(4-(5,7-dimethoxy-4-oxo-3,4-dihydroquinazolin-2-yl)phenyl)piperidine-1-carboxylate (11).

To a solution of tert-butyl 4-(4-(5,7-dimethoxy-4-oxo-3,4-dihydroquinazolin-2-yl)phenyl)piperidine-1-carboxylate (11) (0.45 mmol) in 1,4-dioxane (2 mL) was added 4 M HCl in 1,4-dioxane (1 mL). The resulting solution was stirred at room temperature for 5 hours. Then, the mixture was concentrated in vacuo and the resulting material was purified by flash chromatography on silica gel to afford compound 5,7-dimethoxy-2-(4-(piperidin-4-yl)phenyl)quinazolin-4(3H)-one (12).

To a solution of 5,7-dimethoxy-2-(4-(piperidin-4-yl)phenyl)quinazolin-4(3H)-one (0.16 mmol) in $CH_2Cl_2$ (10 mL) was added $Et_3N$ (0.32 mmol) and acetyl chloride (0.17 mmol). The resulting solution was stirred at 0° C. overnight. The solution was concentrated in vacuo, basified with $NaHCO_3$, extracted with $CH_2Cl_2$, and washed with water and brine. The material was dried ($Na_2SO_4$), filtered, and concentrated to afford the title compound 13 (0.020 g, 30%). $^1H$ NMR (300 MHz, DMSO-$d_6$): δ 11.93 (s, 1H), 8.11 (d, J=8.3 Hz, 2H), 7.40 (d, J=8.3 Hz, 2H), 6.73 (s, 1H), 6.53 (s, 1H), 4.42-4.64 (m, 1H), 3.89 (s, 3H), 3.85 (s, 3H), 3.06-3.21 (m, 1H), 2.77-2.94 (m, 1H), 2.54-2.68 (m, 1H), 2.03 (s, 3H), 1.73-1.91 (m, 2H), 1.56-1.73 (m, 1H), 1.36-1.56 (m, 1H), 1.06-1.36 (m, 1H). ESI MS m/z 408 [M+H]$^+$.

Example 4

Preparation of 2-(4-(3-(cyclopropylmethylamino)pyrrolidin-1-yl)phenyl)-5,7-dimethoxyquinazolin-4(3H)-one (15)

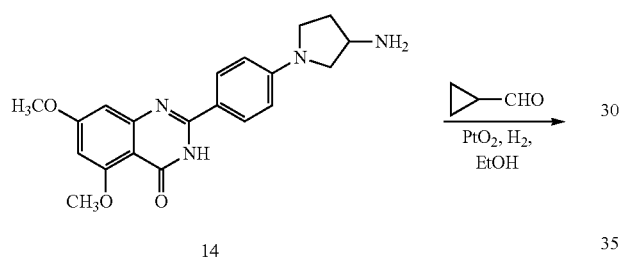

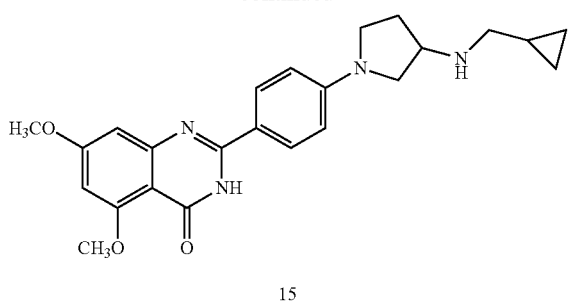

A suspension of 2-(4-(3-aminopyrrolidin-1-yl)phenyl)-5,7-dimethoxyquinazolin-4(3H)-one (14) (0.21 mmol) in ethanol (30 mL) was treated with $PtO_2$ (0.050 g) followed by cyclopropanecarbaldehyde (0.100 mL). The reaction was stirred under 1 atmosphere of hydrogen for 24 hours, filtered through Celite, with ethanol washes, concentrated, and purified by flash chromatography on silica gel, eluting to afford the title compound 15.

Example 5

Preparation of 2-(4-(2-(1-acetylazetidin-3-yl)ethoxy)-3,5-dimethylphenyl)-5,7-dimethoxyquinazolin-4(3H)-one (19)

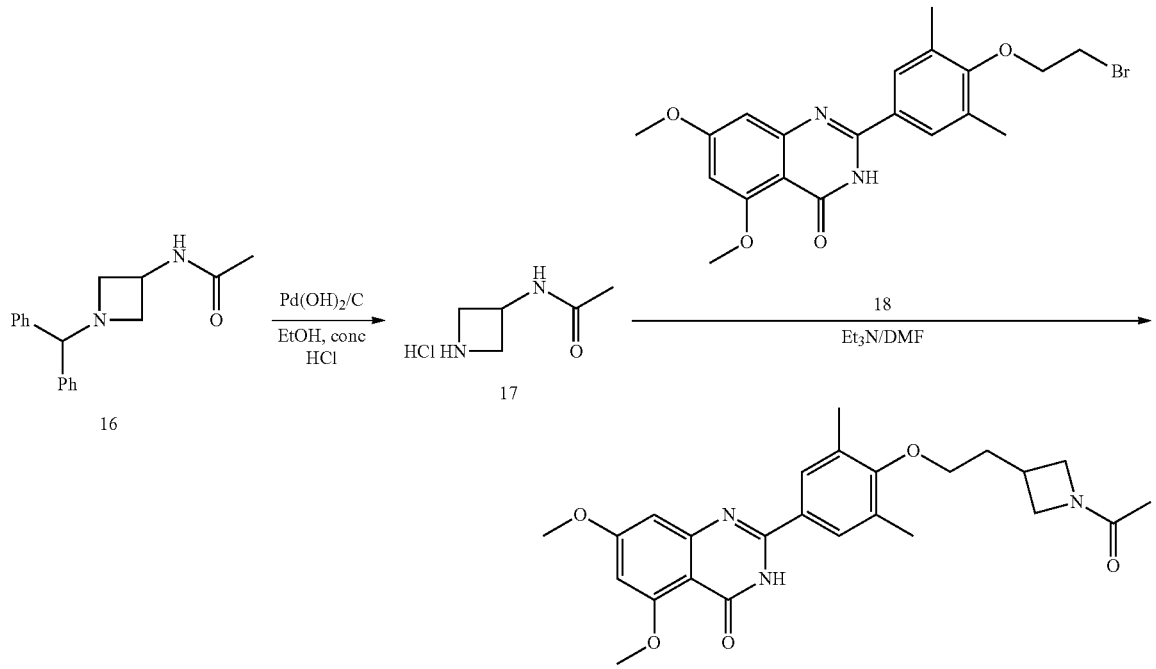

To a solution of N-(1-benzhydryl-azetidin-3-yl)-acetamide (16) (3.57 mmol) in ethanol (20 mL) were added palladium hydroxide on carbon (20 wt %, 0.20 g) and concentrated HCl (0.6 mL). The reaction mixture was hydrogenated at 50 psi at 40° C. for 2 hours, then filtered and washed with methanol (50 mL). The filtrate was collected and the solvent was evaporated, to give N-azetidin-3-yl-acetamide (17).

To a suspension of N-azetidin-3-yl-acetamide (17) (1.99 mmol) and 2-[4-(2-bromo-ethoxy)-3,5-dimethyl-phenyl]-5,7-dimethoxy-3H-quinazolin-4-one (18) (1.00 mmol) in anhydrous DMF (10 mL) was added triethylamine (3 mL). The reaction mixture was stirred at room temperature for 3 days under nitrogen. The solvent was evaporated under reduced pressure, water (50 mL) was added, and the precipitated solid was filtered off. The aqueous layer was extracted with ethyl acetate (2×100 mL). The organic phase was dried over anhydrous Na$_2$SO$_4$ and concentrated. The crude compound was purified by the Simpliflash system (0-5% 7 N ammonia in methanol and CH$_2$Cl$_2$ as eluent) to give the title compound 19 as a white solid.

Example 6

Preparation of 2-(2,6-dimethylpyridin-4-yl)-5-(2-isopropoxyethoxy)-7-methoxyquinazolin-4(3H)-one (23)

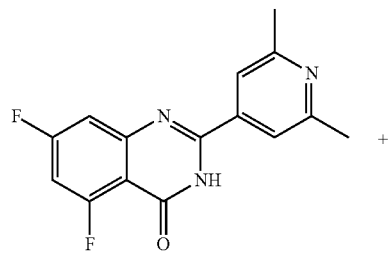

20

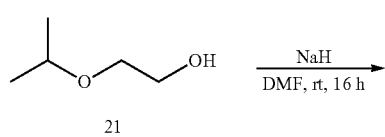

21

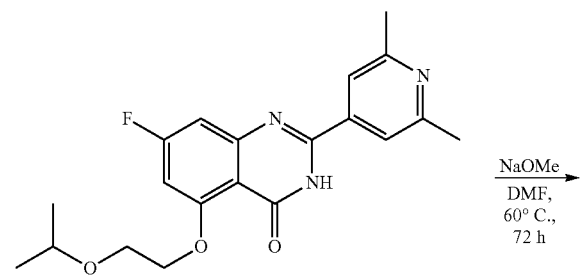

22

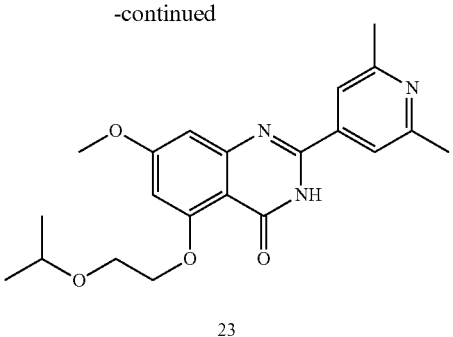

23

To a solution of 2-isopropoxy ethanol (21) (57.0 mmol) in anhydrous DMF (10 mL) was added a sodium hydride (60% suspension in mineral oil, 28.54 mmol) in small portions at room temperature under nitrogen. After the addition, the reaction mixture was stirred at room temperature for 30 minutes. Then, 2-(2,6-dimethyl-pyridin-4-yl)-5,7-difluoro-3H-quinazolin-4-one (20) (2.85 mmol) was added, and the reaction mixture was stirred at room temperature for 16 hours. The reaction mixture was cooled to room temperature and saturated NH$_4$Cl solution was added. The product was extracted with ethyl acetate (3×200 mL). The combined organic layer was washed with water, brine, dried over anhydrous Na$_2$SO$_4$, and evaporated to give crude product (22) as a white solid.

2-(2,6-Dimethyl-pyridin-4-yl)-7-fluoro-5-(2-isopropoxy-ethoxy)-3H-quinazolin-4-one (22) (960 mg, 2.58 mmol) was taken up in anhydrous DMF (10 mL). Sodium methoxide (25% solution in methanol, 12.9 mmol) was added. After the addition, the reaction mixture was stirred at 60° C. for 72 hours. The reaction mixture was cooled to room temperature, and quenched with saturated solution of NH$_4$Cl. The product was extracted with ethyl acetate (3×200 mL). The combined organic layer was washed with water, brine, dried over Na$_2$SO$_4$, and evaporated to give crude product. The crude compound was purified by preparative HPLC, to give the title compound 23 as a white solid.

Example 7

Preparation of 2-(4-((3R,5S)-4-Acetyl-3,5-dimethylpiperazin-1-yl)phenyl)-5,7-dimethoxypyrido[2,3-d]pyrimidin-4(3H)-one

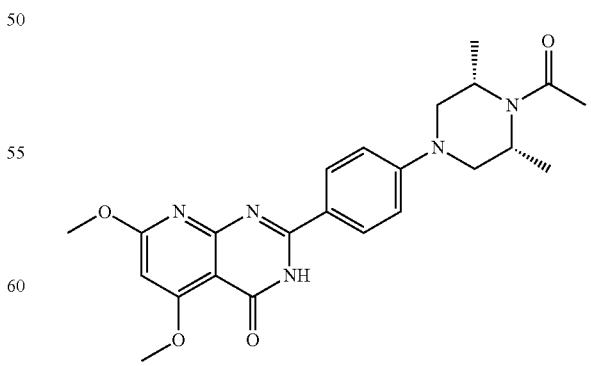

To a solution of 4-fluoro-benzaldehyde (3.0 g, 0.024 mol) and 1-(2,6-dimethyl-piperazin-1-yl)-ethanone (3.0 g, 0.019 mol) in anhydrous DMF (15 mL) was added potassium carbonate (6.6 g, 0.048 mol). The reaction mixture was heated to 130° C. for 32 hours. The DMF was removed and the residue was purified by column chromatography (silica gel 230-400 mesh; eluting with 2:1 ethyl acetate and dichloromethane) to give 4-(4-acetyl-3,5-dimethyl-piperazin-1-yl)-benzaldehyde as light yellow solid (2.31 g, 46.2%).

A mixture of 2-amino-4,6-dimethoxy-nicotinamide (0.25 g, 1.26 mmol), 4-(4-acetyl-3,5-dimethyl-piperazin-1-yl)-benzaldehyde (0.43 g, 1.64 mmol), p-toluenesulfonic acid monohydrate (0.53 mg, 2.77 mmol) and sodium bisulfite (0.45 g, 2.52 mmol) in N,N-dimethylacetamide (5.0 mL) was stirred at 135° C. under $N_2$ for 16 hours and then cooled to room temperature. The mixture was concentrated to dryness under reduced pressure. Water (40 mL) was added to the residue and stirred for 0.5 hours. The precipitate was filtered and the solid was rinsed with water and dried over $Na_2SO_4$. The crude solid was purified by column chromatography (silica gel 230-400 mesh; eluting with 2.5% methanol in dichloromethane) to afford the title compound as yellow solid. Yield: 90 mg (16.3%). MP 279-279.8° C. $^1$H NMR (400 MHz, CDCl$_3$): δ 10.18 (s, 1H), 8.14 (d, J=8.8 Hz, 2H), 6.99 (d, J=8.8 Hz, 2H), 6.20 (s, 1H), 4.78 (bs, 1H), 4.12 (s, 3H), 4.02 (s, 3H), 3.70 (d, J=12.0 Hz, 2H) 3.11 (d, J=10 Hz, 2H), 2.18 (s, 3H), 1.40 (bs, 6H).

Example 8

Preparation of 2-(4-(4-Hydroxypiperidin-1-yl)phenyl)-5,7-dimethoxypyrido[2,3-d]pyrimidin-4(3H)-one

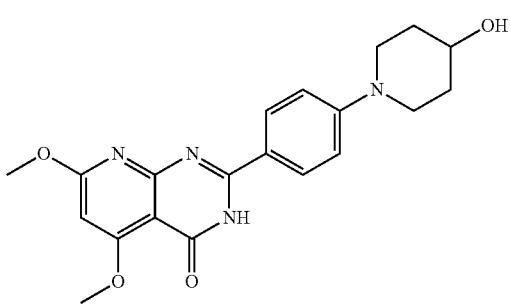 [SMILES: COc1cc(OC)c2c(=O)[nH]c(-c3ccc(N4CCC(O)CC4)cc3)nc2n1]

A mixture of 2-amino-4,6-dimethoxy-nicotinamide (0.60 g, 3.0 mmol), 4-(4-hydroxy-piperidin-1-yl)-benzaldehyde (0.81 g, 3.9 mmol), p-toluenesulfonic acid monohydrate (1.25 g, 6.6 mmol) and sodium bisulfite (1.06 g, 6.0 mmol) in N,N-dimethylacetamide (8.0 mL) was stirred at 135° C. under $N_2$ for 16 hours and then cooled to room temperature. The mixture was concentrated to dryness under reduced pressure. Water (40 mL) was added to the residue and stirred for 0.5 hours. The precipitate was filtered and the solid was rinsed with water and air-dried. The crude solid was purified by column chromatography (silica gel 230-400 mesh; eluting with 4% methanol in dichloromethane) to afford the title compound, as a yellow solid. Yield: 0.29 g (25.2%). MP 284-286° C. $^1$H NMR (400 MHz, DMSO-d$_6$): δ 12.09 (s, 1H), 8.12 (d, J=8.8 Hz, 2H), 7.02 (d, J=8.8 Hz, 2H), 6.32 (s, 1H), 4.73 (d, J=4.4 Hz, 1H), 3.94 (s, 3H), 3.89 (s, 3H), 3.72 (m, 3H), 3.05 (m, 2H), 1.80 (m, 2H), 1.43 (m, 2H). MS (ES$^+$) m/z: 383.06 (M+1).

Example 9

Preparation of 2-(4-((3R,5S)-4-Acetyl-3,5-dimethylpiperazin-1-yl)phenyl)-5-methoxy-7-(2-methoxyethoxy)quinazolin-4(3H)-one

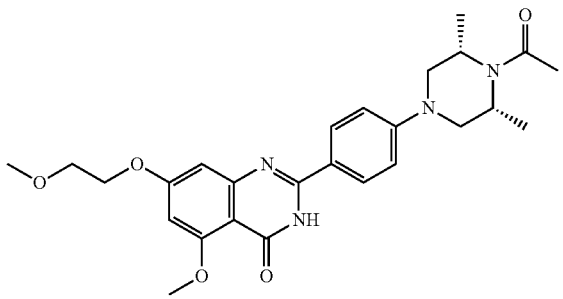 [SMILES: COCCOc1cc(OC)c2c(=O)[nH]c(-c3ccc(N4C[C@@H](C)N(C(C)=O)[C@@H](C)C4)cc3)nc2c1]

To a stirred solution of 2-amino-4,6-difluoro-benzamide (0.66 g, 3.84 mmol) and 4-(4-acetyl-3,5-dimethyl-piperazin-1-yl)-benzaldehyde (1.00 g, 3.84 mmol) in N,N-dimethyl acetamide (20 mL), was added sodium hydrogen sulfite (58.5 wt %, 1.04 g, 5.76 mmol) and p-toluenesulfonic acid monohydrate (0.88 g, 4.61 mmol) and the reaction mixture was stirred at 115° C. for 16 hours. The solvent was evaporated in vacuo, water was added, and the precipitated solid was filtered off, to give 2-[4-(4-acetyl-3,5-dimethyl-piperazin-1-yl)-phenyl]-5,7-difluoro-3H-quinazolin-4-one as a yellow solid, which was used in the next step without further purification.

To a solution of 2-[4-(4-acetyl-3,5-dimethyl-piperazin-1-yl)-phenyl]-5,7-difluoro-3H-quinazolin-4-one (0.66 g, 1.60 mmol) in DMF (10 mL), a solution of sodium methoxide in methanol (25 wt %, 3.5 mL, 16.0 mmol) was added and the reaction mixture was stirred at room temperature for 16 hours. Water was added, acidified to pH approximately 4-5 with acetic acid, and the precipitated solid was filtered and dried under vacuum to give crude compound, which was further purified by column chromatography (silica gel 230-400 mesh; eluting with 2% methanol solution in dichloromethane) to yield 2-[4-(4-acetyl-3,5-dimethyl-piperazin-1-yl)-phenyl]-7-fluoro-5-methoxy-3H-quinazolin-4-one as a light yellow solid.

To a solution of 2-methoxy-ethanol (1.00 g, 13.4 mmol) in dimethyl sulfoxide (4 mL), sodium hydride (60% suspension in mineral oil, 0.50 g, 12.5 mmol) was added in portions, and the reaction mixture was stirred at room temperature for 20 minutes. To this reaction mixture was added 2-[4-(4-acetyl-3,5-dimethyl-piperazin-1-yl)-phenyl]-7-fluoro-5-methoxy-3H-quinazolin-4-one (0.57 g, 1.34 mmol) and the reaction mixture was stirred at 85° C. for 24 hours. Water was added. The mixture was acidified to pH approximately 4-5 with acetic acid, and the precipitated solid was filtered to give crude product, which was purified by column chromatography (silica gel 230-400 mesh; eluting with 2% methanol in dichloromethane). The resulting mixture was purified by preparative HPLC to obtain the title compound as a white solid. Yield: 0.140 g (23.2%). MP 225-227° C. $^1$H NMR (400 MHz, CDCl$_3$): δ 8.10 (d, J=8.8 Hz, 2H), 7.08 (d, J=8.8 Hz, 1H), 6.70 (d, J=2.4 Hz, 1H), 6.49 (d, J=2.4 Hz, 1H), 4.50 (bs, 1H), 4.23

(m, 2H), 4.14 (bs, 1H), 3.84 (s, 3H), 3.81 (m, 2H), 3.69 (m, 2H), 3.32 (s, 3H), 2.99 (bs, 2H), 2.07 (s, 3H), 1.25 (bs, 6H). MS (ES) m/z: 481.11 (M$^+$+1).

Example 10

Preparation of 2-(4-(4-Isopropylpiperazin-1-yl)phenyl)-5,7-dimethoxyquinazolin-4(3H)-one

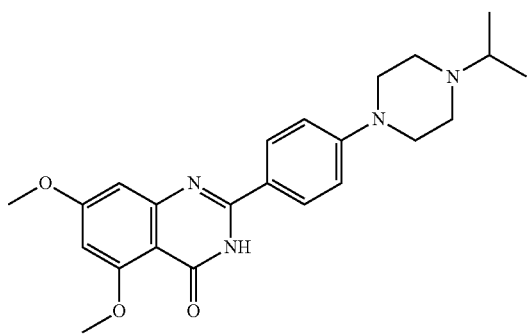 [SMILES: COc1cc(OC)c2c(=O)[nH]c(-c3ccc(N4CCN(C(C)C)CC4)cc3)nc2c1]

A mixture of 4-fluorobenzaldehyde (0.242 g, 1.95 mmol), 1-isopropylpiperazine (0.335 mL, 2.34 mmol), and K$_2$CO$_3$ (0.323 g, 2.34 mmol) in DMF (2.44 mL) was heated at 120° C. overnight. The mixture was diluted with EtOAc (200 mL), washed with 10% aqueous LiCl (3×75 mL) and brine (75 mL), dried over Na$_2$SO$_4$, and filtered. The volatiles were removed under vacuum to yield 4-(4-Isopropylpiperazin-1-yl)benzaldehyde (0.504 g) as an orange solid, which was used without further purification.

A mixture of 2-amino-4,6-dimethoxybenzamide (0.100 g, 0.510 mmol), aldehyde from above (0.118 g, 0.510 mmol), NaHSO$_3$ (94%, 0.0565 g, 0.510 mmol), and p-TsOH.H$_2$O (0.0097 g, 0.051 mmol) in DMA (3.40 mL) was heated at reflux for 1 hour. The mixture was diluted with EtOAc (250 mL), washed with 10% aqueous LiCl (3×75 mL) and brine (75 mL), dried over Na$_2$SO$_4$, filtered and concentrated under vacuum. The resulting residue was purified over silica gel (12 g, CH$_2$Cl$_2$/MeOH) and the product was freeze-dried from MeCN/H$_2$O to provide the title compound (0.0632 g, 30%) as a yellow solid. $^1$H NMR (300 MHz, DMSO-d$_6$): δ 11.74 (s, 1H), 8.09 (d, J=9.05 Hz, 2H), 7.00 (d, J=9.05 Hz, 2H), 6.68 (d, J=2.31 Hz, 1H), 6.47 (d, J=2.31 Hz, 1H), 3.88 (s, 3H), 3.84 (s, 3H), 3.31-3.24 (m, 4H), 2.74-2.63 (m, 1H), 2.61-2.53 (m, 4H), 1.01 (d, J=6.52 Hz, 6H).

Example 11

Preparation of 2-(4-(4-Acetylpiperazin-1-yl)phenyl)-5,7-dimethoxyquinazolin-4(3H)-one

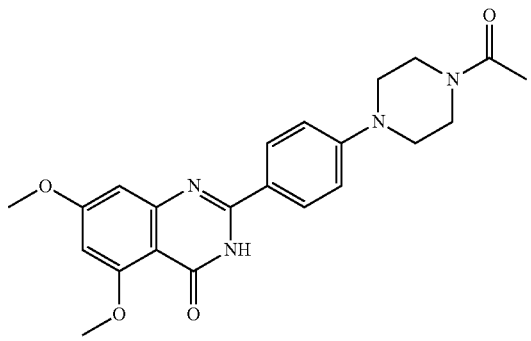 [SMILES: COc1cc(OC)c2c(=O)[nH]c(-c3ccc(N4CCN(C(C)=O)CC4)cc3)nc2c1]

Following the procedure described for Example 10, 4-(4-acetylpiperazin-1-yl)benzaldehyde was made from 1-acetylpiperazine and isolated as an orange oil in 67% yield. Following the procedure described for Example 10, the title compound was made from 4-(4-acetylpiperazin-1-yl)benzaldehyde and refluxing for 5 hours. The title compound was isolated as a yellow solid in 20% yield. $^1$H NMR (300 MHz, DMSO-d$_6$): δ 11.76 (s, 1H), 8.11 (d, J=8.97 Hz, 2H), 7.03 (d, J=8.97 Hz, 2H), 6.69 (d, J=2.26 Hz, 1H), 6.47 (d, J=2.26 Hz, 1H), 3.88 (s, 3H), 3.84 (s, 3H), 3.62-3.53 (m, 4H), 3.41-3.25 (m, 4H), 2.05 (s, 3H); MS (ESI) m/z 409 [C$_{22}$H$_{24}$N$_4$O$_4$+H]$^+$.

Example 12

Preparation of 5,7-Dimethoxy-2-(4-(piperazin-1-yl)phenyl)quinazolin-4(3H)-one

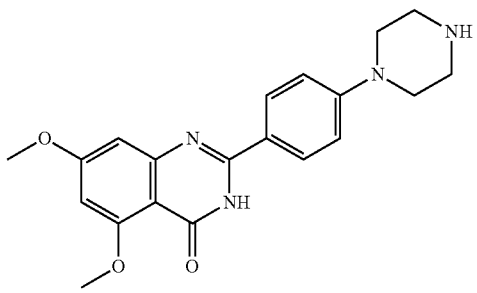

A mixture of 4-(4-acetylpiperazin-1-yl)benzaldehyde (1.34 g, 5.77 mmol) and 2-amino-4,6-dimethoxybenzamide (1.03 g, 5.24 mmol) in DMA (30 mL) was treated with p-TsOH (0.100 g, 0.524 mmol) and NaHSO$_3$ (0.578 g, 5.55 mmol). The mixture was heated at 155° C. for 6 hours, cooled to room temperature, diluted with water (400 mL), and filtered to give brown solids. The filtrate was extracted with EtOAc (3×100 mL), concentrated, and combined with the brown solids from the filter cake. The combined solids were purified by silica gel chromatography, eluting with 92:7:1 CHCl$_3$/MeOH/concentrated NH$_4$OH to afford 2-(4-(4-acetylpiperazin-1-yl)phenyl)-5,7-dimethoxyquinazolin-4(3H)-one as a yellow solid (1.9 g, 90%).

A mixture of 2-(4-(4-acetylpiperazin-1-yl)phenyl)-5,7-dimethoxyquinazolin-4(3H)-one (1.93 g, 4.7 mmol) and 2 M HCl (200 mL) was heated at reflux for 9 hours. Then, the mixture was cooled to room temperature, basified to pH 8 with 2 N NaOH, extracted with CH$_2$Cl$_2$ (3×300 mL), dried over anhydrous MgSO$_4$, filtered, and concentrated. The residue was purified by silica gel chromatography, eluting with 92:7:1 to 6:3:1 CHCl$_3$/MeOH/concentrated NH$_4$OH, to afford the title compound (1.13 g, 66%). $^1$H NMR (300 MHz, DMSO-d$_6$): δ 8.08 (d, J=8.9 Hz, 2H), 6.99 (d, J=8.9 Hz, 2H), 6.68 (d, J=2.3 Hz, 1H), 6.47 (d, J=2.3 Hz, 1H), 3.88 (s, 3H), 3.83 (s, 3H), 3.19-3.23 (m, 4H), 2.81-2.84 (m, 4H); APCI MS m/z 367 [M+H]$^+$.

Example 13

Preparation of N-(1-(4-(5,7-Dimethoxy-4-oxo-3,4-dihydroquinazolin-2-yl)phenyl)piperidin-4-yl)acetamide

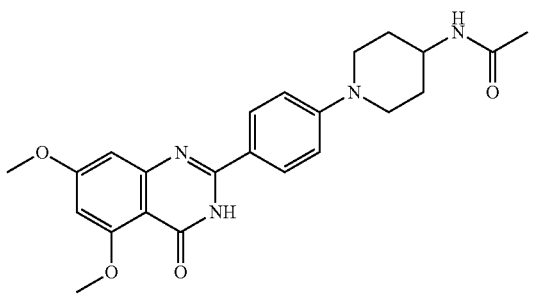 [SMILES: COc1cc(OC)c2c(=O)[nH]c(-c3ccc(N4CCC(NC(C)=O)CC4)cc3)nc2c1]

A solution of ethyl 4-fluorobenzoate (16.5 g, 98.1 mmol) and piperidin-4-ol (10.0 g, 98.8 mmol) in DMSO (20 mL) was heated at 120° C. under nitrogen for 48 hours. The mixture was cooled to room temperature, poured into water (400 mL), and the solids were filtered off, washed with water, followed by hexane, to afford ethyl 4-(4-hydroxypiperidin-1-yl)benzoate (20.0 g, 82%).

To a solution of ethyl 4-(4-hydroxypiperidin-1-yl)benzoate (8.0 g, 32.1 mmol) in $CH_2Cl_2$ (200 mL) was added $Et_3N$ (23 mL, 165 mmol) under nitrogen, followed by MsCl (5.6 g, 48.9 mmol). The mixture was stirred for 5 minutes, washed with water (300 mL), dried over anhydrous $MgSO_4$, filtered, and concentrated to afford ethyl 4-(4-(methylsulfonyloxy)piperidin-1-yl)benzoate as a tan solid (10.5 g, 100%).

To a solution of ethyl 4-(4-(methylsulfonyloxy)piperidin-1-yl)benzoate (10.5 g, 32.1 mmol) in DMF (50 mL) was added sodium azide (4.17 g, 64.2 mmol). The mixture was heated at 80° C. for 5 hours, cooled to room temperature, diluted with brine (300 mL), and extracted with ethyl acetate (400 mL). The organic phase was washed with brine (2×300 mL), dried over anhydrous $MgSO_4$, filtered, and concentrated, to afford ethyl 4-(4-azidopiperidin-1-yl)benzoate as a yellow solid (7.62 g, 87%).

To a solution of ethyl 4-(4-azidopiperidin-1-yl)benzoate (7.62 g, 27.8 mmol) in dioxane (190 mL) was added acetic acid (27 mL) and water (54 mL). Then, 10% Pd/C (0.750 g) was added and the mixture was hydrogenated under 1 atmosphere of hydrogen for 5 hours. The mixture was filtered through Celite, concentrated, and 0.5 M HCl (500 mL) was added. The solution was washed with ethyl acetate (2×300 mL) and the aqueous phase basified with ammonium hydroxide, to pH 12. The aqueous phase was saturated with sodium chloride, extracted with $CH_2Cl_2$ (2×300 mL), dried over anhydrous $MgSO_4$, filtered, and concentrated, to afford ethyl 4-(4-aminopiperidin-1-yl)benzoate.

To a solution of ethyl 4-(4-aminopiperidin-1-yl)benzoate (1.65 g, 6.65 mmol) in $CH_2Cl_2$ (200 mL) was added $Et_3N$ (1.35 g, 13.3 mmol), followed by acetyl chloride (0.573 g, 7.3 mmol). The reaction mixture was stirred at room temperature for 5 minutes, washed with brine (300 mL), dried over anhydrous $Na_2SO_4$, filtered, and concentrated, to afford ethyl 4-(4-acetamidopiperidin-1-yl)benzoate as a white solid (1.9 g, 100%).

A solution of ethyl 4-(4-acetamidopiperidin-1-yl)benzoate (0.123 g, 0.42 mmol) in $CH_2Cl_2$ (10 mL) under nitrogen at −78° C. was treated with DIBAL-H (1.0M in hexanes, 0.950 mL, 0.95 mmol) dropwise, via a syringe. After 20 minutes, the mixture was warmed to room temperature, stirred for 1 hour, and quenched with 10% Rochelle's salt. After stirring for 10 minutes, $CH_2Cl_2$ (50 mL) was added, and the stirring was continued for 15 additional minutes. The layers were separated and the aqueous phase was extracted with $CH_2Cl_2$ (50 mL) and ethyl acetate (50 mL). The combined organic phases were dried ($MgSO_4$), filtered, concentrated, and purified by flash chromatography on silica gel, eluting with 100% ethyl acetate to 10% MeOH/ethyl acetate to afford N-(1-(4-(hydroxymethyl)phenyl)piperidin-4-yl)acetamide as a white solid (0.025 g, 24%).

A mixture of N-(1-(4-(hydroxymethyl)phenyl)piperidin-4-yl)acetamide (0.380 g, 1.53 mmol), TPAP (0.026 g, 0.08 mmol), NMO (0.268 g, 2.30 mmol), and molecular sieves (3 Angstrom, 0.300 g) in $CH_2Cl_2$ was stirred at room temperature for 19 hours. The mixture was filtered through Celite, concentrated, and purified by flash chromatography on silica gel, eluting with 100% ethyl acetate to 10% MeOH/ethyl acetate, to afford N-(1-(4-formylphenyl)piperidin-4-yl)acetamide as a white solid (0.280 g, 74%).

A mixture of N-(1-(4-formylphenyl)piperidin-4-yl)acetamide (0.280 g, 1.14 mmol), 2-amino-4,6-dimethoxybenzamide (0.224 g, 1.14 mmol), p-TsOH (0.022 g, 0.114 mmol), and $NaHSO_3$ (0.125 g, 1.21 mmol) in DMA was heated at 155° C. for 6 hours. The reaction mixture was cooled, diluted with water (100 mL), basified with saturated $NaHCO_3$, and extracted with ethyl acetate (3×150 mL). The organic phase was concentrated and purified by flash chromatography on silica gel, eluting with 1:1 $CH_2Cl_2$/(92:7:1 $CHCl_3$/MeOH/concentrated $NH_4OH$) to 100% 92:7:1 $CHCl_3$/MeOH/concentrated $NH_4OH$. Further purification by reverse-phase HPLC, eluting with 10% to 90% $CH_3CN$ in $H_2O$ with 0.1% TFA, afforded the title compound as a yellow solid (0.140 g, 29%): $^1H$ NMR (300 MHz, DMSO-$d_6$): δ 11.74 (s, 1H), 8.08 (d, J=9.0 Hz, 2H), 7.83 (d, J=7.7 Hz, 1H), 7.01 (d, J=9.0 Hz, 2H), 6.68 (d, J=2.3 Hz, 1H), 6.46 (d, J=2.3 Hz, 1H), 3.7-3.89 (m, 9H), 2.92-3.00 (m, 2H), 1.76-1.85 (m, 5H), 1.36-1.48 (m, 2H); APCI MS m/z 423 $[M+H]^+$.

Example 14

Preparation of N-(1-(4-(5,7-Dimethoxy-4-oxo-3,4-dihydroquinazolin-2-yl)phenyl)piperidin-4-yl)methanesulfonamide

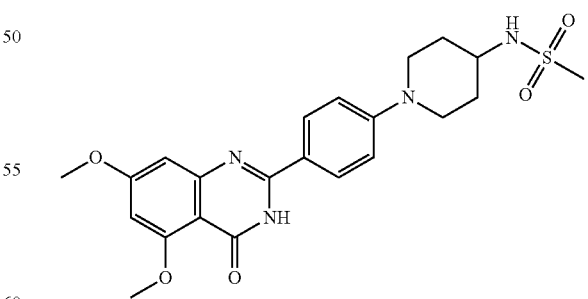

A mixture of 2-(4-(4-aminopiperidin-1-yl)phenyl)-5,7-dimethoxyquinazolin-4(3H)-one (0.105 g, 0.28 mmol), methanesulfonylchloride (0.035 g, 0.30 mmol), and $Et_3N$ (0.057 g. 0.56 mmol) in $CH_2Cl_2$ (10 mL) was stirred at room temperature under nitrogen for 2 hours. The mixture was concentrated, redissolved in THF (5 mL), 2 M NaOH (5 mL)

added and stirred for 20 minutes. The pH was adjusted to 8 with 1 M HCl and the mixture extracted with $CH_2Cl_2$ (3×150 mL). The organic phase was dried over anhydrous $MgSO_4$, filtered, and concentrated. The residue was purified by silica gel chromatography, eluting with 1:1 $CH_2Cl_2$/(92:7:1 $CHCl_3$/ MeOH/concentrated $NH_4OH$) to 100% 92:7:1 $CHCl_3$/ MeOH/concentrated $NH_4OH$. Further purification by reverse-phase HPLC. eluting with 10% to 90% $CH_3CN$ in $H_2O$ with 0.1% TFA. afforded the title compound as a yellow solid (0.075 g, 58%). $^1$H NMR (300 MHz, DMSO-$d_6$): δ 11.75 (s, 1H), 8.08 (d, J=9.0 Hz, 2H), 7.13 (d, J=7.3 Hz, 1H), 7.00 (d, J=9.0 Hz, 2H), 6.66 (d, J=2.3 Hz, 1H), 6.46 (d, J=2.3 Hz, 1H), 3.81-3.94 (m, 8H), 3.34-3.47 (m, 1H), 2.90 (m, 6H), 1.87-1.95 (m, 2H), 1.42-1.54 (m, 2H); ESI MS m/z 459 $[M+H]^+$.

Example 15

Preparation of 3-(1-(4-(5,7-Dimethoxy-4-oxo-3,4-dihydroquinazolin-2-yl)phenyl)piperidin-4-yl)-1,1-dimethylurea

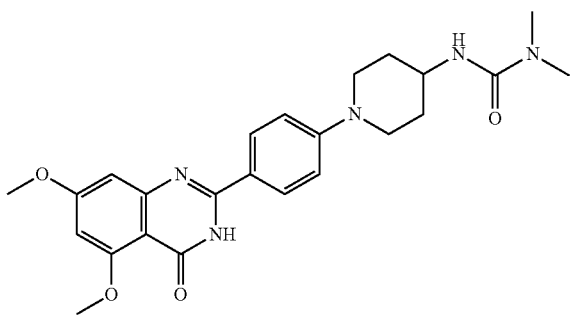

A mixture of N-(1-(4-(5,7-dimethoxy-4-oxo-3,4-dihydroquinazolin-2-yl)phenyl)piperidin-4-yl)acetamide (0.250 g, 0.59 mmol) and 2 M HCl (20 mL) was heated at reflux for 24 hours. The mixture was basified with 2 M NaOH to pH 8, extracted with $CH_2Cl_2$ (3×150 mL), dried over anhydrous MgSO4, filtered, and concentrated to afford 2-(4-(4-aminopiperidin-1-yl)phenyl)-5,7-dimethoxyquinazolin-4(3H)-one as a yellow solid (0.215 g, 96%).

A mixture of 2-(4-(4-aminopiperidin-1-yl)phenyl)-5,7-dimethoxyquinazolin-4(3H)-one (0.105 g, 0.28 mmol), dimethylcarbamic chloride (0.032 g, 0.30 mmol), and $Et_3N$ (0.085 g, 0.84 mmol) in THF (10 mL) was stirred at room temperature for 18 hours. The mixture was then heated at reflux for 24 hours, then cooled to room temperature. 2 M NaOH (20 mL) was added and the mixture was stirred for 30 minutes. The reaction mixture was adjusted to pH 8, extracted with $CH_2Cl_2$ (3×100 mL), dried over anhydrous $MgSO_4$, filtered, and concentrated. The residue was dissolved in $CHCl_3$/MeOH and concentrated, then $CH_3CN$ was added and concentrated to afford the title compound as a white solid (0.065 g, 51%): $^1$H NMR (300 MHz, $CDCl_3$): δ 11.72 (s, 1H), 8.08 (d, J=9.0 Hz, 2H), 7.00 (d, J=9.0 Hz, 2H), 6.78 (d, J=2.2 Hz, 1H), 6.46 (d, J=2.2 Hz, 1H), 5.99 (d, J=7.8 Hz, 1H), 3.90-3.94 (m, 2H), 3.88 (s, 3H), 3.83 (s, 3H), 3.66-3.69 (m, 1H), 2.88-2.93 (m, 2H), 2.76 (s, 6H), 1.75-1.80 (m, 2H), 1.45-1.52 (m, 2H); ESI MS m/z 452 $[M+H]^+$.

Example 16

Preparation of 2-(4-(4-Hexanoylpiperazin-1-yl)phenyl)-5,7-dimethoxyquinazolin-4(3H)-one

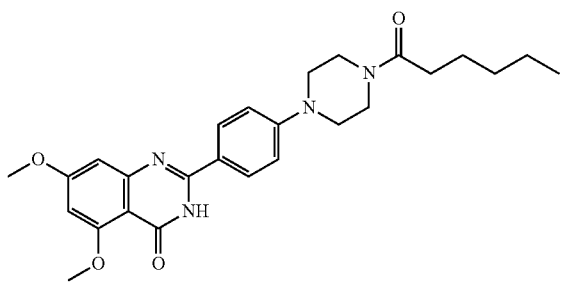 [SMILES: CCCCCC(=O)N1CCN(c2ccc(-c3nc4cc(OC)cc(OC)c4c(=O)[nH]3)cc2)CC1]

To a solution of 5,7-dimethoxy-2-(4-(piperazin-1-yl)phenyl)quinazolin-4(3H)-one (0.120 g, 0.32 mmol) in $CH_2Cl_2$ (10 mL) was added $Et_3N$ (0.06 mL, 0.48 mmol) and hexanoyl chloride (0.03 mL, 0.28 mmol). The resulting solution was stirred at room temperature for 1 hour. The mixture was concentrated in vacuo. The material was purified by flash chromatography, eluting with 2% to 10% of MeOH/$CH_2Cl_2$, to afford the title compound (0.050 g, 38%). $^1$H NMR (300 MHz, DMSO-$d_6$): δ 11.79 (s, 1H), 8.11 (d, J=8.7 Hz, 2H), 7.03 (d, J=8.8 Hz, 2H), 6.68 (s, 1H), 6.47 (s, 1H), 3.75-4.05 (m, 6H), 3.47-3.73 (m, 4H), 3.17-3.43 (m, 4H), 2.20-2.40 (m, 2H), 1.41-1.62 (m, 2H), 1.15-1.38 (m, 4H), 0.76-0.98 (m, 3H); APCI MS m/z 465 $[M+H]^+$.

Example 17

Preparation of 2-(4-(4-Isobutyrylpiperazin-1-yl)phenyl)-5,7-dimethoxyquinazolin-4(3H)-one

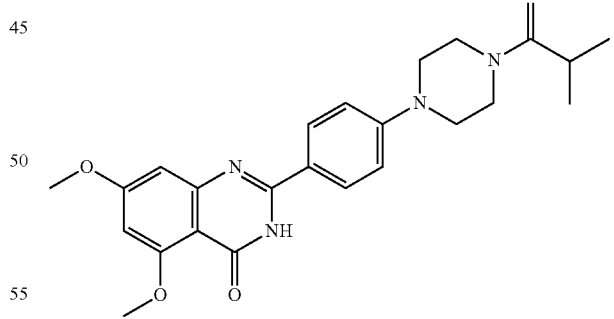

To a solution of 5,7-dimethoxy-2-(4-(piperazin-1-yl)phenyl)quinazolin-4(3H)-one (0.150 g, 0.40 mmol) in $CH_2Cl_2$ (10 mL) was added $Et_3N$ (0.08 mL, 0.60 mmol) and isobutyryl chloride (0.03 mL, 0.36 mmol). The resulting solution was stirred at room temperature for 1 hour. The solution was concentrated in vacuo and the residue was purified by flash chromatography on silica gel, eluting with 2% to 10% of MeOH/$CH_2Cl_2$. The solid was further purified by flash chromatography on silica gel, eluting with 0% to 5% of MeOH/ EtOAc, to afford the title compound (0.080 g, 50%): $^1$H NMR (300 MHz, DMSO-d$_6$): δ 11.78 (s, 1H), 8.11 (d, J=9.0 Hz, 2H), 7.03 (d, J=9.1 Hz, 2H), 6.68 (s, 1H), 6.47 (s, 1H), 3.76-3.92 (m, 6H), 3.52-3.71 (m, 4H), 3.16-3.44 (m, 4H), 2.83-3.00 (m, 1H), 1.02 (d, J=6.8 Hz, 6H); APCI MS m/z 437 [M+H]$^+$.

Example 18

Preparation of 2-(4-(4-Benzoylpiperazin-1-yl)phenyl)-5,7-dimethoxyquinazolin-4(3H)-one

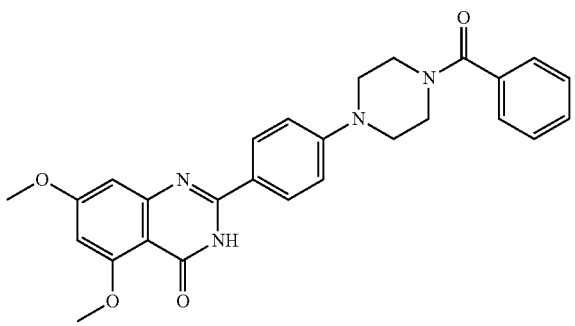 [SMILES: COc1cc(OC)c2c(=O)[nH]c(-c3ccc(N4CCN(C(=O)c5ccccc5)CC4)cc3)nc2c1]

To a solution of 5,7-dimethoxy-2-(4-(piperazin-1-yl)phenyl)quinazolin-4(3H)-one (0.150 g, 0.40 mmol) in CH$_2$Cl$_2$ (10 mL) was added Et$_3$N (0.08 mL, 0.60 mmol) and benzoyl chloride (0.04 mL, 0.36 mmol). The resulting solution was stirred at room temperature for 3 hours. The solution was concentrated in vacuo. The material was purified by flash chromatography on silica gel eluting with 0% to 10% of MeOH/EtOAc to afford the title compound (0.110 g, 64%). $^1$H NMR (300 MHz, DMSO-d$_6$): δ 11.79 (s, 1H), 8.11 (d, J=8.7 Hz, 2H), 7.37-7.54 (m, 5H), 7.04 (d, J=8.9 Hz, 2H), 6.68 (s, 1H), 6.47 (s, 1H), 3.61-4.03 (m, 8H), 3.23-3.62 (m, 6H); ESI MS m/z 471 [M+H]$^+$.

Example 19

Preparation of 2-(4-(4-(4-Fluorobenzoyl)piperazin-1-yl)phenyl)-5,7-dimethoxyquinazolin-4(3H)-one

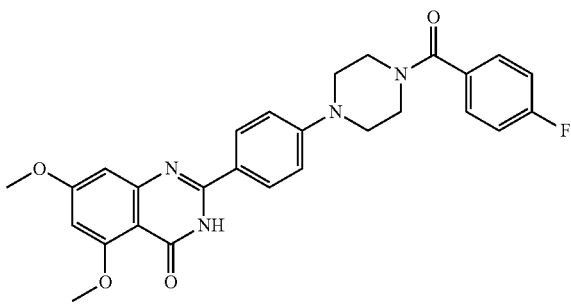 [SMILES: COc1cc(OC)c2c(=O)[nH]c(-c3ccc(N4CCN(C(=O)c5ccc(F)cc5)CC4)cc3)nc2c1]

To a solution of 5,7-dimethoxy-2-(4-(piperazin-1-yl)phenyl)quinazolin-4(3H)-one (0.150 g, 0.40 mmol) in CH$_2$Cl$_2$ (10 mL) was added Et$_3$N (0.08 mL, 0.60 mmol) and 4-fluorobenzoyl chloride (0.04 mL, 0.36 mmol). The resulting solution was stirred at room temperature for 3 hours. The solution was concentrated in vacuo and the residue was purified by flash chromatography on silica gel, eluting with 0% to 10% of MeOH/EtOAc, to afford the title compound (0.080 g, 45%). $^1$H NMR (300 MHz, DMSO-d$_6$): δ 11.79 (s, 1H), 8.11 (d, J=8.8 Hz, 2H), 7.44-7.62 (m, 2H), 7.21-7.39 (m, 2H), 7.04 (d, J=9.0 Hz, 2H), 6.68 (s, 1H), 6.47 (s, 1H), 3.64-3.94 (m, 8H), 3.22-3.60 (m, 6H); APCI MS m/z 489 [M+H]$^+$.

Example 20

Preparation of N-(1-(4-(5,7-Dimethoxy-4-oxo-3,4-dihydroquinazolin-2-yl)phenyl)piperidin-4-yl)benzamide

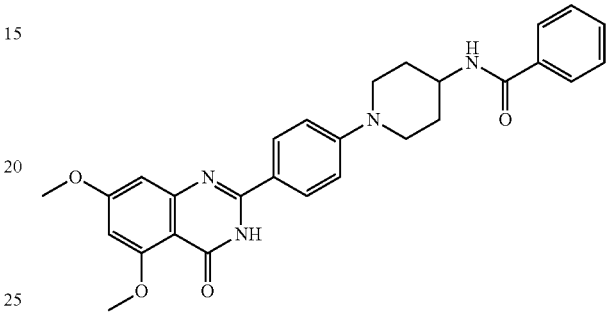

To a solution of ethyl 4-(4-aminopiperidin-1-yl)benzoate (3.0 g, 12.1 mmol) in CH$_2$Cl$_2$ under nitrogen was added Et$_3$N (2.45 g, 24.2 mmol), followed by benzoyl chloride (1.70 g, 12.1 mmol). The mixture was stirred at room temperature overnight, washed with brine (200 mL), dried over anhydrous MgSO$_4$, filtered, and concentrated. The resulting solids were triturated with hexanes to afford ethyl 4-(4-benzamidopiperidin-1-yl)benzoate as a yellow solid (4.2 g, 100%).

A solution of ethyl 4-(4-benzamidopiperidin-1-yl)benzoate (4.2 g, 11.9 mmol) in THF (400 mL) was cooled to 0° C. under nitrogen and treated with DIBAL-H (1.0 M in THF, 47 mL, 47 mmol). The mixture was warmed to room temperature and stirred for 1 hour. Then, the reaction mixture was quenched with Rochelle's salt (10% aqueous), concentrated to remove the THF, brine (300 mL) was added, and the organic phase was extracted with CH$_2$Cl$_2$ (3×200 mL), dried over anhydrous MgSO$_4$, filtered, and concentrated, to afford N-(1-(4-(hydroxymethyl)phenyl)piperidin-4-yl)benzamide as a yellow solid that was used without further purification.

To a solution of N-(1-(4-(hydroxymethyl)phenyl)piperidin-4-yl)benzamide (1.1 g, 3.5 mmol) in CH$_2$Cl$_2$ (250 mL) was added TPAP (0.123 g, 0.35 mmol) and NMO (0.623 g, 5.3 mmol). After 1 hour, the mixture was filtered through Celite, concentrated, and purified by silica gel chromatography, eluting with 30% ethyl acetate/hexanes to 100% ethyl acetate, to afford N-(1-(4-formylphenyl)piperidin-4-yl)benzamide as a white solid (0.350 g, 32%).

A mixture of N-(1-(4-formylphenyl)piperidin-4-yl)benzamide (0.350 g, 1.10 mmol), NaHSO$_3$ (0.180 g, 1.70 mmol) and p-TsOH (0.022 g, 0.11 mmol) and 2-amino-4,6-dimethoxybenzamide (0.223 g, 1.10 mmol) in DMA (10 mL) was heated at 150° C. overnight. The mixture was concentrated in vacuo, and the residue was dissolved in EtOAc and washed with H$_2$O and brine, dried (Na$_2$SO$_4$), filtered and concentrated in vacuo. The resulting solid was purified by silica gel chromatography eluting with 10% to 50% CHCl$_3$/MeOH/concentrated NH$_4$OH in CH$_2$Cl$_2$ to afford the title compound (0.050 g, 10%): $^1$H NMR (300 MHz, DMSO-d$_6$): δ 11.75 (s, 1H), 8.26 (d, J=7.4 Hz, 1H), 8.10 (d, J=9.0 Hz, 2H), 7.83 (d, J=6.9 Hz, 2H), 7.44-7.49 (m, 3H), 7.05 (d, J=8.8 Hz, 2H), 6.68 (s, 1H), 6.46 (s, 1H), 3.93-4.17 (m, 3H), 3.88 (s, 3H), 3.83 (s, 3H), 2.91-3.08 (m, 2H), 1.82-1.93 (m, 2H), 1.52-1.72 (m, 2H); APCI MS m/z 485 [M+H]+.

Example 21

Preparation of 5,7-Dimethoxy-2-(4-(4-picolinoylpiperazin-1-yl)phenyl)quinazolin-4(3H)-one

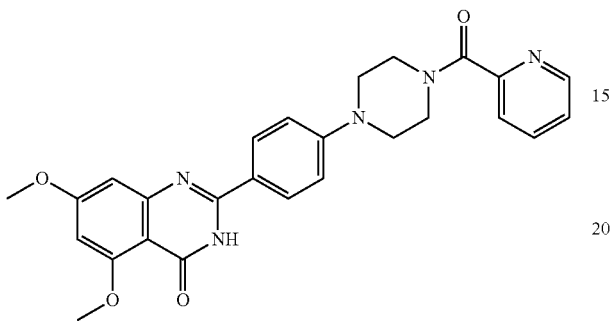

To a solution of picolinic acid (0.066 g, 0.54 mmol) in THF (20 mL) was added HOBt (0.079 g, 0.59 mmol), EDCl (0.113 g, 0.59 mmol), Et₃N (0.08 mL, 0.59 mmol) and 5,7-dimethoxy-2-(4-(piperazin-1-yl)phenyl)quinazolin-4(3H)-one (0.200 g, 0.54 mmol). The resulting solution was stirred overnight at room temperature. The solution was concentrated in vacuo and the resulting solid was purified by flash chromatography on silica gel, eluting with 50% to 100% of 92:7:1 CHCl₃/MeOH/concentrated NH₄OH in CH₂Cl₂, to afford the title compound (0.160 g, 62%): ¹H NMR (300 MHz, DMSO-d₆): δ 11.69 (s, 1H), 8.53-8.70 (m, 1H), 8.11 (d, J=8.9 Hz, 2H), 7.86-8.04 (m, 1H), 7.64 (d, J=7.8 Hz, 1H), 7.44-7.57 (m, 1H), 7.04 (d, J=9.1 Hz, 2H), 6.69 (s, 1H), 6.47 (s, 1H), 3.74-3.97 (m, 8H), 3.53-3.68 (m, 2H), 3.41-3.53 (m, 2H), 3.23-3.39 (m, 2H). APCI MS m/z 472 [M+H]+.

Example 22

Preparation of 5,7-Dimethoxy-2-(4-(4-nicotinoylpiperazin-1-yl)phenyl)quinazolin-4(3H)-one

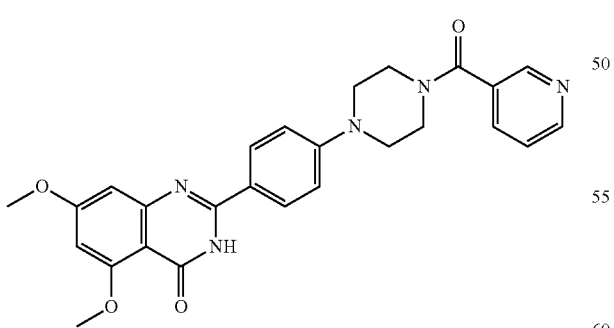

To a solution of nicotinic acid (0.066 g, 0.54 mmol) in THF (20 mL) was added HOBt (0.079 g, 0.59 mmol), EDCl (0.113 g, 0.59 mmol), Et₃N (0.08 mL, 0.59 mmol) and 5,7-dimethoxy-2-(4-(piperazin-1-yl)phenyl)quinazolin-4(3H)-one (0.200 g, 0.54 mmol). The resulting solution was stirred overnight at room temperature. The solution was concentrated in vacuo and the resulting solid was purified by flash chromatography on silica gel, eluting with 10% to 60% of 92:7:1 CHCl₃/MeOH/concentrated NH₄OH in CH₂Cl₂, to afford the title compound (0.050 g, 19%): ¹H NMR (300 MHz, DMSO-d₆): δ 11.79 (s, 1H), 8.59-8.78 (m, 2H), 8.12 (d, J=8.8 Hz, 2H), 7.82-7.99 (m, 1H), 7.37-7.60 (m, 1H), 7.04 (d, J=9.1 Hz, 2H), 6.69 (s, 1H), 6.47 (s, 1H), 3.63-3.97 (m, 8H), 3.20-3.63 (m, 6H). APCI MS m/z 472 [M+H]+.

Example 23

Preparation of 2-(4-(4-Isonicotinoylpiperazin-1-yl)phenyl)-5,7-dimethoxyquinazolin-4(3H)-one

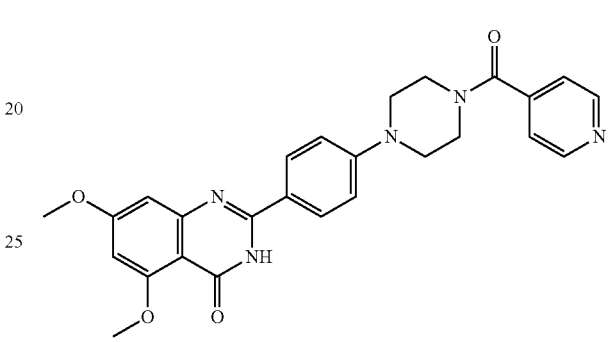

To a solution of isonicotinic acid (0.083 g, 0.68 mmol) in THF (20 mL) was added HOBt (0.099 g, 0.74 mmol), EDCl (0.141 g, 0.74 mmol), Et₃N (0.10 mL, 0.74 mmol) and 5,7-dimethoxy-2-(4-(piperazin-1-yl)phenyl)quinazolin-4(3H)-one (0.250 g, 0.68 mmol). The resulting solution was stirred overnight at room temperature. The solution was concentrated in vacuo and the resulting material was purified by flash chromatography on silica gel, eluting with 10% to 60% of 92:7:1 CHCl₃/MeOH/concentrated NH₄OH in CH₂Cl₂, to afford the title compound (0.110 g, 34%). ¹H NMR (300 MHz, DMSO-d₆): δ 11.79 (s, 1H), 8.58-8.79 (m, 2H), 8.12 (d, J=9.0 Hz, 2H), 7.45 (d, J=6.0 Hz, 2H), 7.04 (d, J=9.0 Hz, 2H), 6.69 (s, 1H), 6.47 (s, 1H), 3.64-4.06 (m, 9H), 3.22-3.54 (m, 5H). APCI MS m/z 472 [M+H]+.

Example 24

Preparation of 5,7-Dimethoxy-2-(4-(4-(thiophene-2-carbonyl)piperazin-1-yl)phenyl)quinazolin-4(3H)-one

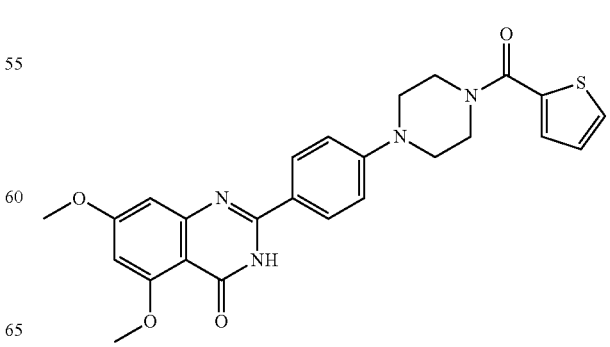

To a solution of 2-thiophenecarboxylic acid (0.087 g, 0.68 mmol) in THF (20 mL) was added HOBt (0.099 g, 0.74 mmol), EDCl (0.141 g, 0.74 mmol), Et$_3$N (0.10 mL, 0.74 mmol) and 5,7-dimethoxy-2-(4-(piperazin-1-yl)phenyl) quinazolin-4(3H)-one (0.250 g, 0.68 mmol). The resulting solution was stirred at room temperature for 4 hours. The solution was concentrated in vacuo. The material was purified by flash chromatography, eluting with 0% to 50% of 92:7:1 CHCl$_3$/MeOH/concentrated NH$_4$OH in CH$_2$Cl$_2$, to afford the title compound (0.100 g, 30%). $^1$H NMR (300 MHz, DMSO-d$_6$): δ 11.78 (s, 1H), 8.12 (d, J=9.0 Hz, 2H), 7.75-7.84 (m, 1H), 7.46-7.53 (m, 1H), 7.12-7.20 (m, 1H), 7.03 (d, J=9.1 Hz, 2H), 6.69 (d, J=2.3 Hz, 1H), 6.47 (d, J=2.3 Hz, 1H), 3.88 (s, 3H), 3.83 (s, 3H), 3.74-3.92 (m, 4H), 3.37-3.49 (m, 4H). APCI MS m/z 477 [M+H]$^+$.

Example 25

Preparation of 2-(4-(4-(5-Chloro-1-methyl-1H-pyrazole-4-carbonyl)piperazin-1-yl)phenyl)-5,7-dimethoxyquinazolin-4(3H)-one

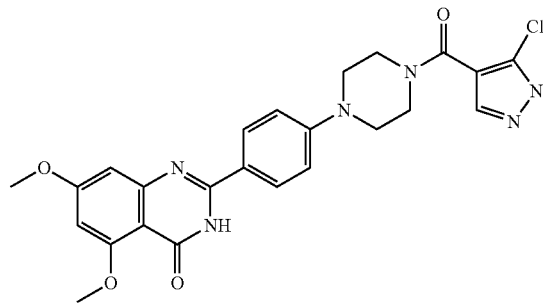

To a mixture of 5,7-dimethoxy-2-(4-(piperazin-1-yl)phenyl)quinazolin-4(3H)-one (0.150 g, 0.41 mmol) and 5-chloro-1-methyl-1H-pyrazole-4-carbonyl chloride (0.073 g, 0.41 mmol) in CH$_2$Cl$_2$ (50 mL), was added Et$_3$N (0.086 mL, 0.62 mmol) and the reaction stirred under nitrogen at room temperature for 1 hour. The residue was concentrated and purified by flash chromatography on silica gel, eluting with 70% CH$_2$Cl$_2$/(92:7:1 CHCl$_3$/MeOH/concentrated NH$_4$OH) to 100% (92:7:1 CHCl$_3$/MeOH/concentrated NH$_4$OH), to afford the title compound as a white solid (0.159 g, 76%). $^1$H NMR (500 MHz, DMSO-d$_6$): δ 11.78 (s, 1H), 8.12 (d, J=9.0 Hz, 2H), 7.77 (s, 1H), 7.04 (d, J=9.1 Hz, 2H), 6.69 (d, J=2.3 Hz, 1H), 6.47 (d, J=2.3 Hz, 1H), 3.88 (s, 3H), 3.80-3.87 (m, 6H), 3.63-3.80 (m, 4H), 3.38-3.44 (m, 4H). APCI MS m/z 509 [M+H]$^+$.

Example 26

Preparation of 5,7-Dimethoxy-2-(4-(4-(3,3,3-trifluoropropanoyl)piperazin-1-yl)phenyl)quinazolin-4(3H)-one

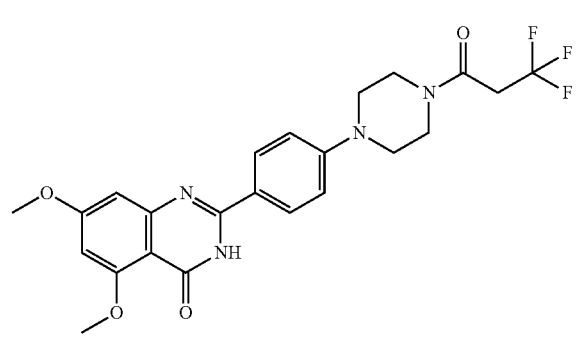 [SMILES: COc1cc(OC)c2c(=O)[nH]c(-c3ccc(N4CCN(C(=O)CC(F)(F)F)CC4)cc3)nc2c1]

To a solution of 5,7-dimethoxy-2-(4-(piperazin-1-yl)phenyl)quinazolin-4(3H)-one (0.200 g, 0.54 mmol) in THF (10 mL) was added EDCl (0.105 g, 0.54 mmol), HOBt (0.074 g, 0.54 mmol), Et$_3$N (0.08 mL, 0.54 mmol) and trifluoropropionic acid (0.070 g, 0.54 mmol). The reaction was stirred at room temperature for 4 hours and concentrated in vacuo. Purification by flash chromatography, eluting with 20% to 100% of 92:7:1 CHCl$_3$/MeOH/concentrate NH$_4$OH in CH$_2$Cl$_2$, afforded the title compound (0.135 g, 52%). $^1$H NMR (300 MHz, DMSO-d$_6$): δ 11.78 (s, 1H), 8.10 (d, J=9.0 Hz, 2H), 7.03 (d, J=9.0 Hz, 2H), 6.68 (d, J=2.3 Hz, 1H), 6.47 (d, J=2.3 Hz, 1H), 3.88 (s, 3H), 3.83 (s, 3H), 3.70-3.78 (m, 2H), 3.60-3.67 (m, 4H), 3.34-3.38 (m, 4H). APCI MS m/z 477 [M+H]$^+$.

Example 27

Preparation of 2-(4-(4-(2,5-Dichlorothiophene-3-carbonyl)piperazin-1-yl)phenyl)-5,7-dimethoxyquinazolin-4(3H)-one

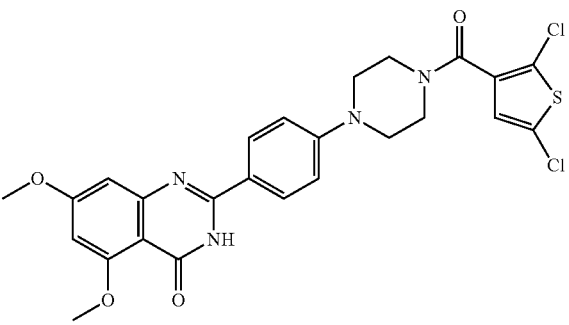 [SMILES: COc1cc(OC)c2c(=O)[nH]c(-c3ccc(N4CCN(C(=O)c5cc(Cl)sc5Cl)CC4)cc3)nc2c1]

To a mixture of 5,7-dimethoxy-2-(4-(piperazin-1-yl)phenyl)quinazolin-4(3H)-one (0.150 g, 0.41 mmol) and 2,5-dichlorothiophene-3-carbonyl chloride (0.088 g, 0.41 mmol) in CH$_2$Cl$_2$ was added Et$_3$N (0.086 mL, 0.62 mmol) and the mixture stirred at room temperature under nitrogen for 30 minutes. The mixture was concentrated and purified by silica gel chromatography, eluting with 70% CH$_2$Cl$_2$/(92:7:1 CHCl$_3$/MeOH/concentrated NH$_4$OH) to 100% (92:7:1 CHCl$_3$/MeOH/concentrated NH$_4$OH), to afford the title compound as a light yellow solid (0.177 g, 79%). $^1$H NMR (300 MHz, DMSO-d$_6$): δ 11.80 (s, 1H), 8.12 (d, J=9.0 Hz, 2H), 7.27 (s, 1H), 7.05 (d, J=9.0 Hz, 2H), 6.69 (d, J=2.3 Hz, 1H), 6.48 (d, J=2.3 Hz, 1H), 3.88 (s, 3H), 3.84 (s, 3H), 3.73-3.82 (m, 2H), 3.38-3.44 (m, 6H). APCI MS m/z 545 [M+H]$^+$.

Example 28

Preparation of 2-(4-(4-(Cyclopropanecarbonyl)piperazin-1-yl)phenyl)-5,7-dimethoxyquinazolin-4(3H)-one

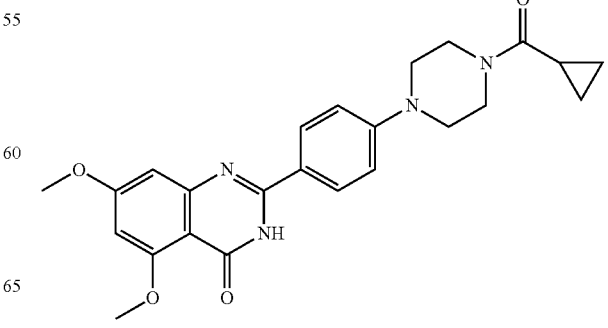

To a solution of 5,7-dimethoxy-2-(4-(piperazin-1-yl)phenyl)quinazolin-4(3H)-one (0.150 g, 0.40 mmol) in CH$_2$Cl$_2$ (10 mL) was added Et$_3$N (0.08 mL, 0.60 mmol), and cyclopropane carbonyl chloride (0.03 mL, 0.36 mmol). The resulting solution was stirred overnight at room temperature. The solution was concentrated in vacuo and the material was purified by flash chromatography on silica gel eluting with 0% to 50% of 92:7:1 CHCl$_3$/MeOH/concentrated NH$_4$OH in CH$_2$Cl$_2$ to afford the title compound (0.100 g, 63%). $^1$H NMR (300 MHz, DMSO-d$_6$): δ 11.78 (s, 1H), 8.12 (d, J=8.9 Hz, 2H), 7.04 (d, J=9.2 Hz, 2H), 6.63-6.74 (m, 1H), 6.39-6.52 (m, 1H), 3.73-3.95 (m, 8H), 3.51-3.73 (m, 2H), 3.21-3.49 (m, 4H), 1.93-2.10 (m, 1H), 0.56-0.83 (m, 4H). APCI MS m/z 435 [M+H]$^+$.

Example 29

Preparation of 2-(4-(4-(4-Fluorobenzyl)piperazin-1-yl)phenyl)-5,7-dimethoxyquinazolin-4(3H)-one

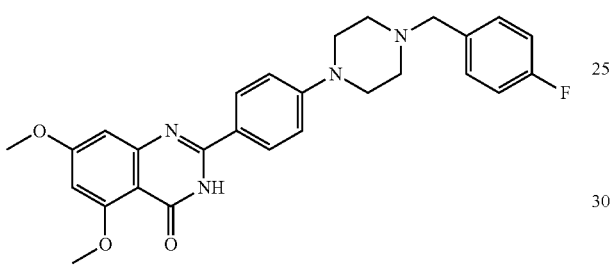

To a solution of 5,7-dimethoxy-2-(4-(piperazin-1-yl)phenyl)quinazolin-4(3H)-one (0.200 g, 0.55 mmol) in DMF (5 mL) was added 4-fluorobenzyl bromide (0.07 mL, 0.55 mmol) and K$_2$CO$_3$ (0.15 g, 1.10 mmol). The reaction was stirred at room temperature for 2 hours then diluted with H$_2$O and the solids filtered off to afford the title compound (0.17 g, 65%) as a light brown solid. $^1$H NMR (300 MHz, DMSO-d$_6$): δ 11.76 (br s, 1H), 8.09 (d, J=8.1 Hz, 2H), 7.26-7.52 (m, 2H), 7.08-7.25 (m, 2H), 7.00 (d, J=8.0 Hz, 2H), 6.68 (s, 1H), 6.46 (s, 1H), 3.87 (s, 3H), 3.83 (s, 3H), 3.51 (s, 2H), 3.08-3.41 (m, 4H), 2.23-2.68 (m, 4H). APCI MS m/z 475 [M+H]$^+$.

Example 30

Preparation of 2-(4-(4-Benzylpiperazin-1-yl)phenyl)-5,7-dimethoxyquinazolin-4(3H)-one

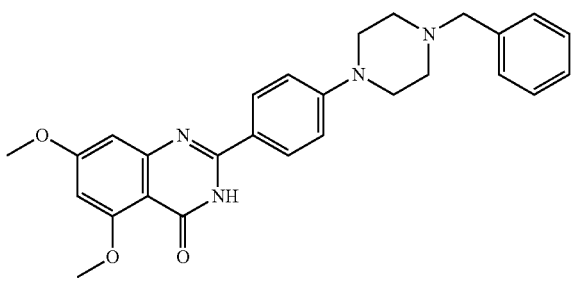 [SMILES: COc1cc(OC)c2c(=O)[nH]c(-c3ccc(N4CCN(Cc5ccccc5)CC4)cc3)nc2c1]

Following the method described for Example 29 above, the title compound was made from benzyl bromide in 45% yield. $^1$H NMR (300 MHz, DMSO-d$_6$): δ 11.76 (s, 1H), 8.09 (d, J=8.6 Hz, 2H), 7.26-7.43 (m, 5H), 7.00 (d, J=8.8 Hz, 2H), 6.68 (s, 1H), 6.46 (s, 1H), 3.87 (s, 3H), 3.85 (s, 3H), 3.53 (s, 2H), 3.23-3.40 (m, 4H), 2.38-2.63 (m, 4H). APCI MS m/z 457 [M+H]$^+$.

Example 31

Preparation of 2-(4-(4-(2,2,2-Trifluoroethyl)piperazin-1-yl)phenyl)quinazolin-4(3H)-one

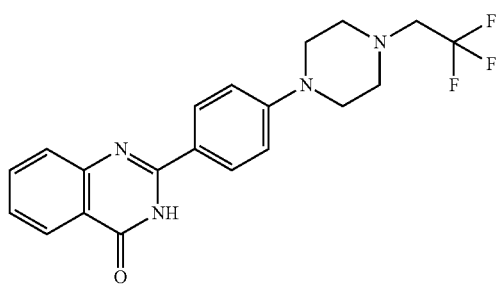 [SMILES: O=c1[nH]c(-c2ccc(N3CCN(CC(F)(F)F)CC3)cc2)nc2ccccc12]

To a mixture of 2-aminobenzamide (1.0 g, 7.35 mmol) and 4-(4-acetylpiperazin-1-yl)benzaldehyde (1.71 g, 7.35 mmol) in DMA (60 mL) was added p-TsOH (0.140 g, 0.73 mmol) and NaHSO$_3$ (0.841 g, 8.1 mmol). The reaction mixture was heated at 150° C. for 21 hours, concentrated to half-volume, diluted with water (300 mL), extracted with CH$_2$Cl$_2$ (2×200 mL), washed with brine (200 mL), dried over anhydrous MgSO$_4$, filtered, and concentrated. The residue was purified by silica gel chromatography, eluting with 100% CH$_2$Cl$_2$ to 100% (92:7:1 CHCl$_3$/MeOH/concentrated NH$_4$OH), to afford 2-(4-(4-acetylpiperazin-1-yl)phenyl)quinazolin-4(3H)-one as a yellow solid (2.27 g, 89%).

A mixture of 2-(4-(4-acetylpiperazin-1-yl)phenyl)quinazolin-4(3H)-one (2.27 g, 6.5 mmol) and 2 N HCl (100 mL) were heated at 100° C. for 4 hours. Then, the mixture was cooled to room temperature, basified to pH 8 with 2 N NaOH, extracted with CH$_2$Cl$_2$ (3×150 mL), dried over anhydrous MgSO$_4$, filtered, and concentrated to afford 2-(4-(piperazin-1-yl)phenyl)quinazolin-4(3H)-one as a pale yellow solid (1.8 g, 90%).

To a mixture of 2-(4-(piperazin-1-yl)phenyl)quinazolin-4(3H)-one (0.325 g, 1.06 mmol) in THF (50 mL) was added Hünig's base (0.192 g, 1.48 mmol), followed by 2,2,2-trifluoroethyl trifluoromethanesulfonate (0.295 g, 1.3 mmol). The reaction mixture was heated at reflux for 15 hours, concentrated, and purified by flash chromatography on silica gel, eluting with 100% CH$_2$Cl$_2$ to 100% ethyl acetate, to afford the title compound as an off-white solid (0.385 g, 94%). $^1$H NMR (300 MHz, DMSO-d$_6$): δ 12.27 (br s, 1H), 8.10-8.14 (m, 3H), 7.76-7.82 (m, 1H), 7.67 (d, J=7.8 Hz, 1H), 7.42-7.47 (m, 1H), 7.05 (d, J=9.1 Hz, 2H), 3.21-3.34 (m, 6H), 2.73-2.78 (m, 4H). APCI MS m/z 389 [M+H]$^+$.

Example 32

Preparation of 2-(4-(4-Acetyl-1,4-diazepan-1-yl)phenyl)-5,7-dimethoxyquinazolin-4(3H)-one

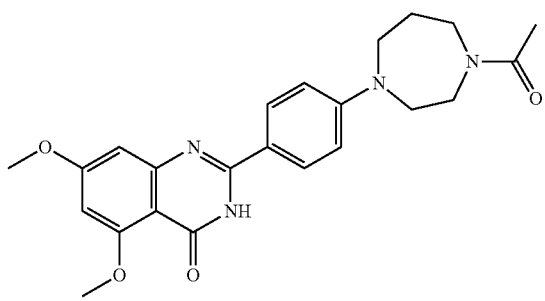 [SMILES: COc1cc(OC)c2c(=O)[nH]c(-c3ccc(N4CCCN(C(C)=O)CC4)cc3)nc2c1]

A mixture of 4-fluorobenzaldehyde (1.56 g, 12.6 mmol), 1-(1,4-diazepan-1-yl)ethanone (1.5 g, 10.5 mmol), and $K_2CO_3$ (1.74 g, 12.6 mmol) in DMF (10 mL) were heated at 120° C. for 20 hours. The mixture was cooled to room temperature and diluted with water. The mixture was extracted with ethyl acetate and the organic phase washed with brine, dried over anhydrous $MgSO_4$, filtered, and concentrated. The residue was purified by flash chromatography on silica gel, eluting with 50% ethyl acetate/hexanes to 100% ethyl acetate to 10% methanol/ethyl acetate, to afford 4-(4-acetyl-1,4-diazepan-1-yl)benzaldehyde (1.8 g, 70%).

To a mixture of 2-amino-4,6-dimethoxybenzamide (0.377 g, 1.92 mmol) and 4-(4-acetyl-1,4-diazepan-1-yl)benzaldehyde (0.520 g, 2.11 mmol) in DMA (20 mL) was added $NaHSO_3$ (0.240 g, 2.3 mmol) followed by p-TsOH (0.037 g, 0.192 mmol) and the reaction heated at 150° C. for 6 hours. The mixture was cooled to room temperature, diluted with $CH_2Cl_2$ (150 mL), washed with brine (2×150 mL), dried over anhydrous $MgSO_4$, filtered, and concentrated. The residue was purified by flash chromatography on silica gel, eluting with 1:1 $CH_2Cl_2$/92:7:1 $CHCl_3$/MeOH/concentrated $NH_4OH$ to 100% 92:7:1 $CHCl_3$/MeOH/concentrated $NH_4OH$, to afford the title compound (0.333 g, 41%) as a yellow solid. $^1H$ NMR (300 MHz, $CDCl_3$): δ 9.12 (s, 1H), 7.88-7.91 (m, 2H), 6.78-6.82 (m, 3H), 6.42 (d, J=2.2 Hz, 1H), 3.98 (s, 3H), 3.93 (s, 3H), 3.62-3.80 (m, 6H), 3.36-3.48 (m, 2H), 1.98-2.12 (m, 5H). ESI MS m/z 421 [M−H]⁻.

Example 33

Preparation of 2-(4-(1,4-Diazepan-1-yl)phenyl)-5,7-dimethoxyquinazolin-4(3H)-one

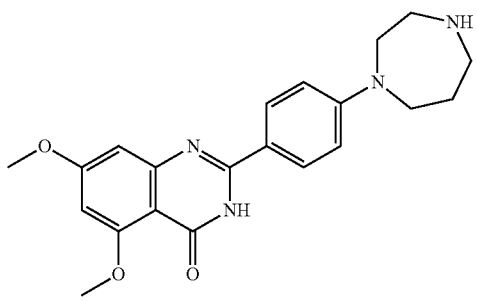 [SMILES: COc1cc(OC)c2c(=O)[nH]c(-c3ccc(N4CCCNCC4)cc3)nc2c1]

A mixture of 2-(4-(4-acetyl-1,4-diazepan-1-yl)phenyl)-5,7-dimethoxyquinazolin-4(3H)-one (0.135 g, 0.32 mmol) and 2 N HCl (10 mL) was heated at 100° C. for 4 hours. Then, the reaction mixture was cooled to room temperature, basified to pH 8, and extracted with $CH_2Cl_2$ (8×125 mL). The residue was purified by flash chromatography on silica gel, eluting with 1:1 $CH_2Cl_2$/92:7:1 $CHCl_3$/MeOH/concentrated $NH_4OH$ to 100% 92:7:1 $CHCl_3$/MeOH/concentrated $NH_4OH$, to afford the title compound (0.040 g, 33%) as a yellow solid. $^1H$ NMR (300 MHz, $CDCl_3$): δ 8.98 (s, 1H), 7.86 (d, J=9.0 Hz, 2H), 6.76-6.79 (m, 3H), 6.40 (d, J=2.3 Hz, 1H), 3.98 (s, 3H), 3.92 (s, 3H), 3.61-3.69 (m, 5H), 3.05 (t, J=4.9 Hz, 2H), 2.83 (t, J=5.7 Hz, 2H), 1.92 (t, J=5.4 Hz, 2H). ESI MS m/z 379 [M−H]⁻.

Example 34

Preparation of 5,7-Dimethoxy-2-(4-(4-methyl-1,4-diazepan-1-yl)phenyl)quinazolin-4(3H)-one

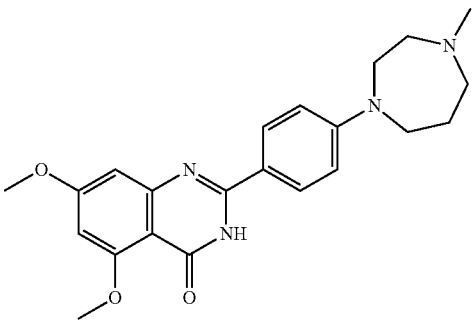

To a solution of 2-(4-(1,4-diazepan-1-yl)phenyl)-5,7-dimethoxyquinazolin-4(3H)-one (0.150 g, 0.39 mmol) in DMF (20 mL) was added $CH_3I$ (0.067 g, 0.47 mmol) and Hünig's Base (0.138 mL, 0.79 mmol). The reaction mixture was heated at 50° C. for 1.5 hours, cooled to room temperature, diluted with ethyl acetate (150 mL), washed with brine (2×100 mL), dried over anhydrous $MgSO_4$, filtered, and concentrated. The residue was purified by flash chromatography on silica gel, eluting with 1:1 $CH_2Cl_2$/92:7:1 $CHCl_3$/MeOH/concentrated $NH_4OH$ to 100% 92:7:1 $CHCl_3$/MeOH/concentrated $NH_4OH$, to afford the title compound (0.035 g, 23%) as a white solid. $^1H$ NMR (300 MHz, DMSO-$d_6$): δ 11.66 (s, 1H), 8.06 (d, J=9.0 Hz, 2H), 6.78 (d, J=9.0 Hz, 2H), 6.65 (d, J=2.2 Hz, 1H), 6.44 (d, J=2.2 Hz, 1H), 3.87 (s, 3H), 3.83 (s, 3H), 3.57-3.59 (m, 2H), 3.52 (t, J=6.1 Hz, 2H), 2.60-2.64 (m, 2H), 2.45-2.50 (m, 2H), 2.26 (s, 3H), 1.89-1.99 (m, 2H). ESI MS m/z 395 [M+H]⁺.

Example 35

Preparation of N-(1-(4-(5,7-Dimethoxy-4-oxo-3,4-dihydroquinazolin-2-yl)phenyl)piperidin-4-yl)-N-ethylacetamide

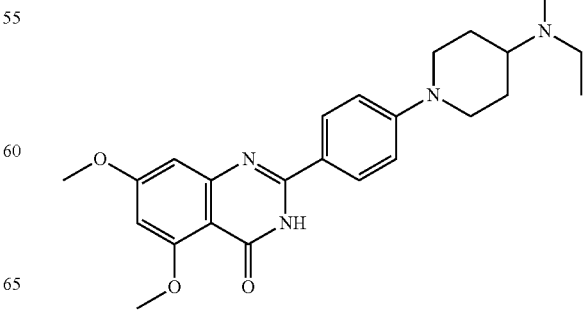

To a solution of 4-acetamidopiperidine (2.5 g, 17.5 mmol) in DMF (10 mL) was added 4-fluorobenzaldehyde (2.2 g, 17.5 mmol) and K$_2$CO$_3$ (2.9 g, 21.2 mmol). The reaction was heated at 120° C. for 4 hours, diluted with H$_2$O, and extracted with EtOAc. The organics were washed sequentially with H$_2$O and brine, dried (Na$_2$SO$_4$), filtered, and concentrated in vacuo, to afford N-(1-(4-formylphenyl)piperidin-4-yl)acetamide (3.1 g, 92%).

A 60% suspension in oil of NaH (0.113 g, 2.8 mmol) was added to a 0° C. solution of N-(1-(4-formylphenyl)piperidin-4-yl)acetamide (0.700 g, 2.8 mmol) in DMF (10 mL) and stirred for 35 minutes. To this mixture was added EtI (0.23 mL, 2.8 mmol) and the reaction was warmed to room temperature for 2 hours, quenched with H$_2$O, and extracted with EtOAc. The organics were washed with brine, dried over anhydrous Na$_2$SO$_4$, filtered, and concentrated in vacuo. Purification by flash chromatography on silica gel, eluting with 0% to 5% MeOH/CH$_2$Cl$_2$, afforded N-ethyl-N-(1-(4-formylphenyl)piperidin-4-yl)acetamide (0.490 g, 64%).

A mixture of N-ethyl-N-(1-(4-formylphenyl)piperidin-4-yl)acetamide (0.385 g, 1.40 mmol), NaHSO$_3$ (0.162 g, 1.50 mmol), and p-TsOH (0.024 g, 0.12 mmol) were added to a solution of 2-amino-4,6-dimethoxybenzamide (0.250 g, 1.20 mmol) in DMA (10 mL). The reaction was stirred at 150° C. for 4 hours and then cooled to room temperature overnight. The mixture was diluted with H$_2$O and extracted with EtOAc. The organics were washed with brine, dried over anhydrous Na$_2$SO$_4$, filtered, and concentrated in vacuo. Purification by flash chromatography on silica gel, eluting with 2% to 10% MeOH/CH$_2$Cl$_2$, afforded the title compound (0.300 g, 55%) as a yellow solid. $^1$H NMR (300 MHz, DMSO-d$_6$): mixture of rotamers δ 11.76 (s, 1H), 8.08 (d, J=8.7 Hz, 2H), 7.02 (d, J=8.7 Hz, 2H), 6.67 (d, J=2.0 Hz, 1H), 6.46 (d, J=2.0 Hz, 1H), 4.29-4.33 (m, 0.5H), 3.99-4.03 (m, 2H), 3.88 (s, 3H), 3.83 (5, 3H), 3.12-3.25 (m, 2H), 2.81-2.93 (m, 2H), 2.07 (s, 1.5H), 2.01 (s, 1.5H), 1.59-1.74 (m, 4.5H), 1.10 (t, J=6.7 Hz, 1.5H), 0.99 (t, J=6.7 Hz, 1.5H). ESI MS m/z 451 [M+H]$^+$.

Example 36

Preparation of 2-(4-((3R,5S)-4-Acetyl-3,5-dimethylpiperazin-1-yl)phenyl)-5,7-dimethoxyquinazolin-4(3H)-one

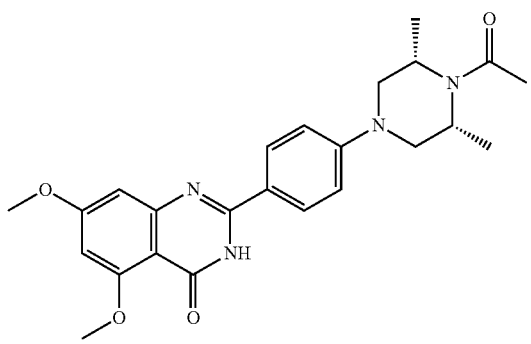 [SMILES: COc1cc(OC)c2c(=O)[nH]c(-c3ccc(N4C[C@@H](C)N(C(C)=O)[C@@H](C)C4)cc3)nc2c1]

A mixture of 4-fluorobenzaldehyde (2.0 g, 16.1 mmol), 2,6-dimethylpiperazine (2.2 g, 19.3 mmol), and K$_2$CO$_3$ (2.7 g, 19.3 mmol) in DMF (10 mL) was heated at 120° C. for 4 hours. Then, the reaction was diluted with H$_2$O and extracted with EtOAc. The organics were washed with brine, dried (Na$_2$SO$_4$), filtered and concentrated in vacuo. Purification by flash chromatography on silica gel eluting with 3% to 10% MeOH/CH$_2$Cl$_2$ afforded 4-(3,5-dimethylpiperazin-1-yl)benzaldehyde (2.0 g, 57%).

A solution of 4-(3,5-dimethylpiperazin-1-yl)benzaldehyde (1.0 g, 4.6 mmol.) in CH$_2$Cl$_2$ (15 mL) was cooled to 0° C. and treated with Et$_3$N (0.64 mL, 4.6 mmol) followed by acetyl chloride (0.33 mL, 4.6 mmol). The reaction stirred for 30 minutes, then concentrated in vacuo. Purification by flash chromatography on silica gel, eluting with 0% to 50% EtOAc/CH$_2$Cl$_2$, afforded 4-(4-acetyl-3,5-dimethylpiperazin-1-yl)benzaldehyde (1.0 g, 83%).

A mixture of 4-(4-acetyl-3,5-dimethylpiperazin-1-yl)benzaldehyde (0.580 g, 2.20 mmol), NaHSO$_3$ (0.260 g, 2.40 mmol), and p-TsOH (0.039 g, 0.20 mmol) was added to a solution of 2-amino-4,6-dimethoxybenzamide (0.400 g, 2.20 mmol) in DMA (15 mL). The reaction was stirred at 120° C. for 4 hours and then cooled to room temperature overnight. The mixture was diluted with H$_2$O and extracted with EtOAc. The organics were washed with brine, dried over anhydrous Na$_2$SO$_4$, filtered, and concentrated in vacuo. Purification by flash chromatography on silica gel, eluting with 2% to 10% MeOH/CH$_2$Cl$_2$, afforded the title compound (0.400 g, 46%) as a yellow solid. $^1$H NMR (300 MHz, DMSO-d$_6$): δ 11.78 (br s, 1H), 8.10 (d, J=8.9 Hz, 2H), 7.05 (d, J=9.0 Hz, 2H), 6.68 (d, J=2.3 Hz, 1H), 6.46 (d, J=2.3 Hz, 1H), 4.01-4.64 (m, 2H), 3.71-3.95 (m, 8H), 2.87-3.07 (m, 2H), 2.06 (s, 3H), 1.25 (d, J=6.2 Hz, 6H). ESI MS m/z 437 [M+H]$^+$.

Example 37

Preparation of 2-(4-((3R,5S)-3,5-Dimethylpiperazin-1-yl)phenyl)-5,7-dimethoxyquinazolin-4(3H)-one

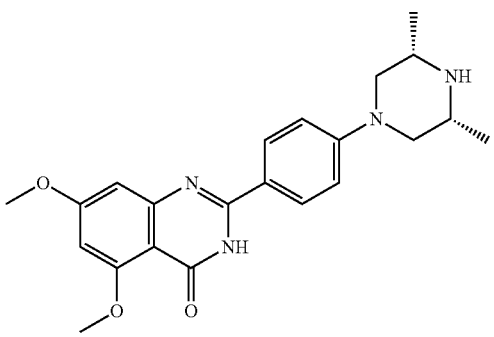

A solution of 2-(4-(4-acetyl-3,5-dimethylpiperazin-1-yl)phenyl)-5,7-dimethoxyquinazolin-4(3H)-one (0.150 g, 0.34 mmol) in 2N HCl was heated at reflux temperature for 3 days. The reaction was cooled to room temperature, basified with 1N NaOH, and extracted with CH$_2$Cl$_2$. Purification by flash chromatography on silica gel, eluting with 0% to 15% MeOH/CH$_2$Cl$_2$, followed by further purification, eluting with 30% to 100% of 92:7:1 CHCl$_3$/MeOH/concentrated NH$_4$OH, afforded the title compound (0.040 g, 30%) as a white solid. $^1$H NMR (300 MHz, DMSO-d$_6$): δ 11.98 (br s, 1H), 8.08 (d, J=9.0 Hz, 2H), 7.00 (d, J=9.0 Hz, 2H), 6.68 (d, J=2.3 Hz, 1H), 6.46 (d, J=2.3 Hz, 1H), 3.88 (s, 3H), 3.83 (s, 3H), 3.73-3.76

(m, 2H), 2.78-2.81 (m, 2H), 2.19-2.26 (m, 2H), 1.03 (d, J=6.2 Hz, 6H). ESI MS m/z 395 [M+H]+.

Example 38

Preparation of 2-(4-(4-Acetyl-3-methylpiperazin-1-yl)phenyl)-5,7-dimethoxyquinazolin-4(3H)-one

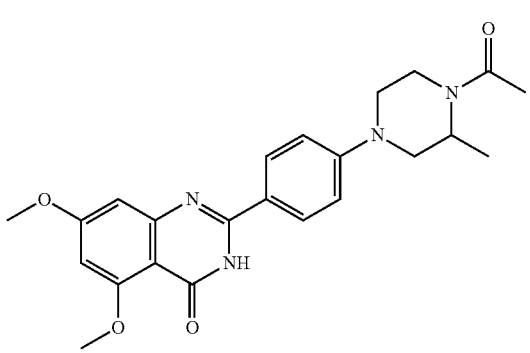 [SMILES: COc1cc(OC)c2c(=O)[nH]c(-c3ccc(N4CCN(C(C)=O)C(C)C4)cc3)nc2c1]

To a solution of 4-fluorobenzaldehyde (2.0 g, 16.1 mmol) in DMF (10 mL) was added 2-methylpiperazine (1.9 g, 19.3 mmol) and K₂CO₃ (2.7 g, 19.3 mmol). The reaction was heated at 120° C. for 6 hours, diluted with H₂O, and extracted with EtOAc. The organics were washed with brine, dried over anhydrous Na₂SO₄, filtered, and concentrated in vacuo, to afford 4-(3-methylpiperazin-1-yl)benzaldehyde (2.3 g, 69%): ¹H NMR (300 MHz, CDCl₃): δ 9.77 (s, 1H), 7.75 (d, J=9.0 Hz, 2H), 6.90 (d, J=9.0 Hz, 2H), 3.67-3.83 (m, 2H), 3.07-3.18 (m, 1H), 2.81-3.06 (m, 3H), 2.50-2.62 (m, 1H), 1.46-1.73 (br s, 1H), 1.15 (d, J=6.3 Hz, 3H). ESI MS m/z 205 [M+H]+.

A solution of 4-(3-methylpiperazin-1-yl)benzaldehyde (1.0 g, 4.89 mmol) in methylene chloride (15 mL) was cooled to 0° C. and treated with Et₃N (0.68 mL, 4.89 mmol), followed by acetyl chloride (0.34 mL, 4.89 mmol). The resulting solution was stirred at 0° C. for 20 minutes and then concentrated in vacuo. The material was purified by flash chromatography on silica gel, eluting with 0% to 5% of EtOAc/CH₂Cl₂, to afford 4-(4-acetyl-3-methylpiperazin-1-yl) benzaldehyde (0.88 g, 73%).

To a solution of 4-(4-acetyl-3-methylpiperazin-1-yl)benzaldehyde (0.400 g, 1.62 mmol) in DMA (15 mL) was added 2-amino-4,6-dimethoxybenzamide (0.349 g, 1.78 mmol), NaHSO₃ (0.201 g, 1.94 mmol) and p-TsOH (0.030 g, 0.16 mmol). The resulting solution was heated to 155° C. for 5 hours. The mixture was cooled to room temperature, diluted with water, extracted with CH₂Cl₂, washed with brine, dried (Na₂SO₄), filtered, and concentrated in vacuo. The material was purified by flash chromatography on silica gel, eluting with 50% to 100% of 92:7:1 CHCl₃/MeOH/concentrated NH₄OH in CH₂Cl₂, to afford the title compound (0.150 g, 21%). ¹H NMR (300 MHz, DMSO-d₆): mixture of rotamers δ 11.57 (s, 1H), 8.10 (d, J=8.9 Hz, 2H), 6.90-7.14 (m, 2H), 6.68 (s, 1H), 6.46 (s, 1H), 4.42-4.75 (m, 0.5H), 4.03-4.42 (m, 1H), 3.61-4.02 (m, 8H), 3.41-3.60 (m, 1H), 2.85-3.13 (m, 2H), 2.63-2.85 (m, 0.5H), 1.88-2.13 (m, 3H), 1.04-1.31 (m, 3H). ESI MS m/z 423 [M+H]+.

Example 39

Preparation of N-(1-(4-(5,7-Dimethoxy-4-oxo-3,4-dihydroquinazolin-2-yl)phenyl)pyrrolidin-3-yl)acetamide

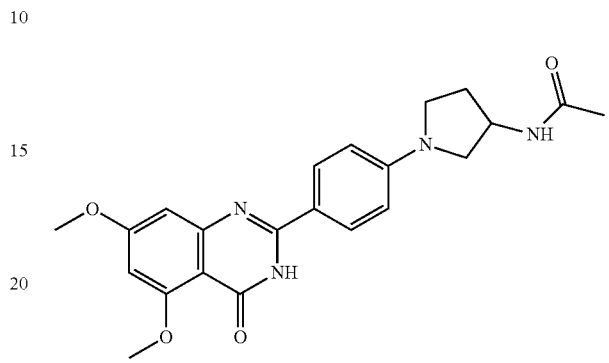

A solution of 2-(4-(3-aminopyrrolidin-1-yl)phenyl)-5,7-dimethoxyquinazolin-4(3H)-one (0.150 g, 0.41 mmol) in CH₂Cl₂ (10 mL) was treated with Et₃N (0.114 mL, 0.82 mmol), cooled to 0° C., and acetyl chloride (0.029 mL, 0.41 mmol) was added. The mixture was stirred for 2 hours at room temperature, concentrated, and purified by flash chromatography on silica gel, eluting with 1:1 CH₂Cl₂/92:7:1 CHCl₃/MeOH/concentrated NH₄OH to 100% 92:7:1 CHCl₃/MeOH/concentrated NH₄OH. The mixture was further purified by flash chromatography on silica gel, eluting with 9:1 methylene chloride/methanol, to afford the title compound (0.130 g, 78%) as a yellow solid. ¹H NMR (300 MHz, DMSO-d₆): δ 11.67 (s, 1H), 8.18 (d, J=6.8 Hz, 1H), 8.14 (d, J=6.8 Hz, 2H), 6.66 (d, J=2.3 Hz, 1H), 6.60 (d, J=9.0 Hz, 2H), 6.44 (d, J=2.3 Hz, 1H), 4.36-4.39 (m, 1H), 3.88 (s, 3H), 3.83 (s, 3H), 3.13-3.59 (m, 5H), 2.15-2.22 (m, 1H), 1.90-1.94 (m, 1H), 1.82 (s, 3H). ESI MS m/z 409 [M+H]+.

Example 40

Preparation of 2-(4-(4-Isopropylpiperazin-1-yl)phenyl)-8-methoxyquinazolin-4(3H)-one

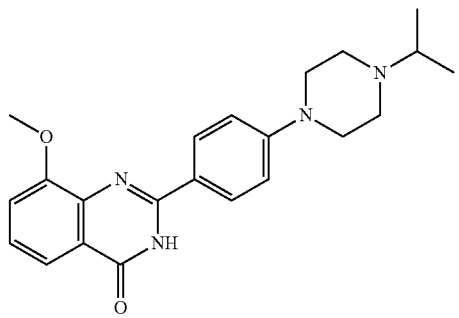 [SMILES: COc1cccc2c(=O)[nH]c(-c3ccc(N4CCN(C(C)C)CC4)cc3)nc12]

To a solution of 2-amino-3-methoxy benzoic acid (2.0 g, 11.90 mmol) in THF (30 mL) was added EDCl (2.7 g, 14.3 mmol), HOBt (1.9 g, 14.3 mmol) and NMM (1.6 mL, 14.3 mmol). The reaction was stirred at room temperature for 2 hours and then NH₄OH (1 mL) in H₂O (1 mL) was added.

After stirring overnight, the reaction was diluted with H₂O and extracted with CH₂Cl₂. The organics were washed with brine, dried over anhydrous Na₂SO₄, filtered, and concentrated in vacuo. The solids were suspended in Et₂O and filtered off to afford 2-amino-3-methoxybenzamide (1.1 g, 56%). ¹H NMR (300 MHz, DMSO-d₆) δ 7.71 (br s, 1H), 7.19 (d, J=8.1 Hz, 1H), 7.08 (br s, 1H), 6.87 (d, J=7.1 Hz, 1H), 6.45-6.53 (m, 1H), 6.26 (br s, 2H), 3.78 (s, 3H).

A mixture of 4-(4-isopropylpiperazin-1-yl)benzaldehyde (0.562 g, 2.40 mmol), NaHSO₃ (0.310 g, 2.90 mmol), and p-TsOH (0.046 g, 0.24 mmol) was added to a solution of 2-amino-3-methoxybenzamide (0.400 g, 2.40 mmol) in DMA (15 mL). The reaction was stirred at 120° C. overnight. The mixture was diluted with H₂O and saturated NaHCO₃ and extracted with CH₂Cl₂. The organics were washed with brine, dried (Na₂SO₄), filtered and concentrated in vacuo. Purification by flash chromatography on silica gel eluting with 0% to 10% MeOH/CH₂Cl₂ afforded the title compound (0.140 g, 15%). ¹H NMR (300 MHz, DMSO-d₆): δ 12.27 (s, 1H), 8.10 (d, J=8.9 Hz, 2H), 7.64-7.70 (m, 1H), 7.31-7.39 (m, 2H), 7.03 (d, J=9.1 Hz, 2H), 3.93 (s, 3H), 3.27-3.32 (m, 4H), 2.64-2.75 (m, 1H), 2.56-2.59 (m, 4H), 1.00 (d, J=6.6 Hz, 6H). ESI MS m/z 379 [M+H]⁺.

Example 41

Preparation of N-(1-(4-(5,7-dimethoxy-4-oxo-3,4-dihydroquinazolin-2-yl)phenyl)piperidin-4-yl)-N-isopropylacetamide

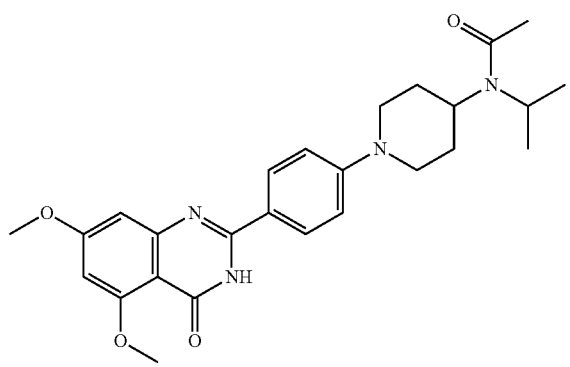 [SMILES: COc1cc(OC)c2c(=O)[nH]c(-c3ccc(N4CCC(N(C(C)=O)C(C)C)CC4)cc3)nc2c1]

To the solution of tert-butyl 4-oxopiperidine-1-carboxylate (5.0 g, 25.09 mmol) in methanol (35 mL) was added isopropylamine (1.07 mL, 12.54 mmol), acetic acid (0.94 mL, 16.30 mmol) and sodium cyanoborohydride (1.0 g, 16.30 mmol). The resulting solution was stirred at room temperature for 1 hour, then quenched with water. The solution was concentrated in vacuo and redissolved in ethyl ether. The organics were extracted with 0.1 N HCl. The aqueous extracts were basified with 1 N NaOH (pH>8) and extracted with ethyl ether. The organic extracts were dried over anhydrous Na₂SO₄, filtered, and concentrated in vacuo, to afford tert-butyl 4-(isopropylamino)piperidine-1-carboxylate (1.2 g, 41%) as a clear liquid.

To a 0° C. solution of tert-butyl 4-(isopropylamino)piperidine-1-carboxylate (1.2 g, 5.19 mmol) in CH₂Cl₂ (18 mL) was added Et₃N (1.44 mL, 10.38 mmol) followed by acetyl chloride (0.55 mL, 7.78 mmol). The resulting solution was stirred for 2.5 hours, then concentrated in vacuo. The material was purified by flash chromatography on silica gel, eluting with 0% to 5% of EtOAc/CH₂Cl₂, to afford tert-butyl 4-(N-isopropylacetamido)piperidine-1-carboxylate (0.88 g, 59%).

A solution of tert-butyl 4-(N-isopropylacetamido)piperidine-1-carboxylate (0.880 g, 3.09 mmol) in hydrogen chloride (4.0 M solution in 1,4-dioxane, 10 mL) was stirred at room temperature overnight. The resulting solution was concentrated in vacuo, basified with aqueous saturated NaHCO₃, and extracted with EtOAc. The organics were dried (Na₂SO₄), filtered, and concentrated in vacuo. The material was purified by flash chromatography on silica gel, eluting with 50% to 100% of 92:7:1 CHCl₃/MeOH/concentrated NH₄OH in CH₂Cl₂. The residue was further purified by flash chromatography on silica gel, eluting with 100% of 92:7:1 CHCl₃/MeOH/concentrated NH₄OH, to afford N-Isopropyl-N-(piperidin-4-yl)acetamide hydrogen chloride (0.260 g, 45%) as a clear liquid.

To a solution of N-isopropyl-N-(piperidin-4-yl)acetamide hydrogen chloride (0.260 g, 1.41 mmol) in DMF (5 mL) was added 4-fluorobenzaldehyde (0.18 mL, 1.69 mmol) and K₂CO₃ (0.233 g, 1.69 mmol). The resulting solution was heated to 120° C. overnight, and cooled. The cooled solution was diluted with water and extracted with CH₂Cl₂. The organics were washed with brine, dried over anhydrous Na₂SO₄, filtered, and concentrated in vacuo. The material was purified by flash chromatography on silica gel, eluting with 0% to 5% MeOH/CH₂Cl₂, to afford N-(1-(4-formylphenyl)piperidin-4-yl)-N-isopropylacetamide (0.290 g, 71%).

To a solution of N-(1-(4-formylphenyl)piperidin-4-yl)-N-isopropylacetamide (0.300 g, 1.04 mmol) in DMA (10 mL) was added 2-amino-4,6-dimethoxybenzamide (0.204 g, 1.04 mmol), NaHSO₃ (0.129 g, 1.24 mmol) and p-TsOH (0.019 g, 0.10 mmol). The resulting solution was heated to 155° C. overnight and then cooled to room temperature. The solution was diluted with water, extracted with CH₂Cl₂, washed with brine, dried over anhydrous Na₂SO₄, filtered, and concentrated in vacuo. The material was purified by flash chromatography on silica gel eluting, with 30% to 100% of 92:7:1 CHCl₃/MeOH/concentrated NH₄OH in CH₂Cl₂, to afford the title compound (0.100 g, 20%). ¹H NMR (300 MHz, DMSO-d₆): mixture of rotamers δ 11.66 (s, 1H), 8.07 (d, J=8.3 Hz, 2H), 6.89-7.15 (m, 2H), 6.67 (s, 1H), 6.46 (s, 1H), 3.90-4.11 (m, 3H), 3.88 (s, 3H), 3.83 (s, 3H), 2.80-3.02 (m, 2H), 2.39-2.66 (m, 1H), 1.92-2.06 (m, 3H), 1.63-1.82 (m, 2H), 1.32-1.47 (m, 1H), 1.21-1.32 (m, 3H), 1.08-1.21 (m, 4H). ESI MS m/z 463 [M−H]⁻.

Example 42

Preparation of 5-Chloro-2-(4-(4-isopropylpiperazin-1-yl)phenyl)quinazolin-4(3H)-one

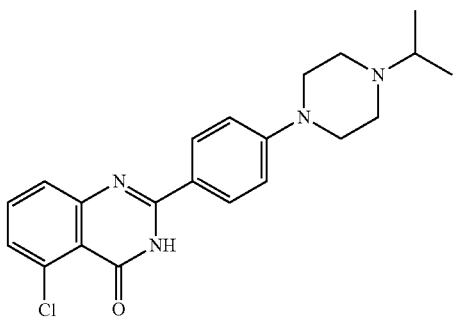 [SMILES: CC(C)N1CCN(c2ccc(-c3nc4cccc(Cl)c4c(=O)[nH]3)cc2)CC1]

A solution of 2-amino-6-chlorobenzamide (0.314 g, 1.85 mmol) and 4-(4-isopropylpiperazin-1-yl)benzaldehyde (0.430 g, 1.85 mmol) in DMA (25 mL) were treated with p-TsOH (0.035 g, 0.185 mmol) and NaHSO$_3$ (0.212 g, 2.04 mmol), and the mixture was heated at 140° C. for 18 hours. Then, the mixture was cooled, diluted with CH$_2$Cl$_2$ (200 mL), and washed with saturated NaHCO$_3$ (100 mL). The organic phase was dried over anhydrous MgSO$_4$, filtered, concentrated, and purified by silica gel chromatography, eluting with 1:1 CH$_2$Cl$_2$/92:7:1 CHCl$_3$/MeOH/concentrated NH$_4$OH to 100% 92:7:1 CHCl$_3$/MeOH/concentrated NH$_4$OH to 100% 6:3:1 CHCl$_3$/MeOH/concentrated NH$_4$OH. The resulting solids were rechromatographed with 9:1 CH$_2$Cl$_2$/MeOH to afford the title compound as a white solid. $^1$H NMR (300 MHz, DMSO-d$_6$): δ 12.24 (br s, 1H), 8.11 (d, J=8.8 Hz, 2H), 7.66-7.71 (m, 1H), 7.59 (d, J=7.9 Hz, 1H), 7.42 (d, J=7.4 Hz, 1H), 7.03 (d, J=8.6 Hz, 2H), 3.28-3.34 (m, 4H), 2.64-2.73 (m, 1H), 2.55-2.59 (m, 4H), 1.01 (d, J=6.4 Hz, 6H). ESI MS m/z 383 [M+H]$^+$.

Example 43

Preparation of 2-(4-((3R,5S)-4-Isopropyl-3,5-dimethylpiperazin-1-yl)phenyl)-5,7-dimethoxyquinazolin-4(3H)-one

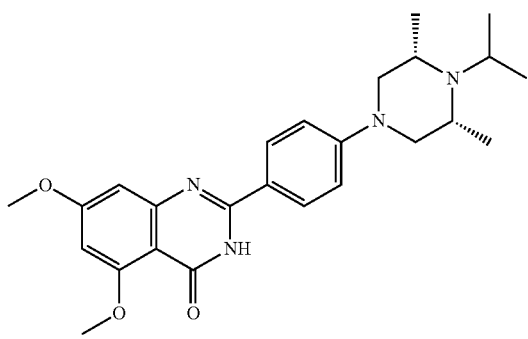 [SMILES: COc1cc(OC)c2c(=O)[nH]c(-c3ccc(N4C[C@@H](C)N(C(C)C)[C@@H](C)C4)cc3)nc2c1]

To a mixture of 4-(3,5-dimethylpiperazin-1-yl)benzaldehyde (1.0 g, 4.6 mmol) and K$_2$CO$_3$ (1.3 g, 9.2 mmol) in CH$_3$CN (10 mL) was added 2-iodopropane (2.3 mL, 22.9 mmol) and the reaction was stirred at reflux temperature overnight. Additional 2-iodopropane (2.3 mL, 22.9 mmol) and K$_2$CO$_3$ (1.3 g, 9.2 mmol) were added and the reaction was continued to reflux overnight. The mixture was concentrated in vacuo and purified by flash chromatography on silica gel, eluting with 1% to 10% MeOH/CH$_2$Cl$_2$, to afford 4-(4-isopropyl-3,5-dimethylpiperazin-1-yl)benzaldehyde (0.550 g, 46%).

A mixture of 4-(4-isopropyl-3,5-dimethylpiperazin-1-yl)benzaldehyde (0.400 g, 1.50 mmol), NaHSO$_3$ (0.195 g, 1.80 mmol), and p-TsOH (0.030 g, 0.15 mmol) was added to a solution of 2-amino-4,6-dimethoxybenzamide (0.400 g, 2.40 mmol) in DMA (10 mL). The reaction was stirred at 140° C. for 4 hours, then at room temperature overnight. The mixture was diluted with H$_2$O and extracted with CH$_2$Cl$_2$. The organics were washed with brine, dried (Na$_2$SO$_4$), filtered, and concentrated in vacuo. Purification by flash chromatography on silica gel, eluting with 1% to 10% MeOH/CH$_2$Cl$_2$, followed by reverse-phase chromatography, eluting with 10% to 90% CH$_3$CN in H$_2$O, afforded the title compound (0.114 g, 17%). $^1$H NMR (300 MHz, DMSO-d$_6$): δ 11.68 (s, 1H), 8.09 (d, J=8.9 Hz, 2H), 6.78 (d, J=9.0 Hz, 2H), 6.66 (s, 1H), 6.44 (s, 1H), 3.87 (s, 3H), 3.83 (s, 3H), 3.41-3.44 (m, 2H), 3.11-3.23 (m, 5H), 1.00-1.03 (m, 12H). ESI MS m/z 437 [M+H]$^+$.

Example 44

Preparation of 5,7-Dimethoxy-2-(4-(piperidin-4-yl)phenyl)quinazolin-4(3H)-one

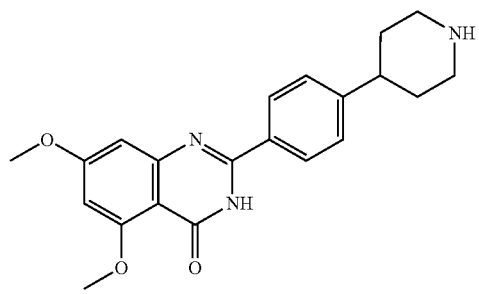 [SMILES: COc1cc(OC)c2c(=O)[nH]c(-c3ccc(C4CCNCC4)cc3)nc2c1]

To a solution of tert-butyl 4-(4-(5,7-dimethoxy-4-oxo-3,4-dihydroquinazolin-2-yl)phenyl)piperidine-1-carboxylate (0.210 g, 0.45 mmol) in 1,4-dioxane (2 mL) was added 4M HCl in 1,4-dioxane (1 mL). The resulting solution was stirred at room temperature for 5 hours. Then, the mixture was concentrated in vacuo and the resulting material was purified by flash chromatography on silica gel, eluting with 0% to 10% of MeOH/CH$_2$Cl$_2$. The residue was further purified by flash chromatography on silica gel, eluting with 100% of 92:7:1 CHCl$_3$/MeOH/concentrated NH$_4$OH followed by 100% of 6:3:1 CHCl$_3$/MeOH/concentrated NH$_4$OH, to afford the title compound (0.030 g, 18%). $^1$H NMR (300 MHz, DMSO-d$_6$): δ 8.11 (d, J=8.3 Hz, 2H), 7.37 (d, J=8.2 Hz, 2H), 6.73 (s, 1H), 6.53 (s, 1H), 3.89 (s, 3H), 3.85 (s, 3H), 2.92-3.20 (m, 2H), 2.56-2.81 (m, 3H), 2.35-2.57 (m, 2H), 1.67-1.88 (m, 2H), 1.38-1.67 (m, 2H). ESI MS m/z 366 [M+H]$^+$.

Example 45

Preparation of 5,7-Dimethoxy-2-(4-(3-(methylamino)pyrrolidin-1-yl)phenyl)quinazolin-4(3H)-one

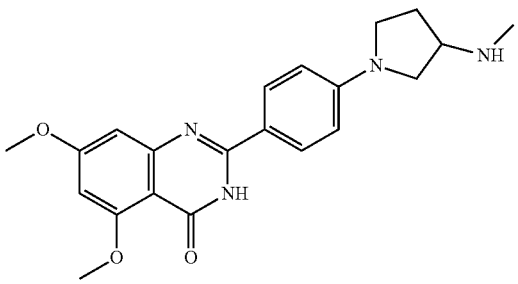

A mixture of N-(1-(4-(5,7-dimethoxy-4-oxo-3,4-dihydroquinazolin-2-yl)phenyl)pyrrolidin-3-yl)-N-methylacetamide (0.500 g, 1.18 mmol) and 2 N HCl (80 mL) was heated at 100° C. for 4 hours, cooled, basified to pH 9, extracted with CH$_2$Cl$_2$ (2×200 mL), dried (MgSO$_4$), filtered, and concentrated. The residue was purified by flash chromatography on silica gel, eluting with 1:1 CH$_2$Cl$_2$/92:7:1 CHCl$_3$/MeOH/concentrated NH$_4$OH to 100% 92:7:1 CHCl$_3$/MeOH/concentrated NH$_4$OH to 6:3:1 CHCl$_3$/MeOH/concentrated NH$_4$OH, to afford the title compound (0.210 g, 47%) as a pale yellow solid. $^1$H NMR (300 MHz, DMSO-d$_6$): δ 11.65 (br s, 1H), 8.08 (d, J=8.7 Hz, 2H), 6.65 (s 1H), 6.55 (d, J=7.8 Hz, 2H), 6.43 (s, 1H), 3.88 (s, 3H), 3.83 (s, 3H), 3.46-3.49 (m, 1H), 3.38-3.42 (m, 1H), 3.26-3.28 (m, 2H), 3.07-3.10 (m, 1H), 2.31 (s, 3H), 2.08-2.11 (m, 1H), 1.81-1.84 (m, 1H). ESI MS m/z 381 [M+H]$^+$.

Example 46

Preparation of Tert-butyl 4-(4-(5,7-dimethoxy-4-oxo-3,4-dihydroquinazolin-2-yl)phenyl)piperidine-1-carboxylate

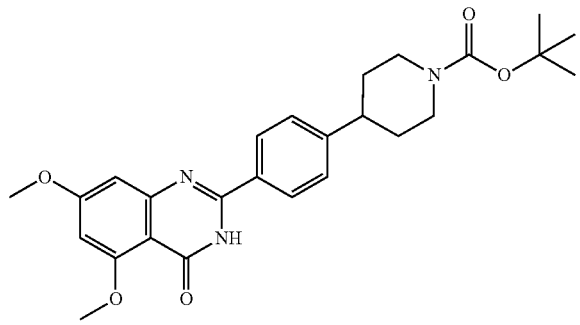 [SMILES: COc1cc(OC)c2c(=O)[nH]c(-c3ccc(C4CCN(C(=O)OC(C)(C)C)CC4)cc3)nc2c1]

A solution of 2-(4-bromophenyl)-5,7-dimethoxyquinazolin-4(3H)-one (1.1 g, 3.23 mmol), K$_2$CO$_3$ (1.3 g, 9.69 mmol), PdCl$_2$(dppf) (0.261 g, 0.32 mmol) and tert-butyl 4-(4,4,5,5-tetramethyl-1,3,2-dioxaborolan-2-yl)-5,6-dihydropyridine-1(2H)-carboxylate (1.0 g, 3.23 mmol) in DMF (50 mL) was heated to 110° C. overnight. The resulting solution was concentrated in vacuo and the material was purified twice by flash chromatography on silica gel, eluting with 0% to 5% of MeOH/CH$_2$Cl$_2$. The residue was further purified by flash chromatography on silica gel, eluting with 10% to 50% of EtOAc/CH$_2$Cl$_2$, to afford tert-butyl 4-(4-(5,7-dimethoxy-4-oxo-3,4-dihydroquinazolin-2-yl)phenyl)-5,6-dihydropyridine-1(2H)-carboxylate (0.030 g, 49%) as a light yellow solid.

A solution of tert-butyl 4-(4-(5,7-dimethoxy-4-oxo-3,4-dihydroquinazolin-2-yl)phenyl)-5,6-dihydropyridine-1(2H)-carboxylate (0.160 g, 0.34 mmol) in EtOH (10 mL) and HOAc (5 mL) was purged with nitrogen, and 10% Pd/C (0.016 g) was added. The mixture was stirred under 1 atmosphere of hydrogen overnight. Then, the solution was filtered through Celite, with MeOH washings, and the filtrate was concentrated in vacuo. The material was purified by flash chromatography on silica gel, eluting with 30% to 70% of 92:7:1 CHCl$_3$/MeOH/concentrated NH$_4$OH in CH$_2$Cl$_2$, to afford the title compound (0.160 g, 100%). $^1$H NMR (300 MHz, DMSO-d$_6$): δ 11.91 (s, 1H), 8.11 (d, J=8.3 Hz, 2H), 7.40 (d, J=8.5 Hz, 2H), 6.73 (s, 1H), 6.53 (s, 1H), 4.00-4.22 (m, 2H), 3.89 (s, 3H), 3.85 (s, 3H), 2.65-2.97 (m, 3H), 1.68-1.88 (m, 2H), 1.48-1.68 (m, 2H), 1.42 (s, 9H). ESI MS m/z 466 [M+H]$^+$.

Example 47

Preparation of N-(1-(4-(5,7-dimethoxy-4-oxo-3,4-dihydroquinazolin-2-yl)phenyl)pyrrolidin-3-yl)-N-methylacetamide

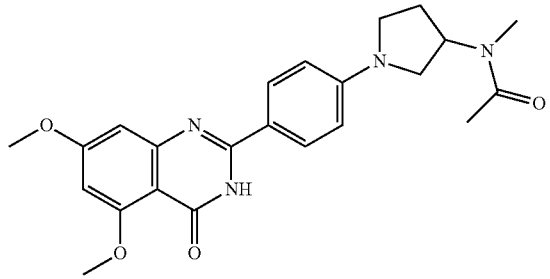 [SMILES: COc1cc(OC)c2c(=O)[nH]c(-c3ccc(N4CCC(N(C)C(C)=O)C4)cc3)nc2c1]

A solution of 4-fluorobenzaldehyde (2.01 g, 16.2 mmol) and N-methyl-N-(pyrrolidin-3-yl)acetamide (1.92 g, 13.5 mmol) in DMF (20 mL) was treated with K$_2$CO$_3$ (2.24 g, 16.2 mmol). The mixture was heated at 120° C. under nitrogen for 18 hours, cooled to room temperature, diluted with ethyl acetate (150 mL), washed with brine, dried (Na$_2$SO$_4$), filtered, and concentrated. The residue was purified by flash chromatography on silica gel, eluting with 100% ethyl acetate to 10% methanol/ethyl acetate, to afford N-(1-(4-formylphenyl)pyrrolidin-3-yl)-N-methylacetamide.

A solution of 2-amino-4,6-dimethoxybenzamide (0.797 g, 4.07 mmol) and N-(1-(4-formylphenyl)pyrrolidin-3-yl)-N-methylacetamide (1.0 g, 4.07 mmol) in DMA (75 mL) was treated with NaHSO$_3$ (0.466 g, 4.5 mmol) and p-TsOH (0.078 g, 0.41 mmol). The mixture was heated at 150° C. for 15 hours, cooled to room temperature, diluted with CH$_2$Cl$_2$ (200 mL), and washed with saturated NaHCO$_3$ (100 mL) and water (200 mL). The organic phase was dried over anhydrous MgSO$_4$, filtered, and concentrated. The residue was purified by flash chromatography on silica gel, eluting with 1:1 CH$_2$Cl$_2$/92:7:1 CHCl$_3$/MeOH/concentrated NH$_4$OH to 100% 92:7:1 CHCl$_3$/MeOH/concentrated NH$_4$OH, to afford the title compound (1.5 g, 88%) as a light brown solid. $^1$H NMR (300 MHz, DMSO-d$_6$): δ 11.68 (s, 1H), 8.10 (d, J=8.8 Hz, 2H), 6.55-6.67 (m, 3H), 6.44 (d, J=2.2 Hz, 1H), 4.67-5.22 (m, 1H), 3.88 (s, 3H), 3.83 (s, 3H), 3.43-3.60 (m, 2H), 3.22-3.26 (m, 2H), 2.76-2.89 (m, 3H), 1.91-2.27 (m, 5H). ESI MS m/z 423 [M+H]$^+$.

Example 48

Preparation of 2-(4-(4-(Isopropylamino)piperidin-1-yl)phenyl)-5,7-dimethoxyquinazolin-4(3H)-one

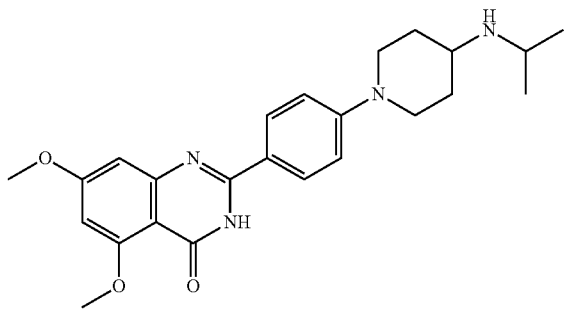 [SMILES: COc1cc(OC)c2c(=O)[nH]c(-c3ccc(N4CCC(NC(C)C)CC4)cc3)nc2c1]

A solution of N-(1-(4-(5,7-dimethoxy-4-oxo-3,4-dihydroquinazolin-2-yl)phenyl)piperidin-4-yl)-N-isopropylacetamide (0.130 g, 0.27 mmol) in 2 N HCl (8 mL) was heated to reflux and stirred overnight. The resulting solution was cooled to room temperature, basified with 2 N NaOH (pH 14), and extracted with CH$_2$Cl$_2$. The solution was concentrated in vacuo and the residue was purified by flash chromatography on silica gel, eluting with 30% to 100% of 92:7:1 CHCl$_3$/MeOH/concentrated NH$_4$OH in CH$_2$Cl$_2$, to afford the title compound (0.060 g, 52%). $^1$H NMR (300 MHz, DMSO-d$_6$): δ 8.07 (d, J=9.0 Hz, 2H), 6.99 (d, J=9.1 Hz, 2H), 6.67 (s, 1H), 6.46 (s, 1H), 3.75-3.95 (m, 8H), 2.81-2.99 (m, 3H), 2.69-2.79 (m, 1H), 1.79-1.92 (m, 2H), 1.14-1.37 (m, 3H), 0.97 (d, J=6.1 Hz, 6H). ESI MS m/z 423 [M+H]$^+$.

Example 49

Preparation of 5,7-Dimethoxy-2-(4-(3-methylpiperazin-1-yl)phenyl)quinazolin-4(3H)-one

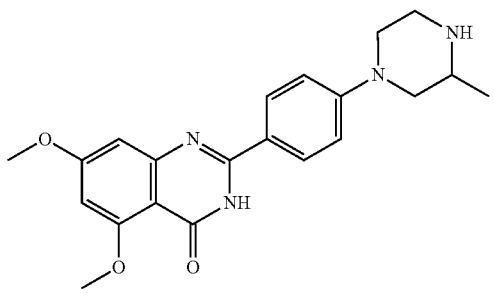

A solution of 2-(4-(4-acetyl-3-methylpiperazin-1-yl)phenyl)-5,7-dimethoxyquinazolin-4(3H)-one (0.340 g, 0.80 mmol) in 2 N HCl (5 mL) was heated to reflux and stirred for 3 days. Then, the resulting solution was cooled to room temperature, basified with 2 N NaOH, extracted with $CH_2Cl_2$, and concentrated in vacuo. The material was purified by flash chromatography on silica gel, eluting with 50% to 100% of 92:7:1 $CHCl_3$/MeOH/concentrate $NH_4OH$ in $CH_2Cl_2$, to afford the title compound (0.03 g, 9%). $^1$H NMR (300 MHz, DMSO-$d_6$): δ 10.76 (s, 1H), 8.08 (d, J=8.9 Hz, 2H), 6.99 (d, J=9.1 Hz, 2H), 6.67 (s, 1H), 6.46 (s, 1H), 3.88 (s, 3H), 3.83 (s, 3H), 3.62-3.79 (m, 2H), 2.90-3.04 (m, 1H), 2.57-2.85 (m, 4H), 2.20-2.39 (m, 1H), 1.03 (d, J=6.3 Hz, 3H). ESI MS m/z 381 [M+H]$^+$.

Example 50

Preparation of N-Benzyl-N-(1-(5-(5,7-dimethoxy-4-oxo-3,4-dihydroquinazolin-2-yl)pyridin-2-yl)piperidin-4-yl)acetamide

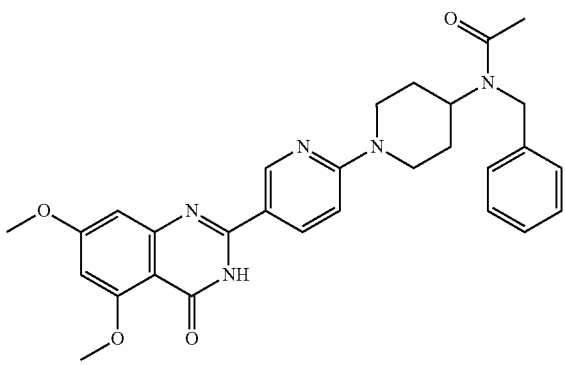 [SMILES: COc1cc(OC)c2c(=O)[nH]c(-c3ccc(N4CCC(N(Cc5ccccc5)C(C)=O)CC4)nc3)nc2c1]

To a solution of tert-butyl 4-oxopiperidine-1-carboxylate (10.0 g, 50.2 mmol) and benzylamine (2.7 mL, 25.1 mmol) in MeOH (30 mL) was added HOAc (1.9 mL, 32.6 mmol), followed by $NaCNBH_3$ (2.0 g, 32.6 mmol) and the reaction was stirred at room temperature overnight. The resulting mixture was quenched with $H_2O$ (5 mL) and concentrated in vacuo. The residue was diluted with 0.1 N HCl and washed with $Et_2O$. The aqueous layer was then basified with 2 N NaOH and extracted with $Et_2O$. The organics were washed with brine, dried over anhydrous $Na_2SO_4$, filtered, and concentrated in vacuo, to afford tert-butyl 4-(benzylamino)piperidine-1-carboxylate (8.1 g, 56%).

To a solution of tert-butyl 4-(benzylamino)piperidine-1-carboxylate (8.1 g, 28.0 mmol) and $Et_3N$ (7.8 mL, 56.0 mmol) in $CH_2Cl_2$ (100 mL) was added acetyl chloride (2.4 mL, 33.5 mmol) and the reaction was stirred at room temperature overnight, then concentrated in vacuo. Purification by flash chromatography on silica gel, eluting with 30% to 60% EtOAc/$CH_2Cl_2$, afforded tert-butyl 4-(N-benzylacetamido)piperidine-1-carboxylate (9.3 g, 99%).

A solution of tert-butyl 4-(N-benzylacetamido)piperidine-1-carboxylate (9.3 g, 28.0 mmol) in dioxane (20 mL) and 4 M HCl/dioxane (14.0 mL, 56.0 mmol) was stirred at room temperature overnight and then concentrated in vacuo. The residue was basified with 2 N NaOH and extracted with EtOAc. The organics were washed with brine, dried ($Na_2SO_4$), filtered, and concentrated in vacuo, to afford N-benzyl-N-(piperidin-4-yl)acetamide (4.4 g, 67%).

To a solution of N-benzyl-N-(piperidin-4-yl)acetamide (1.5 g, 6.3 mmol) and 2-(6-chloropyridin-3-yl)-5,7-dimethoxyquinazolin-4(3H)-one (1.0 g, 3.2 mmol) in DMF (15 mL) was added $K_2CO_3$ (0.875 g, 6.3 mmol) and the reaction was heated at reflux temperature overnight. The resulting mixture was concentrated in vacuo and purified by flash chromatography on silica gel, eluting with 1% to 10% MeOH/$CH_2Cl_2$, to afford the title compound (0.500 g, 30%) as a white solid. $^1$H NMR (300 MHz, DMSO-$d_6$): δ 11.84 (s, 1H), 8.86 (s, 1H), 8.22 (d, J=9.2 Hz, 1H), 7.33-7.37 (m, 1H), 7.14-7.27 (m, 4H), 6.88-6.96 (m, 1H), 6.66 (d, J=1.5 Hz, 1H), 6.46 (d, J=1.5 Hz, 1H), 4.44-4.58 (m, 4.5H), 4.10-4.20 (m, 0.5H), 3.87 (s, 3H), 3.83 (s, 3H), 2.86-2.98 (m, 2H), 2.25 (s, 1.5H), 1.95 (s, 1.5H), 1.45-1.77 (m, 4H). ESI/APCI MS m/z 514 [M+H]$^+$.

Example 51

Preparation of 2-(6-(4-(Benzylamino)piperidin-1-yl)pyridin-3-yl)-5,7-dimethoxyquinazolin-4(3H)-one

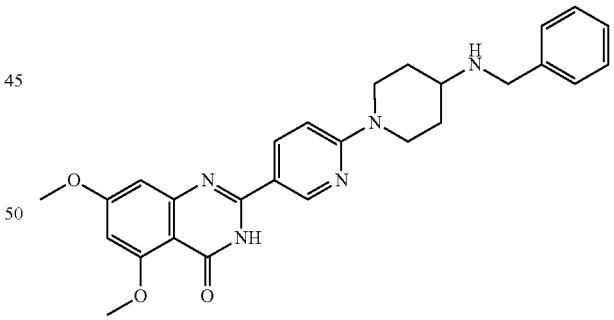

A solution of N-benzyl-N-(1-(5-(5,7-dimethoxy-4-oxo-3,4-dihydroquinazolin-2-yl)pyridin-2-yl)piperidin-4-yl)acetamide (0.200 g, 0.39 mmol) in 2 N HCl (15 mL) was refluxed for 3 days. The resulting mixture was basified with 2 N NaOH and extracted with $CH_2Cl_2$. The organics were washed with brine, dried over anhydrous $Na_2SO_4$, filtered, and concentrated in vacuo. Purification by flash chromatography on silica gel, eluting with 10% to 100% of 92:7:1 $CHCl_3$/MeOH/concentrated $NH_4OH$ in $CH_2Cl_2$, afforded the title compound (0.110 g, 60%) as a white solid. $^1$H NMR (300 MHz, DMSO-$d_6$): δ 11.11 (br s, 1H), 8.89 (d, J=2.3 Hz, 1H), 8.22-8.26 (m, 1H), 7.28-7.37 (m, 4H), 7.18-7.23 (m, 1H), 6.91 (d, J=7.2 Hz, 1H), 6.67 (d, J=2.2 Hz, 1H), 6.46 (d, J=2.2 Hz, 1H), 4.27-4.31 (m, 2H), 3.88 (s, 3H), 3.83 (s, 3H), 3.76 (s, 2H), 3.00-3.11 (m, 2H), 2.62-2.69 (m, 1H), 1.88-1.91 (m, 2H), 1.25-1.31 (m, 2H). ESI MS m/z 472 [M+H]$^+$.

Example 52

Preparation of 4-(4-(5,7-Dimethoxy-4-oxo-3,4-dihydroquinazolin-2-yl)phenyl)piperazine-1-carbaldehyde

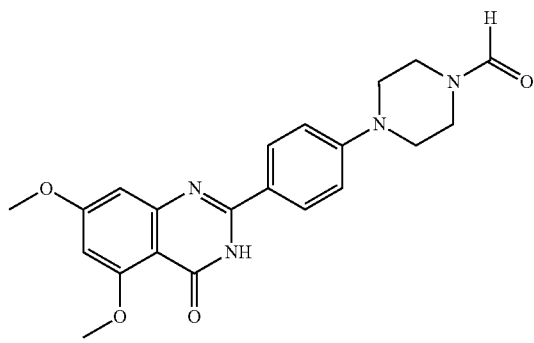 [SMILES: COc1cc(OC)c2c(=O)[nH]c(-c3ccc(N4CCN(C=O)CC4)cc3)nc2c1]

A mixture of methyl formate (75 mL) and 5,7-dimethoxy-2-(4-(piperazin-1-yl)phenyl)quinazolin-4(3H)-one (0.300 g, 0.82 mmol) was heated at reflux for 48 hours. The mixture was concentrated, and purified by silica gel chromatography, eluting with 1:1 CH$_2$Cl$_2$/92:7:1 CHCl$_3$/MeOH/concentrated NH$_4$OH, to afford the title compound (0.320 g, 99%) as a white solid. $^1$H NMR (300 MHz, DMSO-d$_6$): δ 11.79 (br s, 1H), 8.10-8.19 (m, 3H), 7.06 (d, J=9.1 Hz, 2H), 6.69 (d, J=2.3 Hz, 1H), 6.48 (d, J=2.3 Hz, 1H), 3.88 (s, 3H), 3.84 (s, 3H), 3.46-3.59 (m, 4H), 3.32-3.38 (m, 4H). APCI MS m/z 393 [M−H]$^-$.

Example 53

Preparation of 5,7-Dimethoxy-2-(4-(4-oxopiperidin-1-yl)phenyl)pyrido[2,3-d]pyrimidin-4(3H)-one

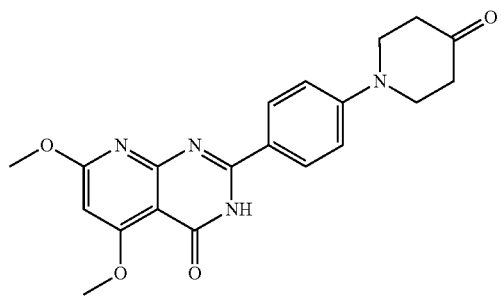 [SMILES: COc1cc(OC)c2c(=O)[nH]c(-c3ccc(N4CCC(=O)CC4)cc3)nc2n1]

To a solution of 2-[4-(4-hydroxy-piperazin-1-yl)-phenyl]-5,7-dimethoxy-3H-pyrido[2,3-d]pyrimidin-4-one (160 mg, 0.418 mmol) in DMSO (4.0 mL), 1,2-benziodexol-3(1H)-one-1-hydroxy-1-oxide (IBX) (178 mg, 0.635 mmol) was added and the reaction mixture was kept at 50° C. for 16 hours. Water was added and the precipitated solid was filtered to give crude product, which was purified by column chromatography (silica gel 230-400 mesh; eluting with 3% methanol in dichloromethane) to obtain the title compound as a yellow solid. Yield: 0.70 g (44.0%). MP>350° C. $^1$H NMR (400 MHz, CDCl$_3$): δ 12.15 (s, 1H), 8.18 (d, J=9.2 Hz, 2H), 7.02 (d, J=9.2 Hz, 2H), 6.33 (s, 1H), 3.95 (s, 3H), 3.90 (s, 3H), 3.77 (t, J=6.4 Hz, 4H), 2.45 (t, J=6.4 Hz, 4H).

Example 54

Preparation of 2-(2-(Hydroxymethyl)-1H-indol-5-yl)-5,7-dimethoxyquinazolin-4(3H)-one

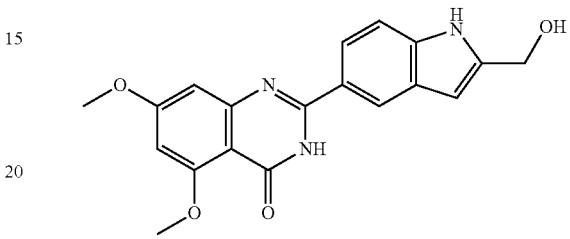

To a solution of N-(4-formyl-phenyl)-acetamide (1.25 g, 7.67 mmol) in trifluoroacetic acid (70 mL) was slowly added thallium(III)trifluoroacetate (5.00 g, 9.20 mmol). The reaction mixture was stirred at room temperature for 30 minutes. Then, a solution of sodium iodide (1.19 g, 7.95 mmol) in water (10 mL) was added slowly. The color changed to dark purple and a lot of solid was formed. Stirring continued at room temperature for 16 hours. Solvent was evaporated to half of the volume, and water (50 mL) was added. The pH was adjusted to approximately 13 with 4 N NaOH solution. The mixture was extracted with ethyl acetate (2×100 mL). The organic phase was dried over anhydrous Na$_2$SO$_4$ and concentrated on a rotary evaporator. The solid obtained was washed with ethyl acetate (2×5 mL), ether (2×10 mL), and dried under vacuum to give N-(4-formyl-2-iodo-phenyl)-acetamide as an off-white solid. Yield: 0.760 g (34%).

To a degassed solution of N-(4-formyl-2-iodo-phenyl)-acetamide (0.760 g, 2.63 mmol) in anhydrous DMF (20 mL) were added bis(triphenylphosphine)palladium(II) dichloride (90 mg, 0.13 mmol), copper (I) iodide (0.03 g, 0.13 mmol), 1,1,3,3-tetramethyl guanidine (1.51 g, 13.1 mmol), and propargyl alcohol (0.210 g, 3.68 mmol). The reaction mixture was stirred at room temperature for 2 hours and then at 80° C. for 24 hours under nitrogen. Solvent was evaporated under reduced pressure. Water (100 mL) was added and the mixture was extracted with ethyl acetate (200 mL). The organic phase was backwashed with water (2×100 mL), brine (100 mL), and dried over anhydrous Na$_2$SO$_4$. Solvent was evaporated and crude compound was purified by the Simpliflash system (60% ethyl acetate in hexanes as eluent) to give 2-hydroxymethyl-1H-indole-5-carbaldehyde as a pale yellow solid. Yield: 0.10 g (22%).

To a solution of 2-hydroxymethyl-1H-indole-5-carbaldehyde (90 mg, 0.51 mmol) and 2-amino-4,6-dimethoxy-benzamide (0.15 g, 0.77 mmol) in N,N-dimethylacetamide (5 mL) were added sodium hydrogen sulfite (58.5 wt %) (0.14 g, 0.77 mmol) and p-toluenesulfonic acid (20 mg, 0.10 mmol). The reaction mixture was stirred at 120° C. for 16 hours under nitrogen, cooled to room temperature, and concentrated under reduced pressure. Water (20 mL) was added. The separated solid was filtered, washed with water (20 mL) and ether (20 mL), and dried under vacuum. Crude compound was purified by column chromatography (silica gel 230-400 mesh; 0-5% methanol in CH$_2$Cl$_2$ as eluent), to give the title compound as an off-white solid. Yield: 0.06 g (33%). MP 264-265° C. $^1$H NMR (400 MHz, DMSO-d$_6$): δ 11.85 (br s, 1H), 11.36 (s, 1H), 8.39 (s, 1H), 7.93 (dd, J=8.6 and 1.6 Hz, 1H), 7.44 (d, J=9.0 Hz, 1H), 6.73 (d, J=2.3 Hz, 1H), 6.49 (d, J=2.4 Hz, 1H), 6.41 (s, 1H). 5.34 (t, J=5.8 Hz, 1H), 4.63 (d, J=5.5 Hz, 2H), 3.90 (s, 3H), 3.85 (s, 3H).

Example 55

Preparation of 2-(2-(2-Hydroxyethyl)-1H-indol-5-yl)-5,7-dimethoxyquinazolin-4(3H)-one

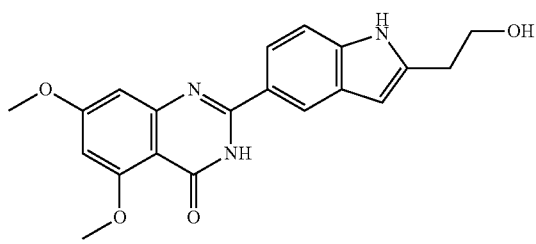 [SMILES: COc1cc(OC)c2c(=O)[nH]c(-c3ccc4[nH]c(CCO)cc4c3)nc2c1]

To a stirred solution of 4-amino-3-iodo-benzoic acid methyl ester (11.1 g, 40.0 mmol) in pyridine (80 mL) was added acetyl chloride (3.30 g, 42.0 mmol) at 0° C. under nitrogen. Stirring continued at 0° C. for 30 minutes. The ice-bath was removed, and stirring continued at room temperature for 16 hours. Pyridine was evaporated under reduced pressure. The residue was taken in ethyl acetate (300 mL). The organic phase was washed with 2 N aqueous HCl (200 mL), water (200 mL), brine (200 mL), and then dried over anhydrous Na$_2$SO$_4$. Removal of solvent gave 4-acetylamino-3-iodo-benzoic acid methyl ester as a white solid. Yield: 12.71 g (99%).

Lithium aluminium hydride (2.43 g, 64.1 mmol) was taken in a dry, three-necked, round bottom flask. Anhydrous THF (80 mL) was added and cooled to −10° C. A solution of 4-acetylamino-3-iodo-benzoic acid methyl ester (10.2 g, 32.0 mmol) in anhydrous THF (60 mL) was added dropwise at −10° C. over a period of 45 minutes under nitrogen. Stirring was continued at −10° C. for 1 hour. The reaction mixture was quenched with saturated sodium sulfate aqueous solution. The reaction mixture was then filtered, and the filtrate was concentrated. The solid was washed with methanol. The combined organic phases were dried over anhydrous Na$_2$SO$_4$. The solvent was evaporated. The crude compound was purified by the Simpliflash system (5% methanol in CH$_2$Cl$_2$ as eluent), to give N-(4-hydroxymethyl-2-iodo-phenyl)-acetamide as a white solid. Yield: 6.36 g (68%).

To a solution of IBX (0.93 g, 3.3 mmol) in dimethylsulfoxide (3.5 mL) was added N-(4-hydroxymethyl-2-iodo-phenyl)-acetamide (0.87 g, 3.0 mmol) and the reaction mixture was stirred at room temperature for 1 hour. Water (50 mL) was added and the solid was separated by filtration, and washed with ethyl acetate (20 mL). The filtrate was collected and extracted with ethyl acetate (200 mL). The organic phase was washed with brine (100 mL) and dried over anhydrous Na$_2$SO$_4$. Removal of solvent gave N-(4-formyl-2-iodo-phenyl)-acetamide as a light brown solid. Yield: 0.82 g (95%).

To a degassed solution of N-(4-formyl-2-iodo-phenyl)-acetamide (0.810 g, 2.82 mmol) in DMF (25 mL) and triethylamine (5 mL) were added PdCl$_2$(PPh$_3$)$_2$ (0.10 g, 0.14 mmol) and copper (I) iodide (0.16 g, 0.85 mmol). A degassed solution of but-3-yn-1-ol (0.27 g, 0.29 mmol) in DMF (8 mL) and triethylamine (2 mL) was added at 80° C. over a period of 1 hour under nitrogen. After the addition, the reaction mixture was stirred at 80° C. for 4 hours, cooled to room temperature, and concentrated under reduced pressure. The residue was diluted with water (100 mL) and extracted with ethyl acetate (200 mL). The organic phase was washed with brine (100 mL) and dried over anhydrous Na$_2$SO$_4$. Removal of solvent gave N-[4-formyl-2-(4-hydroxy-but-1-ynyl)-phenyl]-acetamide as a brown solid. Crude yield: 0.85 g (100%). The crude material was used in next step without further purification.

To a solution of N-[4-formyl-2-(4-hydroxy-but-1-ynyl)-phenyl]-acetamide (0.85 g, approximately 2.80 mmol) in THF (20 mL) was added a THF solution of TBAF (6.0 mL, 6.0 mmol) and the reaction mixture was stirred at reflux for 36 hours under nitrogen and cooled to room temperature. Solvent was evaporated and the residue was taken in ethyl acetate (200 mL). The organic phase was washed with water (2×100 mL), brine (100 mL) and dried over anhydrous Na$_2$SO$_4$. Solvent was evaporated; crude compound was purified by simpliflash system (50% ethyl acetate in hexanes as eluent) to give 2-(2-hydroxy-ethyl)-1H-indole-5-carbaldehyde as yellow solid. Yield: 0.31 g (58% for two steps).

To a solution of 2-(2-hydroxy-ethyl)-1H-indole-5-carbaldehyde (0.300 g, 1.58 mmol) and 2-amino-4,6-dimethoxybenzamide (0.370 g, 1.90 mmol) in N,N-dimethylacetamide (5 mL) were added sodium hydrogen sulfite (58.5 wt %) (0.350 g, 1.90 mmol) and p-toluenesulfonic acid monohydrate (60 mg, 0.32 mmol). The reaction mixture was stirred at 120° C. for 16 hours under nitrogen and cooled to room temperature. The solvent was evaporated under reduced pressure. Water (20 mL) was added and the solid was separated by filtration, washed with water (30 mL) and dried under vacuum. Crude compound was purified by the Simpliflash system (5:20:75 methanol/ethyl acetate/CH$_2$Cl$_2$ as eluent) to give the title compound as an off-white solid. Yield: 0.22 g (38%). MP 237-238° C. $^1$H NMR (400 MHz, DMSO-d$_6$): δ 11.83 (br s, 1H), 11.20 (s, 1H), 8.34 (s, 1H), 7.90 (d, J=8.2 Hz, 1H), 7.37 (d, J=8.6 Hz, 1H), 6.73 (d, J=1.9 Hz, 1H), 6.48 (d, J=1.9 Hz, 1H), 6.30 (s, 1H), 4.81 (t, J=5.1 Hz, 1H), 3.89 (s, 3H), 3.84 (s, 3H), 3.75 (q, J=6.63 Hz, 2H), 2.89 (t, J=7.0 Hz, 2H).

Example 56

Preparation of 5,7-Dimethoxy-2-(2-(pyrrolidin-1-ylmethyl)-1H-indol-5-yl)quinazolin-4(3H)-one

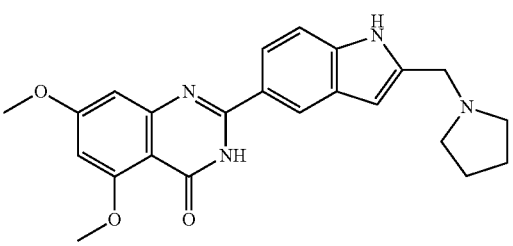 [SMILES: COc1cc(OC)c2c(=O)[nH]c(-c3ccc4[nH]c(CN5CCCC5)cc4c3)nc2c1]

To a mixture of 5-bromo-1H-indole-2-carboxylic acid (1.0 g, 4.2 mmol), 1-ethyl-3-(3'-dimethylaminopropyl)carbodiimide hydrochloride (EDCl) (1.1 g, 5.9 mmol), 1-hydroxybenzotriazole hydrate (HOBt) (0.62 g, 4.6 mmol) in THF (20 mL) was added 4-methylmorpholine (NMM) (0.65 mL, 5.9 mmol). After 10 minutes, pyrrolidine (0.73 mL, 8.8 mmol) was added. The mixture was stirred at room temperature under nitrogen for 17 hours. The solvent was removed under reduced pressure. Water was added, stirred for 0.5 hours. The solid was filtered, washed with water, and dried in air to afford (5-bromo-1H-indol-2-yl)-pyrrolidin-1-yl-methanone as a pale yellow solid. Yield: 1.2 g (95%).

To a suspension of (5-bromo-1H-indol-2-yl)-pyrrolidin-1-yl-methanone (0.53 g, 1.8 mmol) in THF (50 mL) at 0° C. was slowly added lithium aluminum hydride (0.20 g, 5.4 mmol). The mixture was stirred under nitrogen at 0° C. for a while and the cooling bath was allowed to warm to room temperature. The mixture was then stirred at room temperature for 17 hours. The reaction was quenched by careful, successive, dropwise addition of water (0.2 mL), 15% NaOH aqueous solution (0.2 mL), and water (0.6 mL). The solid was filtered and washed with MeOH and $CH_2Cl_2$. The filtrate was concentrated to dryness, and dried under vacuum, to give 5-bromo-2-pyrrolidin-1-ylmethyl-1H-indole as a white solid. Yield: 0.45 g (90%).

To a suspension of potassium hydride (30 wt % dispersion in mineral oil) (96 mg, 0.72 mmol) in ether (20 mL) at 0° C. was added 5-bromo-2-pyrrolidin-1-ylmethyl-1H-indole (0.20 g, 0.72 mmol). After stirring for 30 minutes, the reaction mixture was cooled to −78° C., and t-BuLi solution (1.7 M in pentane; 0.93 mL, 1.58 mmol) was added. The mixture was stirred at −78° C. for 15 minutes, then at −20° C. for approximately 3 min, and then it was cooled down to −78° C. again. DMF was added. The mixture was stirred under nitrogen at −78° C. for a while and the cooling bath was allowed to warm to room temperature. Saturated $NaHCO_3$ aqueous solution (approximately 5 mL) was added. The mixture was extracted with dichloromethane. The organic solution was dried over $Na_2SO_4$, and concentrated to dryness to afford a mixture of the desired product and starting material, at about a 1:1 ratio, from the NMR spectrum. The crude product (approximately 0.2 g) was used for next reaction without any further purification.

A mixture of 2-amino-4,6-dimethoxy-benzamide (0.20 g, 1.0 mmol), crude 2-pyrrolidin-1-ylmethyl-1H-indole-5-carbaldehyde (0.23 g, 1.0 mmol), p-toluenesulfonic acid monohydrate (0.38 g, 2.0 mmol), and sodium bisulfite (0.42 g, 4.0 mmol) in N,N-dimethylacetamide (5 mL) was stirred at 115° C. under $N_2$ for 17 hours and cooled to room temperature. The mixture was diluted with saturated $Na_2CO_3$ aqueous solution and concentrated to dryness under reduced pressure. The residue was purified by column chromatography on silica gel, eluting with $CH_2Cl_2$:7.0 M $NH_3$ in MeOH (95:5), to afford the title compound as a yellow solid. Yield: 87 mg (22%). MP 168-169.5° C. (decomposition). $^1H$ NMR (400 MHz, $CDCl_3$): δ 9.05 (s, 1H), 8.22 (s, 1H), 7.85 (d, 1H), 7.43 (d, 1H), 6.84 (s, 1H), 6.45 (s, 1H), 6.43 (s, 1H), 3.96 (s, 3H), 3.92 (s, 3H), 3.81 (s, 2H), 2.57 (m, 4H), 1.81 (m, 4H).

Example 57

Preparation of 2-(3-(Hydroxymethyl)-1H-indazol-5-yl)-5,7-dimethoxyquinazolin-4(3H)-one

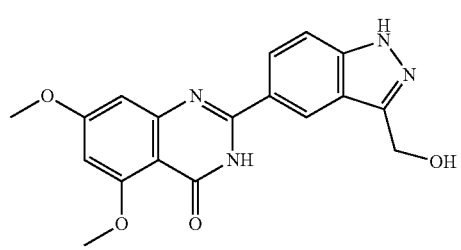 [SMILES: COc1cc(OC)c2c(=O)[nH]c(-c3ccc4[nH]nc(CO)c4c3)nc2c1]

To a solution of sodium nitrite (20.0 g, 290.0 mmol) in THF (1000 mL) and water (50 mL) was added 1H-indole-5-carboxylic acid methyl ester (5.00 g, 28.5 mmol). The mixture was cooled to 0° C. and aqueous 6 N HCl (70 mL) was added dropwise at 0° C. After stirring for 3 days at room temperature, solvent was evaporated, and extracted with ethyl acetate (3×200 mL). The combined organic phase was washed brine (200 mL) and dried over anhydrous $Na_2SO_4$. The solvent was evaporated. The residue was purified by the Simpliflash system (20-30% ethyl acetate in hexanes as eluent), to give 3-formyl-1H-indazole-5-carboxylic acid methyl ester as a yellow solid. Yield: 1.47 g, (25%).

To a solution of 3-formyl-1H-indazole-5-carboxylic acid methyl ester (0.37 g, 1.80 mmol) in anhydrous methanol (15 mL) was added sodium borohydride (68 mg, 1.80 mmol) in small portions at 0° C. After the addition, the reaction mixture was stirred at 0° C. for 30 minutes. Solvent was evaporated; water (100 mL) was added and the mixture was extracted with ethyl acetate (150 mL). The organic phase was washed with brine (100 mL) and dried over anhydrous $Na_2SO_4$. Solvent was evaporated to give 3-hydroxymethyl-1H-indazole-5-carboxylic acid methyl ester as a yellow solid. Yield: 0.32 g (87%).

To a solution of 3-hydroxymethyl-1H-indazole-5-carboxylic acid methyl ester (0.32 g, 1.55 mmol) in a mixture of anhydrous dichloromethane and THF (2:1, 60 mL) was added pyridinium p-toluene sulfonate (0.08 g, 0.31 mmol) and then 3,4-dihydro-2H-pyran (0.19 g, 2.32 mmol) was added. The reaction mixture was stirred at room temperature for 16 hours under nitrogen. Solvent was evaporated; water (100 mL) was added, and the mixture was extracted with ethyl acetate (100 mL). The organic phase was washed with brine (100 mL) and dried over anhydrous $Na_2SO_4$. Removal of solvent gave 3-(tetrahydro-pyran-2-yloxymethyl)-1H-indazole-5-carboxylic acid methyl ester as a yellow gummy material. Yield: 0.55 g (crude). This product was used in next step without further purification.

3-(Tetrahydro-pyran-2-yloxymethyl)-1H-indazole-5-carboxylic acid methyl ester (0.53 g crude, approximately 1.55 mmol) was taken in anhydrous THF (20 mL) and cooled to −10° C. A solution of lithium aluminium hydride (1.0 M solution in THF, 0.12 g, 3.10 mmol) was added drop-wise at −10° C. over a period of 15 minutes under nitrogen. Stirring continued at −10° C. for 1 hour and the reaction was then allowed to warm to room temperature and stirring continued at room temperature for 16 hours. The reaction mixture was carefully quenched with saturated aq. saturated ammonium chloride solution (100 mL). Then, reaction mixture was diluted with ethyl acetate (100 mL). The organic phase was separated, washed with brine (50 mL) and dried over anhydrous $Na_2SO_4$. Solvent was evaporated to give [3-(tetrahydro-pyran-2-yloxymethyl)-1H-indazol-5-yl]-methanol as a yellow gummy material. Yield: 0.40 g (crude). This product was used in the next step without further purification.

To a solution of [3-(tetrahydro-pyran-2-yloxymethyl)-1H-indazol-5-yl]-methanol (0.40 g, 1.50 mmol) in DMSO (3 mL), IBX (0.42 g, 1.50 mmol) was added and the reaction mixture was stirred at room temperature for 3 hours under nitrogen. Water (50 mL) was added; the separated solid was filtered, and the solid was washed with ethyl acetate (100 mL). The filtrate was collected and the organic phase was separated, washed with brine (100 mL), and dried over anhydrous $Na_2SO_4$. Removal of solvent gave 3-(tetrahydro-pyran-2-yloxymethyl)-1H-indazole-5-carbaldehyde as an off-white solid. Yield: 0.33 g (84%).

To a solution of 3-(tetrahydro-pyran-2-yloxymethyl)-1H-indazole-5-carbaldehyde (0.32 g, 1.23 mmol) and 2-amino-4,6-dimethoxy-benzamide (0.24 g, 1.23 mmol) in N,N-dimethylacetamide (10 mL) were added NaHSO$_3$ (58.5 wt %, 0.27 g, 1.48 mmol) and p-toluenesulfonic acid monohydrate (0.05 g, 0.25 mmol); the reaction mixture was heated at 120° C. for 16 hours, then cooled to room temperature. Solvent was removed under reduced pressure. The residue was diluted with water (100 mL). The separated solid was filtered and washed with water and dried under vacuum. The residue was purified by the Simpliflash system (0-5% methanol in CH$_2$Cl$_2$ as eluent) to give the title compound as an off-white solid. Yield: 30 mg (7%). MP 264-266° C. $^1$H NMR (400 MHz, CD$_3$OD): δ 8.60 (s, 1H), 8.10 (d, J=8.98 Hz, 1H), 7.65 (d, J=8.98 Hz, 1H), 6.85 (d, J=1.95 Hz, 1H), 6.55 (d, J=1.95 Hz, 1H), 5.05 (s, 2H), 3.96 (s, 6H).

Example 58

Preparation of 5,7-Dimethoxy-2-(2-(2-(pyrrolidin-1-yl)ethyl)-1H-indol-5-yl)quinazolin-4(3H)-one

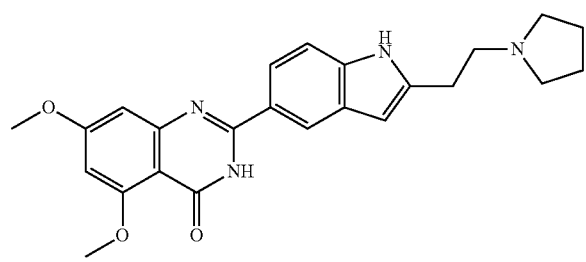 [SMILES: COc1cc(OC)c2c(=O)[nH]c(-c3ccc4[nH]c(CCN5CCCC5)cc4c3)nc2c1]

To a stirred solution of 4-amino-3-iodo-benzoic acid methyl ester (11.1 g, 40.0 mmol) in anhydrous pyridine (80 mL) was added acetyl chloride (3.30 g, 42.0 mmol) at 0° C. under nitrogen. Stirring was continued at 0° C. for 30 minutes. The ice-bath was removed, and stirring continued at room temperature for 16 hours. Pyridine was evaporated under reduced pressure. The residue was taken in ethyl acetate (300 mL). The organic phase washed with 2 N aqueous HCl (200 mL), water (200 mL), brine (200 mL), and was dried over anhydrous Na$_2$SO$_4$. Removal of solvent gave 4-acetylamino-3-iodo-benzoic acid methyl ester as a white solid. Yield: 12.7 g (99%).

To but-3-yn-1-ol (40.0 g, 570.0 mmol) and 3,4-dihydro-2H-pyran (48.0 g, 570.0 mmol) in anhydrous dichloromethane (350 mL) was added pyridium p-toluenesulfonate (0.45 g, 1.80 mmol). The mixture was stirred at room temperature for 16 hours. Solvent was evaporated, and the residue was purified by vacuum distillation to give 2-but-3-ynyloxy-tetrahydro-pyran as a light yellow liquid. Yield: 60.0 g (68%).

To a degassed solution of 4-acetylamino-3-iodo-benzoic acid methyl ester (41.4 g, 130 mmol) in DMF (200 mL) and triethylamine (40 mL) were added PdCl$_2$(PPh$_3$)$_2$ (3.99 g, 5.68 mmol) and copper (I) iodide (7.43 g, 39.0 mmol). A degassed solution of 2-but-3-ynyloxy-tetrahydro-pyran (30.1 g, 195 mmol) in DMF (100 mL) and triethylamine (20 mL) was added at 80° C. over a period of 1 hour under nitrogen. After the addition, the reaction mixture was stirred at 80° C. for 2 hours and then cooled to room temperature. Solvent was evaporated under reduced pressure. Ethyl acetate (200 mL) was added. The solid was filtered, and washed with ethyl acetate. The ethyl acetate solution was washed with brine, and dried over anhydrous Na$_2$SO$_4$. The organic phase was concentrated to dryness, to afford 66.8 g crude 4-acetylamino-3-[4-(tetrahydro-pyran-2-yloxy)-but-1-ynyl]-benzoic acid methyl ester. This was used in next step without further purification.

A solution of crude 4-acetylamino-3-[4-(tetrahydro-pyran-2-yloxy)-but-1-ynyl]-benzoic acid methyl ester (33.4 g, approximately 65 mmol) in anhydrous THF (300 mL) was mixed with a 1.0 M solution of tetrabutylammonium fluoride in THF (110 mL, 110 mmol); the reaction mixture was stirred at 90° C. for 4 hours under nitrogen, and then cooled to room temperature. Solvent was evaporated and the residue was taken in ethyl acetate (300 mL). The organic phase was washed with water (300 mL), brine (200 mL), and dried over anhydrous Na$_2$SO$_4$. The solvent was evaporated and the crude compound was purified by column chromatography on silica gel, eluting with hexanes and ethyl acetate (3:1), to give 2-[2-(tetrahydro-pyran-2-yloxy)-ethyl]-1H-indole-5-carboxylic acid methyl ester. Yield: 14.9 g (76%).

Lithium aluminum hydride (3.38 g, 89.0 mmol) in anhydrous THF (100 mL) was cooled to –30° C. 2-[2-(Tetrahydro-pyran-2-yloxy)-ethyl]-1H-indole-5-carboxylic acid methyl ester (13.5 g, 44.5 mmol) in anhydrous THF (100 mL) was added dropwise. The reaction mixture was stirred at –20° C. for 1 hour and then at room temperature for 4 hours. The reaction mixture was cooled to 0° C. and water (6 mL) was added slowly. Ammonium chloride solution (200 mL) was added and extracted with ethyl acetate (2×200 mL). The organic phase was washed with water (100 mL), then brine (100 mL), and dried over anhydrous sodium sulfate. The solvent was evaporated to give {2-[2-(tetrahydro-pyran-2-yloxy)-ethyl]-1H-indol-5-yl}-methanol as a white solid. Yield: 11.50 g (94%).

{2-[2-(Tetrahydro-pyran-2-yloxy)-ethyl]-1H-indol-5-yl}-methanol (11.5 g 41.7 mmol) in anhydrous DMSO (45 mL) was added IBX (12.3 g, 43.8 mmol) and the reaction was stirred at room temperature for 2 hours. The reaction mixture was poured into water (300 mL) and extracted with ethyl acetate (300 mL), the organic phase was washed with water, then brine, and was purified by column chromatography on silica gel, eluting with dichloromethane, to give 2-[2-(tetrahydro-pyran-2-yloxy)-ethyl]-1H-indole-5-carbaldehyde as a white solid. Yield: 8.50 g (75%).

To a solution of 2-amino-4,6-dimethoxy-benzamide (6.10 g, 31.1 mmol) and 2-[2-(tetrahydro-pyran-2-yloxy)-ethyl]-1H-indole-5-carbaldehyde (8.50 g, 31.1 mmol) in N,N-dimethylacetamide (45 mL) was added NaHSO$_3$ (58.5 wt %, 6.08 g, 34.2 mmol) and p-TSA (0.60 g, 3.11 mmol). The reaction mixture was heated at 115° C. for 16 hours and then cooled to room temperature. N,N-dimethylacetamide was removed under reduced pressure, the residue was diluted with water (50 mL) and the solid was collected and mixed with dichloromethane (100 mL), ether (100 mL), and then filtered to give a mixture of 5,7-dimethoxy-2-{2-[2-(tetrahydro-pyran-2-yloxy)-ethyl]-1H-indol-5-yl}-3H-quinazolin-4-one and 2-[2-(2-hydroxy-ethyl)-1H-indol-5-yl]-5,7-dimethoxy-3H-quinazolin-4-one as a white solid, which was used in next step without further purification. Yield: 7.50 g (crude).

A mixture of 5,7-dimethoxy-2-{2-[2-(tetrahydro-pyran-2-yloxy)-ethyl]-1H-indol-5-yl}-3H-quinazolin-4-one and 2-[2-(2-hydroxy-ethyl)-1H-indol-5-yl]-5,7-dimethoxy-3H-quinazolin-4-one (7.50 g, 16.6 mmol) was dissolved in anhydrous methanol (60 mL). 1.0 M HCl in ether (42 mL) was added and the reaction was stirred at room temperature for 2 hours. The solid was filtered and the mother liquor was evaporated to dryness and the residue was combined with the solid. Sodium bicarbonate solution (200 mL) was added and stirred for 1 hours. The separated solid was filtered and washed with cold water and dried under vacuum to give 2-[2-(2-hydroxy-ethyl)-1H-indol-5-yl]-5,7-dimethoxy-3H-quinazolin-4-one as a white solid. Yield: 6.2 g (55%; 3 steps).

To a solution of 2-[2-(2-hydroxy-ethyl)-1H-indol-5-yl]-5,7-dimethoxy-3H-quinazolin-4-one (6.20 g, 16.9 mmol) in anhydrous DMF (25 mL) was added carbon tetrabromide (6.47 g, 19.5 mmol) and triphenylphosphine (5.11 g, 19.5 mmol). The reaction mixture was stirred at 40° C. for 16 hours. DMF was removed under vacuum and water (150 mL) was added. The separated solid was filtered and mixed with ether (150 mL) and heated for 10 minutes. The solid was filtered and dried under vacuum to give 2-[2-(2-bromo-ethyl)-1H-indol-5-yl]-5,7-dimethoxy-3H-quinazolin-4-one as a white solid. Yield: 6.1 g (84%).

To a solution of 2-[2-(2-bromo-ethyl)-1H-indol-5-yl]-5,7-dimethoxy-3H-quinazolin-4-one (6.10 g, 14.2 mmol) in anhydrous DMF (45 mL) was added pyrrolidine (6.07 g, 85.4 mmol) and the reaction mixture was stirred at 45° C. for 15 hours. DMF was removed under reduced pressure, the residue was taken in water (150 mL), and stirred for 30 minutes. Separated solid was filtered, washed with water, and dried under vacuum. Crude compound was purified by column chromatography (silica gel 230-400 mesh, eluting with 5% 7.0 M ammonia in methanol solution in dichloromethane) to give the title compound as a white solid. Yield: 3.4 g (57%). MP 215-217° C. $^1$H NMR (400 MHz, DMSO-d$_6$): δ 11.79 (s, 1H), 11.21 (s, 1H), 8.31 (s, 1H), 7.88 (dd, J=8.8 and 1.6 Hz, 1H), 7.35 (d, J=8.8 Hz, 1H), 6.71 (d, J=2.4 Hz, 1H), 6.46 (d, J=2.4 Hz, 1H), 6.28 (s, 1H), 3.87 (s, 3H), 3.83 (s, 3H), 2.89 (t, J=8.0 Hz, 2H), 2.74 (t, J=8.0 Hz, 2H), 2.48 (m, 4H), 1.67 (m, 4H).

Example 59

Preparation of 2-(2-((Dimethylamino)methyl)-1H-indol-5-yl)-5,7-dimethoxyquinazolin-4(3H)-one

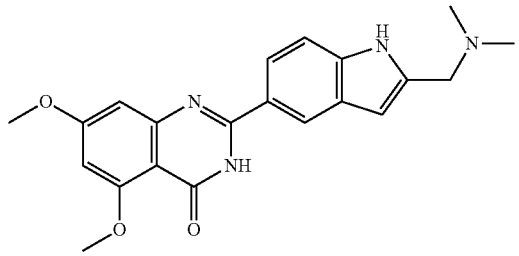

To a solution of 5-bromo-1H-indole-2-carboxylic acid (2.40 g, 10.0 mmol) in THF (100 mL) were added EDCl (2.11 g, 30.0 mmol), HOBt (1.49 g, 11.0 mmol). The reaction mixture was stirred at room temperature for 10 minutes. Then, a solution of N,N-dimethyl amine (2.0 M solution in THF, 15 mL, 30.0 mmol) was added. The mixture was stirred for 16 hours at room temperature. Solvent was evaporated, the residue was taken in ethyl acetate (200 mL), and water (200 mL) was added. The organic phase was separated; the aqueous phase was extracted with ethyl acetate (200 mL). The combined organic phase was washed with water (100 mL), then brine (100 mL), and dried over anhydrous sodium sulfate. Solvent was evaporated and dried under vacuum to give 5-bromo-1H-indole-2-carboxylic acid dimethylamide as an off-white solid. Yield: 2.56 g (96%).

5-Bromo-1H-indole-2-carboxylic acid dimethylamide (1.34 g, 5.00 mmol) was taken in anhydrous THF (50 mL) (suspension), and cooled to −20° C. A solution of lithium aluminium hydride (1.0 M solution in THF, 10.0 mL, 10.0 mmol) was added dropwise at −20° C. over a period of 15 minutes under nitrogen, and allowed to warm to 10° C.; stirring was continued at 10° C. for 1 hour. The reaction mixture was carefully quenched with aq. saturated ammonium chloride solution (10 mL). The reaction mixture was diluted with ethyl acetate (150 mL). The organic phase was separated, washed with water (100 mL), then brine (100 mL), and dried over anhydrous Na$_2$SO$_4$. Solvent was evaporated, to give (5-bromo-1H-indole-2-ylmethyl)-dimethyl amine as an off-white solid. Yield: 1.27 g (crude).

To a cold (0° C.) solution of potassium hydride (suspension in mineral oil, 0.79 g, 5.90 mmol) in anhydrous THF (60 mL) was added a solution of (5-bromo-1H-indole-2-ylmethyl)-dimethyl amine (1.24 g, 4.90 mmol) in anhydrous THF (20 mL) was added dropwise at 0° C. over a period of 15 minutes under nitrogen. Stirring was continued for 30 minutes at 0° C., then cooled to −10° C. n-Butyl lithium (1.6 M solution in hexanes, 7.4 mL, 11.7 mmol) was added rapidly. Stirring was continued at −10° C. for 1 h. Then, anhydrous DMF (5.0 mL) was added, and the mixture was allowed to warm to room temperature over 2 h. The reaction mixture was carefully quenched with 1N aq. HCl (10 mL). The reaction mixture was diluted with ethyl acetate (150 mL). The organic phase was separated, washed with water (100 mL), then brine (100 mL), and dried over anhydrous Na$_2$SO$_4$. The solvent was evaporated to give 2-dimethylaminomethyl-1H-indole-5-carbaldehyde as an orange-colored gummy material. Yield: 0.91 g (crude). This product was used in next step without further purification.

To a solution of 2-dimethylaminomethyl-1H-indole-5-carbaldehyde (0.88 g crude, 4.35 mmol) and 2-amino-4,6-dimethoxy-benzamide (0.85 g, 4.35 mmol) in N,N-dimethylacetamide (15 mL) were added sodium hydrogen sulfite (58.5 wt %, 0.95 g, 5.22 mmol) and p-toluenesulfonic acid (0.99 g, 5.22 mmol). The reaction mixture was stirred at 120° C. for 5 hours under nitrogen, then cooled to room temperature, and concentrated under reduced pressure. 30% aqueous sodium carbonate (50 mL) was then added. The separated solid was filtered, washed with water (50 mL), and dried under vacuum. Crude compound was purified by the Simpliflash system (0-5% methanol in CH$_2$Cl$_2$ and 7 N ammonia in methanol 5% in CH$_2$Cl$_2$ as eluent) to give the title compound as an off-white solid. Yield: 0.83 g (50%). MP 187-188° C. $^1$H NMR (400 MHz, DMSO-d$_6$): δ 11.82 (s, 1H), 11.34 (s, 1H), 8.38 (s, 1H), 7.93 (d, J=8.59 Hz, 1H), 7.40 (d, J=8.59 Hz, 1H), 6.73 (s, 1H), 6.49 (s, 1H), 6.40 (s, 1H), 3.90 (s, 3H), 3.85 (s, 3H), 3.57 (s, 2H), 2.21 (s, 6H).

Example 60

Preparation of N-(4-(5,7-Dimethoxy-4-oxo-3,4-dihydroquinazolin-2-yl)phenyl)methanesulfonamide

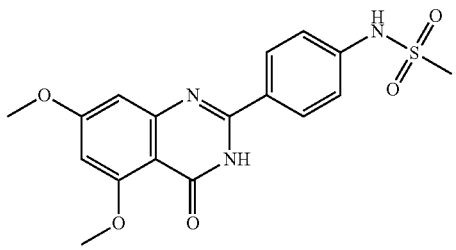

A mixture of 4-bromobenzaldehyde (0.250 g, 1.40 mmol), methanesulfonamide (0.154 g, 1.62 mmol), copper iodide (0.0510 g, 0.270 mmol), N,N-dimethylglycine (0.0280 g, 0.270 mmol), and potassium phosphate tribasic (0.716 g, 3.38 mmol) in DMF (5.00 mL) was stirred at reflux for 16 hours. The mixture was diluted with EtOAc (50 mL), washed with water (50 mL), and then saturated aqueous LiCl (5 mL). The combined aqueous layers were then back-extracted with EtOAc (50 mL). The organic layers were combined, washed with brine (50 mL), dried over $Na_2SO_4$, filtered, and the solvent was removed under reduced pressure, to provide N-(4-formylphenyl)methanesulfonamide (0.161 g, 58%) as a yellow oil.

A mixture of N-(4-formylphenyl)methanesulfonamide (0.161 g, 0.0800 mmol), 2-amino-4,6-dimethoxybenzamide (0.159 g, 0.0800 mmol), $NaHSO_3$ (94%, 0.00460 g, 0.0240 mmol), and p-TsOH.$H_2O$ (0.0125 g, 0.120 mmol) in DMA (1.00 mL) was heated at 155° C. for 16 hours. The mixture was diluted with EtOAc (50 mL), washed with water (2×50 mL), then brine (50 mL), dried over $Na_2SO_4$, filtered, and the solvent was removed under vacuum. The residue was purified over silica gel (12 g, $CH_2Cl_2$/MeOH) and the product was freeze-dried from MeCN/$H_2O$ to provide the title compound (0.0341 g, 11%) as a pale yellow solid. $^1$H NMR (300 MHz, DMSO-$d_6$): δ 11.94 (s, 1H), 10.21 (s, 1H), 8.16 (d, J=8.76 Hz, 2H), 7.30 (d, J=8.76 Hz, 2H), 6.72 (d, J=2.25 Hz, 1H), 6.52 (d, J=2.25 Hz, 1H), 3.89 (s, 3H), 3.85 (s, 3H), 3.09 (s, 3H). MS (ESI) m/z 376 $[C_{17}H_{17}N_3O_5S+H]^+$.

Example 61

Preparation of 5,7-Dimethoxy-2-(4-(pyridin-4-ylamino)phenyl)quinazolin-4(3H)-one

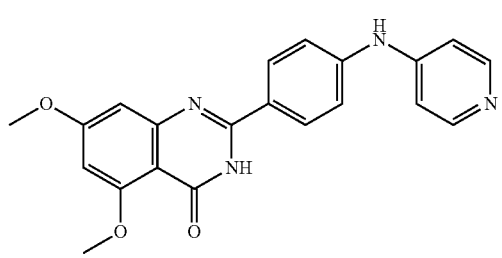 [SMILES: COc1cc(OC)c2c(=O)[nH]c(-c3ccc(Nc4ccncc4)cc3)nc2c1]

A mixture of compound 2-(4-bromophenyl)-5,7-dimethoxyquinazolin-4(3H)-one) (0.200 g, 0.554 mmol), 4-aminopyridine (0.0573 g, 0.609 mmol), $Pd_2(dba)_3$ (0.0025 g, 0.0028 mmol), Xantphos (0.0018 g, 0.0031 mmol), and $Cs_2CO_3$ (0.253 g, 0.776 mmol) in 1,4-dioxane (2.22 mL) under nitrogen was heated at 105° C. for 2 days. The mixture was cooled to room temperature, diluted with EtOAc (200 mL), washed with water (3×75 mL), then brine (75 mL), dried over anhydrous $Na_2SO_4$, filtered, and the solvent was removed under vacuum. The resulting residue was purified over silica gel (12 g, EtOAc/$CHCl_3$/MeOH/$NH_4OH$), to provide the title compound as a white solid. $^1$H NMR (300 MHz, DMSO-$d_6$): δ 11.90 (s, 1H), 9.19 (s, 1H), 8.29 (d, J=6.29 Hz, 2H), 8.17 (d, J=8.75 Hz, 2H), 7.30 (d, J=8.75 Hz, 2H), 7.05 (d, J=6.29 Hz, 2H), 6.72 (d, J=2.26 Hz, 1H), 6.51 (d, J=2.26 Hz, 1H), 3.89 (s, 3H), 3.85 (s, 3H). MS (ESI) m/z 375 $[C_{21}H_{18}N_4O_3+H]^+$.

Example 62

Preparation of 5,7-Dimethoxy-2-(4-(p-tolylamino)phenyl)quinazolin-4(3H)-one

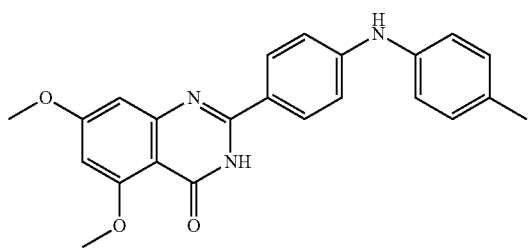

To a mixture of $Pd(OAc)_2$ (0.0112 g, 0.0166 mmol) and (S)-(−)-BINAP (0.0155 g, 0.0249 mmol) was added a degassed solution of toluene/t-BuOH (5:1, 3.00 mL) and the mixture was heated at 100° C. for 1 minute. In a second flask, 2-(4-bromophenyl)-5,7-dimethoxyquinazolin-4(3H)-one) (0.300 g, 0.831 mmol) and degassed toluene/t-BuOH (5:1, 4.00 mL) was heated at 100° C. for 1 minute, t-BuOK (0.130 g, 1.17 mmol) was added, and the mixture heated until most of the solids dissolved. This mixture was then cooled, additional t-BuOK (0.130 g, 1.17 mmol) was added, followed by p-toluidine (0.107 g, 0.997 mmol), the Pd catalyst/ligand mixture, and additional toluene/t-BuOH (5:1, 3.00 mL). The reaction was heated at 105° C. for 3 days, then cooled to room temperature, diluted with water (100 mL), and extracted with EtOAc (2×100 mL). The combined organic layers were washed with brine (50 mL), dried over $Na_2SO_4$, filtered, and the solvent was removed under vacuum. The resulting residue was purified over silica gel (4 g, $CH_2Cl_2$/MeOH) and the product was freeze-dried from MeCN/$H_2O$ to provide the title compound (0.0212 g, 6%) as a yellow solid. $^1$H NMR (300 MHz, DMSO-$d_6$): δ 11.71 (s, 1H), 8.54 (s, 1H), 8.06 (d, J=8.82 Hz, 2H), 7.18-6.99 (m, 6H), 6.67 (d, J=2.21 Hz, 1H), 6.47 (d, J=2.21 Hz, 1H), 3.88 (s, 3H), 3.84 (s, 3H), 2.27 (s, 3H). MS (ESI) m/z 388 $[C_{23}H_{21}N_3O_3+H]^+$.

Example 63

Preparation of 5,7-Dimethoxy-2-(4-(pyridin-3-ylamino)phenyl)quinazolin-4(3H)-one

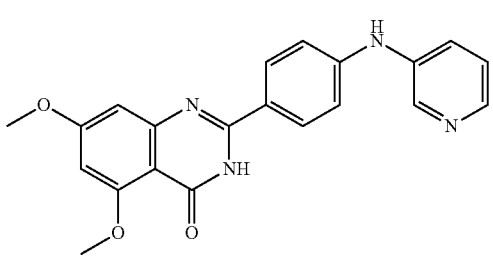 [SMILES: COc1cc(OC)c2c(=O)[nH]c(-c3ccc(Nc4cccnc4)cc3)nc2c1]

A mixture of 2-(4-bromophenyl)-5,7-dimethoxyquinazolin-4(3H)-one (0.200 g, 0.55 mmol), 3-aminopyridine (0.057 g, 0.61 mmol), $Cs_2CO_3$ (0.253 g, 0.776 mmol), Xantphos (0.002 g, 0.003 mmol), and Pd$_2$(dba)$_3$ (0.003 g, 0.003 mmol) in dioxane (2 mL) were combined in a microwave tube under nitrogen and irradiated at 300 W, 105° C. for 30 minutes. Then, DMF (1 mL) was added and the flask was irradiated for 1 hour at 300 W, 105° C. Then, the mixture was concentrated and purified by silica gel chromatography, eluting with 92:7:1 CHCl$_3$/MeOH/concentrated NH$_4$OH. The residue was further purified by reverse-phase HPLC, eluting with 10% to 90% CH$_3$CN in H$_2$O with 0.1% TFA, to afford the title compound (0.105 g, 51%) as a white solid. $^1$H NMR (300 MHz, DMSO-d$_6$): δ 11.83 (s, 1H), 8.82 (s, 1H), 8.44 (d, J=2.4 Hz, 1H), 8.11-8.16 (m, 3H), 7.59-7.62 (m, 1H), 7.31-7.35 (m, 1H), 7.13 (d, J=8.7 Hz, 2H), 6.68 (d, J=1.8 Hz, 1H), 6.46 (d, J=1.8 Hz, 1H), 3.88 (s, 3H), 3.83 (s, 3H). APCI MS m/z 375 [M+H]$^+$.

Example 64

Preparation of 4-(4-(5,7-Dimethoxy-4-oxo-3,4-dihydroquinazolin-2-yl)phenoxy)-N,N-dimethylpiperidine-1-carboxamide

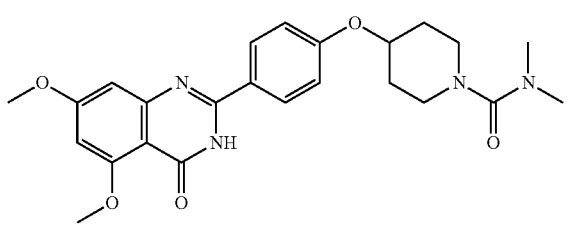

To a solution of 4-hydroxypiperidine (5.0 g, 49 mmol) in THF (70 mL) was added triethylamine (14.4 mL, 103 mmol) and dimethylcarbamyl chloride (9.0 mL, 98 mmol) slowly. The mixture was stirred at room temperature for 1.5 hours. The white precipitate was filtered off, washed with THF. The THF solution was concentrated to dryness then purified with column chromatography (SiO$_2$, MeOH/CH$_2$Cl$_2$=1:19) to afford 4-hydroxypiperidine-1-carboxylic acid dimethylamide as colorless oil. Yield: 7.8 g (94%).

4-Hydroxypiperidine-1-carboxylic acid dimethylamide (1.45 g, 8.40 mmol), 4-hydroxbenzenaldehyde (1.02 g, 8.40 mmol) and triphenylphosphine (3.31 g, 12.6 mmol) were stirred in THF (6 mL). Diisopropylazodicarboxylate (2.51 mL, 12.6 mmol) was added dropwise to the reaction mixture at room temperature over the course of 5 minutes. The mixture was stirred at room temperature for 21 hours, concentrated, and purified by column chromatography (SiO$_2$, hexanes/ethyl acetate=1:1 to neat ethyl acetate), to afford 4-(4-formylphenoxy)-piperidine-1-carboxylic acid dimethylamide a white solid. Yield: 0.7 g (30%).

To a 100 mL round-bottom flask was added 2-amino-4,6-dimethoxybenzamide (196 mg, 1.00 mmol), 4-(4-formylphenoxy)-piperidine-1-carboxylic acid dimethylamide (300 mg, 1.10 mmol), p-toluenesulfonic acid monohydrate (21 mg, 0.10 mmol), sodium hydrogensulfite (216 mg, 1.20 mmol) and dimethylacetamide (5 mL). The mixture was stirred at 115° C. under N$_2$ for 17 hours and cooled to room temperature. Water (20 mL) was added and stirred for 0.5 hours. The precipitate was filtered off, washed with water, and air dried. The crude product was purified by column chromatography (SiO$_2$, neat ethyl acetate, then ethyl acetate/methanol=19:1, then CH$_2$Cl$_2$/methanol=19:1) to afford the title compound as a white solid. Yield: 110 mg (24%). MP 248-249° C. $^1$H NMR (400 MHz, DMSO-d$_6$): δ 11.91 (s, 1H), 8.15 (d, J=8.8 Hz, 2H), 7.10 (d, J=8.8 Hz, 2H), 6.72 (s, 1H), 6.51 (s, 1H), 4.71-4.69 (m, 1H), 3.89 (s, 3H), 3.85 (s, 3H), 3.44-3.39 (m, 2H), 3.06-2.99 (m, 2H), 2.74 (s, 6H), 2.00-1.96 (m, 2H), 1.64-1.59 (m, 2H).

Example 65

Preparation of 2-(4-(1-Acetylpiperidin-4-yloxy)phenyl)-5,7-dimethoxyquinazolin-4(3H)-one

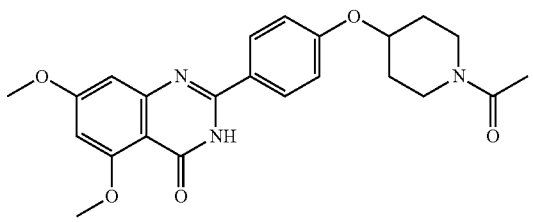 [SMILES: COc1cc(OC)c2c(=O)[nH]c(-c3ccc(OC4CCN(C(C)=O)CC4)cc3)nc2c1]

To a solution of 4-hydroxypiperidine (5.00 g, 49.4 mmol) in anhydrous THF (30 mL) and triethylamine (10 mL, 75 mmol) was added acetyl chloride (3.52 mL, 49.4 mmol). After the addition, the mixture was stirred for another 2 hours at room temperature. The solid formed was filtered and the mother liquid was concentrated to yield 5.0 g of crude product, which was purified by column chromatography on silica gel (230-400 mesh), using 5% methanol in dichloromethane as eluent, to give 1-(4-hydroxy-piperidin-1-yl)-ethanone. Yield: 2.40 g (34%).

To a solution of 1-(4-hydroxy-piperidin-1-yl)-ethanone (1.00 g, 6.90 mmol), 4-hydroxybenzaldehyde (0.854 g, 6.90 mmol) and triphenylphosphine (1.83 g, 6.90 mmol) in THF (10 mL) was added dropwise diisopropyl azodicarboxylate (DIAD) (1.41 g, 6.90 mmol). The reaction mixture was stirred at room temperature for 16 hours, THF was evaporated, and the residue was purified by column chromatography, using dichloromethane:ethyl acetate:methanol (1:2:0.05) as eluent, to give 4-(1-acetyl-piperidin-4-yloxy)-benzaldehyde. Yield: 0.40 g (23%).

To a solution of 2-amino-4,6-dimethoxy-benzamide (0.20 g, 1.0 mmol) and 4-(1-acetyl-piperidin-4-yloxy)-benzaldehyde (0.25 g, 1.0 mmol) in N,N-dimethyl acetamide (5 mL), NaHSO$_3$ (0.20 g, 1.1 mmol) and p-TSA (20 mg, 0.10 mmol) were added and the reaction mixture was heated at 115° C. for 16 hours. The reaction mixture was cooled to room temperature. N,N-dimethylacetamide was removed under reduced pressure. The residue was diluted with water and the solid was collected; the crude product was purified by column chromatography on silica gel (230-400 mesh), using 5% methanol in CH$_2$Cl$_2$ as eluent, to give the title compound. Yield: 0.2 g (47%). MP 275-277° C. $^1$H NMR (400 Hz, CDCl$_3$): δ 11.94 (s, 1H), 8.16 (d, 2H), 7.10 (d, 2H), 6.70 (d, 1H), 6.50 (d, 1H), 4.76 (m, 1H), 3.88 (s, 3H), 3.82 (s, 3H), 3.70 (m, 1H), 3.30 (m, 2H), 3.20 (m, 1H), 2.04 (s, 3H), 1.95 (m, 2H), 1.64 (m, 1H), 1.52 (m, 1H).

Example 66

Preparation of 2-(4-(2-(Isoindolin-2-yl)ethoxy)-3,5-dimethylphenyl)-5,7-dimethoxyquinazolin-4(3H)-one

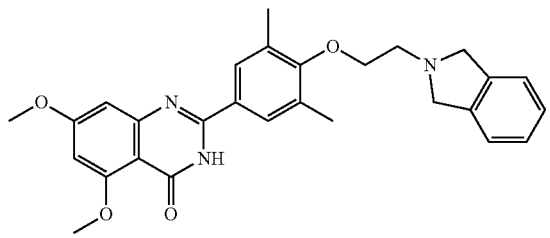 [SMILES: COc1cc(OC)c2c(=O)[nH]c(-c3cc(C)c(OCCN4Cc5ccccc5C4)c(C)c3)nc2c1]

To a suspension of 2-[4-(2-bromoethoxy)-3,5-dimethylphenyl]-5,7-dimethoxy-3H-quinazolin-4-one (0.50 g, 1.15 mmol) in anhydrous DMF (9 mL) was added isoindoline (0.41 mL, 3.46 mmol) and the reaction mixture was stirred at room temperature for 16 hours under nitrogen. The solvent was removed under reduced pressure and the residue was triturated with water (50 mL). The separated solid was filtered, washed with water and ether, and dried under vacuum to give the title compound as a white solid. Yield: 0.45 g (83%). MP 202-202.5° C. $^1$H NMR (400 MHz, CDCl$_3$): δ 10.09 (br s, 1H), 7.77 (s, 2H), 7.22 (br s, 4H), 6.83 (d, J=2.4 Hz, 1H), 6.46 (d, J=2.4 Hz, 1H), 4.11 (s, 4H), 4.03 (t, J=6.0 Hz, 2H), 3.96 (s, 3H), 3.93 (s, 3H), 3.22 (t, J=6.0 Hz, 2H), 2.42 (s, 6H).

Example 67

Preparation of 2-(3,5-Dimethyl-4-(2-(pyrrolidin-1-yl)ethoxy)phenyl)-5-methoxyquinazolin-4(3H)-one

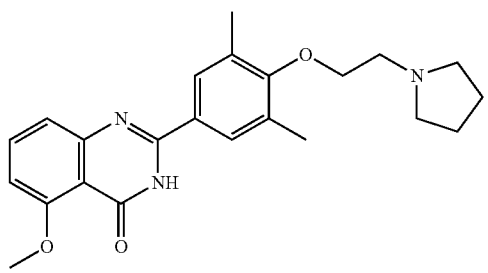 [SMILES: COc1cccc2nc(-c3cc(C)c(OCCN4CCCC4)c(C)c3)[nH]c(=O)c12]

To a stirred solution of 2-amino-6-methoxy-benzoic acid (3.00 g, 17.9 mmol) in THF (90 mL), EDCl (7.89 g, 41.1 mmol) and HOBt (7.95 g, 51.9 mmol) were added and stirred at room temperature for 30 minutes then N-methylmorpholine (6.15 g, 60.0 mmol) and aqueous 50% v/v NH$_4$OH (12 mL, 171.4 mmol) was added. The mixture was stirred for 16 hours at room temperature. The solvent was removed under reduced pressure and the residue was extracted with ethylacetate (4×100 mL), the combined organic phase was washed with water and brine, and dried over anhydrous sodium sulfate; the solvent was evaporated to give 2-amino-6-methoxy-benzamide as an off-white solid. Yield: 1.90 g, (65%).

To a solution of 2-amino-6-methoxy-benzamide (1.00 g, 6.01 mmol) and 4-(2-hydroxy-ethoxy)-3,5-dimethyl-benzaldehyde (1.28 g, 6.59 mmol) in N,N-dimethylacetamide (15 mL) were added NaHSO$_3$ (58.5 wt %, 0.68 g, 6.50 mmol) and p-TSA (0.23 g, 1.20 mmol) and the reaction mixture was heated at 115° C. for 20 hours, and cooled to room temperature. N,N-dimethylacetamide was removed under reduced pressure. The residue was diluted with water (50 mL), stirred for 30 minutes, and then filtered. The solid was suspended in dichloromethane (30 mL), stirred for 1 h, filtered, and dried under vacuum to give 2-[4-(2-hydroxy-ethoxy)-3,5-dimethyl-phenyl]-5-methoxy-3H-quinazolin-4-one as an off-white solid. Yield: 1.1 g (55%).

To a solution of 2-[4-(2-hydroxy-ethoxy)-3,5-dimethyl-phenyl]-5-methoxy3H-quinazolin-4-one (1.10 g, 3.20 mmol) in anhydrous N,N-dimethylformamide (16 mL) were added triphenylphosphine (0.92 g, 3.50 mmol) and carbontetrabromide (1.17 g, 3.50 mmol). The reaction mixture was stirred at room temperature for 16 hours. DMF was removed under reduced pressure. The residue was purified by column chromatography (silica gel 230-400 mesh; 3% methanol in dichloromethane as eluent) to give 2-[4(2-bromo-ethoxy)-3,5-dimethyl-phenyl]-5-methoxy3H-quinazolin-4-one as an off-white solid. Yield: 0.60 g (46%).

To a solution of 2-[4(2-bromo-ethoxy)-3,5-dimethyl-phenyl]-5-methoxy3H-quinazolin-4-one (0.50 g, 1.20 mmol) in N,N-dimethylformamide (10 mL) was added pyrrolidine (0.53 g, 7.40 mmol) and the reaction mixture was stirred at room temperature for 15 hours. DMF was removed under reduced pressure, the residue was purified by column chromatography (silica gel 230-400 mesh; 5% methanol in dichloromethane as eluent) to give the title compound as a white solid. Yield: 0.25 g (52%). MP 157-158° C. $^1$H NMR (400 MHz, DMSO-d$_6$): 11.95 (s, 1H), 7.89 (s, 2H), 7.70 (t, J=8.19 Hz, 1H), 7.24 (d, J=7.8 Hz, 1H), 6.99 (d, J=8.1 Hz, 1H), 3.91-3.89 (m, 2H), 3.87 (s, 3H), 2.82 (t, J=6.2 Hz 2H), 2.53-2.50 (m, 4H), 2.30 (s, 6H), 1.69 (m, 4H). MS (ES$^+$) m/z: 394.61 (M+1).

Example 68

Preparation of 5,7-Dichloro-2-(3,5-dimethyl-4-(2-(pyrrolidin-1-yl)ethoxy)phenyl)quinazolin-4(3H)-one

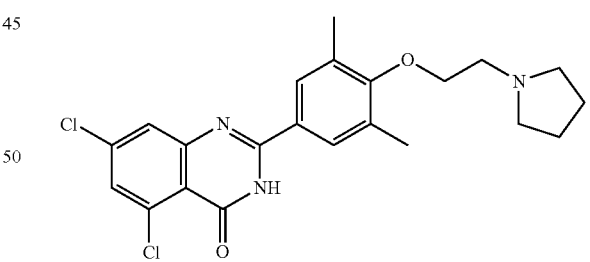

To a solution of 2-amino-4,6-dichloro-benzoic acid (4.12 g, 20.0 mmol) in THF (120 mL) were added EDCl (4.22 g, 22.0 mmol), HOBt (2.70 g, 20.0 mmol) and N-methylmorpholine (2.22 g, 22.0 mmol). The reaction mixture was stirred at room temperature for 20 minutes, then 50% (v/v) aqueous NH$_4$OH solution (2.8 mL, 40.0 mmol) was added. The mixture was stirred for 20 hours at room temperature. The solvent was evaporated, the residue was taken in ethyl acetate (200 mL), and water (200 mL) was added. The organic phase was separated; the aqueous phase was extracted with ethyl acetate (200 mL). The combined organic phase was washed with water (100 mL), then brine (100 mL), and dried over anhydrous sodium sulfate. The solvent was evaporated and dried under vacuum to give 2-amino-4,6-dichloro-benzamide as an off-white solid. Yield: 3.83 g (93%).

To a solution of 2-amino-4,6-dichloro-benzamide (1.54 g, 7.50 mmol) and 4-(2-hydroxy-ethoxy)-3,5-dimethyl-benzaldehyde (1.46 g, 7.50 mmol) in N,N-dimethylacetamide (15 mL) were added sodium hydrogen sulfite (58.5 wt %, 1.51 g, 8.25 mmol) and p-toluenesulfonic acid monohydrate (0.28 g, 1.50 mmol). The reaction mixture was stirred at 120° C. for 16 hours under nitrogen, and then cooled to room temperature. Solvent was evaporated under reduced pressure. Water (100 mL) was added. The separated solid was filtered, washed with water (50 mL), and dried under vacuum. Crude compound was further washed with ether and dried under vacuum to give 5,7-dichloro-2-[4-(2-hydroxy-ethoxy)-3,5-dimethylphenyl]-3H-quinazolin-4-one as a white solid. Yield: 2.42 g (85%).

To a solution of 5,7-dichloro-2-[4-(2-hydroxy-ethoxy)-3,5-dimethylphenyl]-3H-quinazolin-4-one (1.14 g, 3.00 mmol) in anhydrous DMF (15 mL) was added carbon tetrabromide (1.10 g, 3.30 mmol). Then, triphenylphosphine (0.86 g, 3.30 mmol) was added in small portions. The reaction mixture was stirred at room temperature for 16 hours under nitrogen. Solvent was evaporated under reduced pressure. The residue was washed with ethyl acetate (50 mL) and dried under vacuum to give 2-[4-(2-bromo-ethoxy)-3,5-dimethylphenyl]-5,7-dichloro-3H-quinazolin-4-one as a white solid. Yield: 0.46 g (35%).

To a solution of 2-[4-(2-bromo-ethoxy)-3,5-dimethylphenyl]-5,7-dichloro-3H-quinazolin-4-one (0.44 g, 1.00 mmol) in anhydrous DMF (10 mL) was added pyrrolidine (0.28 g, 4.00 mmol). The reaction mixture was stirred at room temperature for 6 hours under nitrogen. Solvent was evaporated under reduced pressure. Water (50 mL) was added. The separated solid was filtered, washed with water (20 mL), and dried under vacuum. The crude compound was purified by the Simpliflash system (0-5% methanol in $CH_2Cl_2$ and 5% methanol (containing 7.0 M ammonia) in $CH_2Cl_2$ as eluent) to give the title compound as a white solid. Yield: 0.31 g (72%). MP 209-210° C. $^1$H NMR (400 MHz, DMSO-$d_6$): δ 12.39 (br s, 1H), 7.90 (s, 2H), 7.71 (d, J=1.95 Hz, 1H), 7.60 (d, J=1.95 Hz, 1H), 3.91 (t, J=5.85 Hz, 2H), 2.83 (t, J=6.05 Hz, 2H), 2.55 (m, 4H), 2.31 (s, 6H), 2.01 (m, 4H). MS (ES+) m/z 432.54 (100%), 434.49 (90%).

Example 69

Preparation of 2-(3,5-Dimethyl-4-(3-(pyrrolidin-1-yl)propoxy)phenyl)-5,7-dimethoxy-3-(3-(pyrrolidin-1-yl)propyl)quinazolin-4(3H)-one

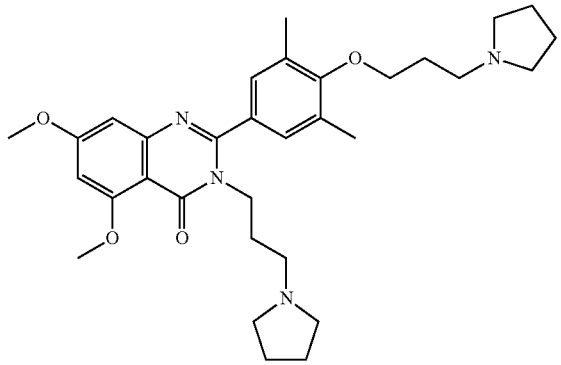 [SMILES: COc1cc(OC)c2c(=O)n(CCCN3CCCC3)c(-c3cc(C)c(OCCCN4CCCC4)c(C)c3)nc2c1]

To a solution of 2-(4-hydroxy-3,5-dimethyl-phenyl)-5,7-dimethoxy-3H-quinazolin-4-one (0.70 g, 2.14 mmol) in anhydrous THF (50 mL) were added triphenyl phosphine (1.69 g, 6.43 mmol), 3-bromo-1-propanol (0.60 g, 4.34 mmol) and N,N-diisopropylethyl amine (0.42 g, 3.22 mmol). To this stirred solution was added diethyl azodicarboxylate (1.13 g, 6.43 mmol). The reaction mixture was stirred at room temperature for 48 hours under nitrogen. Ethyl acetate (400 mL) was added; the organic phase was separated, washed with water (100 mL), then brine (100 mL), and dried over anhydrous $Na_2SO_4$. Solvent was removed under reduced pressure. The crude material was purified by the Simpliflash system (5:95 ethyl acetate:hexane as eluent) to give 2-[4-(3-bromo-propoxy)-3,5-dimethyl-phenyl]-3-(3-bromo-propyl)-5,7-dimethoxy-3H-quinazolin-4-one as a white solid. Yield: 0.765 g (63%).

To a solution of 2-[4-(3-bromo-propoxy)-3,5-dimethyl-phenyl]-3-(3-bromo-propyl)-5,7-dimethoxy-3H-quinazolin-4-one (0.76 g, 1.35 mmol) in DMF (10 mL) were added pyrrolidine (0.77 g, 10.77 mmol). The reaction mixture was stirred at room temperature for 16 hours. Then, water was added and product was extracted with ethyl acetate (2×200 mL). The combined organic layer was washed with water, then brine, and dried over $Na_2SO_4$. Solvent was evaporated to give the title compound as a white solid. Yield: 0.12 g (16%). MP 109-111° C. $^1$H NMR (400 MHz, CDCl$_3$): δ 8.16 (s, 2H), 6.93 (d, J=2.4 Hz, 1H), 6.44 (d, J=2.4 Hz, 1H), 4.71 (t, J=6.4 Hz, 2H), 3.94 (s, 3H), 3.93 (s, 3H), 3.87 (t, J=6.0 Hz, 2H), 2.75 (m, 4H), 2.60 (m, 8H), 2.37 (s, 6H), 2.16 (m, 2H), 2.05 (m, 2H), 1.82 (m, 8H). MS (ES) m/z: 549.75 (M+1). Analysis calculated for $C_{32}H_{44}N_4O_4 \cdot 0.5H_2O$ (FW 557.73), %: C, 68.91; H, 8.13; N, 10.05. Found, %: C, 68.71; H, 8.56; N, 9.74.

Example 70

Preparation of 2-(4-(2-(4-Acetylpiperazin-1-yl)ethoxy)-3,5-dimethylphenyl)-5,7-dimethoxyquinazolin-4(3H)-one

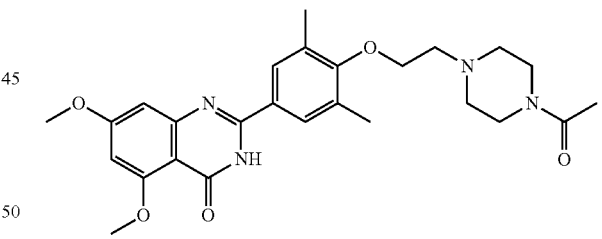

To a suspension of 2-[4-(2-bromoethoxy)-3,5-dimethylphenyl]-5,7-dimethoxy-3H-quinazolin-4-one (0.35 g, 0.81 mmol) in anhydrous DMF (9 mL) was added 1-acetylpyperazine (0.31 g, 2.42 mmol) and the reaction mixture was stirred at room temperature under nitrogen for 32 hours. Solvent was removed under reduced pressure and water (50 mL) was added. The separated solid was filtered, washed with water and ether, and dried under vacuum, to give the title compound as a white solid. Yield: 0.28 g (72%). MP 213-214° C. $^1$H NMR (400 MHz, CDCl$_3$): δ 9.87 (br s, 1H), 7.74 (s, 2H), 6.83 (d, J=2.4 Hz, 1H), 6.46 (d, J=2.4 Hz, 1H), 3.97 (s, 3H), 3.95 (t, J=6.0 Hz, 2H), 3.93 (s, 3H), 3.69 (t, J=5.0 Hz, 2H), 3.53 (t, J=5.0 Hz, 2H), 2.84 (t, J=5.6 Hz, 2H), 2.62 (t, J=5.0 Hz, 2H), 2.57 (t, J=5.0 Hz, 2H), 2.39 (s, 6H), 2.11 (s, 3H). MS (ES$^-$) m/z 479.65 (100%, M−1).

Example 71

Preparation of 2-(4-(2-(1H-Imidazol-1-yl)ethoxy)-3,5-dimethylphenyl)-5,7-dimethoxyquinazolin-4(3H)-one

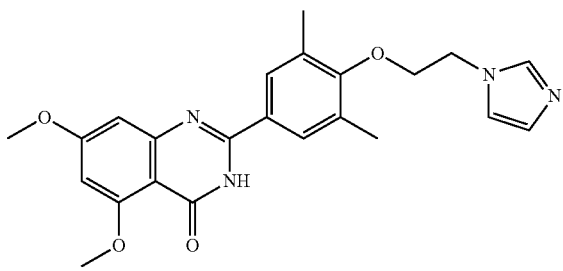 [SMILES: COc1cc(OC)c2c(=O)[nH]c(-c3cc(C)c(OCCn4ccnc4)c(C)c3)nc2c1]

To a solution of 2-[4-(2-bromoethoxy)-3,5-dimethylphenyl]-5,7-dimethoxy-3H-quinazolin-4-one (0.12 g, 0.27 mmol) in acetone (5 mL) was added imidazole (0.18 g, 2.70 mmol) and $Cs_2CO_3$ (0.26 g, 0.80 mmol). The reaction mixture was stirred at room temperature for 16 hours. Solvent was removed under reduced pressure, and the residue was purified by column chromatography (silica gel 230-400 mesh; 3% methanol in dichloromethane as eluent) to give the title compound as a white solid. Yield: 0.04 g (35%). MP 218-219° C. $^1$H NMR (400 MHz, DMSO-$d_6$): δ 11.80 (br s, 1H), 7.83 (s, 2H), 7.72 (s, 1H), 7.29 (s, 1H), 6.92 (s, 1H), 6.70 (d, J=2.4 Hz, 1H), 6.49 (d, J=2.4 Hz, 1H), 4.36 (t, J=4.8 Hz, 2H), 4.02 (t, J=4.8 Hz, 2H), 3.86 (s, 3H), 3.81 (s, 3H), 2.06 (s, 6H). MS (ES) m/z: 419.57 (M−1).

Example 72

Preparation of 2-(3,5-Dimethyl-4-(2-(pyrrolidin-1-yl)ethoxy)phenyl)-7-methoxyquinazolin-4(3H)-one

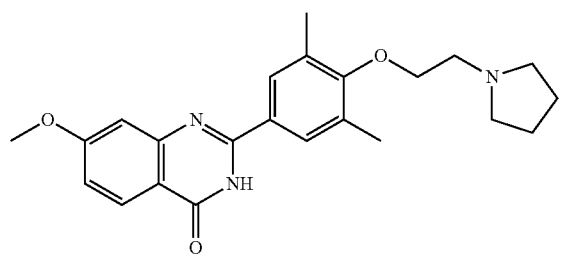 [SMILES: COc1ccc2c(=O)[nH]c(-c3cc(C)c(OCCN4CCCC4)c(C)c3)nc2c1]

To a stirred solution of 2-amino-4-methoxy-benzoic acid (3.00 g, 17.9 mmol) in THF (90 mL), EDCl (7.89 g, 41.1 mmol) and HOBt (7.95 g, 51.9 mmol) were added and stirred at room temperature for 30 minutes. Then, N-methylmorpholine (6.15 g, 60.0 mmol) and aqueous 50% (v/v) $NH_4OH$ (12 mL, 171.4 mmol) were added. The mixture was stirred for 16 hours at room temperature. The solvent was removed under reduced pressure and the residue was extracted with ethyl acetate (4×100 mL). The combined organic phase was washed with water, then brine, and dried over anhydrous sodium sulfate. Solvent was evaporated to give 2-amino-4-methoxy-benzamide as an off-white solid. Yield: 1.80 g, (60%).

To a solution of 2-amino-4-methoxy-benzamide (1.00 g, 6.01 mmol) and 4-(2-hydroxy-ethoxy)-3,5-dimethyl-benzaldehyde (1.28 g, 6.59 mmol) in N,N-dimethylacetamide (15 mL) were added $NaHSO_3$ (58.5 wt %, 0.68 g, 6.50 mmol) and p-TSA (0.23 g, 1.20 mmol) and the reaction mixture was stirred at 115° C. for 16 hours, and cooled to room temperature. Solvent was removed under reduced pressure. The residue was diluted with water (50 mL), stirred for 30 minutes, and then filtered. The solid was suspended in dichloromethane (30 mL), stirred for 1 hour, filtered, and dried under vacuum, to give 2-[4-(2-hydroxy-ethoxy)-3,5-dimethyl-phenyl]-7-methoxy-3H-quinazolin-4-one as an off-white solid. Yield: 1.20 g (58%).

To a solution of 2-[4-(2-hydroxy-ethoxy)-3,5-dimethyl-phenyl]-7-methoxy-3H-quinazolin-4-one (1.20 g, 3.52 mmol) in anhydrous DMF (15 mL) were added triphenylphosphine (1.00 g, 3.80 mmol) and carbontetrabromide (1.27 g, 3.80 mmol). The reaction mixture was stirred at room temperature for 16 hours. DMF was removed under reduced pressure. The residue was purified by column chromatography (silica gel 230-400 mesh; 3% methanol in dichloromethane as eluent) to give 2-[4(2-bromo-ethoxy)-3,5-dimethyl-phenyl]-7-methoxy3H-quinazolin-4-one as an off-white solid. Yield: 0.37 g (26%).

To a solution of 2-[4-(2-bromo-ethoxy)-3,5-dimethyl-phenyl]-7-methoxy-3H-quinazolin-4-one (0.30 g, 0.74 mmol) in DMF (5 mL) was added pyrrolidine (0.31 g, 4.36 mmol) and the reaction mixture was stirred at room temperature for 15 hours. DMF was removed under reduced pressure, and the residue was purified by column chromatography (silica gel 230-400 mesh; 5% methanol in dichloromethane as eluent) to give the title compound as a white solid. Yield: 0.13 g (44%). MP 218-220° C. $^1$H NMR (400 MHz, DMSO-$d_6$): δ 12.13 (br s, 1H), 8.03 (d, J=8.98 Hz, 1H), 7.90 (s, 2H), 7.16 (d, J=2.3 Hz, 1H), 7.07 (dd, J=8.9 and 2.7 Hz, 1H), 3.92-3.89 (m, 5H), 2.83 (t, J=5.8 Hz, 2H), 2.54-2.50 (m, 4H), 2.31 (s, 6H), 1.73 (m, 4H). MS ($ES^+$) m/z: 394.62 (M+1).

Example 73

Preparation of 2-(3,5-Dimethyl-4-(2-(4-methylpiperazin-1-yl)ethoxy)phenyl)-5,7-dimethoxyquinazolin-4(3H)-one

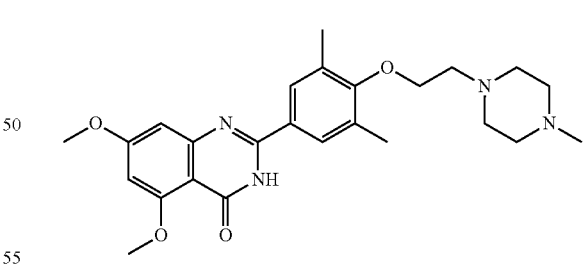

To a solution of 2-[4-(2-bromo-ethoxy)-3,5-dimethyl-phenyl]-5,7-dimethoxy-3H-quinazolin-4-one (0.17 g, 0.39 mmol) in N,N-dimethylformamide (0.5 mL) was added N-methylpiperazine (0.44 mL, 3.92 mmol) and the reaction mixture was stirred at room temperature for 15 hours. N,N-dimethylformamide was removed under reduced pressure. The residue was purified by column chromatography (silica gel 230-400 mesh; 5% methanol in dichloromethane as eluent) to give the title compound as a white solid. Yield: 60 mg (33.8%). MP 180-182° C. $^1$H NMR (400 MHz, DMSO-$d_6$): δ 11.76 (s, 1H), 7.89 (s, 2H), 6.73 (d, J=2.4 Hz, 1H), 6.51 (d, J=2.4 Hz, 1H), 3.88 (m, 5H), 3.84 (s, 3H), 2.68 (t, J=5.6 Hz, 2H), 2.50 (br s, 4H), 2.32 (br s, 4H), 2.30 (s, 6H), 2.15 (s, 3H). MS (ES⁺) m/z: 453.21 (M+1).

Example 74

Preparation of 2-(3,5-Dimethyl-4-(2-(piperidin-1-yl) ethoxy)phenyl)-5,7-dimethoxyquinazolin-4(3H)-one

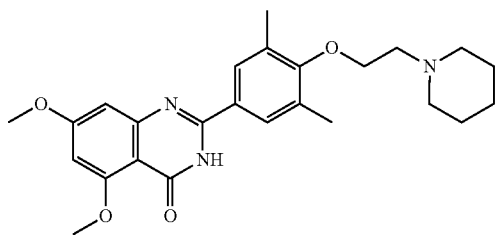 [SMILES: COc1cc(OC)c2c(=O)[nH]c(-c3cc(C)c(OCCN4CCCCC4)c(C)c3)nc2c1]

To a solution of 2-[4-(2-bromo-ethoxy)-3,5-dimethyl-phenyl]-5,7-dimethoxy-3H-quinazolin-4-one (0.34 g, 0.78 mmol) in DMF (10 mL) was added piperidine (0.27 g, 3.14 mmol). The reaction mixture was stirred at room temperature for 16 hours. Then, water was added and the product was extracted with ethyl acetate (2×200 mL). The combined organic layer was washed with water, then brine, and dried over anhydrous Na₂SO₄. Solvent was evaporated to give the title compound as a white solid. Yield: 0.33 g (96%). ¹H NMR (400 MHz, DMSO-d₆): δ 11.80 (br s, 1H), 7.87 (s, 2H), 6.72 (d, J=2.4 Hz, 1H), 6.49 (d, J=2.0 Hz, 1H), 3.86 (m, 6H), 3.82 (s, 2H), 2.63 (t, J=5.6 Hz, 2H), 2.42 (m, 4H), 2.28 (s, 6H), 1.50 (m, 4H), 1.37 (m, 2H). MS (ES) m/z 438.63 (M+1).

Example 75

Preparation of 5,7-Dimethoxy-2-(3-methyl-4-(2-(pyrrolidin-1-yl)ethoxy)phenyl)quinazolin-4(3H)-one

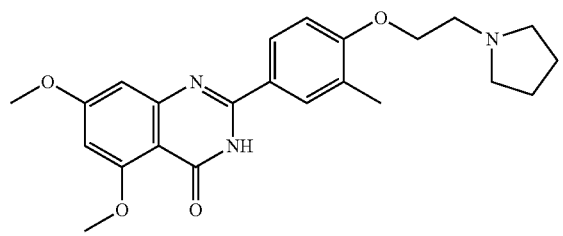 [SMILES: COc1cc(OC)c2c(=O)[nH]c(-c3ccc(OCCN4CCCC4)c(C)c3)nc2c1]

To a solution of 4-hydroxy-3-methylbenzaldehyde (1.10 g, 8.08 mmol) in anhydrous DMF (12 mL) was added K₂CO₃ (2.23 g, 16.16 mmol) and ethylene carbonate (1.42 g, 16.16 mmol) at room temperature. The resulting reddish-orange suspension was stirred at 110° C. for 6 hours under nitrogen. DMF was removed and the residue was diluted with water (50 mL) and dichloromethane (50 mL). The organic phase was separated, and the aqueous phase was extracted with dichloromethane (2×20 mL). The combined organic phase was washed with brine and dried over anhydrous magnesium sulfate. The solvent was removed under reduced pressure to obtain 4-(2-hydroxy-ethoxy)-3-methylbenzaldehyde as a brown oil. Yield: 1.46 g (100%).

To a solution of 4-(2-hydroxy-ethoxy)-3-methylbenzaldehyde (1.46 g, 8.08 mmol) and 2-amino-4,6-dimethoxybenzamide (1.58 g, 8.08 mmol) in N,N-dimethylacetamide (20 mL) were added NaHSO₃ (58.5 wt %, 2.20 g, 12.12 mmol) and p-toluenesulfonic acid monohydrate (0.38 g, 2.02 mmol). The reaction mixture was stirred at 110° C. for 16 hours, then cooled to room temperature. N,N-dimethylacetamide was removed under reduced pressure. The residue was triturated with water (50 mL). The resulting slurry was filtered and solid was washed with water, ether, and hexanes to obtain 2-[4-(2-hydroxy-ethoxy)-3-methyl-phenyl]-5,7-dimethoxy-3H-quinazolin-4-one as a beige solid. Yield: 2.75 g (95%).

Tetrabromomethane (3.26 g, 9.82 mmol) was added to a solution of triphenylphosphine (2.58 g, 9.82 mmol) in anhydrous DMF (20 mL) at 0° C. A solution of 2-[4-(2-hydroxy-ethoxy)-3-methyl-phenyl]-5,7-dimethoxy-3H-quinazolin-4-one (1.75 g, 4.91 mmol) in DMF (7 mL) was then added dropwise and stirred the reaction mixture at room temperature for 16 hours. The solvent was removed under reduced pressure and the residue was diluted with water (50 mL) and extracted with dichloromethane (4×25 mL). The combined organic phase was washed with brine and dried over anhydrous magnesium sulfate. The solvent was removed and the solid was triturated with ether. The resulting slurry was filtered and washed with ether several times (to remove the triphenylphosphine oxide) and finally with a solution of dichloromethane-ether (1:1) to obtain 2-[4-(2-bromo-ethoxy)-3-methyl-phenyl]-5,7-dimethoxy-3H-quinazolin-4-one as an off-white solid. Yield: 0.70 g (34%).

To a suspension of 2-[4-(2-bromo-ethoxy)-3-methyl-phenyl]-5,7-dimethoxy-3H-quinazolin-4-one (0.70 g, 1.67 mmol) in anhydrous DMF (9 mL) was added pyrrolidine (0.55 mL, 6.68 mmol) and the reaction mixture was stirred at room temperature under nitrogen for 20 hours. Solvent was removed under reduced pressure and the residue was purified by column chromatography (silica gel 230-400 mesh; 9% methanol in dichloromethane as eluent) to give the title compound as an off-white solid. Yield: 0.62 g (90.6%). MP 230-231° C. ¹H NMR (400 MHz, CDCl₃): δ 9.96 (br s, 1H), 7.91-7.89 (m, 2H), 6.93 (d, J=7.6 Hz, 1H), 6.82 (d, J=2.4 Hz, 1H), 6.44 (d, J=2.4 Hz, 1H), 4.21 (t, J=6.0 Hz, 2H), 3.98 (s, 3H), 3.93 (s, 3H), 2.98 (t, J=6.0 Hz, 2H), 2.69 (br s, 4H), 2.32 (s, 3H), 1.84-1.81 (m, 4H). MS (ES⁻) m/z 408.13 (M−1, 100%), MS (ES⁺) m/z 410.14 (M+1, 75%).

Example 76

Preparation of 3-(2-(4-(5,7-Dimethoxy-4-oxo-3,4-dihydroquinazolin-2-yl)-2,6-dimethylphenoxy) ethyl)-1-isopropylimidazolidine-2,4-dione

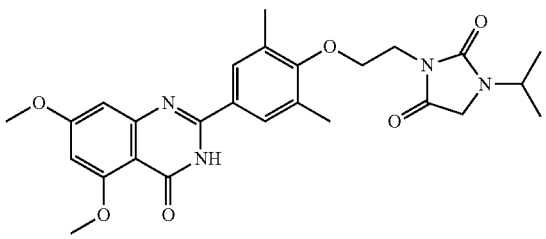 [SMILES: COc1cc(OC)c2c(=O)[nH]c(-c3cc(C)c(OCCN4C(=O)CN(C(C)C)C4=O)c(C)c3)nc2c1]

To a mixture of urea (5.00 g, 83.0 mmol) in anhydrous toluene (13 mL) was added chloroacetyl chloride (6.6 mL, 83.0 mmol) and the reaction mixture was heated to reflux for 2 hours. The reaction mixture was cooled to room temperature and toluene was removed by filtration. The resulting solid was further washed with toluene (10 mL) and mixed with water (100 mL). The solid was filtrated and washed with cold water (50 mL) and dried to give (2-chloroacetyl)-urea as a white solid. Yield: 10.3 g (91%).

(2-Chloroacetyl)-urea (0.68 g, 5.00 mmol) and isopropylamine (0.86 mL, 10.0 mmol) in DMF (10 mL) was stirred for 6 h at room temperature and then heated to 135° C. for 4 hours. DMF was removed under vacuum and the residue was purified by column chromatography (silica gel 230-400 mesh; eluting with hexane:dichloromethane:ethyl acetate 2.5:1.0:0.5) to give 1-isopropyl-imidazolidine-2,4-dione as a white solid. Yield: 0.20 g (28%).

To a solution of 1-isopropyl-imidazolidine-2,4-dione (0.10 g, 0.70 mmol) in N,N-dimethylformamide (5 mL) was added sodium hydride (60% in mineral oil, 31 mg, 0.77 mmol) and the reaction mixture was stirred for 10 minutes. Then, 2-[4-(2-bromo-ethoxy)-3,5-dimethyl-phenyl]-5,7-dimethoxy-3H-quinazolin-4-one (0.32 g, 0.73 mmol) was added. The reaction mixture was stirred at 55° C. for 16 hours, then poured into water (100 mL). The solid was filtered and dried. The crude compound was purified by column chromatography (silica gel 230-400 mesh; eluting with 2:1 ethyl acetate and dichloromethane) to give the title compound as a white solid. Yield: 0.09 g (26.0%). MP 219-221° C. $^1$H NMR (400 MHz, DMSO): δ 9.64 (s, 1H), 7.69 (s, 2H), 6.82 (d, J=2.4 Hz, 1H), 6.45 (d, J=2.4 Hz, 1H), 4.42 (m, 1H), 4.02 (m, 2H), 3.98 (m, 2H), 3.96 (s, 3H), 3.92 (s, 3H), 3.85 (s, 2H), 2.32 (s, 6H) 1.22 (d, J=6.4 Hz, 6H). MS (ES$^+$) m/z: 495.16 (M+1).

Example 77

Preparation of 2-(3,5-Dimethyl-4-(3-(pyrrolidin-1-yl)propoxy)phenyl)-5,7-dimethoxyquinazolin-4(3H)-one

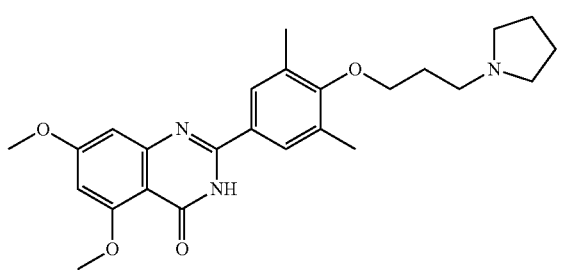 [SMILES: COc1cc(OC)c2c(=O)[nH]c(-c3cc(C)c(OCCCN4CCCC4)c(C)c3)nc2c1]

To a solution of 4-hydroxy-3,5-dimethyl benzaldehyde (5.0 g, 33.29 mmol) in DMF (30 mL) were added 3-bromo propan-1-ol (5.56 g, 39.95 mmol) and Cs$_2$CO$_3$ (16.24 g, 50.0 mmol). Then, the reaction mixture was stirred at room temperature for 48 hours. Then, water was added and the products were extracted with ethyl acetate (2×250 mL). The combined organic phase was washed with water (100 mL), then brine (100 mL), and dried over anhydrous Na$_2$SO$_4$. Removal of solvent gave 4-(3-hydroxypropoxy)-3,5-dimethyl benzaldehyde as a colorless liquid. Yield: 5.38 g (77%).

To a solution of 2-amino-4,6-dimethoxy-benzamide (1.3 g, 6.63 mmol) and 4-(3-hydroxypropoxy)-3,5-dimethyl benzaldehyde (1.38 g, 6.63 mmol) in N,N-dimethyl acetamide (10 mL), NaHSO$_3$ (1.30 g, 7.3 mmol), and p-TSA (252 mg, 1.32 mmol) were added and the reaction mixture was heated at 115° C. for 26 hours, then cooled to room temperature. The solvent was removed under reduced pressure. Then, water (100 mL) was added and stirred for 1 hour at room temperature. The separated solids were filtered and dried. The solids were again washed with diethyl ether to give crude product 2-[4-(3-hydroxy-propoxy)-3,5-dimethyl-phenyl]-5,7-dimethoxy-3H-quinazolin-4-one as an off-white solid. Yield: 1.69 g (66%).

To a solution of 2-[4-(3-hydroxy-propoxy)-3,5-dimethyl-phenyl]-5,7-dimethoxy-3H-quinazolin-4-one (1.39 g, 3.62 mmol) in DMF (15 mL) were added PPh$_3$ (1.04 g, 3.98 mmol) and CBr$_4$ (1.32 g, 3.98 mmol). The reaction mixture was stirred at room temperature for 16 hours. Then, solvent was removed under reduced pressure. The residue was triturated with ether and ethyl acetate. The solids were dried and purified by the Simpliflash system, using 2% methanol in CH$_2$Cl$_2$, to give 2-[4-(3-bromo-propoxy)-3,5-dimethyl-phenyl]-5,7-dimethoxy-3H-quinazolin-4-one as a white solid. Yield: 940 mg (58%).

To a solution of 2-[4-(3-bromo-propoxy)-3,5-dimethyl-phenyl]-5,7-dimethoxy-3H-quinazolin-4-one (340 mg, 0.76 mmol) in DMF (10 mL) was added pyrrolidine (433 mg, 6.08 mmol). Then, the reaction mixture was stirred at room temperature for 16 hours. Then, water was added and the solids were filtered. The solids were washed with water and dried to give the title compound as a white solid. Yield: 307 mg (92%). $^1$H NMR (400 MHz, DMSO-d$_6$): δ 11.80 (s, 1H), 7.87 (s, 2H), 6.71 (d, J=2.0 Hz, 1H), 6.49 (d, J=2.0 Hz, 1H), 3.86 (s, 3H), 3.82 (m, 5H), 2.59 (t, J=6.8 Hz, 2H), 2.42 (m, 4H), 2.26 (s, 6H), 1.89 (m, 2H), 1.67 (m, 4H). MS (ES) m/z: 438.16 (M+1).

Example 78

Preparation of 5,7-Dimethoxy-2-(4-(2-(pyrrolidin-1-yl)ethoxy)phenyl)quinazolin-4(3H)-one

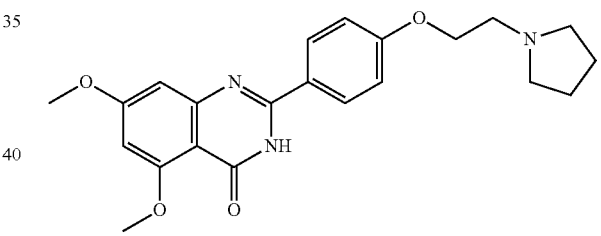

Carbon tetrabromide (0.26 g, 0.77 mmol) was added to a solution of triphenylphosphine (0.24 g, 0.92 mmol) in anhydrous DMF (5 mL) at 0° C. A solution of 2-[4-(2-hydroxy-ethoxy)-phenyl]-5,7-dimethoxy-3H-quinazolin-4-one (0.21 g, 0.61 mmol) in DMF (2 mL) was then added dropwise and stirred at room temperature for 16 hours. Solvent was removed under reduced pressure and the residue was diluted with water (10 mL) and extracted with dichloromethane (4×10 mL). The combined organic phase was washed with brine and dried over anhydrous magnesium sulfate. Solvent was removed and the residual solid was triturated with ether. The resulting slurry was filtered and washed with ether several times (to remove the triphenylphosphine oxide) and finally with a solution of dichloromethane-ether (1:4) to obtain 2-[4-(2-bromo-ethoxy)-phenyl]-5,7-dimethoxy-3H-quinazolin-4-one as an off-white solid. Yield: 0.25 g (quantitative).

To a suspension of 2-[4-(2-bromo-ethoxy)-phenyl]-5,7-dimethoxy-3H-quinazolin-4-one (0.25 g, 0.61 mmol) in anhydrous DMF (10 mL) was added pyrrolidine (0.20 mL, 2.45 mmol) and the reaction mixture was stirred at room temperature under nitrogen for about 20 hours. Solvent was removed under reduced pressure and the residual solid was triturated with water. The resulting slurry was filtered and washed with ether and hexanes. The crude product was purified by column chromatography (silica gel 230-400 mesh; 10% methanol in dichloromethane as eluent) to give the title compound as a white solid. Yield: 0.11 g (44%). MP 226-227° C. $^1$H NMR (400 MHz, CDCl$_3$): δ 10.08 (br s, 1H), 8.07 (d, J=8.4 Hz, 2H), 7.06 (d, J=8.8 Hz, 2H), 6.81 (d, J=1.95 Hz, 1H), 6.45 (d, J=1.95 Hz, 1H), 4.21 (t, J=5.6 Hz, 2H), 3.99 (s, 3H), 3.93 (s, 3H), 2.97 (t, J=5.6 Hz, 2H), 2.68 (br s, 4H), 1.84 (br s, 4H). MS (ES$^+$): m/z 198.65 (100%), 396.10 (M+1, 70%).

Example 79

Preparation of 2-(3,5-Dimethyl-4-(3-(pyrrolidin-1-yl)propyl)phenyl)-5,7-dimethoxyquinazolin-4(3H)-one

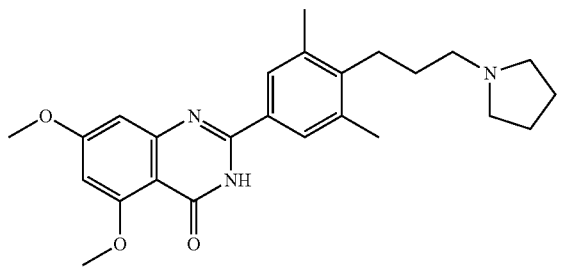 [SMILES: COc1cc(OC)c2c(=O)[nH]c(-c3cc(C)c(CCCN4CCCC4)c(C)c3)nc2c1]

To a solution of 2-amino-4,6-dimethoxy-benzamide (0.80 g, 4.00 mmol) and 4-(3-hydroxy-propyl)-3,5-dimethyl-benzaldehyde (0.98 g, 5.1 mmol) in N,N-dimethylacetamide (15 mL) were added NaHSO$_3$ (58.5 wt %, 0.80 g, 4.40 mmol) and p-TSA (0.155 g, 0.81 mmol) and the reaction mixture was heated at 115° C. for 16 hours, then cooled to room temperature. N,N-dimethylacetamide was removed under reduced pressure. The residue was diluted with water (50 mL), stirred for 30 minutes, and then filtered and washed with water. The crude compound was purified by column chromatography (silica gel 230-400 mesh; 5% methanol in dichloromethane as eluent) to give 2-[4-(3-hydroxy-propyl)-3,5-dimethyl-phenyl]-5,7-dimethoxy-3H-quinazolin-4-one as an off-white solid. Yield: 1.10 g (73%).

To a solution of 2-[4-(3-hydroxy-propyl)-3,5-dimethyl-phenyl]-5,7-dimethoxy-3H-quinazolin-4-one (1.00 g, 2.70 mmol) in anhydrous N,N-dimethylformamide (15 mL) were added triphenylphosphine (0.78 g, 3.00 mmol) and carbon tetrabromide (1.00 g, 3.00 mmol). The reaction mixture was stirred at room temperature for 16 hours. DMF was removed under reduced pressure. The residue was purified by column chromatography (silica gel 230-400 mesh; 3% methanol in dichloromethane as eluent) to give 2-[4-(3-bromo-propyl)-3,5-dimethyl-phenyl]-5,7-dimethoxy-3H-quinazolin-4-one as an off-white solid. Yield: 0.60 g (51%).

To a solution of 2-[4-(3-bromo-propyl)-3,5-dimethyl-phenyl]-5,7-dimethoxy-3H-quinazolin-4-one (0.40 g, 0.92 mmol) in N,N-dimethylformamide (10 mL) was added pyrrolidine (0.39 g, 5.52 mmol) and the reaction mixture was stirred at room temperature for 16 hours. DMF was removed under reduced pressure, the residue was purified by column chromatography (silica gel 230-400 mesh; 5% methanol ammonia in dichloromethane as eluent) to give the title compound as a white solid. Yield: 0.27 g (69%). MP 194-196° C. $^1$H NMR (400 MHz, DMSO-d$_6$): δ 11.79 (br s, 1H), 7.81 (s, 2H), 6.72 (d, J=2.3 Hz, 1H), 6.50 (d, J=2.3 Hz, 1H), 4.00 (s, 3H), 3.87 (s, 3H), 2.67-2.63 (m, 2H), 2.49-2.46 (m, 6H), 2.33 (s, 6H), 1.70-1.67 (m, 4H), 1.59-1.53 (m, 2H). MS (ES$^+$) m/z: 422.17 (M+1).

Example 80

Preparation of 2-(3,5-Dimethyl-4-(4-(pyrrolidin-1-yl)butoxy)phenyl)-5,7-dimethoxyquinazolin-4(3H)-one

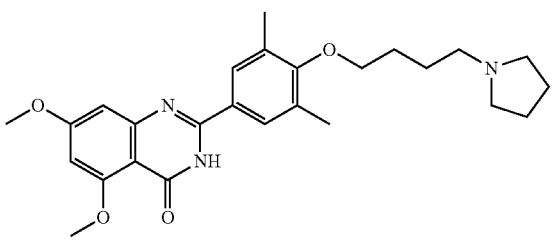 [SMILES: COc1cc(OC)c2c(=O)[nH]c(-c3cc(C)c(OCCCCN4CCCC4)c(C)c3)nc2c1]

To a solution of 4-hydroxy-3,5-dimethyl benzaldehyde (5.00 g, 33.3 mmol) in DMF (30 mL) were added 4-bromo-butan-1-ol (6.11 g, 39.9 mmol) and Cs$_2$CO$_3$ (16.2 g, 50.0 mmol). The reaction mixture was stirred at room temperature for 48 hours, then water (100 mL) was added, and the products were extracted with ethyl acetate (2×200 mL). The combined organic phase was washed with water (100 mL), then brine (100 mL), and dried over anhydrous Na$_2$SO$_4$. Solvent was removed and the crude product was purified by the Simpliflash system, using 40% ethyl acetate in hexane as eluent, to give 4-(4-hydroxybutoxy)-3,5-dimethyl benzaldehyde as a colorless liquid. Yield: 0.66 g (7%).

To a solution of 2-amino-4,6-dimethoxy-benzamide (497 mg, 2.53 mmol) and 4-(4-hydroxybutoxy)-3,5-dimethyl benzaldehyde (660 mg, 2.53 mmol) in N,N-dimethyl acetamide (10 mL), NaHSO$_3$ (58.5 wt %, 496 mg, 2.79 mmol) and p-TSA (96 mg, 0.50 mmol) were added and the reaction mixture was heated at 115° C. for 16 hours and then cooled to room temperature. The solvent was removed under reduced pressure. Water (100 mL) was added and stirred for 1 hour at room temperature. The solid separated was filtered and dried. The solid was further washed with diethyl ether to give product 2-[4-(4-hydroxy-butoxy)-3,5-dimethyl-phenyl]-5,7-dimethoxy-3H-quinazolin-4-one as a white solid. Yield: 1.69 g (82%).

To a solution of 2-[4-(4-hydroxy-butoxy)-3,5-dimethyl-phenyl]-5,7-dimethoxy-3H-quinazolin-4-one (675 mg, 1.69 mmol) in DMF (10 mL) were added PPh$_3$ (489 mg, 1.86 mmol) and CBr$_4$ (619 mg, 1.86 mmol). The reaction mixture was stirred at room temperature for 16 hours. Solvent was removed under reduced pressure. The residue was triturated with ether and ethyl acetate. The solid was dried and then purified by the Simpliflash system using 5% methanol in CH$_2$Cl$_2$ as the eluent to give 2-[4-(4-bromo-butoxy)-3,5-dimethyl-phenyl]-5,7-dimethoxy-3H-quinazolin-4-one as a white solid. Yield: 494 mg (63%).

To a solution of 2-[4-(4-bromo-butoxy)-3,5-dimethyl-phenyl]-5,7-dimethoxy-3H-quinazolin-4-one (494 mg, 1.07 mmol) in DMF (10 mL) was added pyrrolidine (609 mg, 8.57 mmol). The reaction mixture was stirred at room temperature for 16 hours. Water (100 mL) was added and the product was extracted with ethyl acetate (2×200 mL). The combined organic phase was washed with water, then brine, and dried over anhydrous Na$_2$SO$_4$. Solvent was evaporated to give the title compound as a white solid. Yield: 278 mg (57%). MP 180-181° C. $^1$H NMR (400 MHz, CDCl$_3$): δ 7.68 (s, 2H), 6.83 (d, J=2.4 Hz, 1H), 6.46 (d, J=2.4 Hz, 1H), 3.97 (s, 3H), 3.92 (s, 3H), 3.83 (t, J=6.4 Hz, 2H), 2.56 (m, 6H), 2.36 (s, 6H), 1.88 (m, 2H), 1.79 (m, 6H). MS (ES) m/z: 452.21 (M+1).

Example 81

Preparation of 2-(3,5-Dimethyl-4-(2-(pyrrolidin-1-yl)ethoxy)phenyl)-8-methoxyquinazolin-4(3H)-one

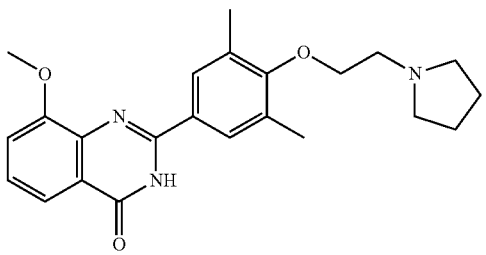 [SMILES: COc1cccc2c(=O)[nH]c(-c3cc(C)c(OCCN4CCCC4)c(C)c3)nc12]

To a solution of 2-amino-3-methoxy benzoic acid (5.00 g, 29.9 mmol) in THF (50 mL) were added EDCl (6.88 g, 35.9 mmol), HOBt (4.85 g, 35.9 mmol), N-methylmorpholine (3.60 g, 35.9 mmol), and aqueous ammonia (50% v/v, 30 mL). Then, the reaction mixture was stirred at room temperature for 48 hours. Then, water was added and the product was extracted with ethyl acetate (2×250 mL). The combined organic phase was washed with water, then brine, and dried over anhydrous Na$_2$SO$_4$. Removal of solvent gave product 2-amino-3-methoxy-benzamide as a light orange solid. Yield: 1.70 g (34%).

To a solution of 2-amino-3-methoxy-benzamide (700 mg, 4.22 mmol) and 4-(2-hydroxyethoxy)-3,5-dimethyl benzaldehyde (823 mg, 4.22 mmol) in N,N-dimethyl acetamide (10 mL) were added NaHSO$_3$ (58.5 wt %, 841 mg, 4.64 mmol) and p-TSA (160 mg, 0.84 mmol). The reaction mixture was heated at 115° C. for 16 hours, then cooled to room temperature. Solvent was removed under reduced pressure. Water (100 mL) was added and stirred for 1 hour at room temperature. The solid separated was filtered and dried. The solid was further washed with diethyl ether to give crude product 2-[4-(2-hydroxy-ethoxy)-3,5-dimethyl-phenyl]-8-methoxy-3H-quinazolin-4-one as an off-white solid. Yield: 1.2 g (84%).

To a solution of 2-[4-(2-hydroxy-ethoxy)-3,5-dimethyl-phenyl]-8-methoxy-3H-quinazolin-4-one (1.20 g, 3.53 mmol) in DMF (10 mL) were added PPh$_3$ (1.02 g, 3.88 mmol) and CBr$_4$ (1.29 g, 3.88 mmol). The reaction mixture was stirred at room temperature for 16 hours. Solvent was removed under reduced pressure. The residue was triturated with ether and ethyl acetate. The solid was dried under vacuum and purified by the Simpliflash system, using 2% methanol in CH$_2$Cl$_2$ as eluent, to give 2-[4-(2-bromo-ethoxy)-3,5-dimethyl-phenyl]-8-methoxy-3H-quinazolin-4-one as a white solid. Yield: 0.547 g (38%).

To a solution of 2-[4-(2-bromo-ethoxy)-3,5-dimethyl-phenyl]-8-methoxy-3H-quinazolin-4-one (537 mg, 1.33 mmol) in DMF (10 mL) was added a pyrrolidine (758 mg, 10.66 mmol). The reaction mixture was stirred at room temperature for 16 hours. Water (100 mL) was added and the solid separated was filtered and dried under vacuum. The solid was triturated with ether and dried to give the title compound as a white solid. Yield: 232 mg (44%). MP 231-232° C. $^1$H NMR (400 MHz, CDCl$_3$): δ 10.30 (s, 1H), 7.90 (dd, J=8.0 Hz, 1H), 7.806 (br s, 2H), 7.42 (t, J=8.4 Hz, 1H), 7.24 (d, J=8.4 Hz, 1H), 4.04 (s, 3H), 3.95 (t, J=6.4 Hz, 2H), 2.93 (t, J=6.0 Hz, 2H), 2.65 (m, 4H), 2.40 (s, 6H), 1.84 (m, 4H). MS (ES) m/z: 394.15 (M+1).

Example 82

Preparation of 3-(2-(4-(5,7-Dimethoxy-4-oxo-3,4-dihydroquinazolin-2-yl)-2,6-dimethylphenoxy)ethyl)-5-phenylimidazolidine-2,4-dione

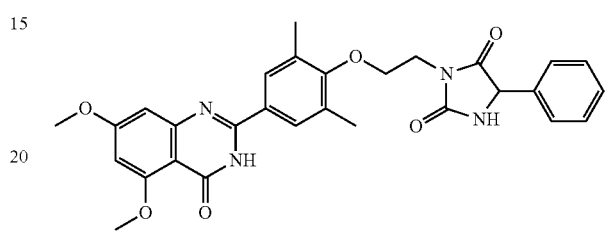

To a suspension of 2-[4-(2-hydroxy-ethoxy)-3,5-dimethyl-phenyl]-5,7-dimethoxy-3H-quinazolin-4-one (0.50 g, 1.35 mmol) in THF (20 mL), were added 5-phenyl-imidazolidine-2,4-dione (0.24 g, 1.35 mmol) and triphenyl phosphine (0.35 g, 1.35 mmol), then diethyl azodicarboxylate (0.43 mL, 2.70 mmol) was added and the reaction mixture was stirred at room temperature for 16 hours. Solvent was evaporated in vacuo and the residue was washed with dichloromethane and ether. The residue was dissolved in acetic acid and purified by preparative HPLC. The compound was further washed with dichloromethane and ether (1:1, 20 mL) to obtain the title compound as a white solid. Yield: 0.07 g (10%). MP 219.6-221.4° C. $^1$H NMR (400 MHz, DMSO-d$_6$): δ 8.81 (s, 1H), 7.86 (s, 2H), 7.37 (m, 5H), 6.71 (s, 1H), 6.48 (s, 1H), 3.94 (m, 4H), 3.86 (s, 3H), 3.82 (s, 3H), 2.18 (s, 6H). MS (ES) m/z: 529.29 (M$^+$+1).

Example 83

Preparation of 3-(4-(5,7-Dimethoxy-4-oxo-3,4-dihydroquinazolin-2-yl)benzyl)imidazolidine-2,4-dione

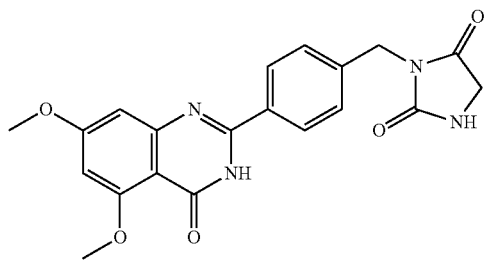 [SMILES: COc1cc(OC)c2c(=O)[nH]c(-c3ccc(CN4C(=O)CNC4=O)cc3)nc2c1]

Hydantoin (0.80 g, 8.00 mmol) was dissolved in DMF (10 mL) and cooled to 0° C. Sodium hydride (60% in mineral oil, 88 mg, 2.20 mmol) was added. The mixture was stirred at room temperature for 3 hours. 4-(Bromomethyl)benzaldehyde (0.40 g, 2.00 mmol) was added. The mixture was stirred at room temperature for 2.5 days. Saturated aqueous NH$_4$Cl (1 mL) was added. The mixture was concentrated to dryness.

Water (10 mL) was added, extracted with dichloromethane, and the organic phase was dried over anhydrous $Na_2SO_4$. Solvent was removed and the crude compound was purified by column chromatography (silica gel 230-400 mesh; 5% methanol in $CH_2Cl_2$ as eluent) to give 4-(2,5-dioxo-imidazolidin-1-ylmethyl)-benzaldehyde as a white solid. Yield: 0.28 g (64%).

To a solution of 2-amino-4,6-dimethoxy-benzamide (0.19 g, 0.98 mmol) in N,N-dimethylacetamide (4 mL) were added 4-(2,5-dioxo-imidazolidin-1-ylmethyl)-benzaldehyde (0.19 g, 0.89 mmol), sodium hydrogen sulfite (58.5 wt %, 0.24 g, 1.30 mmol) and p-toluenesulfonic acid monohydrate (34 mg, 0.18 mmol) and the reaction mixture was stirred at 115° C. for 17 hours under nitrogen, then cooled to room temperature. The precipitate was filtered, washed with methanol, water, then methanol, and dried in air. The solid was suspended in hot DMSO (approximately 3 mL); saturated aqueous $NaHCO_3$ (approximately 3 mL) and water were added. The solid was filtered, washed with water, then methanol, and air dried to give the title compound as a light yellow solid. Yield: 0.16 g (46%). MP 317-318° C. $^1$H NMR (400 MHz, DMSO-$d_6$): δ 12.05 (s, 1H), 8.17 (s, 1H), 8.12 (d, J=8.4 Hz, 2H), 7.40 (d, J=8.4 Hz, 2H), 6.74 (d, J=2.0 Hz, 1H), 6.54 (d, J=2.0 Hz, 1H), 4.61 (s, 2H), 4.02 (s, 2H), 3.89 (s, 3H), 3.85 (s, 3H). MS ($ES^+$) m/z: 395.09 (M+1).

Example 84

Preparation of 2-(3,5-Dimethyl-4-(2-(pyrrolidin-1-yl)ethoxy)phenyl)-6-methoxyquinazolin-4(3H)-one

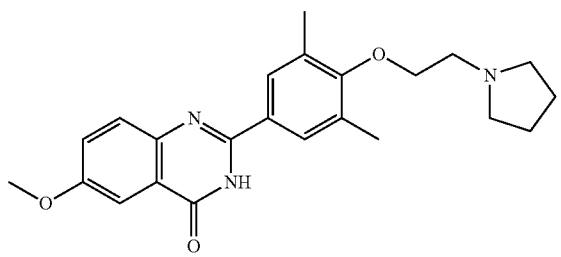 [SMILES: COc1ccc2nc(-c3cc(C)c(OCCN4CCCC4)c(C)c3)[nH]c(=O)c2c1]

To a suspension of 2-amino-5-methoxy-benzoic acid (5.00 g, 30.0 mmol) in THF (50 mL) were added 1-(3-dimethylaminopropyl)-3-ethylcarbodiimide hydrochloride (7.50 g, 39.0 mmol), 1-hydroxybenzotriazole (4.50 g, 33.0 mmol) and 4-methylmorpholine (3.6 mL, 33.0 mmol) and the reaction mixture was stirred at room temperature for 1 hours. Then, 50% aqueous $NH_3$ (8 mL, 105.0 mmol) was added and the reaction mixture was stirred at room temperature for 16 hours. Water (100 mL) was added and the product was extracted with ethyl acetate. Solvent was evaporated in vacuo and the residue was washed with ether to give 2-amino-5-methoxy-benzamide as a white solid. Yield: 2.62 g (53%).

To a stirred solution of 2-amino-5-methoxy-benzamide (2.62 g, 15.80 mmol) and 4-(2-hydroxy-ethoxy)-3,5-dimethyl-benzaldehyde (3.23 g, 16.60 mmol) in N,N-dimethyl acetamide (20 mL), were added sodium hydrogen sulfite (58.5 wt %, 3.44 g, 19.00 mmol) and p-toluenesulfonic acid monohydrate (0.60 g, 3.20 mmol) and the reaction mixture was stirred at 115° C. for 16 hours. Solvent was evaporated in vacuo, water (50 mL) was added, and the separated solid was filtered. The solid was triturated with ether to give 2-[4-(2-hydroxy-ethoxy)-3,5-dimethyl-phenyl]-6-methoxy-3H-quinazolin-4-one as a white solid. Yield: 3.56 g (66%).

To a suspension of 2-[4-(2-hydroxy-ethoxy)-3,5-dimethyl-phenyl]-6-methoxy-3H-quinazolin-4-one (1.50 g, 4.41 mmol) in N,N-dimethylformamide (15 mL), carbon tetrabromide (1.60 g, 4.85 mmol), and triphenylphosphine (1.30 g, 4.85 mmol) were added and the reaction mixture was stirred at room temperature for 16 hours. The solvent was evaporated in vacuo and the product was purified by the Simpliflash system, using 1-2% methanol in $CH_2Cl_2$ as eluent, to give 2-[4-(2-bromo-ethoxy)-3,5-dimethyl-phenyl]-6-methoxy-3H-quinazolin-4-one as a white solid. Yield: 1.77 g (quantitative).

To a suspension of 2-[4-(2-bromo-ethoxy)-3,5-dimethyl-phenyl]-6-methoxy-3H-quinazolin-4-one (1.94 g, 4.80 mmol) in N,N-dimethylformamide (20 mL), pyrrolidine (4 mL) was added and the reaction mixture was stirred at room temperature for 16 hours. Solvent was evaporated in vacuo, water (50 mL) was added, and the separated solid was filtered. The solid was washed with ether to give the title compound as a light brown solid. Yield: 0.30 g (16%). MP 201.2-203.1° C. $^1$H NMR (400 MHz, $CDCl_3$): δ 7.73 (m, 4H), 7.39 (m, 1H), 3.98 (t, J=6.0 Hz, 3H), 3.94 (s, 3H), 2.97 (t, J=6.0 Hz, 2H), 2.69 (br s, 4H), 2.41 (s, 6H), 1.86 (br s, 4H). MS (ES) m/z: 394.21 ($M^+$+1).

Example 85

Preparation of 2-(3,5-Dimethyl-4-(2-(pyrrolidin-1-yl)ethoxy)phenyl)-5,7-dimethoxypyrido[2,3-d]pyrimidin-4(3H)-one

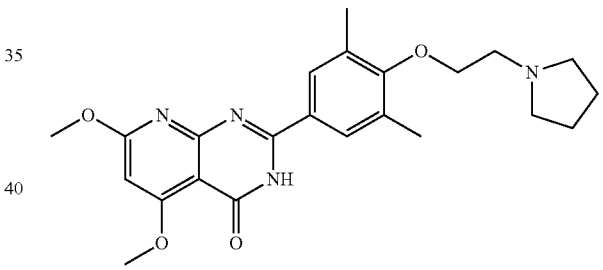

To a solution of 2-amino-4,6-dimethoxy-nicotinamide (0.60 g, 3.00 mmol) and 4-(2-hydroxy-ethoxy)-3,5-dimethyl-benzaldehyde (0.59 g, 3.00 mmol) in N,N-dimethylacetamide (8 mL) was added $NaHSO_3$ (58.5 wt %, 0.59 g, 3.30 mmol) and p-TSA (0.22 g, 1.20 mmol). The reaction mixture was heated to 145-148° C. for 16 hours, then cooled to room temperature. N,N-dimethylacetamide was removed under reduced pressure, the residue was diluted with sodium bicarbonate solution (50 mL), and the solid separated was filtered and dried under vacuum. The crude compound was purified by column chromatography (silica gel 230-400 mesh; 5% methanol in dichloromethane as eluent) to give 2-[4-(2-hydroxy-ethoxy)-3,5-dimethyl-phenyl]-5,7-dimethoxy-3H-pyrido[2,3-d]pyrimidin-4-one as a white solid. Yield: 0.50 g (49%).

To a solution of 2-[4-(2-hydroxy-ethoxy)-3,5-dimethyl-phenyl]-5,7-dimethoxy-3H-pyrido[2,3-d]pyrimidin-4-one (0.50 g, 1.34 mmol) in anhydrous DMF (6 mL) was added carbon tetrabromide (0.53 g, 1.61 mmol) and triphenylphosphine (0.42 g, 1.61 mmol). The reaction mixture was stirred at 25° C. for 16 hours. DMF was removed under vacuum and dichloromethane (200 mL) was added. The organic phase was washed with water (100 mL), then brine (100 mL), and dried over anhydrous sodium sulfate. Solvent was removed and the residue was washed with ether (100 mL) to give 2-[4-(2-bromo-ethoxy)-3,5-dimethyl-phenyl]-5,7-dimethoxy-3H-pyrido[2,3-d]pyrimidin-4-one as a white solid. Yield: 0.23 g (40%).

A solution of 2-[4-(2-bromo-ethoxy)-3,5-dimethyl-phenyl]-5,7-dimethoxy-3H-pyrido[2,3-d]pyrimidin-4-one (0.20 g, 0.46 mmol) in pyrrolidine (2 mL) was stirred at room temperature for 3 hours. The excess pyrrolidine was removed under reduced pressure, and the residue was purified by column chromatography (silica gel 230-400 mesh; eluting with 2% 2.0 M ammonia in methanol solution and dichloromethane) to give the title compound as a white solid. Yield: 0.17 g (87%). MP 228-230° C. $^1$H NMR (400 MHz, CDCl$_3$): δ 10.06 (s, 1H), 7.83 (s, 2H), 6.22 (s, 1H), 4.12 (s, 3H), 4.00 (s, 3H), 3.95 (t, J=6.0 Hz, 2H), 2.93 (t, J=6.0 Hz, 2H), 2.64 (m, 4H), 2.37 (s, 6H), 1.80 (m, 4H). MS (ES$^+$) m/z: 425.19 (M+1).

Example 86

Preparation of 2-(3,5-Dimethyl-4-(2-(pyrrolidin-1-yl)ethoxy)phenyl)-7-fluoro-5-(pyrrolidin-1-yl)quinazolin-4(3H)-one

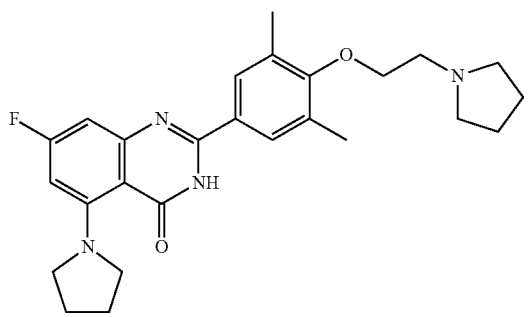 [SMILES: Cc1cc(-c2nc3cc(F)cc(N4CCCC4)c3c(=O)[nH]2)cc(C)c1OCCN1CCCC1]

A mixture of 2-amino-4,6-difluoro-benzamide (0.96 g, 5.60 mmol), 4-(2-hydroxy-ethoxy)-3,5-dimethyl-benzaldehyde (1.09 g, 5.60 mmol), NaHSO$_3$ (58.5 wt %, 1.00 g, 5.60 mmol) and p-toluenesulfonic acid monohydrate (1.44 g, 7.06 mmol) in N,N-dimethylacetamide (25 mL) was stirred at 120° C. for 16 hours, then cooled to room temperature. Solvent was removed under reduced pressure. The residue was diluted with water (100 mL). The solid separated was filtered and washed with water and dried under vacuum to give 5,7-difluoro-2-[4-(2-hydroxy-ethoxy)-3,5-dimethyl-phenyl]-3H-quinazolin-4-one as a white solid. Yield: 1.55 g (79%).

A mixture of 5,7-difluoro-2-[4-(2-hydroxy-ethoxy)-3,5-dimethyl-phenyl]-3H-quinazolin-4-one (1.54 g, 4.44 mmol), PPh$_3$ (1.52 g, 5.78 mmol), and CBr$_4$ (1.92 g, 5.78 mmol) in anhydrous DMF (30 mL) was stirred at room temperature for 36 hours. DMF was evaporated under vacuum, water (100 mL) was added, and stirred for 30 minutes. The solid separated was filtered, washed with water, then ether, and dried under vacuum to give 2-[4-(2-bromo-ethoxy)-3,5-dimethyl-phenyl]-5,7-difluoro-3H-quinazolin-4-one as pale yellow solid. Yield: 1.38 g (crude). This product was used in the next step without further purification.

A solution of 2-[4-(2-bromo-ethoxy)-3,5-dimethyl-phenyl]-5,7-difluoro-3H-quinazolin-4-one (1.38 g, crude) and pyrrolidine (10 mL) was stirred at room temperature for 16 hours. Excess pyrrolidine was evaporated, the residue was purified by column chromatography (silica gel 230-400 mesh; 30-50% ethyl acetate in hexanes as eluent). The compound was further purified by preparative HPLC to give the title compound as a white solid. Yield: 260 mg (13% for two steps). MP 206.6-206.8° C. $^1$H NMR (400 MHz, DMSO-d$_6$): δ 11.85 (s, 1H), 6.63 (d, J=8 Hz, 1H), 6.51 (d, J=12 Hz, 1H), 3.90 (t, J=4 Hz, 2H), 2.83 (t, J=4 Hz, 2H), 2.50 (s, 6H), 2.30 (s, 4H), 1.89 (s, 4H), 1.70 (s, 4H).

Example 87

Preparation of 5-Chloro-2-(3,5-dimethyl-4-(2-(pyrrolidin-1-yl)ethoxy)phenyl)quinazolin-4(3H)-one

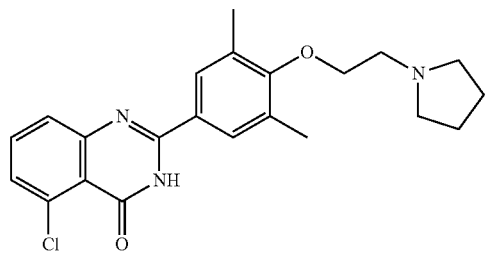 [SMILES: Cc1cc(-c2nc3cccc(Cl)c3c(=O)[nH]2)cc(C)c1OCCN1CCCC1]

To a solution of 2-amino-6-chlorobenzoic acid (2.00 g, 11.65 mmol) in anhydrous THF (20 mL) were added 4-methylmorpholine (1.40 mL, 12.82 mmol), HOBT (1.73 g, 12.82 mmol), and EDCl (2.45 g, 12.82 mmol); the reaction mixture was stirred at room temperature for 30 minutes. 50% (v/v) Ammonium hydroxide solution (10 mL, 132.0 mmol) was added and the mixture was stirred at room temperature for 23 hours. Solvent was evaporated to about 20 mL, poured into aqueous NaHCO$_3$ solution (200 mL) and extracted with ethyl acetate (7×100 mL). The organic phase was washed with water (3×100 mL), dried (Na$_2$SO$_4$), filtered, and evaporated, to give 2-amino-6-chlorobenzamide as a white solid. Yield: 1.65 g (83%).

4-(2-Hydroxyethoxy)-3,5-dimethylbenzaldehyde (0.70 g, 3.58 mmol), 2-amino-6-chlorobenzamide (0.60 g, 3.51 mmol), sodium bisulfite (0.71 g, 3.86 mmol) and p-toluenesulfonic acid monohydrate (0.133 g, 0.699 mmol) in anhydrous N,N-dimethyl acetamide (14 mL) were heated at 120° C. under nitrogen for 23 hours. The solvent was evaporated and the white solid was triturated with water (50 mL), filtered, and washed with water (20 mL). The solid was dried in vacuo and triturated with Et$_2$O (20 mL), filtered, and dried to give 5-chloro-2-(4-(2-hydroxyethoxy)-3,5-dimethylphenyl)quinazolin-4(3H)-one as a white solid. Yield: 0.77 g, (64%).

To a solution of 5-chloro-2-(4-(2-hydroxyethoxy)-3,5-dimethylphenyl)quinazolin-4(3H)-one (0.40 g, 1.16 mmol) in anhydrous DMF (10 mL) was added carbon tetrabromide (0.42 g, 1.27 mmol) and triphenylphosphine (0.33 g, 1.27 mmol). The reaction mixture was stirred at room temperature for 27 hours. Solvent was evaporated to dryness in vacuo and the residue triturated with Et$_2$O (15 mL)/EtOAc (15 mL) to give 2-(4-(2-bromoethoxy)-3,5-dimethylphenyl)-5-chloro-quinazolin-4(3H)-one (0.42 g). It was used without further purification. The $^1$H NMR indicated a purity of about 45%.

To a solution of 2-(4-(2-bromoethoxy)-3,5-dimethylphenyl)-5-chloroquinazolin-4(3H)-one (0.40 g, crude) in anhydrous DMF (10 mL) was added pyrrolidine (0.36 mL, 4.35 mmol) and the reaction mixture was stirred at room temperature, under nitrogen, for 25 hours. Solvent was evaporated to dryness in vacuo. The residue was triturated with water (50 mL), filtered, and the brown solid washed with Et$_2$O (20 mL).

The crude material was purified by column chromatography (silica gel 230-400 mesh; 6% methanol in dichloromethane as the eluent) and then by reverse-phase HPLC (0.1% aqueous trifluoroacetic acid/acetonitrile as the eluent), to give a white solid. The solid was dissolved in CH$_2$Cl$_2$ (20 mL)/MeOH (4.5 mL), washed with 1 M Na$_2$CO$_3$ (4.5 mL) and the organic phase separated. The aqueous phase was extracted with CH$_2$Cl$_2$ (4×20 mL). The combined organic phase was washed with water (10 mL), dried (Na$_2$SO$_4$), filtered, and evaporated to give the title compound as a white solid. Yield: 0.091 g (21%, for two steps). MP 179-180° C. $^1$H NMR (400 MHz, DMSO-d$_6$): δ 12.30 (br s, 1H), 7.89 (s, 2H), 7.77-7.66 (m, 1H), 7.66-7.60 (m, 1H), 7.47 (d, J=7.42 Hz, 1H), 3.89 (t, J=5.85 Hz, 2H), 2.80 (t, J=5.85 Hz, 2H), 2.53 (br s, 4H), 2.30 (s, 6H), 1.68 (br s, 4H). MS (ES+) m/z: 398.11 (100%), 400.13, 401.07.

Example 88

Preparation of 2-(4-(2-(Azepan-1-yl)ethoxy)-3,5-dimethylphenyl)-5,7-dimethoxyquinazolin-4(3H)-one

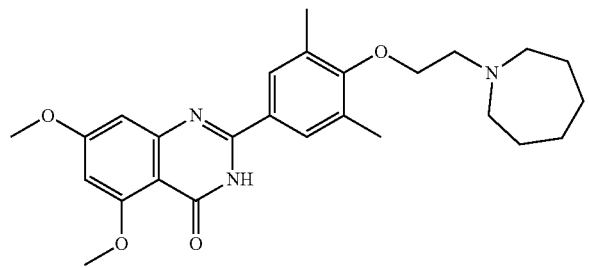 [SMILES: COc1cc(OC)c2c(=O)[nH]c(-c3cc(C)c(OCCN4CCCCCC4)c(C)c3)nc2c1]

To a suspension of 2-[4-(2-bromo-ethoxy)-3,5-dimethyl-phenyl]-5,7-dimethoxy-3H-quinazolin-4-one (0.22 g, 0.50 mmol) in DMF (2 mL) was added hexamethyleneimine(azepane) (0.22 mL, 2.0 mmol) and the reaction mixture was stirred at room temperature for 17 hours. Saturated aqueous NaHCO$_3$ solution (2 mL) was added and stirred for 2 hours. Water (10 mL) was added and stirred for another 0.5 hours. The solid was filtered, washed with water, and dried under vacuum to give the title compound as a white solid. Yield: 0.22 g (95%). MP 198-199° C. $^1$H NMR (400 MHz, CD$_3$OD): δ 7.70 (s, 2H), 6.79 (s, 1H), 6.55 (s, 1H), 3.97 (t, J=6.0 Hz, 2H), 3.92 (s, 3H), 3.91 (s, 3H), 2.98 (t, J=6.0 Hz, 2H), 2.82 (t, J=5.2 Hz, 4H), 2.37 (s, 6H), 1.72 (m, 4H), 1.66 (m, 4H). MS (ES$^+$) m/z: 452.27 (M+1). Analysis calculated for C$_{26}$H$_{33}$N$_3$O$_4$ (451.56), %: C, 69.16; H, 7.37; N, 9.31. Found, %: C, 68.94; H, 6.90; N, 9.30.

Example 89

Preparation of 2-(3,5-Dimethyl-4-(2-(pyrrolidin-1-yl)ethoxy)phenyl)-5,7-difluoroquinazolin-4(3H)-one

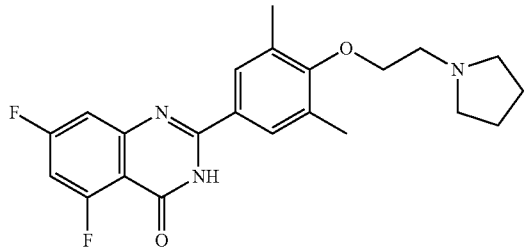 [SMILES: Cc1cc(-c2nc3cc(F)cc(F)c3c(=O)[nH]2)cc(C)c1OCCN1CCCC1]

To a solution of 2-amino-4,6-difluoro-benzamide (0.80 g, 4.60 mmol) and 3,5-dimethyl-4-(2-pyrrolidin-1-yl-ethoxy)-benzaldehyde (1.14 g, 4.60 mmol) in N,N-dimethylacetamide (60 mL) were added sodium hydrogen sulfite (58.5 wt %, 1.25 g, 6.9 mmol) and p-toluenesulfonic acid monohydrate (3.50 g, 18.4 mmol). The reaction mixture was stirred at 145° C. for 16 hours under nitrogen atmosphere, then cooled to room temperature. Solvent was evaporated under reduced pressure. Water (50 mL) was added, followed by saturated aqueous sodium bicarbonate solution (15 mL). The mixture was extracted with CH$_2$Cl$_2$ (2×100 mL) and washed with water. The organic phase was evaporated and the residue was washed with hexane/ether (90:10, 100 mL). The solid was filtered and dried under vacuum to give the title compound as a brown solid. Yield: 1.48 g (80%). MP 234-235° C. $^1$H NMR (400 MHz, DMSO-d$_6$): δ 12.36 (s, 1H), 7.90 (s, 1H), 7.32 (m, 2H), 3.91 (t, J=4 Hz, 2H), 2.83 (t, J=4 Hz, 2H), 2.55 (s, 4H), 2.31 (s, 6H), 1.70 (s, 4H).

Example 90

Preparation of 2-(4-(2-(Azetidin-1-yl)ethoxy)-3,5-dimethylphenyl)-5,7-dimethoxyquinazolin-4(3H)-one

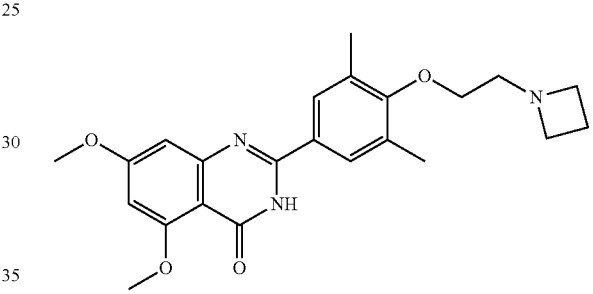

To a suspension of 2-[4-(2-bromoethoxy)-3,5-dimethyl-phenyl]-5,7-dimethoxy-3H-quinazolin-4-one (216 mg, 0.50 mmol) in DMF (5 mL) was added azetidine (154 mg, 2.70 mmol). The reaction mixture was stirred at room temperature for 2 days. The solid was collected by filtration, washed with methanol, ethyl acetate, and water, and dried under vacuum to give the title compound as a white solid. Yield: 58 mg (28%). MP 204-205° C. $^1$H NMR (400 MHz, DMSO-d$_6$): δ 7.85 (s, 2H), 6.71 (d, J=2.4 Hz, 1H), 6.49 (d, J=2.4 Hz, 1H), 3.86 (s, 3H), 3.81 (s, 3H), 3.70 (t, J=6.0 Hz, 2H), 3.18 (t, J=6.8 Hz, 4H), 2.70 (t, J=6.0 Hz, 2H), 2.26 (s, 6H), 1.97 (m, 2H). MS (ES) m/z: 410.20 (M+1) (100%).

Example 91

Preparation of N-(1-(2-(4-(5,7-Dimethoxy-4-oxo-3,4-dihydroquinazolin-2-yl)-2,6-dimethylphenoxy)ethyl)azetidin-3-yl)acetamide

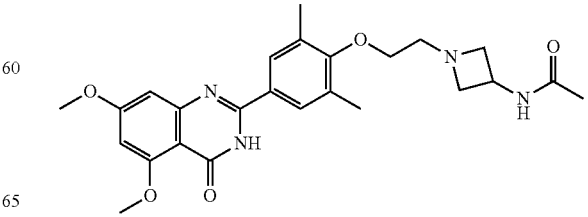

To a solution of N-(1-benzhydryl-azetidin-3-yl)-acetamide (1.00 g, 3.57 mmol) in ethanol (20 mL) were added palladium hydroxide on carbon (20 wt %, 0.20 g) and concentrated HCl (0.6 mL). The reaction mixture was hydrogenated at 50 psi at 40° C. for 2 hours. Then, the solid was filtered and washed with methanol (50 mL). The filtrate was collected; the solvent was evaporated to give N-azetidin-3-yl-acetamide as a green gummy material. Yield: 0.40 g (crude). This product was used in next step without further purification.

To a suspension of N-azetidin-3-yl-acetamide (0.30 g crude, 1.99 mmol) and 2-[4-(2-bromo-ethoxy)-3,5-dimethyl-phenyl]-5,7-dimethoxy-3H-quinazolin-4-one (0.43 g, 1.00 mmol) in anhydrous DMF (10 mL) was added triethylamine (3 mL). The reaction mixture was stirred at room temperature for 3 days under nitrogen. Solvent was evaporated under reduced pressure, water (50 mL) was added, and the precipitated solid was filtered. The aqueous phase was extracted with ethyl acetate (2×100 mL). The organic phase was dried over anhydrous $Na_2SO_4$. Solvent was evaporated, and crude compound was purified by the Simpliflash system (0-5% 7 N ammonia in methanol and $CH_2Cl_2$ as eluent) to give the title compound as a white solid. Yield: 0.30 g (63%). MP 111.8-113.6° C. $^1$H NMR (400 MHz, $CDCl_3$): δ 9.60 (br s, 1H), 7.69 (s, 2H), 6.82 (d, J=2.34 Hz, 1H), 6.46 (d, J=2.34 Hz, 1H), 6.10 (d, J=7.81 Hz, 1H), 4.71-4.44 (m, 1H), 3.97 (s, 3H), 3.93 (s, 3H), 3.85-3.67 (m, 4H), 3.26-3.13 (m, 2H), 2.90 (t, J=5.46 Hz, 2H), 2.36 (s, 6H), 2.01 (s, 3H). MS ($ES^+$) m/z: 467.20 (M+1).

Example 92

Preparation of 2-(3,5-Dimethyl-4-(2-(pyrrolidin-1-yl)ethoxy)phenyl)-5,7-diisopropoxyquinazolin-4(3H)-one

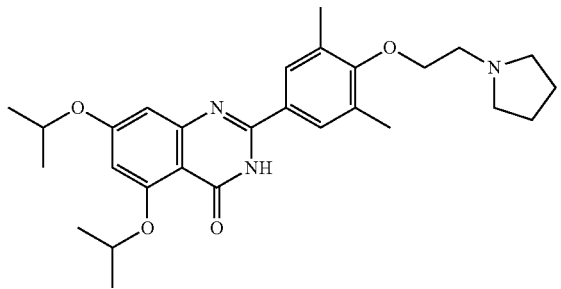 [SMILES: Cc1cc(-c2nc3cc(OC(C)C)cc(OC(C)C)c3c(=O)[nH]2)cc(C)c1OCCN1CCCC1]

To a solution of 2-[4-(2-hydroxy-ethoxy)-3,5-dimethyl-phenyl]-5,7-diisopropoxy-3H-quinazolin-4-one (0.73 g, 1.70 mmol) in DMF (10 mL) were added $PPh_3$ (0.49 g, 1.87 mmol) and $CBr_4$ (0.62 g, 1.87 mmol). The reaction mixture was stirred at room temperature for 16 hours. Then, solvent was removed under reduced pressure. The residue was triturated with ether and ethyl acetate. The solid was dried and purified by the Simpliflash system (2% methanol in $CH_2Cl_2$ as eluent) to give 2-[4-(2-bromo-ethoxy)-3,5-dimethyl-phenyl]-5,7-diisopropoxy-3H-quinazolin-4-one as a white solid. Yield: 0.39 g (47%).

To a solution of 2-[4-(2-bromo-ethoxy)-3,5-dimethyl-phenyl]-5,7-diisopropoxy-3H-quinazolin-4-one (0.39 g, 0.79 mmol) in DMF (10 mL) was added pyrrolidine (0.45 g, 6.37 mmol). The reaction mixture was stirred at room temperature for 4 hours. Then, water was added and product was extracted with ethyl acetate (2×200 mL). The combined organic phase was washed with water, then brine, and dried over anhydrous $Na_2SO_4$. Solvent was evaporated to give the title compound as a white solid. Yield: 0.32 g (83%). MP 65-68° C. $^1$H NMR (400 MHz, $CDCl_3$): δ 9.05 (br s, 1H), 7.63 (s, 2H), 6.78 (s, 1H), 6.42 (s, 1H), 4.70 (m, 1H), 4.63 (m, 1H), 3.94 (m, 2H), 2.94 (m, 2H), 2.64 (br s, 4H), 2.38 (s, 6H), 1.84 (m, 4H), 1.46 (m, 3H), 1.42 (m, 3H). MS (ES) m/z: 480.29 (M+1).

Example 93

Preparation of 8-Chloro-2-(3,5-dimethyl-4-(2-(pyrrolidin-1-yl)ethoxy)phenyl)quinazolin-4(3H)-one

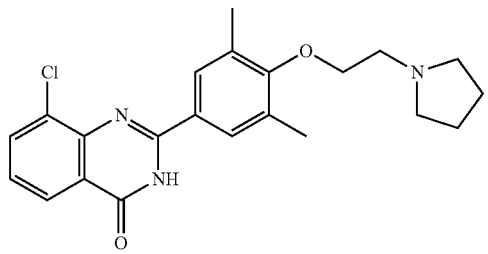 [SMILES: Cc1cc(-c2nc3c(Cl)cccc3c(=O)[nH]2)cc(C)c1OCCN1CCCC1]

To a solution of 2-amino-3-chloro-benzoic acid (2.57 g, 15.0 mmol) in THF (100 mL) were added EDCl (3.16 g, 16.5 mmol), HOBt (2.23 g, 16.5 mmol) and N-methylmorpholine (1.67 g, 16.5 mmol). The reaction mixture was stirred at room temperature for 20 minutes then 50% (v/v) aq. $NH_4OH$ solution (4.2 mL, 60.0 mmol) was added. The mixture was stirred for 20 hours at room temperature. Solvent was evaporated and the residue was taken in ethyl acetate (200 mL). Water (100 mL) was added. The organic phase was separated; the aqueous phase was extracted with ethyl acetate (200 mL). The combined organic phase was washed with water (100 mL), then brine (100 mL), and dried over anhydrous sodium sulfate. Solvent was evaporated and dried under vacuum to give 2-amino-3-chloro-benzamide as a white solid. Yield: 2.07 g (81%).

To a solution of 2-amino-3-chloro-benzamide (0.85 g, 5.00 mmol) and 3,5-dimethyl-4-(2-pyrrolidin-1-yl-ethoxy)-benzaldehyde (1.23 g, 5.00 mmol) in N,N-dimethylacetamide (20 mL) were added sodium hydrogen sulfite (58.5 wt %, 1.37 g, 7.50 mmol) and p-toluenesulfonic acid monohydrate (3.80 g, 20.0 mmol). The reaction mixture was stirred at 140° C. for 16 hours under nitrogen, then cooled to room temperature. Solvent was evaporated under reduced pressure. Water (100 mL) was added, and the mixture was neutralized, to pH approximately 8 with 2 N aqueous NaOH solution. The separated solid was filtered, washed with water (50 mL), and dried under vacuum. Crude compound was purified by the Simpliflash system (0-5% methanol in $CH_2Cl_2$ and then 5% 7.0 M ammonia in methanol and $CH_2Cl_2$ as eluent) to give the title compound as a brown solid. Yield: 0.49 g (25%). MP 216-217° C. $^1$H NMR (400 MHz, DMSO-$d_6$): δ 8.07 (d, J=7.81 Hz, 1H), 8.01-7.87 (m, 3H), 7.43 (t, J=7.81 Hz, 1H), 3.89 (t, J=5.85 Hz, 2H), 2.81 (t, J=5.85 Hz, 2H), 2.53 (br s, 4H), 2.30 (s, 6H), 1.75-1.60 (m, 4H). MS (ES+) m/z 398.11 (100%), 400.13 (40%).

Example 94

Preparation of 2-(3,5-Dimethyl-4-(2-(pyrrolidin-1-yl)ethoxy)phenyl)-5,7-dimethylquinazolin-4(3H)-one

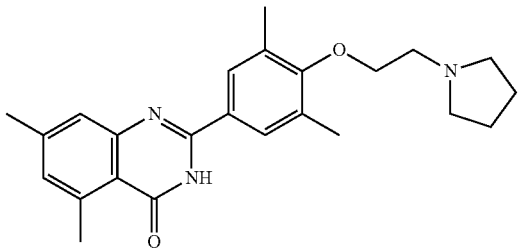 [SMILES: Cc1cc(C)c2c(=O)[nH]c(-c3cc(C)c(OCCN4CCCC4)c(C)c3)nc2c1]

Chloral hydrate (15.29 g, 92.42 mmol) was taken in water (335 mL). Sodium sulfate (78.14 g, 550.13 mmol) was added at room temperature. Then, a suspension of hydroxylamine hydrochloride (18.35 g, 264.06 mmol), 3.5-dimethylaniline (10.0 g, 82.52 mmol) and concentrated hydrochloric acid (36.5%, 10 mL) was added. The mixture was heated at 45° C. for 1.5 hours, then 75° C. for 1 hour. The reaction mixture was cooled to room temperature. The precipitated brown solid was filtered and washed with cold water (50 mL) and hexane (50 mL). The crude compound was dried under vacuum to give N-(3,5-dimethyl-phenyl)-2-hydroxyimino-acetamide as a brown solid. Yield: 13.7 g (86%). The crude compound was used in the next step without further purification.

N-(3,5-Dimethyl-phenyl)-2-hydroxyimino-acetamide (13.7 g, 71.3 mmol) was added to concentrated sulfuric acid (70 mL) in a 250 mL flask. The reaction mixture was then heated at 80° C. for 30 minutes, then cooled to room temperature, and poured into ice-water (200 mL). The precipitated solid was filtered and washed with water (100 mL) and dried under vacuum to give 4,6-dimethyl-1H-indole-2,3-dione as an orange solid. Yield: 5.53 g (44%).

To a heated (70° C. bath temperature) deep red solution of 4,6-dimethyl-1H-indole-2,3-dione (1.00 g, 5.71 mmol) in 33% aqueous sodium hydroxide (35 mL) was added 35% hydrogen peroxide (3.33 g, 34.3 mmol) over a period of 5 minutes. The reaction mixture was heated for another 15 min, then cooled to room temperature, and ice was added. The pH was adjusted to approximately 8 with concentrated HCl at 0° C. and acidified further to pH approximately 6 with glacial acetic acid. The solid precipitated was filtered, washed well with cold water, and dried under vacuum at 40° C. overnight to obtain 2-amino-4,6-dimethyl-benzoic acid as a pale brown solid. Yield: 0.35 g (37%).

To a solution of 2-amino-4,6-dimethyl-benzoic acid (0.35 g, 2.08 mmol) in anhydrous THF (10 mL) was added EDCl (0.80 g, 4.17 mmol), HOBt (0.80 g, 5.22 mmol) and N-methyl-morpholine (0.7 mL, 6.24 mmol). The reaction mixture was stirred at room temperature for 30 minutes, then ammonium hydroxide (50% v/v, 2.5 mL) was added. The mixture was stirred at room temperature for 17 hours. The solvent was removed under reduced pressure. Water (50 mL) was added, and the mixture was extracted with dichloromethane (2×100 mL). The combined organic phase was washed with water, and dried over anhydrous $Na_2SO_4$. Removal of the solvent gave the crude product. The crude product was purified by column chromatography (silica gel 230-400 mesh; 3% methanol in dichloromethane as eluent) to give 2-amino-4,6-dimethyl-benzamide. Yield: 0.20 g (59%).

To a solution of 2-amino-4,6-dimethyl-benzamide (0.20 g, 1.22 mmol) and 3,5-dimethyl-4-(2-pyrrolidin-1-yl-ethoxy)-benzaldehyde (0.36 g, 1.46 mmol) in N,N-dimethylacetamide (10 mL) was added $NaHSO_3$ (58.5 wt %, 0.55 g, 3.05 mmol) and p-TSA (0.46 g, 2.44 mmol). The reaction mixture was heated to 110° C. for 2 hours, then cooled to room temperature. N,N-dimethylacetamide was removed under reduced pressure, the residue was diluted with sodium bicarbonate solution (50 mL), and the solid separated was filtered and dried under vacuum. The crude compound was purified by column chromatography (silica gel 230-400 mesh; 6% methanol in dichloromethane as eluent) to give the title compound as a white solid. Yield: 0.145 g (30%). MP 181-182° C. $^1$H NMR (400 MHz, DMSO-$d_6$): δ 10.62 (s, 1H), 7.75 (s, 2H), 7.44 (s, 1H), 7.03 (s, 1H), 3.95 (t, J=6.0 Hz, 2H), 2.94 (t, J=6.0 Hz, 2H), 2.85 (s, 3H), 2.65 (s, 4H), 2.44 (s, 3H), 2.39 (s, 6H), 1.84 (s, 4H). MS (ES$^+$) m/z: 392.13 (M+1).

Example 95

Preparation of 2-(2-(4-(6,8-Dimethoxy-1-oxo-1,2-dihydroisoquinolin-3-yl)-2,6-dimethylphenoxy)ethyl)isoindoline-1,3-dione

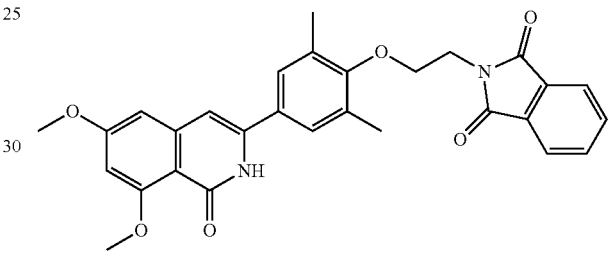

To a suspension of 3-[4-(2-hydroxy-ethoxy)-3,5-dimethyl-phenyl]-6,8-dimethoxy-2H-isoquinolin-1-one (0.80 g, 2.16 mmol), isoindole-1,3-dione (0.35 g, 2.38 mmol), and triphenylphosphine (0.85 g, 3.25 mmol) in THF (30 mL), was added diethyl azodicarboxylate (0.56 g, 3.25 mmol) and the reaction mixture was stirred at room temperature for 16 hours. The solvent was evaporated in vacuo and the residue was washed with ether to give the title compound as an off-white solid. Yield: 1.11 g (crude). $^1$H NMR (400 MHz, CDCl$_3$): δ 8.34 (s, 1H), 7.89 (m, 2H), 7.77 (m, 2H), 7.21 (s, 2H), 6.49 (br s, 2H), 6.44 (s, 1H), 4.16 (m, 2H), 4.08 (m, 2H), 3.97 (s, 3H), 3.89 (s, 3H), 2.25 (s, 6H). MS (ES) m/z: 499.06 (M+1) (100%).

Example 96

Preparation of 2-(3,5-Dimethyl-4-(2-(pyrrolidin-1-yl)ethoxy)phenyl)-5,7-diisopropoxypyrido[2,3-d]pyrimidin-4(3H)-one

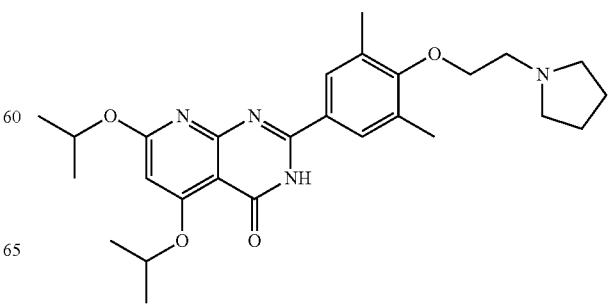

To a suspension of 2-amino-4-hydroxy-6-oxo-1,6-dihydro-pyridine-3-carboxylic acid methyl ester (7.0 g, 38.04 mmol), 2-iodopropane (14.22 g, 83.69 mmol), and $K_2CO_3$ (11.56 g, 83.69 mmol) in DMF (200 mL), was heated at 60° C. for 48 hours, then cooled to the room temperature and filtered. Water (400 mL) was added to the filtrate and the product was extracted with ethyl acetate (3×200 mL). The combined organic layer was washed with water, then brine, dried over $Na_2SO_4$, and evaporated to give crude product. The crude product was purified by Simpliflash, using 10% ethyl acetate in hexane, to give 2-amino-4,6-diisopropoxy-nicotinic acid methyl ester as a colorless oil. Yield: 1.30 g (13%). $^1$H NMR (400 MHz, DMSO-$d_6$): δ 6.91 (s, 2H), 5.57 (s, 1H), 5.19 (m, 1H), 4.59 (m, 1H), 3.66 (s, 3H), 1.23 (d, J=2.0 Hz, 6H), 1.21 (d, J=1.2 Hz, 6H).

To the solution of 2-amino-4,6-diisopropoxy-nicotinic acid methyl ester (1.6 g, 5.97 mmol) in methanol (9.0 mL) and water (1.0 mL), was added lithium hydroxide (750 mg, 17.91 mmol). The reaction mixture was heated to 50° C. for 8 hours. The solvent was removed; the residue was diluted with water and neutralized with 2 N HCl. The product was extracted with ethyl acetate (3×100 mL). The combined organic layer was washed with water, then brine, dried over $Na_2SO_4$, and evaporated, to give crude 2-amino-4,6-diisopropoxy-nicotinic acid as a light yellow solid. Yield: 1.48 g (98%, crude).

To a solution of 2-amino-4,6-diisopropoxy-nicotinic acid (1.48 g, 5.83 mmol) in THF (30 mL) were added EDCl (1.34 g, 6.99 mmol), HOBt (0.94 g, 6.99 mmol), NMM (0.70 g, 6.99 mmol) and liquid $NH_3$ (10 mL). Then, the reaction mixture was stirred at room temperature for 24 hours. Then, water (100 mL) was added and the products were extracted with ethyl acetate (2×200 mL). The combined organic phase was washed with water, then brine, and dried over anhydrous $Na_2SO_4$. Removal of solvent gave crude 2-amino-4,6-diisopropoxy-nicotinamide as a yellow oil. Yield: 450 mg (26%, crude).

To a solution of 2-amino-4,6-diisopropoxy-nicotinamide (450 mg, 1.78 mmol) and 3,5-dimethyl-4-(2-pyrrolidin-1-yl-ethoxy)-benzaldehyde (440 mg, 1.78 mmol) in N,N-dimethyl acetamide (10 mL) were added $NaHSO_3$ (790 mg, 4.44 mmol) and p-TSA (845 mg, 4.44 mmol). The reaction mixture was heated at 120° C. for 16 hours, then cooled to room temperature. The solvent was removed under reduced pressure. Then, water (100 mL) was added and stirred for 30 min at room temperature. The separated solids were filtered and dried to give crude product, which was purified by the Simpliflash system, using 2% methanol in dichloromethane, to give a yellow oil, which dissolved in ether. 2N HCl in ether was added, and the separated solids were filtered and dried to give the hydrochloride salt of the title compound as a yellow solid. Yield: 59 mg (6%). $^1$H NMR (400 MHz, DMSO-$d_6$): δ 10.7 (br s, 1H), 7.88 (s, 2H), 6.31 (s, 1H), 5.41 (m, 1H), 4.80 (m, 1H), 4.14 (t, J=4.8 Hz, 2H), 3.61 (m, 2H), 3.16 (m, 4H), 2.34 (s, 6H), 2.03 (m, 2H), 1.91 (m, 2H), 1.32 (s, 6H), 1.30 (s, 6H). MS (ES) m/z: 481.18 (M+1).

Example 97

Preparation of (S)-2-(3,5-Dimethyl-4-((5-oxopyrrolidin-2-yl)methoxy)phenyl)-5,7-dimethoxyquinazolin-4(3H)-one To a solution of (S)-5-(hydroxymethyl)pyrrolidin-2-one (3.85 g, 33.5 mmol) in acetonitrile (60 mL) under nitrogen was added $PPh_3$ (9.16 g, 34.8 mmol). The mixture was cooled to 0° C. and $CBr_4$ (11.55 g, 34.8 mmol) added dropwise as a solution in acetonitrile (40 mL) over 15 minutes. Then, the reaction mixture was warmed to room temperature and stirred for 18 hours. The mixture was then concentrated and heptane (100 mL) and water (100 mL) added. After stirring for 1 hour, the solids were filtered and washed with 1:1 heptane/water (100 mL). The filtrate layers were separated and the aqueous layer extracted with $Et_2O$ (2×100 mL) and $CHCl_3$ (2×100 mL). The combined organic phase was dried over anhydrous $Na_2SO_4$, filtered, concentrated, and purified by silica gel chromatography, eluting with 100% $CHCl_3$ to 10% MeOH/$CHCl_3$, to afford (S)-5-(bromomethyl)pyrrolidin-2-one as a white solid (3.15 g, 53%).

To a solution of 4-hydroxy-3,5-dimethylbenzaldehyde (2.65 g, 17.7 mmol) in DMF (100 mL) was added $K_2CO_3$ (3.66 g, 26.6 mmol). The mixture was stirred at room temperature under nitrogen for 30 minutes. Then, a solution of (S)-5-(bromomethyl)pyrrolidin-2-one (3.15 g, 17.7 mmol) in DMF (100 mL) was added, and the mixture heated at reflux for 16 hours. The mixture was then concentrated, ethyl acetate (250 mL) added, and the organic phase washed sequentially with water (2×150 mL), and brine (200 mL), dried ($Na_2SO_4$), filtered, and concentrated. The residue was purified by silica gel chromatography, eluting with 100% ethyl acetate to 10% MeOH/ethyl acetate, followed by a second chromatography, eluting with 1:1 $CH_2Cl_2$/92:7:1 $CHCl_3$/MeOH/concentrated $NH_4OH$ to 100% 92:7:1 $CHCl_3$/MeOH/concentrated $NH_4OH$, to afford (S)-3,5-dimethyl-4-((5-oxopyrrolidin-2-yl)methoxy)benzaldehyde as a white solid (0.200 g, 5%).

A mixture of (S)-3,5-dimethyl-4-((5-oxopyrrolidin-2-yl)methoxy)benzaldehyde (0.200 g, 0.81 mmol), 2-amino-4,6-dimethoxybenzamide (0.159 g, 0.81 mmol), $NaHSO_3$ (0.093 g, 0.89 mmol), and p-TsOH (0.015 g, 0.08 mmol) in DMA (10 mL) was heated at 150° C. for 48 hours. The reaction mixture was cooled to room temperature, diluted with ethyl acetate (200 mL), washed with water (2×200 mL), dried over anhydrous $Na_2SO_4$, filtered, and concentrated. The residue was purified by flash chromatography on silica gel, eluting with 1:1 $CH_2Cl_2$/92:7:1 $CHCl_3$/MeOH/concentrated $NH_4OH$ to 100% 92:7:1 $CHCl_3$/MeOH/concentrated $NH_4OH$ to 6:3:1 $CHCl_3$/MeOH/concentrated $NH_4OH$, to afford the title compound as an off-white solid (0.108 g, 31%). $^1$H NMR (300 MHz, DMSO-$d_6$): δ 11.85 (s, 1H), 7.79-7.91 (m, 3H), 6.74 (d, J=2.2 Hz, 1H), 6.52 (d, J=2.2 Hz, 1H), 3.88-3.94 (m, 4H), 3.84 (s, 3H), 3.63-3.75 (m, 2H), 2.30 (s, 6H), 2.09-2.27 (m, 3H), 1.91-2.00 (m, 1H). APCI MS m/z 424 [M+H]$^+$.

Example 98

Preparation of 2-(4-((4-Isopropylpiperazin-1-yl)methyl)phenyl)-5,7-dimethoxyquinazolin-4(3H)-one

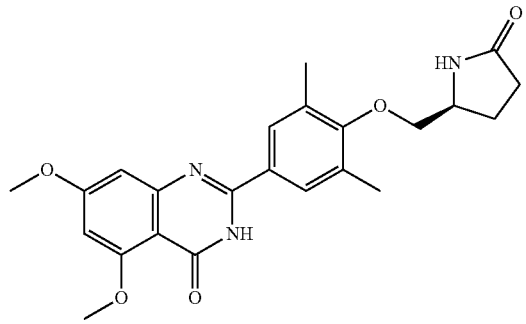 [SMILES: COc1cc(OC)c2c(=O)[nH]c(-c3cc(C)c(OC[C@@H]4CCC(=O)N4)c(C)c3)nc2c1]

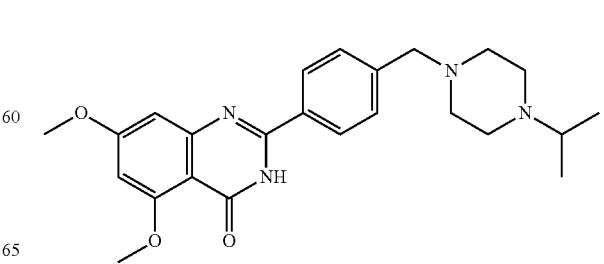

To a mixture of 4-(bromoethyl)benzaldehyde (0.200 g, 1.0 mmol) and K$_2$CO$_3$ (0.277 g, 2.0 mmol) in DMF (5 mL) was added N-isopropylpiperazine (0.129 g, 1.0 mmol) and the reaction was stirred at room temperature for 5 hours, then concentrated in vacuo. The resulting mixture was diluted with H$_2$O and extracted with EtOAc. The organics were washed with brine, dried over anhydrous Na$_2$SO$_4$, filtered, and concentrated in vacuo to afford 4-((4-Isopropylpiperazin-1-yl)methyl)benzaldehyde (0.240 g, 97%).

A mixture of 4-((4-isopropylpiperazin-1-yl)methyl)benzaldehyde (0.240 g, 0.97 mmol), NaHSO$_3$ (0.155 g, 1.50 mmol), and p-TsOH (0.019 g, 0.10 mmol) was added to a solution of 2-amino-4,6-dimethoxybenzamide (0.190 g, 0.97 mmol) in DMA (7 mL). The reaction was stirred at 130° C. overnight. Then, the mixture was diluted with H$_2$O and extracted with CH$_2$Cl$_2$. The organics were washed with brine, dried over anhydrous Na$_2$SO$_4$, filtered, and concentrated in vacuo. Purification by flash chromatography on silica gel, eluting with 2% to 10% MeOH/CH$_2$Cl$_2$, afforded the title compound (0.122 g, 30%) as a light yellow solid. $^1$H NMR (300 MHz, DMSO-d$_6$): δ 12.02 (s, 1H), 8.12 (d, J=8.0 Hz, 2H), 7.43 (d, J=8.0 Hz, 2H), 6.74 (s, 1H), 6.53 (s, 1H), 3.89 (s, 3H), 3.85 (s, 3H), 3.51 (s, 2H), 2.54-2.71 (m, 1H), 2.27-2.44 (m, 8H), 0.95 (d, J=6.4 Hz, 6H). ESI MS m/z 423 [M+H]$^+$.

Example 99

Preparation of N-(1-(4-(5,7-Dimethoxy-4-oxo-3,4-dihydroquinazolin-2-yl)benzyl)piperidin-4-yl)-N-isopropylacetamide

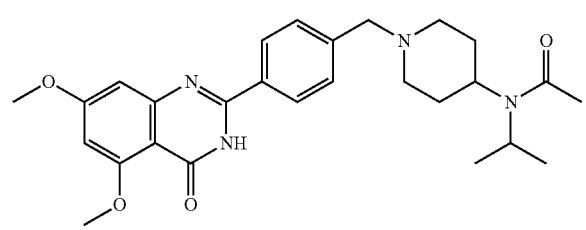 [SMILES: COc1cc(OC)c2c(=O)[nH]c(-c3ccc(CN4CCC(N(C(C)=O)C(C)C)CC4)cc3)nc2c1]

To a mixture of 4-(bromoethyl)benzaldehyde (0.840 g, 4.2 mmol) and K$_2$CO$_3$ (1.75 g, 12.6 mmol) in DMF (15 mL) was added N-isopropyl-N-(piperidin-4-yl)acetamide (0.92 g, 4.2 mmol) and the reaction was stirred at room temperature 5 hours, then concentrated in vacuo. The resulting mixture was diluted with H$_2$O and extracted with EtOAc. The organics were washed with brine, dried over anhydrous Na$_2$SO$_4$, filtered, and concentrated in vacuo. Purification by flash chromatography on silica gel, eluting with 1% to 10% MeOH/CH$_2$Cl$_2$, afforded N-(1-(4-formylbenzyl)piperidin-4-yl)-N-isopropylacetamide (0.770 g, 61%).

A mixture of N-(1-(4-formylbenzyl)piperidin-4-yl)-N-isopropylacetamide (0.770 g, 2.5 mmol), NaHSO$_3$ (0.350 g, 3.3 mmol), and p-TsOH (0.100 g, 0.51 mmol) was added to a solution of 2-amino-4,6-dimethoxybenzamide (0.500 g, 2.5 mmol) in DMA (20 mL). The reaction was stirred at 130° C. for 5 hours and concentrated in vacuo. The residue was diluted with H$_2$O and saturated NaHCO$_3$, then extracted with CH$_2$Cl$_2$. The organics were washed with brine, dried over anhydrous Na$_2$SO$_4$, filtered, and concentrated in vacuo. Purification by flash chromatography on silica gel, eluting with 1% to 10% MeOH/CH$_2$Cl$_2$, afforded the title compound (0.670 g, 56%) as a light yellow solid. $^1$H NMR (300 MHz, DMSO-d$_6$): δ 12.02 (s, 1H), 8.13 (d, J=8.1 Hz, 2H), 7.43 (d, J=8.0 Hz, 2H), 6.74 (d, J=1.9 Hz, 1H), 6.54 (d, J=2.0 Hz, 1H), 3.85-3.95 (m, 7H), 3.43-3.71 (m, 3H), 2.55-3.00 (m, 3H), 1.97-2.09 (m, 5H), 1.70-1.77 (m, 1H), 1.58-1.61 (m, 1H), 1.25-1.30 (m, 4H), 1.11-1.13 (m, 3H). ESI MS m/z 479 [M+H]$^+$.

Example 100

Preparation of 2-(4-((4-(Isopropylamino)piperidin-1-yl)methyl)phenyl)-5,7-dimethoxyquinazolin-4(3H)-one

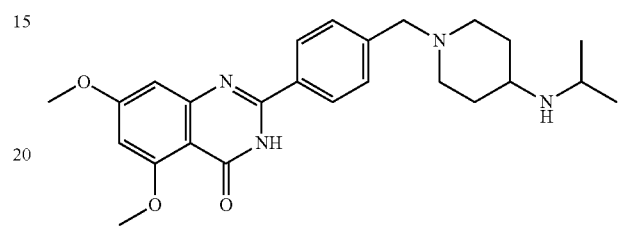

A solution of 2-(4-((4-isopropylpiperazin-1-yl)methyl)phenyl)-5,7-dimethoxyquinazolin-4(3H)-one (0.470 g, 0.98 mmol) in 2N HCl (20 mL) was refluxed for 3 days. The resulting mixture was basified with 2N NaOH and extracted with CH$_2$Cl$_2$. The organics were washed with brine, dried over anhydrous Na$_2$SO$_4$, filtered and concentrated in vacuo. Purification by flash chromatography on silica gel, eluting with 30% to 100% of 92:7:1 CHCl$_3$/MeOH/concentrated NH$_4$OH in CH$_2$Cl$_2$, afforded the title compound (0.090 g, 21%) as a light yellow solid. $^1$H NMR (300 MHz, DMSO-d$_6$): δ 8.12 (d, J=8.3 Hz, 2H), 7.42 (d, J=8.3 Hz, 2H), 6.73 (d, J=2.3 Hz, 1H), 6.53 (d, J=2.3 Hz, 1H), 3.89 (s, 3H), 3.85 (s, 3H), 3.50 (s, 2H), 2.86-2.92 (m, 1H), 2.73-2.77 (m, 2H), 1.85-2.01 (m, 2H), 1.72-1.77 (m, 2H), 1.09-1.38 (m, 4H), 0.94 (d, J=6.2 Hz, 6H). ESI/APCI MS m/z 437 [M+H]$^+$.

Example 101

Preparation of 2-(4-((1H-Tetrazol-5-yl)methyl)phenyl)-5,7-dimethoxyquinazolin-4(3H)-one

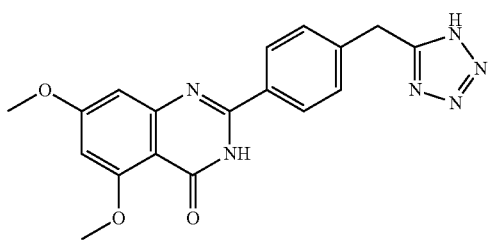 [SMILES: COc1cc(OC)c2c(=O)[nH]c(-c3ccc(Cc4nnn[nH]4)cc3)nc2c1]

To a solution of 4-cyanomethyl benzoic acid methyl ester (2.63 g, 15 mmol) in anhydrous toluene (100 mL) was added sodium azide (1.95 g, 30 mmol) and triethylamine hydrochloride (4.13 g, 30 mmol). The reaction mixture was stirred at 100° C. for 24 hours under nitrogen. The reaction mixture was cooled to room temperature, then extracted with water (2×100 mL). The aqueous layer was acidified with concentrated HCl to pH approximately 4. The white solid was filtered off, washed with water, and dried under vacuum at 40°

C. overnight, to give methyl-4-(1H-tetrazol-5-ylmethyl)benzoate (2.88 g, 88%) as an off-white solid.

Lithium aluminium hydride (0.142 g, 3.75 mmol) was taken in a dry, three-necked flask, fitted with a reflux condenser. Anhydrous ether (10 mL) was added. A solution of methyl-4-(1H-tetrazol-5-ylmethyl)benzoate (0.654 g, 3.0 mmol) in anhydrous THF (5 mL) was added dropwise. After the addition was complete, the mixture was heated to reflux for 2 hours. Then, the reaction mixture was cooled to 0° C. and quenched by cautious addition of water (10 mL) and 15% sodium hydroxide solution (10 mL). The reaction mixture was stirred for 30 minutes and then allowed to warm to room temperature. The aqueous phase was acidified to pH 4 and left for 2 days. A white precipitate was formed and filtered off, washed with water, and dried under vacuum, to give [4-(1H-tetrazol-5-ylmethyl)-phenyl]-methanol as a white solid. Yield: 0.290 g (51%).

IBX (0.437 g, 1.562 mmol) was dissolved in anhydrous DMSO (5 mL) and [4-(1H-tetrazol-5-ylmethyl)-phenyl]-methanol (0.270 g, 1.562 mmol) was added. The reaction mixture was stirred at room temperature under nitrogen for 4 hours. Water (20 mL) was added. The white precipitate was filtered off, washed with water, and dried under vacuum. The crude compound was mixed with methanol (20 mL) and stirred for 30 minutes, before being filtered. The filtrate was concentrated to give 4-(1H-tetrazol-5-ylmethyl)-benzaldehyde as a white solid. Yield: 0.267 g (99%). To a solution of 2-amino-4,6-dimethoxybenzamide (0.157 g, 0.8 mmol) in N,N-dimethyl acetamide (5 mL) were added 4-(1H-tetrazol-5-ylmethyl)-benzaldehyde (0.260 g, 1.4 mmol), sodium hydrogen sulfite (58.5%, 0.159 g, 0.88 mmol) and p-toluenesulfonic acid (19 mg, 0.08 mmol). The reaction mixture was stirred at 150° C. for 3 h, then cooled to room temperature. Water (40 mL) was then added. A yellow precipitate was formed and filtered off, washed with water, and small amount of methanol. It was triturated with 10% methanol in ether to give 0.107 g of solid, which was further purified by preparative HPLC, to give the title compound (0.082 g, 28%) as a white solid. MS (ES) m/z: 365.1 (M+1). MP 295-296° C.

Example 102

Preparation of 1-(2-(4-(5,7-Dimethoxy-4-oxo-3,4-dihydroquinazolin-2-yl)-2,6-dimethylphenoxy)ethyl)pyrrolidine-2,5-dione

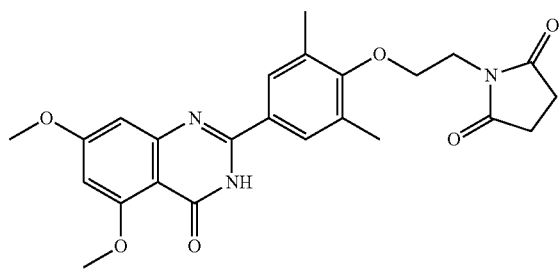 [SMILES: COc1cc(OC)c2c(=O)[nH]c(-c3cc(C)c(OCCN4C(=O)CCC4=O)c(C)c3)nc2c1]

To a solution of 2-[4-(2-hydroxy-ethoxy)-3,5-dimethyl-phenyl]-5,7-dimethoxy-3H-quinazolin-4-one (0.50 g, 1.35 mmol) in anhydrous THF (20 mL) were added triphenyl phosphine (0.53 g, 2.02 mmol), pyrrolidine-2,5-dione (0.20 g, 2.02 mmol), and N,N-diisopropylethyl amine (0.44 g, 3.38 mmol). To this stirred solution was added diethylazodicarboxylate (0.35 g, 2.02 mmol). The reaction mixture was stirred at room temperature for 8 hours under nitrogen. Ethyl acetate (400 mL) was added. The organic phase was separated, washed with water (100 mL), then brine (100 mL), and dried over anhydrous $Na_2SO_4$. The solvent was removed under reduced pressure. The crude material was purified by the Simpliflash system (4:96 methanol:$CH_2Cl_2$ as eluent) to give the title compound as a white solid. Yield: 0.3 g. (49%). $^1$H NMR (400 MHz, CDCl$_3$): δ 9.30 (br s, 1H), 7.66 (s, 2H), 6.82 (d, J=2.4 Hz, 1H), 6.46 (d, J=1.6 Hz, 1H), 3.99 (s, 3H), 3.97 (s, 3H), 3.92 (s, 4H), 2.78 (s, 4H), 2.31 (s, 6H). MS (ES) m/z: 452.51 (M+1) (100%).

Example 103

Preparation of 7-(2-(Benzyloxy)ethoxy)-5-methoxy-2-(pyridin-4-yl)quinazolin-4(3H)-one

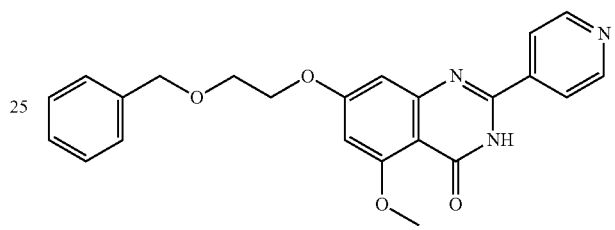

To a stirred solution of 2-amino-4,6-difluoro-benzamide (0.50 g, 2.9 mmol) and pyridine-4-carbaldehyde (0.35 g, 3.2 mmol) in N,N-dimethylacetamide (10 mL) were added sodium hydrogen sulfite (0.63 g, 3.5 mmol) and p-toluenesulfonic acid (0.06 g, 0.3 mmol); the reaction mixture was stirred at 115° C. for 16 hours. The solvent was evaporated in vacuo, water was added, and the precipitated solid was filtered off to obtain 5,7-difluoro-2-pyridin-4-yl-3H-quinazolin-4-one as a yellow solid, which was used in the next step without further purification. Yield: 0.4 g (53%).

To a suspension of 5,7-difluoro-2-pyridin-4-yl-3H-quinazolin-4-one (0.20 g, 0.80 mmol) in DMF (3 mL) was added sodium methoxide in methanol (0.43 g, 8.0 mmol) and the reaction mixture was stirred at room temperature for 16 hours. Water was added, the mixture was acidified with acetic acid to pH approximately 4-5, and the precipitated solid was filtered off to obtain 7-fluoro-5-methoxy-2-pyridin-4-yl-3H-quinazolin-4-one as a yellowish solid. Yield: 0.20 g (83%).

To a solution of 2-benzyloxy-ethanol (2 mL) in dimethyl sulfoxide (3 mL) was added sodium hydride (0.30 g, 7.4 mmol) in portions, and the reaction mixture was stirred at room temperature for 45 minutes. To this mixture was added 7-fluoro-5-methoxy-2-pyridin-4-yl-3H-quinazolin-4-one (0.20 g, 0.74 mmol) and the reaction mixture was heated at 80° C. for 16 hours. Water was added, the mixture was acidified with acetic acid to pH approximately 4-5, and the precipitated solid was filtered off, to obtain a crude product, which was purified by preparative HPLC to obtain the title compound as a light yellow solid. Yield: 0.12 g (40%). MP 228.2-229.9° C. $^1$H NMR (400 MHz, DMSO-d$_6$): δ12.29 (s, 1H), 8.77 (d, 2H), 8.08 (d, 2H), 7.36 (m, 5H), 6.82 (s, 1H), 6.62 (s, 1H), 4.58 (s, 2H), 4.32 (t, 2H), 3.87 (s, 3H), 3.83 (t, 2H). MS (ES+) m/z: 404.51 (M+1).

Example 104

Preparation of 2-(2,6-Dimethylpyridin-4-yl)-5,7-dimethoxyquinazolin-4(3H)-one

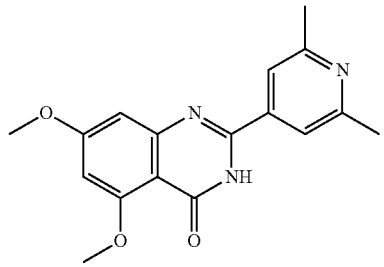

A solution of 2,6-lutidine N-oxide (24.0 g, 0.20 mol) in anhydrous dichloromethane (400 mL) was added to trimethyloxonium tetrafluoroborate (29.6 g, 0.20 mol) at room temperature under nitrogen atmosphere and the reaction mixture was stirred at room temperature for 3 hours. The mixture was concentrated in vacuo to give the crude product, 1-methoxy-2,6-dimethyl-pyridinium tetrafluoroborate.

The crude product was dissolved in MeOH (300 mL) and heated to reflux under nitrogen. Then, a solution of ammonium persulfate (14.2 g, 0.06 mol) in water (57 mL) was added. The mixture was stirred under reflux for 16 hours; TLC showed completion of the reaction. Half of the solvent was removed in vacuo, then quenched with 10% aqueous NaOH solution to pH 7, and evaporated to dryness in vacuo. The residue was dissolved in methanol and filtered, the filtrate was concentrated in vacuo, and the crude compound was purified by column chromatography (silica gel 230-400 mesh; 5-15% methanol in CH$_2$Cl$_2$ as eluent) to give 4-hydroxymethyl-2,6-dimethylpyridine as a white solid. Yield: 11.0 g (40.0%).

4-Hydroxymethyl-2,6-dimethylpyridine (1.00 g, 7.28 mmol) was dissolved in ethanol (20 mL), and activated MnO$_2$ (2.24 g, 21.8 mmol) was added; the reaction mixture was refluxed for 17 hours. The mixture was cooled and concentrated, purified by column chromatography (silica gel 230-400 mesh; 20% ethyl acetate in hexanes as eluent) to give 2,6-dimethyl-4-pyridinecarboxaldehyde as a yellow oil. Yield: 0.14 g (14%).

To a solution of 2,6-dimethylpyridine-4-carbaldehyde (0.14 g, 1.00 mmol) in N,N-dimethyl acetamide (10 mL) were added 2-amino-4,6-dimethoxybenzamide (0.20 g, 1.00 mmol), sodium hydrogen sulfite (0.21 g, 2.00 mmol), and p-toluenesulfonic acid (0.28 g, 1.50 mmol). The reaction mixture was stirred at 110° C. for 16 hours under nitrogen. After cooling to room temperature, solvent was evaporated under reduced pressure. The residue was dissolved in ethyl acetate, washed with saturated NaHCO$_3$ solution (30 mL), water (30 mL), and brine (30 mL), and dried over anhydrous sodium sulfate. Solvent was evaporated, and the residue was purified by column chromatography (silica gel 230-400 mesh; 2-5% methanol in dichloromethane as eluent) to give the title compound as a yellow solid. Yield: 0.030 g (10%).

MP 291-292° C. $^1$H NMR (400 MHz, CDCl$_3$): δ 9.86 (br s, 1H), 7.60 (s, 2H), 6.87 (d, J=2.2 Hz, 1H), 6.53 (d, J=2.2 Hz, 1H), 3.99 (s, 3H), 3.95 (s, 3H), 2.66 (s, 6H). MS (ES) m/z: 312.50 (M+1) (100%).

Example 105

Preparation of 2-(2,6-Dimethylpyridin-4-yl)-5-methoxy-7-(2-methoxyethoxy)quinazolin-4(3H)-one

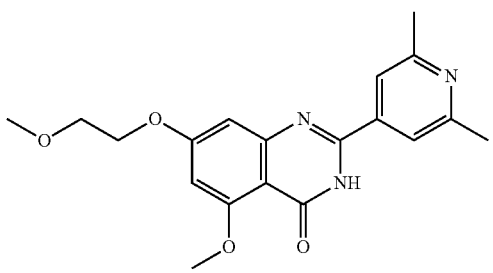

To a suspension of 2,6-dimethyl-pyridin-4-yl)-methanol (1.00 g, 7.30 mmol) in acetonitrile (20 mL), 1,2-benziodexol-3(1H)-one-1-hydroxy-1-oxide (IBX) (2.00 g, 7.30 mmol) was added and the reaction mixture was refluxed for 6 hours. The solid was filtered off and washed with acetonitrile. The filtrate was evaporated in vacuo to give 2,6-dimethyl-pyridine-4-carbaldehyde as a brown liquid. Yield: 0.81 g (82%).

To a stirred solution of 2-amino-4,6-difluoro-benzamide (1.03 g, 6.00 mmol) and 2,6-dimethyl-pyridine-4-carbaldehyde (0.81 g, 6.00 mmol) in N,N-dimethyl acetamide (15 mL), sodium hydrogen sulfite (58.5 wt %, 1.31 g, 7.20 mmol), and p-toluenesulfonic acid monohydrate (0.11 g, 0.60 mmol) were added and the reaction mixture was stirred at 115° C. for 16 hours. The solvent was evaporated in vacuo, water was added, and the precipitated solid was filtered, to give 2-(2,6-dimethyl-pyridin-4-yl)-5,7-difluoro-3H-quinazolin-4-one as a yellow solid, which was used in the next step without further purification. Yield: 0.72 g (42%).

To a suspension of 2-(2,6-dimethyl-pyridin-4-yl)-5,7-difluoro-3H-quinazolin-4-one (0.72 g, 2.51 mmol) in DMF (10 mL), a solution of sodium methoxide in methanol (25 wt %, 1.36 g, 25.1 mmol) was added and the reaction mixture was stirred at room temperature for 16 h. Water was added, the mixture was acidified to pH approximately 4-5 with acetic acid, and the precipitated solid was filtered and dried under vacuum to give 2-(2,6-dimethyl-pyridin-4-yl)-7-fluoro-5-methoxy-3H-quinazolin-4-one as a light yellow solid. Yield: 0.28 g (37%).

To a solution of 2-methoxyethanol (3 mL) in dimethyl sulfoxide (8 mL), sodium hydride (60% suspension in mineral oil, 0.40 g, 9.40 mmol) was added in portions and the reaction mixture was stirred at room temperature for 1 hour. To this reaction mixture was added 2-(2,6-dimethyl-pyridin-4-yl)-7-fluoro-5-methoxy-3H-quinazolin-4-one (0.28 g, 0.94 mmol) and the reaction mixture was stirred at 90° C. for 16 hours. Water was added, acidified to pH approximately 4-5 with acetic acid, and the precipitated solid was filtered to give crude product, which was purified by preparative HPLC, to obtain the title compound as a white solid. Yield: 0.12 g (36%). MP 228.8-230.4° C. MS (ES) m/z: 356.05 (M$^+$+1). $^1$H NMR (400 MHz, CDCl$_3$): δ 10.45 (s, 1H), 7.65 (s, 2H), 6.85

(d, J=1.6 Hz, 1H), 6.61 (d, J=1.6 Hz, 1H), 4.27 (t, J=4.8 Hz, 2H), 3.97 (s, 3H), 3.82 (t, J=4.8 Hz, 2H), 3.49 (s, 3H), 2.66 (s, 6H).

Example 106

Preparation of 2-(2,6-Dimethylpyridin-4-yl)-5,7-bis(2-methoxyethoxy)quinazolin-4(3H)-one

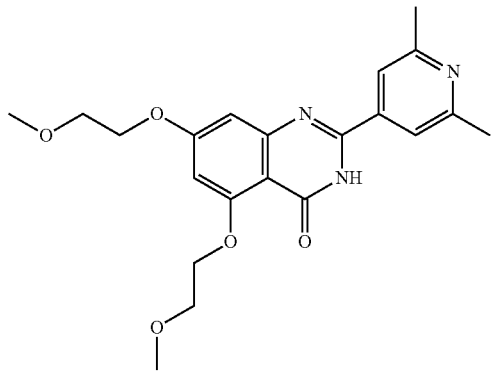

To a suspension of 2,6-dimethyl-pyridin-4-yl)-methanol (1.00 g, 7.30 mmol) in acetonitrile (20 mL), 1,2-benziodexol-3(1H)-one-1-hydroxy-1-oxide (IBX) (2.00 g, 7.30 mmol) was added and the reaction mixture was refluxed for 6 hours. The solid was filtered off and washed with acetonitrile. The filtrate was evaporated in vacuo, to give 2,6-dimethyl-pyridine-4-carbaldehyde as a brown liquid. Yield: 0.81 g (82%).

To a stirred solution of 2-amino-4,6-difluoro-benzamide (1.03 g, 6.00 mmol) and 2,6-dimethyl-pyridine-4-carbaldehyde (0.81 g, 6.00 mmol) in N,N-dimethyl acetamide (15 mL), sodium hydrogen sulfite (58.5 wt %, 1.31 g, 7.20 mmol) and p-toluenesulfonic acid monohydrate (0.11 g, 0.60 mmol) were added and the reaction mixture was stirred at 115° C. for 16 hours. The solvent was evaporated in vacuo, water was added, and the precipitated solid was filtered to give 2-(2,6-dimethyl-pyridin-4-yl)-5,7-difluoro-3H-quinazolin-4-one as a yellow solid, which was used in the next step without further purification. Yield: 0.72 g (42%).

To a suspension of 2-(2,6-dimethyl-pyridin-4-yl)-5,7-difluoro-3H-quinazolin-4-one (0.72 g, 2.51 mmol) in DMF (10 mL), a solution of sodium methoxide in methanol (25 wt %, 1.36 g, 25.1 mmol) was added and the reaction mixture was stirred at room temperature for 16 hours. Water was added, the mixture was acidified to pH approximately 4-5 with acetic acid, and the precipitated solid was filtered and dried under vacuum, to give 2-(2,6-dimethyl-pyridin-4-yl)-7-fluoro-5-methoxy-3H-quinazolin-4-one as a light yellow solid. Yield: 0.28 g (37%).

To a solution of 2-methoxyethanol (3 mL) in dimethyl sulfoxide (8 mL), sodium hydride (60% suspension in mineral oil, 0.40 g, 9.40 mmol) was added in portions and the reaction mixture was stirred at room temperature for 1 hour. To this reaction mixture was added 2-(2,6-dimethyl-pyridin-4-yl)-7-fluoro-5-methoxy-3H-quinazolin-4-one (0.28 g, 0.94 mmol); the reaction mixture was stirred at 90° C. for 16 hours. Water was added, the mixture was acidified to pH approximately 4-5 with acetic acid, and the precipitated solid was filtered, to give crude product, which was purified by preparative HPLC to obtain the title compound. Yield: 0.03 g (8%).

MP 149.8-151.4° C. MS (ES) m/z: 400.13 (M$^+$+1). $^1$H NMR (400 MHz, CDCl$_3$): δ 7.54 (s, 2H), 6.85 (s, 1H), 6.61 (s, 1H), 4.24 (m, 4H), 3.87 (t, J=5.2 Hz, 2H), 3.81 (t, J=5.2 Hz, 2H), 3.49 (br s, 6H), 2.65 (s, 6H).

Example 107

Preparation of 2-(2,6-Dimethylpyridin-4-yl)-7-methoxy-5-(2-(pyrrolidin-1-yl)ethoxy)quinazolin-4(3H)-one

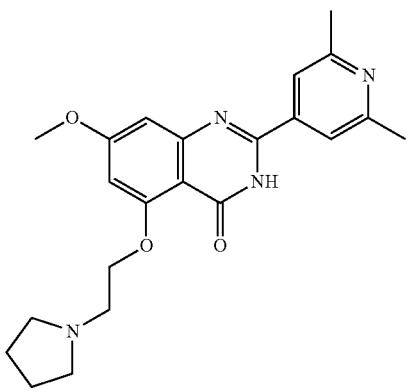 [SMILES: COc1cc(OCCN2CCCC2)c2c(=O)[nH]c(-c3cc(C)nc(C)c3)nc2c1]

To a solution of 2,6-dimethyl-pyridine-4-carbaldehyde (0.99 g, 7.32 mmol) and 2-amino-4,6-difluorobenzamide (1.26 g, 7.32 mmol) in N,N-dimethyl acetamide (20 mL) were added sodium hydrogen sulfite (58.5 wt %, 1.59 g, 8.78 mmol) and p-toluenesulfonic acid (0.21 g, 1.09 mmol). The reaction mixture was stirred at 115° C. for 16 hours under nitrogen. After cooling to room temperature, the solvent was evaporated under reduced pressure. Water (50 mL) was added, the precipitated solid was filtered, washed with water, and dried under vacuum, to give 2-(2,6-dimethyl-pyridin-4-yl)-5,7-difluoro-3H-quinazolin-4-one as a yellow solid. Yield: 0.63 g (30%).

To a solution of 2-pyrrolidin-1-yl-ethanol (5.09 g, 44.2 mmol) in DMF (10 mL) was added sodium hydride (60% suspension in mineral oil, 0.88 g, 22.1 mmol) in small portions and the reaction mixture was stirred at room temperature for 30 minutes. To this mixture was added 2-(2,6-dimethyl-pyridin-4-yl)-5,7-difluoro-3H-quinazolin-4-one 0.63 g, 2.21 mmol) and the reaction mixture was stirred at room temperature for 16 hours. Water (20 mL) was added, and the mixture was neutralized, to pH approximately 6 with acetic acid. Solvent was evaporated, and the residue was dissolved in ethyl acetate, washed with water, and dried over anhydrous sodium sulfate, and concentrated in vacuo. The crude compound was purified by the Simpliflash system (0-4% methanol in CH$_2$Cl$_2$ as eluent) to give 2-(2,6-dimethyl-pyridin-4-yl)-7-fluoro-5-(2-pyrrolidin-1-yl-ethoxy)-3H-quinazolin-4-one as a yellow solid. Yield: 0.61 g (72%).

To a solution of 2-(2,6-dimethyl-pyridin-4-yl)-7-fluoro-5-(2-pyrrolidin-1-yl-ethoxy)-3H-quinazolin-4-one (0.30 g, 0.80 mmol) in anhydrous DMF (5 mL) was added a solution of sodium methoxide in methanol (25 wt %, 0.43 g, 8.00 mmol) and the reaction mixture was stirred at 70° C. for 16 h. After cooling to room temperature, water (10 mL) was added, and the mixture was neutralized to pH approximately 6 with acetic acid. The solvent was evaporated, and the residue was purified by the Simpliflash system (2% methanol in CH$_2$Cl$_2$ and then 4% 7.0 M ammonia in methanol and CH$_2$Cl$_2$ as eluent) to give the title compound as a yellow solid. Yield: 0.100 g (32%). MP 190-191° C. $^1$H NMR (400 MHz, CDCl$_3$): δ 7.59 (s, 2H), 6.86 (d, J=1.95 Hz, 1H), 6.53 (d, J=1.95 Hz, 1H), 4.25 (t, J=6.05 Hz, 2H), 3.93 (s, 3H), 3.03 (t, J=6.24 Hz, 2H), 2.69 (br s, 4H), 2.64 (s, 6H), 1.93-1.70 (m, 4H). MS (ES$^+$) m/z: 395.22 (M+1) and 298.12 (100%).

Example 108

Preparation of 2-(2,6-Dimethylpyridin-4-yl)-6-((4-methylpiperazin-1-yl)methyl)quinazolin-4(3H)-one

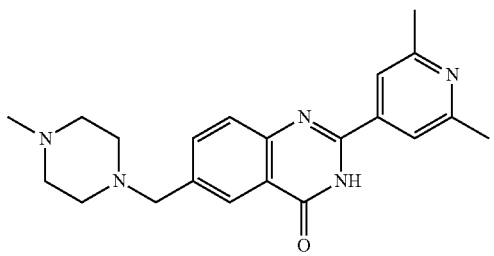

To a mixture of 5-methyl-2-nitrobenzoic acid (45.0 g, 0.248 mol) and potassium carbonate (138.2 g, 1.0 mol) in acetonitrile (700 mL), methyl iodide (78 mL, 1.25 mol) was added. The reaction mixture was stirred at room temperature for 12 hours, then the solution was filtered. The filtrate was concentrated under reduced pressure. The resulting solid was dissolved in ethyl acetate and washed with water and brine. The crude 5-methyl-2-nitrobenzoic acid methyl ester was used in the next step without further purification. Yield: 27.1 g (56%).

5-Methyl-2-nitrobenzoic acid methyl ester (27.1 g, 138.8 mmol) was dissolved in carbon tetrachloride (500 mL), and N-bromosuccinimide (29.6 g, 166.6 mmol) was added, followed by benzoyl peroxide (6.72 g, 27.7 mmol). The mixture was illuminated and gently refluxed for 4 hours. Then, the mixture was cooled and concentrated, then purified by column chromatography silica gel 230-400 mesh; 10% ethyl acetate in hexanes as eluent) to give 5-bromomethyl-2-nitrobenzoic acid methyl ester. Yield: 17.9 g (47%).

To a solution of 5-bromomethyl-2-nitrobenzoic acid methyl ester (3.00 g, 10.9 mmol) in CH$_2$Cl$_2$ (100 mL) was added triethylamine (3.30 g, 33.0 mmol) and 1-methylpiperazine (3.30 g, 33.0 mmol). The mixture was heated at 50° C. under nitrogen for 16 hours, then concentrated to give crude 5-(4-methylpiperazin-1-ylmethyl)-2-nitrobenzoic acid methyl ester, which was purified by column chromatography (silica gel 230-400 mesh; 1-5% methanol in dichloromethane as eluent). Yield: 3.0 g (93%). It was further converted to its hydrochloride salt (3.7 g) by stirring in 1 M HCl in ether and was isolated by filtration.

To a solution of 5-(4-methylpiperazin-1-ylmethyl)-2-nitrobenzoic acid methyl ester hydrochloride salt (3.70 g, 10.0 mmol) in acetic acid (50 mL) was added iron powder (1.80 g, 32.1 mmol), and the mixture was stirred at 70° C. for 2 hours; TLC indicated completion of the reaction. The mixture was cooled and concentrated; the residue was taken in 7 N ammonia in methanol (50 mL) and filtered. The filtrate was evaporated to dryness and purified by column chromatography (silica gel 230-400 mesh; 5-10% methanol in dichloromethane as eluent). Yield: 4.3 g (crude). The crude 2-amino-5-(4-methyl-piperazin-1-ylmethyl)benzoic acid methyl ester was used in the next step without further purification.

To a suspension of 2-amino-5-(4-methyl-piperazin-1-ylmethyl)benzoic acid methyl ester (4.30 g, 10.0 mmol) in water (30 mL) and methanol (10 mL) was added lithium hydroxide (1.26 g, 30.0 mmol); the mixture was stirred at room temperature for 12 hours. An additional amount of lithium hydroxide (0.6 g, 15.0 mmol) was added, and heated at 40° C. for 15 hours; TLC indicated completion of the reaction. The mixture was cooled, concentrated, the residue was adjusted to pH ~5 with 6 N HCl, and evaporated to dryness, to provide crude 2-amino-5-(4-methyl-piperazin-1-ylmethyl)benzoic acid. Yield: 6.2 g, along with inorganic salt. It was used in the next step without further purification.

To a suspension of 2-amino-5-(4-methyl-piperazin-1-ylmethyl)benzoic acid (crude 1.28 g, 3.00 mmol) in THF (18 mL) and DMF (7 mL), EDCl (0.77 g, 4.00 mmol), and HOBT (0.50 g, 3.30 mmol) were added and stirred at room temperature for 20 minutes. Then, N-methylmorpholine (0.33 g, 3.30 mmol) and NH$_4$OH (aq. 50% v/v, 3.50 mL, 50.0 mmol) were added. The mixture was stirred at room temperature for 48 hours. The solvent was evaporated, the residue was purified by column chromatography (silica gel 230-400 mesh; 5-10% 2 M ammonia in methanol and dichloromethane as eluent) to give 2-amino-5-(4-methyl-piperazin-1-ylmethyl)benzamide as a white solid. Yield: 0.416 g (55% for two steps).

To a solution of 2,6-dimethylpyridine-4-carbaldehyde (0.14 g, 1.00 mmol) in N,N-dimethyl acetamide (8 mL) were added 2-amino-5-(4-methyl-piperazin-1-ylmethyl)benzamide (0.25 g, 1.00 mmol), sodium hydrogensulfite (0.18 g, 1.20 mmol), and p-toluenesulfonic acid (0.057 g, 0.30 mmol). The reaction mixture was stirred at 115° C. for 20 hours under nitrogen, then cooled to room temperature. Solvent was evaporated under reduced pressure. The residue was dissolved in dichloromethane, washed with sat. NaHCO$_3$, water, then brine, and dried over anhydrous sodium sulfate. Solvent was evaporated and the residue was purified by column chromatography (silica gel 230-400 mesh; 2-3% 7 M ammonia in methanol and dichloromethane as eluent) to give the title compound. Yield: 0.035 g (9.6%). MP 229-230° C. $^1$H NMR (400 MHz, CDCl$_3$): δ 8.30 (br s, 1H), 7.88 (s, 2H), 7.84 (m, 2H), 3.66 (s, 2H), 2.72 (s, 6H), 2.50 (br s, 8H), 2.30 (s, 3H). MS (ES) m/z: 364.17 (M+1), 182.67 (100%).

Example 109

Preparation of 2-(2,6-Dimethylpyridin-4-yl)-5-methoxy-7-(2-phenoxyethoxy)quinazolin-4(3H)-one

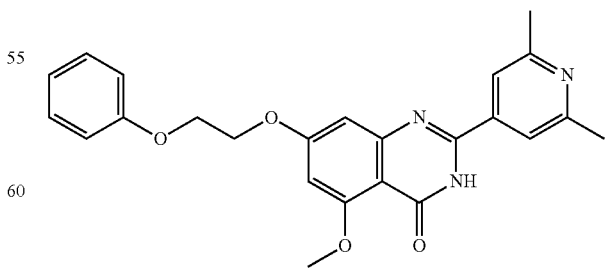

To a solution of 2-phenoxy-ethanol (0.90 g, 6.50 mmol) in DMSO (5 mL) was added sodium hydride (60% in mineral oil, 0.16 g, 4.00 mmol) in small portions. The reaction mixture was stirred at room temperature under nitrogen for 1 hour. 2-(2,6-Dimethyl-pyridin-4-yl)-7-fluoro-5-methoxy-3H-quinazolin-4-one (0.20 g, 0.67 mmol) was added and stirring continued at 90° C. for 17 hours. The reaction was then cooled to room temperature, water (100 mL) was added, and was extracted with ethyl acetate (200 mL). The organic phase was washed with brine and dried over anhydrous $Na_2SO_4$. Solvent was removed and the crude compound was purified by column chromatography (silica gel 230-400 mesh; 5% methanol in $CH_2Cl_2$ as eluent) to give the title compound as a white solid. Yield: 70 mg (25%). MP 223-224° C. $^1$H NMR (400 MHz, $CDCl_3$): δ 11.35 (s, 1H), 7.75 (s, 2H), 7.32 (t, J=8.0 Hz, 2H), 7.02-6.97 (m, 3H), 6.91 (d, J=2.0 Hz, 1H), 6.60 (d, J=1.6 Hz, 1H), 4.49-4.47 (m, 2H), 4.41-4.39 (m, 2H), 3.97 (s, 3H), 2.67 (s, 6H). MS ($ES^+$) m/z: 418.08 (M+1).

Example 110

Preparation of 2-(2,6-Dimethylpyridin-4-yl)-7-methoxy-5-(2-phenoxyethoxy)quinazolin-4(3H)-one

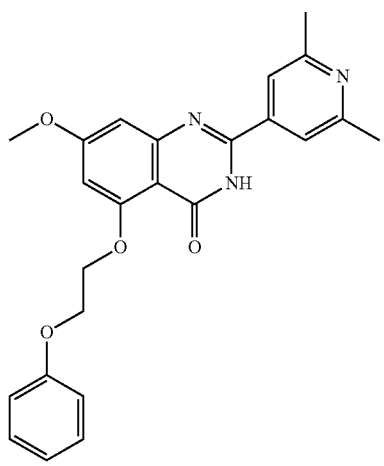

A solution of 2,6-lutidine N-oxide (41.6 g, 0.337 mol, 1.0 equiv.) in dry DCM (650 mL) was added to a flask containing trimethyloxonium tetrafluoroborate (50.0 g, 0.337 mol, 1.0 equiv.) at room temperature. under a nitrogen atmosphere. The mixture was stirred at room temperature for 3.0 hours, then concentrated in vacuo to give 78 g of crude 4-hydroxymethyl-2,6-dimethylpyridine. The crude product was dissolved in methanol (500 mL) and the solution was heated to reflux under a nitrogen atmosphere, then a solution of ammonium persulfate (24.6 g, 0.101 mol) in water (100 mL) was added dropwise. The mixture was stirred at reflux for 16 hours; TLC indicated complete reaction. Half of the solvents were removed in vacuo, then quenched with 10% NaOH solution to pH approximately 7, and evaporated to dryness. The residue was dissolved in methanol and filtered, the filtrate was concentrated in vacuum, and purified by column chromatography (eluting with methanol: DCM=5-15%) to give the title compound as a white solid. Yield: 24.7 g (52%).

4-Hydroxymethyl-2,6-dimethylpyridine (24.7 g, 180 mmol, 1.0 equiv.) was dissolved in DMSO (200 mL), and IBX (53.0 g, 189 mmol, 1.05 equiv.) was added in portions, the mixture was stirred at room temperature for 2 hours; TLC indicated complete reaction. The mixture was filtered, washed with water and ether. The filtrate was extracted with ether (4×150 mL); the combined extracts were washed with water and brine, dried over anhydrous sodium sulfate, and concentrated to give the crude product, which was purified by column chromatography (20% ether in hexanes as eluent) to give 2,6-dimethyl-4-pyridinecarboxaldehyde as a yellow oil. Yield: 20.0 g (82%).

To a solution of 2,6-dimethyl-pyridine-4-carbaldehyde (5.0 g, 36.5 mmol) and 2-amino-4,6-difluorobenzamide (6.28 g, 36.5 mmol) in N,N-dimethyl acetamide (80 mL) were added sodium hydrogen sulfite (7.95 g, 43.8 mmol) and p-toluenesulfonic acid (0.7 g, 3.65 mmol). The reaction mixture was stirred at 115° C. for 16 hours under nitrogen. The reaction mixture was cooled to room temperature, diluted with water, the precipitate was collected by filtration, washed with sat. $NaHCO_3$ and brine, and dried in vacuo to give 2-(2,6-dimethylpyridin-4-yl)-5,7-difluoro-3H-quinazolin-4-one as a white solid. Yield: 2.82 g (26.8%).

To a solution of 2-phenoxyethanol (4.81 g, 34.8 mmol) in DMF (20 mL) was added sodium hydride (60% suspension in mineral oil, 0.70 g, 17.4 mmol) in portions and the reaction mixture was stirred at room temperature for 1 hour. To this mixture was added 2-(2,6-dimethylpyridin-4-yl)-5,7-difluoro-3H-quinazolin-4-one (0.50 g, 1.74 mmol) and the reaction mixture was stirred at room temperature for 16 hours. Water (1 mL) was added, neutralized to pH approximately 6-7 with acetic acid, concentrated, dissolved in ethyl acetate, washed with water, dried over anhydrous sodium sulfate, and concentrated in vacuo. The residue was purified by column chromatography (eluted with 50% ethyl acetate in hexanes, then 5% methanol in DCM) to give 2-(2,6-dimethylpyridin-4-yl)-7-fluoro-5-(2-phenoxyethoxy)-3H-quinazolin-4-one as a light yellow solid. Yield: 0.59 g (83%).

To a suspension of 2-(2,6-dimethylpyridin-4-yl)-7-fluoro-5-(2-phenoxyethoxy)-3H-quinazolin-4-one (0.59 g, 1.45 mmol) in DMF (10 mL) was added a solution of sodium methoxide in methanol (25 wt %, 3.15 g, 14.5 mmol) and the reaction mixture was stirred at approximately 70-80° C. for 48 hours, then cooled to room temperature. Water (1 mL) was added, the mixture was neutralized to pH approximately 6-7 with acetic acid, concentrated, dissolved in DCM, washed with water and brine, dried over anhydrous sodium sulfate, concentrated in vacuo, and the residue was passed through a column (eluted with 2% methanol in DCM), to give 0.12 g of the desired product. The crude product was washed with acetonitrile, then solubilized in dioxane, and precipitated by adding water to afford the title compound as a white solid. Yield: 70 mg (11%). $^1$H NMR (400 MHz, DMSO-$d_6$): δ 12.08 (br s, 1H), 7.77 (s, 2H), 7.31 (t, J=7.81 Hz, 2H), 7.04 (d, J=8.20 Hz, 2H), 6.96 (t, J=7.42 Hz, 1H), 6.83 (d, J=1.56 Hz, 1H), 6.69 (s, 1H), 4.40-4.53 (m, 2H), 3.90 (s, 3H), 3.33 (s, 6H). MS ($ES^+$) m/z: 418.14 (M+1)$^+$; MP 172.3-173.2° C.

Example 111

Preparation of 2-(2,6-Dimethylpyridin-4-yl)-7-methoxy-5-(2-methoxyethoxy)quinazolin-4(3H)-one

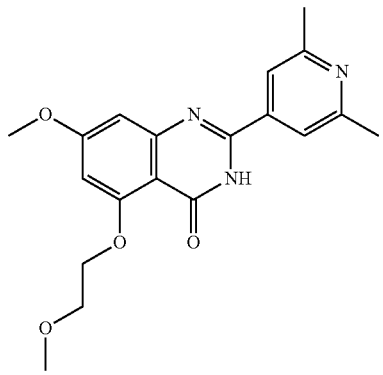

To a solution of 2-methoxyethanol (2.65 g, 34.8 mmol) in DMF (38 mL) was added sodium hydride (60% suspension in mineral oil, 0.70 g, 17.4 mmol) in portions and the reaction mixture was stirred at room temperature for 0.5 hours. To this mixture was added 2-(2,6-dimethylpyridin-4-yl)-5,7-difluoro-3H-quinazolin-4-one (0.50 g, 1.74 mmol) and the reaction mixture was stirred at room temperature for 16 hours. Water (1.5 mL) was added, the mixture was neutralized to pH approximately 6-7 with acetic acid, concentrated, dissolved in ethyl acetate (200 mL), washed with water and brine, dried over anhydrous sodium sulfate, and concentrated in vacuo. The residue was washed with hexanes to give 2-(2,6-dimethylpyridin-4-yl)-7-fluoro-5-(2-methoxyethoxy)-3H-quinazolin-4-one) as a pale solid. Yield: 0.52 g (87%).

To a suspension of 2-(2,6-dimethylpyridin-4-yl)-7-fluoro-5-(2-methoxyethoxy)-3H-quinazolin-4-one (0.42 g, 1.22 mmol) in DMF (10 mL) was added a solution of sodium methoxide in methanol (25 wt %, 2.8 g, 12.8 mmol) and the reaction mixture was stirred at 70° C. for 16 hours, then cooled to room temperature. Water (1 mL) was added, the mixture was neutralized to pH approximately 6 with acetic acid, diluted with water (50 mL), and extracted with ethyl acetate. The combined extracts were washed with water and brine, dried over anhydrous sodium sulfate, and concentrated in vacuo, to give 0.30 g of crude compound. Further purification by crystallization in acetone:Et$_2$O (1:3) gave the title compound as a white solid. Yield: 91 mg (15%). $^1$H NMR (400 MHz, CDCl$_3$): δ 10.08 (br s, 1H), 7.60 (br s, 2H), 6.87 (d, J=1.95 Hz, 2H), 6.55 (d, J=1.95 Hz, 2H), 4.25 (t, J=4.88 Hz, 2H), 3.93 (s, 3H), 3.83 (d, J=4.29 Hz, 2H), 3.44 (s, 3H), 2.64 (s, 6H). MS (ES$^+$) m/z: 356.11 (M+1)$^+$ Example 112

Preparation of 2-(2,6-Dimethylpyridin-4-yl)-5-methoxy-7-(2-(pyrrolidin-1-yl)ethoxy)quinazolin-4(3H)-one

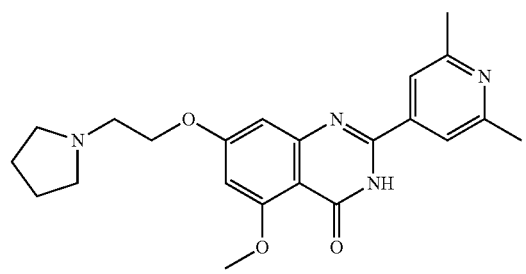 [SMILES: COc1cc(OCCN2CCCC2)cc2nc(-c3cc(C)nc(C)c3)[nH]c(=O)c12]

To a suspension of 2,6-dimethyl-pyridin-4-yl)-methanol (6.00 g, 0.043 mol) in acetonitrile (150 mL), 1,2-benziodexol-3(1H)-one-1-hydroxy-1-oxide (IBX) (14.8 g, 0.0503 mol) was added and the reaction mixture was refluxed for 2 hours. The solid was filtered off and washed with acetonitrile. The filtrate was evaporated in vacuo to give 2,6-dimethylpyridine-4-carbaldehyde as a brown liquid. Yield: 4.30 g (72.7%).

To a stirred solution of 2-amino-4,6-difluoro-benzamide (4.00 g, 0.0237 mol) and 2,6-dimethyl-pyridine-4-carbaldehyde (3.20 g, 0.0237 mol) in N,N-dimethyl acetamide (15 mL), sodium hydrogen sulfite (58.5 wt %, 5.05 g, 0.0284 mol) and p-toluenesulfonic acid monohydrate (0.90 g, 4.74 mmol) were added and the reaction mixture was stirred at 130° C. for 16 hours. The solvent was evaporated in vacuo, water was added, and the precipitated solid was filtered to give 2-(2,6-dimethyl-pyridin-4-yl)-5,7-difluoro-3H-quinazolin-4-one as a yellow solid, which was used in the next step without further purifications. Yield: 3.70 g (42%).

To a suspension of 2-(2,6-dimethyl-pyridin-4-yl)-5,7-difluoro-3H-quinazolin-4-one (2.70 g, 9.4 mmol) in DMF (15 mL), a solution of sodium methoxide in methanol (25 wt %, 6.0 g, 28.2 mmol) was added and the reaction mixture was stirred at room temperature for 16 hours. Water was added, the mixture was acidified to pH approximately 4-5 with acetic acid, and the precipitated solid was filtered and dried under vacuum to give crude 2-(2,6-dimethyl-pyridin-4-yl)-7-fluoro-5-methoxy-3H-quinazolin-4-one (2.40 g), which was further purified by column chromatography (silica gel 230-400 mesh; eluting with 2% methanol solution in dichloromethane) to yield pure compound as a light yellow solid. Yield: 0.35 g (12.4%).

To a solution of 2-pyrrolidin-1-yl-ethanol (1.15 g, 10 mmol) in dimethyl sulfoxide (4 mL), sodium hydride (60% suspension in mineral oil, 0.20 g, 5.0 mmol) was added in portions and the reaction mixture was stirred at room temperature for 20 minutes. To this reaction mixture was added 2-(2,6-dimethyl-pyridin-4-yl)-7-fluoro-5-methoxy-3H-quinazolin-4-one (0.30 g, 1.0 mmol) and the reaction mixture was stirred at 75° C. for 16 hours. The reaction mixture was loaded onto a column and purified by column chromatography (silica gel 230-400 mesh; eluting with 5% 7.0 M ammonia in methanol solution in dichloromethane), to obtain the title compound as a white solid. Yield: 0.163 g (41.3%). MP 227-229° C. MS (ES) m/z: 395.15 (M$^+$+1). $^1$H NMR (400 MHz, CDCl$_3$): δ 7.78 (s, 2H), 6.87 (d, J=2.4 Hz, 1H), 6.58 (d, J=2.4 Hz, 1H), 4.25 (t, J=6.0 Hz, 2H), 3.95 (s, 3H), 2.97 (t, J=6.0 Hz, 2H), 2.66 (s, 6H), 2.63 (m, 4H), 1.83 (m, 4H).

Example 113

Preparation of 2-(2,6-Dimethylpyridin-4-yl)-7-(2-isopropoxyethoxy)-5-methoxyquinazolin-4(3H)-one

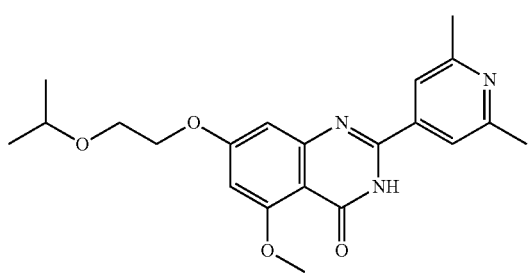 [SMILES: COc1cc(OCCOC(C)C)cc2nc(-c3cc(C)nc(C)c3)[nH]c(=O)c12]

To a suspension of 2-(2,6-dimethyl-pyridin-4-yl)-5,7-difluoro-3H-quinazolin-4-one (0.97 g, 3.38 mmol) in anhydrous DMF (10 mL) was added a solution of sodium methoxide in methanol (25 wt %, 1.09 g, 20.3 mmol). The reaction mixture became clear. The reaction mixture was stirred at room temperature for 16 hours. Water (100 mL) was added, neutralized to pH approximately 6 with aqueous 2N HCl. The separated solid was filtered, washed with water (50 mL), and dried under vacuum to give an off-white solid. Yield: 0.94 g (93%).

To a suspension of sodium hydride (60% suspension in mineral oil, 0.24 g, 6.00 mmol) in anhydrous DMSO (10 mL) was added 2-isopropoxy-ethanol at room temperature under nitrogen. The mixture was stirred for 20 minutes at room temperature, then 2-(2,6-dimethyl-pyridin-4-yl)-7-fluoro-5- methoxy-3H-quinazolin-4-one (0.30 g, 1.00 mmol) was added and the reaction mixture was stirred at 80° C. for 16 hours, then cooled to room temperature. Water (50 mL) was added, and the mixture was extracted with a mixture of ethyl acetate and THF (4:1, 200 mL). The organic phase was washed with brine and dried over anhydrous sodium sulfate. Solvent was evaporated, and the crude compound was purified by the Simpliflash system (3:15:82 methanol, ethyl acetate and dichloromethane as eluent) to give the title compound as a white solid. Yield: 127 mg (33%). MP 188-189° C. $^1$H NMR (400 MHz, CDCl$_3$): δ 11.14 (br s, 1H), 7.72 (s, 2H), 6.86 (d, J=2.34 Hz, 1H), 6.59 (d, J=2.34 Hz, 1H), 4.35-4.15 (m, 2H), 3.97 (s, 3H), 3.89-3.79 (m, 2H), 3.78-3.64 (m, 1H), 2.66 (s, 6H), 1.23 (d, J=5.85 Hz, 6H). MS (ES$^+$) m/z: 384.20 (100%).

Example 114

Preparation of 2-(2,6-dimethylpyridin-4-yl)-5,7-bis (2-isopropoxyethoxy)quinazolin-4(3H)-one

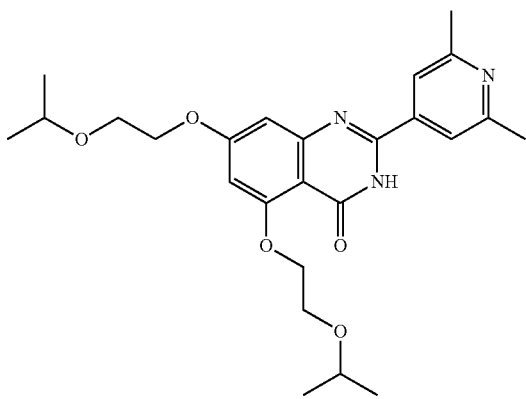 [SMILES: Cc1cc(-c2nc3cc(OCCOC(C)C)cc(OCCOC(C)C)c3c(=O)[nH]2)cc(C)n1]

The title compound was isolated using the process described for Example 113 as a white solid. Yield: 124 mg (27%). MP 124-125° C. $^1$H NMR (400 MHz, CDCl$_3$): δ 10.04 (br s, 1H), 7.60 (s, 2H), 6.85 (d, J=2.34 Hz, 1H), 6.63 (d, J=2.34 Hz, 1H), 4.23 (t, J=4.88 Hz, 4H), 3.85 (dt, J=10.54 and 5.27 Hz, 4H), 3.80-3.64 (m, 2H), 2.64 (s, 6H), 1.23 (d, J=6.24 Hz, 6H), 1.17 (d, J=6.24 Hz, 6H). MS (ES$^+$) m/z: 456.17 (100%).

Example 115

Preparation of 7-(2-(Benzyloxy)ethoxy)-2-(2,6-dimethylpyridin-4-yl)-5-methoxyquinazolin-4(3H)-one

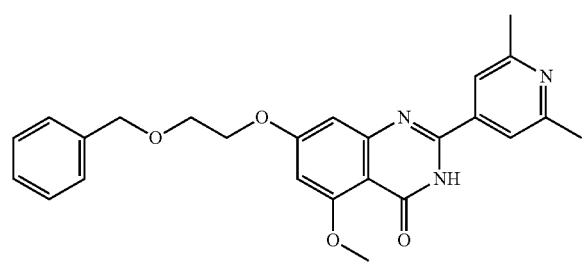 [SMILES: COc1cc(OCCOCc2ccccc2)cc2nc(-c3cc(C)nc(C)c3)[nH]c(=O)c12]

To a suspension of 2,6-dimethyl-pyridin-4-yl)-methanol (6.00 g, 0.043 mol) in acetonitrile (150 mL), 1,2-benziodexol-3(1H)-one-1-hydroxy-1-oxide (IBX) (14.8 g, 0.0503 mol) was added and the reaction mixture was refluxed for 2 hours. The solid was filtered off and washed with acetonitrile. The filtrate was evaporated in vacuo to give 2,6-dimethyl-pyridine-4-carbaldehyde as a brown liquid. Yield: 4.30 g (72.7%).

To a stirred solution of 2-amino-4,6-difluoro-benzamide (4.00 g, 0.0237 mol) and 2,6-dimethyl-pyridine-4-carbaldehyde (3.20 g, 0.0237 mol) in N,N-dimethyl acetamide (15 mL), sodium hydrogen sulfite (58.5 wt %, 5.05 g, 0.0284 mol), and p-toluene sulfonic acid monohydrate (0.90 g, 4.74 mmol) were added and the reaction mixture was stirred at 130° C. for 16 hours. The solvent was evaporated in vacuo, water was added, and the precipitated solid was filtered to give 2-(2,6-dimethyl-pyridin-4-yl)-5,7-difluoro-3H-quinazolin-4-one as a yellow solid, which was used in the next step without further purification. Yield: 3.70 g (54.3%).

To a suspension of 2-(2,6-dimethyl-pyridin-4-yl)-5,7-difluoro-3H-quinazolin-4-one (2.70 g, 9.4 mmol) in DMF (15 mL), a solution of sodium methoxide in methanol (25 wt %, 6.0 g, 28.2 mmol) was added and the reaction mixture was stirred at room temperature for 16 h. Water was added, acidified to pH approximately 4-5 with acetic acid and the precipitated solid was filtered and dried under vacuum to give crude 2-(2,6-dimethyl-pyridin-4-yl)-7-fluoro-5-methoxy-3H-quinazolin-4-one (2.40 g), which was further purified by column chromatography (silica gel 230-400 mesh; eluting with 2% methanol solution in dichloromethane) to yield pure compound as a light yellow solid. Yield: 0.35 g (12.4%).

To a solution of 2-benzyloxy-ethanol (1.15 g, 10.0 mmol) in dimethyl sulfoxide (4 mL), sodium hydride (60% suspension in mineral oil, 0.20 g, 5.0 mmol) was added in portions and the reaction mixture was stirred at room temperature for 20 minutes. To this reaction mixture was added 2-(2,6-dimethyl-pyridin-4-yl)-7-fluoro-5-methoxy-3H-quinazolin-4-one (0.30 g, 1.0 mmol) and the reaction mixture was stirred at 85° C. for 24 hours. Water was added, and the mixture was acidified to pH approximately 4-5 with acetic acid and the precipitated solid was filtered to give crude product, which was purified by column chromatography (silica gel 230-400 mesh; eluting with hexane and ethyl acetate 10:1) to obtain the title compound as a white solid. Yield: 0.140 g (32.4%). MP 178-180° C. MS (ES) m/z: 432.18 (M$^+$+1). $^1$H NMR (400 MHz, CDCl$_3$): δ 10.90 (s, 1H), 7.69 (s, 2H), 7.29-7.40 (m, 5H), 6.85 (d, J=2.0 Hz, 1H), 6.59 (d, J=2.0 Hz, 1H), 4.66 (s, 2H), 4.29 (m, 2H), 3.97 (s, 3H), 3.89 (m, 2H), 2.66 (s, 6H).

Example 116

Preparation of 2-(2,6-Dimethylpyridin-4-yl)-6-(2-morpholinoethyl)quinazolin-4(3H)-one

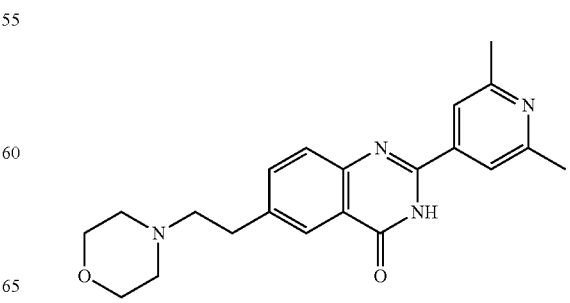

To a solution of 2-amino-5-(2-morpholin-4-yl-ethyl)-benzamide (0.18 g, 0.70 mmol) in N,N-dimethyl acetamide (7 mL) under nitrogen atmosphere were added 2,6-dimethyl-pyridine-4-carbaldehyde (0.10 g, 0.70 mmol), sodium hydrogensulfite (58.5 wt %, 0.15 g, 1.40 mmol) and p-toluenesulfonic acid (0.34 g, 1.80 mmol). The resulting mixture was heated at 120° C. for 16 hours, then cooled to room temperature. The solvent was removed under reduced pressure, and the residue was diluted with methylene chloride (100 mL). The organic phase was washed with saturated aqueous sodium bicarbonate solution, then water, and dried over anhydrous sodium sulfate. The crude orange solid (0.21 g) was purified by column chromatography (silica gel 230-400 mesh; 95:5 methylene chloride and MeOH as eluent) to give the title compound as a yellow solid. Yield: 0.11 g (42%). MP 248.5-249.3° C. $^1$H NMR (400 MHz, CDCl$_3$): δ 11.6 (s, 1H), 8.18 (s, 1H), 7.87-7.76 (m, 3H), 7.76-7.65 (m, 1H), 3.76 (t, J=4.49 Hz, 4H), 2.99 (t, J=8.01 Hz, 4H), 2.71 (s, 6H), 2.75-2.65 (m, 2H), 2.56 (br s, 4H). MS (ES$^+$) m/z: 363.16 (M+1).

Example 117

Preparation of 2-(2-methylpyridin-4-yl)-6-(morpholinomethyl)quinazolin-4(3H)-one

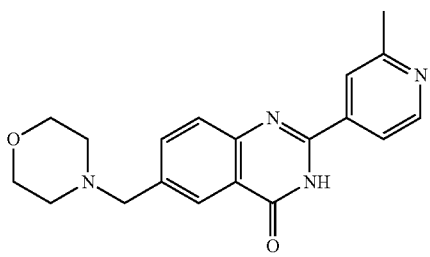 [SMILES: Cc1cc(-c2nc3ccc(CN4CCOCC4)cc3c(=O)[nH]2)ccn1]

A solution of n-butyllithium (1.6 M solution in hexanes, 6.32 mL, 12.6 mmol) in THF (50 mL) was cooled to −78° C. A solution of 4-bromo-2-methyl-pyridine (2.00 g, 11.6 mmol.) in anhydrous THF (5 mL) was added. The resulting mixture was stirred for 5 minutes, then anhydrous N,N dimethylformamide (3.39 g, 46.4 mmol,) was added. The solution was stirred for 90 min at −78° C. and quenched with saturated aqueous NH$_4$Cl solution (30 mL). The reaction mixture was warmed to room temperature. The mixture was extracted with ethyl acetate (3×100 mL), and the combined organic phase was washed with brine (100 mL) and dried over anhydrous Na$_2$SO$_4$. The solvent was evaporated under reduced pressure to give 2-methyl-pyridine-4-carbaldehyde. Yield: 1.20 g, (85%).

To a solution of 2-amino-5-morpholin-4-ylmethyl-benzamide (0.58 g, 2.4 mmol) and 2-methyl-pyridine-4-carbaldehyde (0.3 g, 2.4 mmol) in N,N-dimethylacetamide (10 mL) were added NaHSO$_3$ (58.5 wt %, 0.48 g, 2.7 mmol) and p-TSA (0.23 g, 1.2 mmol) and the reaction mixture was heated at 115° C. for 16 hours, and the solvent was removed under reduced pressure. The crude compound was purified by column chromatography (silica gel 230-400 mesh; eluting with 4% methanolic ammonia in dichloromethane) to give the title compound as a white solid. Yield: 0.18 g (22%). MP 267-268° C. $^1$H NMR (400 MHz, DMSO-d$_6$): δ 11.74 (br s, 1H), 8.77 (d, J=5.4 Hz, 1H), 8.29 (s, 1H), 8.07 (s, 1H), 7.94-7.83 (m, 3H), 3.75 (t, J=4.2 Hz, 4H), 3.74 (s, 2H), 2.77 (s, 6H), 2.53-2.46 (m, 4H). MS (ES$^+$) m/z: 337.41 (M+1).

Example 118

Preparation of 5-methoxy-7-(2-methoxyethoxy)-2-(2-methylpyridin-4-yl)quinazolin-4(3H)-one

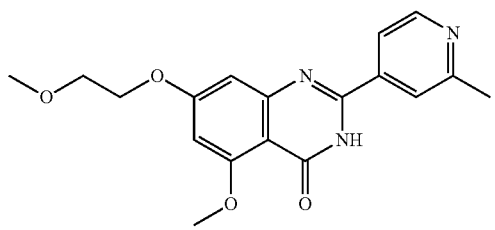

To a solution of 2-amino-4,6-difluoro-benzamide (0.71 g, 4.10 mmol) and 2-methyl-pyridine-4-carbaldehyde (0.50 g, 4.10 mmol) in N,N-dimethylacetamide (10 mL) were added NaHSO$_3$ (58.5 wt %, 1.00 g, 5.70 mmol) and p-TSA (0.16 g, 0.08 mmol). The reaction mixture was heated at 115° C. for 30 hours, then cooled to room temperature. The solvent was removed under reduced pressure. The crude compound was purified by column chromatography (silica gel 230-400 mesh; 5% methanol in dichloromethane) to afford 5,7-difluoro-2-(2-methyl-pyridin-4-yl)-3H-quinazolin-4-one as a light yellow solid. Yield: 0.30 g (26%).

To a suspension of 5,7-difluoro-2-(2-methyl-pyridin-4-yl)-3H-quinazolin-4-one (0.30 g, 1.09 mmol) in anhydrous DMF (8 mL) was added a solution of sodium methoxide in methanol (25 wt %, 0.59 g, 10.9 mmol) and the reaction mixture was stirred at room temperature for 3 hours. Water was added, the mixture was acidified to pH approximately 5 with acetic acid, and the precipitated solid was filtered and dried under vacuum to give 7-fluoro-5-methoxy-2-(2-methyl-pyridin-4-yl)-3H-quinazolin-4-one as a light yellow solid. Yield: 0.24 g (76%).

To a solution of 2-methoxy-ethanol (0.64 g, 8.40 mmol) in anhydrous DMSO (4 mL) was added sodium hydride (60% suspension in mineral oil, 0.12 g, 5.00 mmol) in small portions and the reaction mixture was stirred at room temperature for 30 minutes. To this mixture was added a solution of 7-fluoro-5-methoxy-2-(2-methyl-pyridin-4-yl)-3H-quinazolin-4-one (0.24 g, 0.84 mmol) in anhydrous DMSO (12 mL). The reaction mixture was stirred at 80° C. for 3 hours, then cooled to room temperature, and diluted with ether (500 mL). The solid was filtered and washed with ether. The crude compound was purified by column chromatography (silica gel 230-400 mesh; 4% methanol in dichloromethane). The compound was further purified by preparative HPLC to give the title compound as a white solid. Yield: 60 mg (21%). MP 260-262° C. $^1$H NMR (400 MHz, DMSO-d$_6$): δ 8.62 (d, J=5.07 Hz, 1H), 7.98 (s, 1H), 7.88 (d, J=5.07 Hz, 1H), 6.80 (d, J=2.34 Hz, 1H), 6.61 (d, J=2.34 Hz, 1H), 4.25 (t, J=4.68 Hz, 2H), 3.86 (s, 3H), 3.71 (t, J=3.90 Hz, 2H), 3.33 (s, 3H), 2.57 (s, 3H). MS (ES) m/z: 342.07 (M+1) (100%).

Example 119

Preparation of 2-(2,6-Dimethylpyridin-4-yl)-6-(2-(pyrrolidin-1-yl)ethyl)quinazolin-4(3H)-one

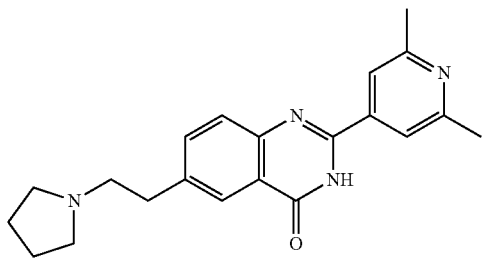 [SMILES: Cc1cc(-c2nc3ccc(CCN4CCCC4)cc3c(=O)[nH]2)cc(C)n1]

To a suspension of 1H-benzotriazole (10.0 g, 83.9 mmol) in water (84 mL) was added pyrrolidine 2 (6.3 mL, 226.6 mmol). After 10 minutes of vigorous stirring at room temperature, formaldehyde 37% aqueous solution was added. The reaction mixture was stirred for 1 hour, then the precipitate was filtered off, and washed with water to afford 1-pyrrolidin-1-ylmethyl-1H-benzoimidazole as an off-white solid. Yield: 14.58 g (85.9%).

To a mixture of zinc powder (1.05 g, 16.05 mmol) and 1-pyrrolidin-1-ylmethyl-1H-benzoimidazole (2.95 g, 14.59 mmol) in N,N-dimethyl formamide (40 mL) under a nitrogen atmosphere was added 5-bromomethyl-2-nitro-benzoic acid methyl ester (4.0 g, 14.59 mmol). The reaction mixture was stirred at room temperature for 24 hours, then quenched at 0° C. with an ice-cold 25% aqueous solution of ammonium hydroxide (108 mL). The stirring was continued until most of the solid had dissolved. Undissolved solid was filtered off and the filtrate was extracted with diethyl ether. The combined organic layers were washed with 1 N aqueous sodium hydroxide, then water, and were dried over anhydrous sodium sulfate and concentrated under high vacuum to give 2-nitro-5-(2-pyrrolidin-1-yl-ethyl)-benzoic acid methyl ester as an orange oil. Yield: 1.3 g (32%). The crude material was used for the next step without further purification.

To a solution of 2-nitro-5-(2-pyrrolidin-1-yl-ethyl)-benzoic acid methyl ester in THF (16 mL) was added 10% palladium on charcoal (0.23 g). The resulting reaction mixture was hydrogenated under 40 psi for 2 hours, then the catalyst was filtered off and the filtrate concentrated under high vacuum to give 2-amino-5-(2-pyrrolidin-1-yl-ethyl)-benzoic acid methyl ester as a yellow oil. Yield: 1.04 g (89.6%). The crude material was used in the next step without further purification.

To a solution of 2-amino-5-(2-pyrrolidin-1-yl-ethyl)-benzoic acid methyl ester (1.04 g, 4.19 mmol) in a mixture of THF (8 mL) and methanol (5 mL) was added lithium hydroxide (0.36 g), followed by water (3 mL). The reaction mixture was stirred at room temperature overnight, and then refluxed for 4 hours. After cooling to room temperature, the was solvent concentrated. The pH was adjusted to approximately 5 with 2 N aqueous hydrochloric acid and the residue was evaporated to dryness to give 2-amino-5-(2-pyrrolidin-1-yl-ethyl)-benzoic acid as a chloride salt. Yield: 1.84 g. The crude material was used in the next step without further purification.

To a solution of 2-amino-5-(2-pyrrolidin-1-yl-ethyl)-benzoic acid (0.41 g, 1.75 mmol) in a mixture of THF (5.1 mL) and N,N-dimethyl formamide (1.75 mL) was added EDCl (0.84 g, 4.37 mmol), followed by HOBt (0.71 mL, 5.25 mmol). The reaction mixture was stirred for 30 minutes. Then, N-methyl morpholine (0.67 mL, 6.12 mmol) was added, followed by 50% aqueous ammonium hydroxide (1.2 mL, 17.5 mmol). The resulting mixture was stirred at room temperature for 24 hours. Then, the solvent was reduced and the residue was extracted with methylene chloride. The combined organic layers were washed with brine, water, and dried over sodium sulfate. After solvent evaporation under high vacuum, the crude orange oil (0.72 g) was purified by column chromatography (silica gel 230-400 mesh; 5/95 methylene chloride/7 N ammonia in MeOH as eluent) to give pure 2-amino-5-(2-pyrrolidin-1-yl-ethyl)-benzamide as a light yellow viscous oil. Yield: 0.16 g (39.2%).

To a solution of 2-amino-5-(2-pyrrolidin-1-yl-ethyl)-benzamide (0.16 g, 0.69 mmol) in N,N-dimethyl acetamide (7 mL) under a nitrogen atmosphere was added 2,6-dimethyl-pyridine-4-carbaldehyde (0.09 g, 0.68 mmol), followed by sodium hydrogensulfite (0.14 g, 1.36 mmol) and p-toluenesulfonic acid (0.32 g, 1.7 mmol). The resulting mixture was heated at 120° C. overnight. Then, the solvent was removed under reduced pressure, the residue was diluted with ethyl acetate, and was extracted with water. The pH of the water layer was made basic by adding sodium bicarbonate, then the layer was extracted with methylene chloride, dried over anhydrous sodium sulfate, and was evaporated under high vacuum. The crude yellow solid (0.09 g) was purified by column chromatography (silica gel 230-400 mesh; 95/5 methylene chloride/MeOH as eluent) to afford the title compound as a yellow solid. Yield: 54 mg (23%). MP 212.3-213.2° C. $^1$H NMR (400 MHz, CDCl$_3$): δ 8.19 (s, 1H), 8.19 (br s, 1H), 7.83-7.77 (m, 1H), 7.76-7.70 (m, 3H), 3.0-3.15 (m, 2H), 2.78-2.88 (m, 2H), 2.7 (s, 6H), 2.58-2.68 (m, 4H), 1.8-1.95 (m, 4H). MS (ES$^+$) m/z: 347.11 (M+1).

Example 120

Preparation of 2-(2,6-Dimethylpyridin-4-yl)-7-(2-methoxyethoxy)-5-(2-(pyrrolidin-1-yl)ethoxy)quinazolin-4(3H)-one

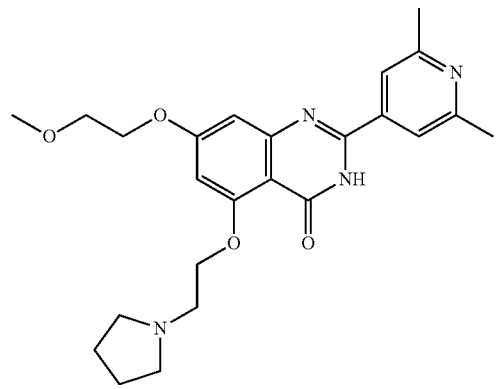

To a solution of 2-pyrrolidin-1-yl-ethanol (5.09 g, 44.2 mmol) in DMF (10 mL) was added sodium hydride (60% suspension in mineral oil, 0.88 g, 22.1 mmol) in small portions and the reaction mixture was stirred at room temperature for 30 minutes. To this mixture was added 2-(2,6-dimethyl-pyridin-4-yl)-5,7-difluoro-3H-quinazolin-4-one (0.63 g, 2.21 mmol) and the reaction mixture was stirred at room temperature for 16 hours. Water (20 mL) was added, and the mixture was neutralized to pH approximately 6 with acetic acid. Solvent was evaporated, the residue was dissolved in ethyl acetate, washed with water, dried over anhydrous sodium sulfate, and concentrated in vacuo. Crude compound was purified by the Simpliflash system (0-4% methanol in $CH_2Cl_2$ as eluent) to afford 2-(2,6-dimethyl-pyridin-4-yl)-7-fluoro-5-(2-pyrrolidin-1-yl-ethoxy)-3H-quinazolin-4-one as a yellow solid. Yield: 0.61 g (72%).

To a solution of 2-methoxy-ethanol (1.35 g, 17.8 mmol) in DMF (10 mL) was added sodium hydride (60% suspension in mineral oil, 0.36 g, 8.89 mmol) in small portions and the reaction mixture was stirred at room temperature for 30 minutes. To this mixture was added 2-(2,6-dimethyl-pyridin-4-yl)-7-fluoro-5-(2-pyrrolidin-1-yl-ethoxy)-3H-quinazolin-4-one (0.34 g, 0.89 mmol) and the reaction mixture was stirred at 70-80° C. for 16 h, then cooled to room temperature. Water (10 mL) was added, and the mixture was neutralized to pH approximately 6 with acetic acid. Solvent was evaporated; the residue was purified by the Simpliflash system (2-5% 7.0M ammonia in methanol and $CH_2Cl_2$ as eluent). The compound was further purified by preparative HPLC to give the title compound as a yellow solid. Yield: 72 mg (18%). MP 60.4-62.3° C. $^1$H NMR (400 MHz, $CDCl_3$): δ 10.23 (br s, 1H), 8.50 (br s, 1H), 7.60 (s, 2H), 6.76 (br s, 1H), 6.43 (br s, 1H), 4.35 (m., 2H), 4.21 (m, 2H), 3.79 (s, 3H), 3.47-3.38 (m, 6H), 2.64 (s, 6H), 1.99 (m, 4H). MS (ES) m/z: 437.09 (M−1) (100%).

Example 121

Preparation of 2-(3-(2-Hydroxyethoxy)phenyl)-5,7-dimethoxyquinazolin-4(3H)-one

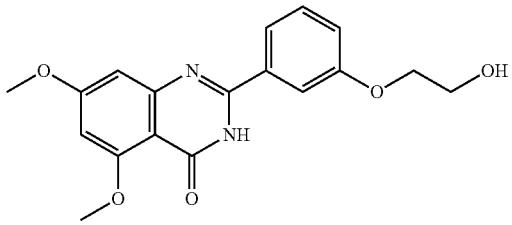 [SMILES: COc1cc(OC)c2c(=O)[nH]c(-c3cccc(OCCO)c3)nc2c1]

To a suspension of sodium hydride (0.426 g, 10.7 mmol) in DMF (30 mL) at room temperature was added 3-hydroxybenzaldehyde (1.00 g, 8.20 mmol). The resulting suspension was stirred at room temperature for 1 hour and (2-bromo-ethoxy)-tert-butyl-dimethyl-silane (4.4 mL, 20.5 mmol), was then added. The resulting mixture was stirred at 60° C. under nitrogen for 14 hours, cooled to room temperature, diluted with water (100 mL), extracted with ethyl acetate (250 mL), and concentrated. The crude product was purified by column chromatography ($SiO_2$, hexane/ethyl acetate=4:1) to afford 3-[2-(tert-butyl-dimethyl-silanyloxy)-ethoxy]-benzaldehyde. It was re-dissolved in THF (50 mL), mixed with 1 N tetra-n-butylammonium fluoride in THF (15 mL), and stirred at room temperature for 8 h. The reaction mixture was then concentrated and the residue was purified by column chromatography ($SiO_2$, hexane/ethyl acetate=4:1) to afford 3-(2-hydroxy-ethoxy)-benzaldehyde as a colorless oil. Yield: 0.68 g (50% for two steps).

A mixture of 2-amino-4,6-dimethoxy-benzamide (195 mg, 1.00 mmol), 3-(2-hydroxy-ethoxy)-benzaldehyde (166 mg, 1.00 mmol), p-toluenesulfonic acid monohydrate (38 mg, 0.20 mmol), and sodium bisulfite (264 mg, 1.50 mmol) in N,N-dimethylacetamide (10 mL) was stirred at 130° C. under nitrogen for 14 hours, cooled to room temperature, and diluted with 0.2 N potassium carbonate aqueous solution (50 mL). It was extracted with ethyl acetate (250 mL), dried over sodium sulfate, and concentrated. The solid residue was re-dissolved in dichloromethane (5 mL), and precipitated with ethyl acetate (15 mL) and hexanes (50 mL). It was filtered and washed with hexanes to afford the title compound as a yellow solid. Yield: 70 mg (20%). MP 244.8-246.0° C. $^1$H NMR (400 MHz, $CDCl_3$): δ 7.64 (d, 1H), 7.60 (d, 1H), 7.45 (t, 1H), 7.12 (dd, 1H), 6.84 (d, 1H), 6.48 (d, 1H), 4.21 (t, 2H), 4.03 (t, 2H), 3.99 (s, 3H), 3.94 (s, 3H). MS ($ES^+$) m/z: 343.55 (M+1).

Example 122

Preparation of 2-(3-(2-Hydroxyethoxy)-5-methylphenyl)-5,7-dimethoxyquinazolin-4(3H)-one

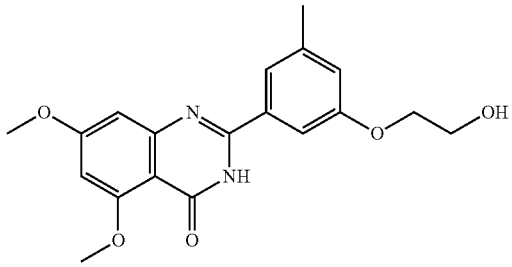 [SMILES: COc1cc(OC)c2c(=O)[nH]c(-c3cc(C)cc(OCCO)c3)nc2c1]

To a solution of 3,5-dimethyl-phenol (3.000 g, 24.55 mmol) in N,N-dimethylformamide (120 mL) under nitrogen were added potassium carbonate (16.96 g, 122.7 mmol) and (2-bromoethoxy)-tert-butyldimethylsilane (7.90 mL, 36.8 mmol). The resulting slurry was heated at reflux for 20 hours; then, the solvent was removed under high vacuum. The residue was dissolved in ethyl acetate and the solution was backwashed with 0.2 N aqueous sodium hydroxide, water, and then brine, dried over sodium sulfate, and concentrated. The crude material (5.69 g) was purified by column chromatography (silica gel 230-400 mesh; methylene chloride as eluent) to give tert-butyl-[2-(3,5-dimethyl-phenoxy)-ethoxy]-dimethylsilane as light yellow oil. Yield: 3.72 g (47%).

To a solution of tert-butyl-[2-(3,5-dimethyl-phenoxy)-ethoxy]-dimethylsilane (2.22 g, 7.91 mmol) in carbon tetrachloride (50 mL) under nitrogen was added N-bromosuccinimide (1.57 g, 8.70 mmol) and benzoyl peroxide (0.38 g, 1.58 mmol). The resulting mixture was heated at reflux for 3 hours with simultaneous illumination by a sun lamp. The precipitate was filtered off and the filtrate was concentrated under reduced pressure. The crude material (3.99 g) was purified by column chromatography (silica gel 230-400 mesh; 1/0 to 4/1 hexanes/EtOAc as eluent) to give [2-(3-bromomethyl-5-methyl-phenoxy)-ethoxy]-tert-butyl-dimethyl-silane as a light yellow oil. Yield: 2.17 g (75%).

To a solution of [2-(3-bromomethyl-5-methyl-phenoxy)-ethoxy]-tert-butyl-dimethyl-silane (2.17 g, 6.04 mmol) under nitrogen in 2-nitropropane (2.0 mL, 20 mmol) was added sodium ethoxide (0.620 g, 9.06 mmol). The resulting mixture was heated at 90° C. for 15 hours, and was then diluted with ethyl acetate and quenched with saturated aqueous ammonium chloride. The aqueous layer was extracted with ethyl acetate and the combined organic layers were backwashed with water and brine, dried over sodium sulfate, and concentrated. The crude material (1.81 g) was purified by column chromatography (silica gel 230-400 mesh; 1/0 to 4/1 hexanes/EtOAc as eluent) to give 3-[2-(tert-butyl-dimethyl-silanyloxy)-ethoxy]-5-methyl-benzaldehyde as a yellow oil. Yield: 0.97 g (55%).

To a solution of 2-amino-4,6-dimethoxy-benzamide (0.350 g, 1.78 mmol) in N,N-dimethylacetamide (20 mL) under nitrogen was added 3-[2-(tert-butyl-dimethyl-silanyloxy)-ethoxy]-5-methyl-benzaldehyde (0.520 g, 1.78 mmol) followed by sodium hydrogensulfite (0.270 g, 2.67 mmol), and p-toluenesulfonic acid (0.033 g, 0.18 mmol). The resulting mixture was heated at 120° C. for 24 hours, then the solvent was concentrated to 5 mL under reduced pressure, and water was added to obtain a precipitate, which was filtered off and washed with $Et_2O$ and methylene chloride. The resulting solid was dissolved in hot $CH_2Cl_2$/MeOH, and then precipitated by adding $Et_2O$, and purified by preparative thin-layer chromatography (DC-Fertigplatten SIL G-100 UV, 9/1 methylene chloride/MeOH as eluent) to give the title compound as a yellow solid. Yield: 81 mg (13%). MP 106.9-109.1° C. $^1$H NMR (400 MHz, $CDCl_3$): δ 7.86 (s, 1H), 7.41 (d, 2H), 6.82 (s, 1H), 6.57 (s, 1H), 4.15-4.13 (m, 2H), 3.94-3.90 (m, 8H), 2.43 (s, 3H). MS ($ES^+$) m/z: 357.53 (M+1).

Example 123

Preparation of 5,7-Dimethoxy-2-(3-methoxy-5-(2-(pyrrolidin-1-yl)ethoxy)phenyl)quinazolin-4(3H)-one

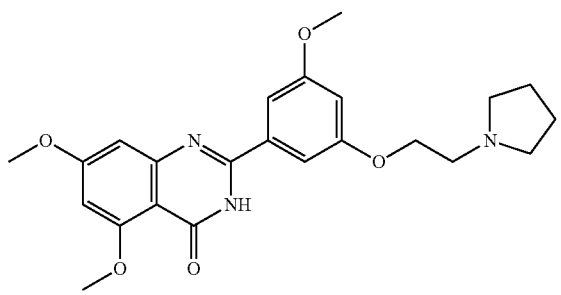 [SMILES: COc1cc(OCCN2CCCC2)cc(-c2nc3cc(OC)cc(OC)c3c(=O)[nH]2)c1]

To a 1.0-L three-neck flask was added sodium ethanethiolate (80%, 28.5 g, 271.0 mmol) and anhydrous DMF (225 mL). The mixture was heated to 145° C. for 1.5 hours. Then, 3,5-dimethoxy-benzaldehyde (15.0 g, 90.0 mmol) in anhydrous DMF (350 mL) was added over a period of 8 minutes. The reaction was kept at 145° C. for another 1 hour, then cooled to room temperature. Saturated sodium chloride solution (2.5 L) and formaline (37%, 240 mL) together with acetic acid (500 mL) was added. The resulting solution was thoroughly extracted with ethyl acetate, the organic phase was dried with sodium sulfate, and the solvent was removed under vacuum. The crude compound was purified by column chromatography (silica gel 230-400 mesh; eluting with dichloromethane and ethyl acetate 7:1) to give 3-hydroxy-5-methoxy-benzaldehyde as a white solid. Yield: 12.0 g (88%).

3-Hydroxy-5-methoxy-benzaldehyde (12.0 g, 78.9 mmol) and [1,3]dioxolan-2-one (13.9 g, 157.0 mmol) in anhydrous DMF (50 mL) was added potassium carbonate (21.6 g, 157.0 mmol). The mixture was then heated to 110° C. for 16 hours. The reaction mixture was cooled to room temperature. Solid potassium carbonate was filtered and washed with ethyl acetate. The organic phase was collected and solvent was removed. The residue was purified by column chromatography (silica gel 230-400 mesh; eluting with dichloromethane and ethyl acetate 7:1), to give 3-(2-hydroxy-ethoxy)-5-methoxy-benzaldehyde as a brown liquid. Yield: 10.0 g (65%).

To a solution of 2-amino-4,6-dimethoxy-benzamide (7.50 g, 38.2 mmol) and 3-(2-hydroxy-ethoxy)-5-methoxy-benzaldehyde (7.50 g, 38.2 mmol) in N,N-dimethylacetamide (30 mL) was added $NaHSO_3$ (58.5 wt %, 4.37 g, 42.0 mmol) and p-TSA (0.72 g, 3.8 mmol). The reaction mixture was heated to 115-120° C. for 16 hours, and then cooled to room temperature. N,N-dimethylacetamide was removed under reduced pressure, the residue was diluted with water (50 mL), and the solid was filtered, collected, and mixed with ether (50 mL), then filtered and dried under vacuum, to give 2-[3-(2-hydroxy-ethoxy)-5-methoxy-phenyl]-5,7-dimethoxy-3H-quinazolin-4-one as a white solid. Yield: 10 g (70%).

To a solution of 2-[3-(2-hydroxy-ethoxy)-5-methoxy-phenyl]-5,7-dimethoxy-3H-quinazolin-4-one (8.00 g, 21.5 mmol) in anhydrous DMF (30 mL) was added carbon tetrabromide (9.80 g, 29.5 mmol) and triphenylphosphine (7.78 g, 29.5 mmol). The reaction mixture was stirred at 40° C. for 7 hours. DMF was removed under vacuum and dichloromethane (200 mL) was added. The organic phase was washed with water (150 mL), brine (100 mL), and dried over anhydrous sodium sulfate. Solvent was removed and the residue was washed three times with a mixture of ether and dichloromethane (20:1, 200 mL) to give 2-[3-(2-bromo-ethoxy)-5-methoxy-phenyl]-5,7-dimethoxy-3H-quinazolin-4-one (5) as a white solid. Yield: 8.9 g (95%).

To a solution of 2-[3-(2-bromo-ethoxy)-5-methoxy-phenyl]-5,7-dimethoxy-3H-quinazolin-4-one (7.10 g, 16.0 mmol) in THF (20 mL) was added pyrrolidine (11.38 g, 160.0 mmol) and the reaction mixture was stirred at room temperature for 15 hours. THF was removed under reduced pressure, the residue was purified by column chromatography (silica gel 230-400 mesh; eluting with 5% 2.0 M ammonia in methanol solution in dichloromethane) to give the title compound as a white solid. Yield: 3.2 g (47%). MP 159-160° C. $^1$H NMR (400 MHz, $CDCl_3$): δ 10.66 (s, 1H), 7.25 (m, 2H), 6.84 (d, J=2.0 Hz, 1H), 6.67 (t, J=2.4 Hz, 1H), 6.45 (d, J=2.0 Hz, 1H), 4.21 (t, J=6.0 Hz, 2H), 3.95 (s, 3H), 3.93 (s, 3H), 3.89 (s, 3H), 2.93 (t, J=6.0 Hz, 2H), 2.64 (m, 4H), 1.80 (m, 4H). MS ($ES^+$) m/z: 426.20 (M+1).

Example 124

Preparation of N-(2-(3-(5,7-dimethoxy-4-oxo-3,4-dihydroquinazolin-2-yl)-5-methoxyphenoxy)ethyl)acetamide

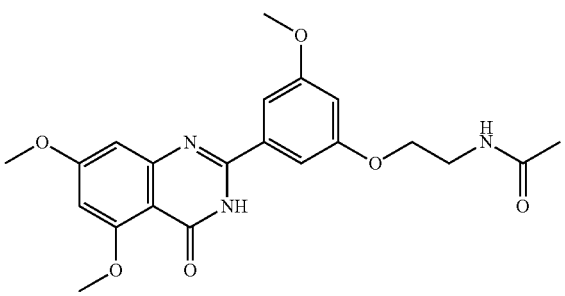 [SMILES: COc1cc(OCCNC(C)=O)cc(-c2nc3cc(OC)cc(OC)c3c(=O)[nH]2)c1]

To a 1.0-L three-neck flask was added sodium ethanethiolate (80%, 28.5 g, 271.0 mmol) and anhydrous DMF (225 mL). The mixture was heated to 145° C. for 1.5 hours; then, a solution of 3,5-dimethoxy-benzaldehyde (15.0 g, 90.0 mmol) in anhydrous DMF (350 mL) was added over a period of 8 minutes. The reaction was kept at 145° C. for 1 hour, then cooled to room temperature. Saturated sodium chloride solution (2.5 L) and formaline (37%, 240 mL), together with acetic acid (500 mL), was added. The resulting solution was thoroughly extracted with ethyl acetate, and the organic phase was dried over anhydrous sodium sulfate. Solvent was removed under vacuum, and the crude compound was purified by column chromatography (silica gel 230-400 mesh; eluting with 7:1 dichloromethane and ethyl acetate) to give 3-hydroxy-5-methoxy-benzaldehyde as a white solid. Yield: 12.0 g (88%).

To a solution of 3-hydroxy-5-methoxy-benzaldehyde (12.0 g, 78.9 mmol) in anhydrous DMF (50 mL) was added [1,3]dioxolan-2-one (13.9 g, 157.0 mmol) and potassium carbonate (21.6 g, 157.0 mmol). The reaction mixture was then heated to 110° C. for 16 hours, then cooled to room temperature. Solid potassium carbonate was filtered and washed with ethyl acetate. The organic phase was collected and solvent was removed. The residue was purified by column chromatography (silica gel 230-400 mesh; eluting with 7:1 dichloromethane and ethyl acetate) to give 3-(2-hydroxy-ethoxy)-5-methoxy-benzaldehyde as a brown liquid. Yield: 10.0 g (65%).

To a solution of 2-amino-4,6-dimethoxy-benzamide (7.50 g, 38.2 mmol) and 3-(2-hydroxy-ethoxy)-5-methoxy-benzaldehyde (7.50 g, 38.2 mmol) in N,N-dimethylacetamide (30 mL) were added NaHSO$_3$ (58.5 wt %, 4.37 g, 42.0 mmol) and p-TSA (0.72 g, 3.8 mmol). The reaction mixture was heated to 115-120° C. for 16 hours, and then cooled to room temperature. N,N-dimethylacetamide was removed under reduced pressure, the residue was diluted with water (50 mL), and the solid was filtered, collected and mixed with ether (50 mL), filtered, and dried under vacuum, to give 2-[3-(2-hydroxy-ethoxy)-5-methoxy-phenyl]-5,7-dimethoxy-3H-quinazolin-4-one as a white solid. Yield: 10 g (70%).

To a solution of 2-[3-(2-hydroxy-ethoxy)-5-methoxy-phenyl]-5,7-dimethoxy-3H-quinazolin-4-one (8.00 g, 21.5 mmol) in anhydrous DMF (30 mL) was added carbon tetrabromide (9.80 g, 29.5 mmol) and triphenylphosphine (7.78 g, 29.5 mmol). The reaction mixture was stirred at 40° C. for 7 hours. DMF was removed under vacuum and dichloromethane (200 mL) was added. The organic phase was washed with water (150 mL), then brine (100 mL), and dried over anhydrous sodium sulfate. Solvent was removed and the residue was washed three times with a mixture of ether and dichloromethane (20:1, 200 mL) to give 2-[3-(2-bromo-ethoxy)-5-methoxy-phenyl]-5,7-dimethoxy-3H-quinazolin-4-one as a white solid. Yield: 8.9 g (95%).

To a solution of 2-[3-(2-bromo-ethoxy)-5-methoxy-phenyl]-5,7-dimethoxy-3H-quinazolin-4-one (0.37 g, 0.84 mmol) in DMF (10 mL) was added sodium azide (0.14 g, 2.11 mmol) and the reaction mixture was stirred at 70° C. for 7 hours. DMF was removed under reduced pressure and dichloromethane (100 mL) was added. The organic phase was washed with water (50 mL), then brine (50 mL), and dried over anhydrous sodium sulfate. Solvent was removed and the residue was purified by column chromatography (silica gel 230-400 mesh; 30-40% ethyl acetate in dichloromethane as eluent) to give a white solid. Yield: 0.23 g (69%).

2-[3-(2-Azido-ethoxy)-5-methoxy-phenyl]-5,7-dimethoxy-3H-quinazolin-4-one (90 mg, 0.22 mmol) was taken in thioacetic acid (2 mL) and the reaction mixture was stirred at room temperature for 2 hours. Thioacetic acid was removed under reduced pressure, and the residue was purified by column chromatography (silica gel 230-400 mesh; 3.5% methanol in dichloromethane as eluent) to give the title compound as a white solid. Yield: 45 mg (49%). MP 264-265° C. $^1$H NMR (400 MHz, DMSO-d$_6$): δ 12.05 (s, 1H), 8.13 (t, J=5.86 Hz, 1H), 7.39 (d, J=1.56 Hz, 2H), 6.76 (d, J=2.34 Hz, 1H), 6.69 (t, J=2.15 Hz, 1H), 6.55 (d, J=2.34 Hz, 1H), 4.07 (t, J=5.67 Hz, 2H), 3.90 (s, 3H), 3.85 (s, 3H), 3.83 (s, 3H), 3.43 (q, J=5.47 Hz, 2H), 1.84 (s, 3H). MS (ES$^+$) m/z: 414.11 (M+1).

Example 125

Preparation of 2-(3,5-Dimethoxyphenyl)-6-(pyridin-4-ylamino)quinazolin-4(3H)-one

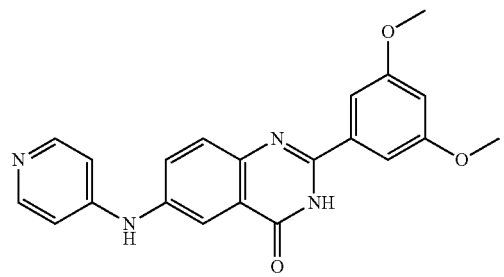 [SMILES: COc1cc(OC)cc(-c2nc3ccc(Nc4ccncc4)cc3c(=O)[nH]2)c1]

To a mixture of 2-amino-5-nitro-benzoic acid (12.9 g, 81.9 mmol), 1-ethyl-3-(3'-dimethylaminopropyl)carbodiimide hydrochloride (EDCl) (17.3 g, 90.1 mmol), 1-hydroxybenzotriazole hydrate (HOBt) (12.2 g, 90.1 mmol) in THF (200 mL) was added 4-methylmorpholine (NMM) (9.91 mL, 90.1 mmol). After 10 minutes, ammonium hydroxide (50% v/v, 50 mL) was added. The mixture was stirred at room temperature under nitrogen for 17 hours. Solvent was removed under reduced pressure. Water was added. The solid separated was filtered, washed with aqueous NaHCO$_3$ solution, and with water, and dried in air, to afford 2-amino-5-nitro-benzamide as a yellow solid. Yield: 9.88 g (66%).

A mixture of 2-amino-5-nitro-benzamide (1.81 g, 10.0 mmol), 3,5-dimethoxy-benzaldehyde (1.83 g, 11.0 mmol), sodium hydrogen sulfite (58.5 wt %, 3.94 g, 22.0 mmol), and p-toluenesulfonic acid monohydrate (0.38 g, 2.00 mmol) in N,N-dimethylacetamide (20 mL) was stirred at 150° C. for 17 hours under nitrogen and then cooled to room temperature. Saturated aqueous NaHCO$_3$ (approximately 1 mL) was added. The mixture was stirred at room temperature for 2 hours, then concentrated to dryness. Water (80 mL) was added, stirred for 0.5 hours, and filtered. The solid was air dried. The crude compound was purified by column chromatography (silica gel 230-400 mesh; ethyl acetate as eluent) to give 6-amino-2-(3,5-dimethoxy-phenyl)-3H-quinazolin-4-one as a yellow solid. Yield: 1.50 g (50%).

6-Amino-2-(3,5-dimethoxy-phenyl)-3H-quinazolin-4-one (297 mg, 1.00 mmol), 4-bromopyridine hydrochloride (194 mg, 1.00 mmol), tris(dibenzylideneacetone)dipalladium(0) (18 mg, 0.02 mmol), 1,1'-bis(diphenylphosphino)ferrocene (17 mg, 0.03 mmol), sodium tert-butoxide (230 mg, 2.40 mmol) and pyridine (3 mL) were heated at 140° C. in microwave oven (150 W) for 1 hour. The mixture was concentrated under vacuum to dryness. The residue was purified by column chromatography (silica gel 230-400 mesh; 5% methanol in dichloromethane and then 10% 2 N NH$_3$ in methanol and dichloromethane as eluent) to give the title compound as a brown/beige solid. Yield: 176 mg (47%). MP 289-290° C. $^1$H NMR (400 MHz, DMSO-d$_6$): δ 9.24 (s, 1H), 8.29 (d, J=5.6 Hz, 2H), 7.90 (s, 1H), 7.75 (d, J=8.8 Hz, 1H), 7.65 (d, J=8.4 Hz, 1H), 7.38 (s, 2H), 7.03 (d, J=5.2 Hz, 2H), 6.69 (s, 1H), 3.85 (s, 6H). MS (ES+) m/z: 375.13 (M+1).

Example 126

Preparation of 5,7-Dimethoxy-2-(3-methoxyphenyl)quinazolin-4(3H)-one

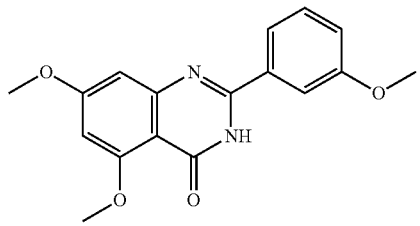

A mixture of 2-amino-4,6-dimethoxybenzamide (0.0600 g, 0.306 mmol), 3-methoxybenzaldehyde (0.306 mmol), NaHSO$_3$ (94%, 0.0474 g, 0.428 mmol), and p-TsOH.H$_2$O (0.0175 g, 0.0918 mmol) in DMA (3.06 mL) was heated at 140° C. for 20 hours. The mixture was diluted with EtOAc (300 mL), washed with water (3×75 mL), then brine (75 mL), dried over sodium sulfate, filtered, and concentrated under vacuum. The residue was purified on silica gel (40 g, CH$_2$Cl$_2$/MeOH) and the product was freeze-dried from MeCN/H$_2$O to provide the title compound (69%) as an off-white solid. $^1$H NMR (300 MHz, DMSO-d$_6$): δ 12.04 (s, 1H), 7.82-7.70 (m, 2H), 7.43 (t, J=7.98 Hz, 1H), 7.13 (dd, J=8.19, 2.46 Hz, 1H), 6.76 (d, J=2.19 Hz, 1H), 6.55 (d, J=2.19 Hz, 1H), 3.92-3.82 (m, 9H); MS (APCI) m/z 313 [C$_{17}$H$_{16}$N$_2$O$_4$+H]$^+$.

Example 127

Quantification of hIL-6 mRNA

In this example, hIL-6 mRNA in tissue culture cells was quantitated to measure the transcriptional inhibition of hIL-6 when treated with a compound of the invention.

A human leukemic monocyte lymphoma cell line (U937) was plated (3.2×10$^5$ cells per well) in a 96-well plate in 100 μL RPMI-1640, and differentiated for 3 days prior to the addition of the compound of interest. The cells were pre-treated for 1 h with the test compound prior to stimulation with lipolysaccharide from *Escherichia coli*. The cells were incubated at 37° C. for 3 h before the cells were harvested. At time of harvest, the spent media was removed from the cells and the cells were rinsed in 200 μL PBS. Cell lysis solution (70 μL) was added the cells in each well and incubated for 5-10 min at room temperature, to allow for complete cell lysis and detachment. mRNA was then prepared using the "mRNA Catcher PLUS plate" (Invitrogen), according to the protocol supplied. After the last wash, as much wash buffer as possible was aspirated without allowing the wells to dry. Elution buffer (E3, 70 μL) was then added to each well. mRNA was then eluted by incubating the mRNA Catcher PLUS plate with Elution Buffer for 5 min at 68° C. and then immediately placing the plate on ice.

The eluted mRNA isolated was then used in a one-step quantitative real-time PCR reaction, using components of the Ultra Sense Kit together with Applied Biosystems primer-probe mixes. Real-time PCR data was analyzed, normalizing the Ct values for hIL-6 to an internal control, prior to determining the fold induction of each unknown sample, relative to the control.

In Table 2, an active compound is one that causes a ≥20% inhibition in IL-6 mRNA at a concentration less than or equal to 10 μM.

TABLE 2

| Example | Inhibition of IL-6 expression |
|---|---|
| 5,7-dimethoxy-2-(4-morpholinophenyl)quinazolin-4(3H)-one | Active |
| 2-(4-((3R,5S)-4-acetyl-3,5-dimethylpiperazin-1-yl)phenyl)-5,7-dimethoxypyrido[2,3-d]pyrimidin-4(3H)-one | Active |
| 2-(4-(4-hydroxypiperidin-1-yl)phenyl)-5,7-dimethoxypyrido[2,3-d]pyrimidin-4(3H)-one | Active |
| 2-(4-((3R,5S)-4-acetyl-3,5-dimethylpiperazin-1-yl)phenyl)-5-methoxy-7-(2-methoxyethoxy)quinazolin-4(3H)-one | Active |
| 2-(4-(4-isopropylpiperazin-1-yl)phenyl)-5,7-dimethoxyquinazolin-4(3H)-one | Active |
| 2-(4-(4-acetylpiperazin-1-yl)phenyl)-5,7-dimethoxyquinazolin-4(3H)-one | Active |
| 5,7-dimethoxy-2-(4-(piperazin-1-yl)phenyl)quinazolin-4(3H)-one | Active |
| N-(1-(4-(5,7-dimethoxy-4-oxo-3,4-dihydroquinazolin-2-yl)phenyl)piperidin-4-yl)acetamide | Active |
| N-(1-(4-(5,7-dimethoxy-4-oxo-3,4-dihydroquinazolin-2-yl)phenyl)piperidin-4-yl)methanesulfonamide | Active |
| 3-(1-(4-(5,7-dimethoxy-4-oxo-3,4-dihydroquinazolin-2-yl)phenyl)piperidin-4-yl)-1,1-dimethylurea | Active |
| 2-(4-(4-hexanoylpiperazin-1-yl)phenyl)-5,7-dimethoxyquinazolin-4(3H)-one | Active |
| 2-(4-(4-isobutyrylpiperazin-1-yl)phenyl)-5,7-dimethoxyquinazolin-4(3H)-one | Active |
| 2-(4-(4-benzoylpiperazin-1-yl)phenyl)-5,7-dimethoxyquinazolin-4(3H)-one | Active |
| 2-(4-(4-(4-fluorobenzoyl)piperazin-1-yl)phenyl)-5,7-dimethoxyquinazolin-4(3H)-one | Active |
| N-(1-(4-(5,7-dimethoxy-4-oxo-3,4-dihydroquinazolin-2-yl)phenyl)piperidin-4-yl)benzamide | Active |
| 5,7-dimethoxy-2-(4-(4-picolinoylpiperazin-1-yl)phenyl)quinazolin-4(3H)-one | Active |
| 5,7-dimethoxy-2-(4-(4-nicotinoylpiperazin-1-yl)phenyl)quinazolin-4(3H)-one | Active |
| 2-(4-(4-isonicotinoylpiperazin-1-yl)phenyl)-5,7-dimethoxyquinazolin-4(3H)-one | Active |
| 5,7-dimethoxy-2-(4-(4-(thiophene-2-carbonyl)piperazin-1-yl)phenyl)quinazolin-4(3H)-one | Active |
| 2-(4-(4-(5-chloro-1-methyl-1H-pyrazole-4-carbonyl)piperazin-1-yl)phenyl)-5,7-dimethoxyquinazolin-4(3H)-one | Active |

TABLE 2-continued

| Example | Inhibition of IL-6 expression |
|---|---|
| 5,7-dimethoxy-2-(4-(4-(3,3,3-trifluoropropanoyl)piperazin-1-yl)phenyl)quinazolin-4(3H)-one | Active |
| 2-(4-(4-(2,5-dichlorothiophene-3-carbonyl)piperazin-1-yl)phenyl)-5,7-dimethoxyquinazolin-4(3H)-one | Active |
| 2-(4-(4-(cyclopropanecarbonyl)piperazin-1-yl)phenyl)-5,7-dimethoxyquinazolin-4(3H)-one | Active |
| 2-(4-(4-(4-fluorobenzyl)piperazin-1-yl)phenyl)-5,7-dimethoxyquinazolin-4(3H)-one | Active |
| 2-(4-(4-benzylpiperazin-1-yl)phenyl)-5,7-dimethoxyquinazolin-4(3H)-one | Active |
| 2-(4-(4-(2,2,2-trifluoroethyl)piperazin-1-yl)phenyl)quinazolin-4(3H)-one | Active |
| 2-(4-(4-butylpiperazin-1-yl)phenyl)-5,7-dimethoxyquinazolin-4(3H)-one | Active |
| 2-(4-(4-acetyl-1,4-diazepan-1-yl)phenyl)-5,7-dimethoxyquinazolin-4(3H)-one | Active |
| 2-(4-(1,4-diazepan-1-yl)phenyl)-5,7-dimethoxyquinazolin-4(3H)-one | Active |
| 5,7-dimethoxy-2-(4-(4-methyl-1,4-diazepan-1-yl)phenyl)quinazolin-4(3H)-one | Active |
| N-(1-(4-(5,7-dimethoxy-4-oxo-3,4-dihydroquinazolin-2-yl)phenyl)piperidin-4-yl)-N-ethylacetamide | Active |
| 2-(4-((3R,5S)-4-acetyl-3,5-dimethylpiperazin-1-yl)phenyl)-5,7-dimethoxyquinazolin-4(3H)-one | Active |
| 2-(4-((3R,5S)-3,5-dimethylpiperazin-1-yl)phenyl)-5,7-dimethoxyquinazolin-4(3H)-one | Active |
| 2-(4-(4-acetyl-3-methylpiperazin-1-yl)phenyl)-5,7-dimethoxyquinazolin-4(3H)-one | Active |
| N-(1-(4-(5,7-dimethoxy-4-oxo-3,4-dihydroquinazolin-2-yl)phenyl)pyrrolidin-3-yl)acetamide | Active |
| 2-(4-(4-isopropylpiperazin-1-yl)phenyl)-8-methoxyquinazolin-4(3H)-one | Active |
| 2-(4-(4-(2-hydroxyethyl)piperazin-1-yl)phenyl)-5,7-dimethoxyquinazolin-4(3H)-one | Active |
| N-(1-(4-(5,7-dimethoxy-4-oxo-3,4-dihydroquinazolin-2-yl)phenyl)piperidin-4-yl)-N-isopropylacetamide | Active |
| 5-chloro-2-(4-(4-isopropylpiperazin-1-yl)phenyl)quinazolin-4(3H)-one | Active |
| 2-(4-((3R,5S)-4-isopropyl-3,5-dimethylpiperazin-1-yl)phenyl)-5,7-dimethoxyquinazolin-4(3H)-one | Active |
| 5,7-dimethoxy-2-(4-(piperidin-4-yl)phenyl)quinazolin-4(3H)-one | Active |
| 5,7-dimethoxy-2-(4-(3-(methylamino)pyrrolidin-1-yl)phenyl)quinazolin-4(3H)-one | Active |
| 2-(4-((4-isopropylpiperazin-1-yl)methyl)phenyl)-5,7-dimethoxyquinazolin-4(3H)-one | Active |
| 2-(4-(4-(isopropylamino)piperidin-1-yl)phenyl)-5,7-dimethoxyquinazolin-4(3H)-one | Active |
| 2-(4-(1-acetylpiperidin-4-yl)phenyl)-5,7-dimethoxyquinazolin-4(3H)-one | Active |
| 5,7-dimethoxy-2-(4-(3-methylpiperazin-1-yl)phenyl)quinazolin-4(3H)-one | Active |
| N-benzyl-N-(1-(5-(5,7-dimethoxy-4-oxo-3,4-dihydroquinazolin-2-yl)pyridin-2-yl)piperidin-4-yl)acetamide | Active |
| 2-(6-(4-(benzylamino)piperidin-1-yl)pyridin-3-yl)-5,7-dimethoxyquinazolin-4(3H)-one | Active |
| 4-(4-(5,7-dimethoxy-4-oxo-3,4-dihydroquinazolin-2-yl)phenyl)piperazine-1-carbaldehyde | Active |
| 5,7-dimethoxy-2-(4-(4-oxopiperidin-1-yl)phenyl)pyrido[2,3-d]pyrimidin-4(3H)-one | Active |
| tert-butyl 4-(4-(5,7-dimethoxy-4-oxo-3,4-dihydroquinazolin-2-yl)phenyl)piperidine-1-carboxylate | Active |
| 2-(4-(dimethylamino)naphthalen-1-yl)-6,7-dimethoxyquinazolin-4(3H)-one | Active |
| 2-(4-(bis(2-hydroxyethyl)amino)phenyl)-5,7-dimethoxypyrido[2,3-d]pyrimidin-4(3H)-one | Active |
| 2-(2-(hydroxymethyl)-1H-indol-5-yl)-5,7-dimethoxyquinazolin-4(3H)-one | Active |
| 2-(2-(2-hydroxyethyl)-1H-indol-5-yl)-5,7-dimethoxyquinazolin-4(3H)-one | Active |
| 5,7-dimethoxy-2-(2-(pyrrolidin-1-ylmethyl)-1H-indol-5-yl)quinazolin-4(3H)-one | Active |
| 2-(3-(hydroxymethyl)-1H-indazol-5-yl)-5,7-dimethoxyquinazolin-4(3H)-one | Active |
| 5,7-dimethoxy-2-(2-(2-(pyrrolidin-1-yl)ethyl)-1H-indol-5-yl)quinazolin-4(3H)-one | Active |
| 2-(2-((dimethylamino)methyl)-1H-indol-5-yl)-5,7-dimethoxyquinazolin-4(3H)-one | Active |
| N-(4-(5,7-dimethoxy-4-oxo-3,4-dihydroquinazolin-2-yl)phenyl)methanesulfonamide | Active |
| 5,7-dimethoxy-2-(4-(pyridin-4-ylamino)phenyl)quinazolin-4(3H)-one | Active |
| 5,7-dimethoxy-2-(4-(p-tolylamino)phenyl)quinazolin-4(3H)-one | Active |
| 5,7-dimethoxy-2-(4-(pyridin-3-ylamino)phenyl)quinazolin-4(3H)-one | Active |
| 3-(3,5-dimethyl-4-(2-morpholinoethoxy)phenyl)-6,8-dimethoxyisoquinolin-1(2H)-one | Active |
| 2-(3,5-dimethyl-4-(2-morpholinoethoxy)phenyl)-5,7-dimethoxyquinazolin-4(3H)-one | Active |
| 3-(3,5-dimethyl-4-(2-(4-methylpiperazin-1-yl)ethoxy)phenyl)-6,8-dimethoxyisoquinolin-1(2H)-one | Active |

TABLE 2-continued

| Example | Inhibition of IL-6 expression |
|---|---|
| 2-(3,5-dimethyl-4-(2-morpholinoethoxy)phenyl)quinazolin-4(3H)-one | Active |
| 7-(3,5-dimethyl-4-(2-morpholinoethoxy)phenyl)-2,4-dimethoxy-1,6-naphthyridin-5(6H)-one | Active |
| 5,7-dimethoxy-2-(4-((4-methylpiperazin-1-yl)methyl)phenyl)quinazolin-4(3H)-one | Active |
| 5,7-dimethoxy-2-(4-(morpholinomethyl)phenyl)quinazolin-4(3H)-one | Active |
| 2-(4-((4-ethylpiperazin-1-yl)methyl)phenyl)-5,7-dimethoxyquinazolin-4(3H)-one | Active |
| 2-(3,5-dimethyl-4-(2-(pyrrolidin-1-yl)ethoxy)phenyl)-5,7-dimethoxyquinazolin-4(3H)-one | Active |
| 4-(4-(5,7-dimethoxy-4-oxo-3,4-dihydroquinazolin-2-yl)phenoxy)-N,N-dimethylpiperidine-1-carboxamide | Active |
| 2-(4-(1-acetylpiperidin-4-yloxy)phenyl)-5,7-dimethoxyquinazolin-4(3H)-one | Active |
| 2-(4-(2-(isoindolin-2-yl)ethoxy)-3,5-dimethylphenyl)-5,7-dimethoxyquinazolin-4(3H)-one | Active |
| 2-(3,5-dimethyl-4-(2-(pyrrolidin-1-yl)ethoxy)phenyl)-5-methoxyquinazolin-4(3H)-one | Active |
| 5,7-dichloro-2-(3,5-dimethyl-4-(2-(pyrrolidin-1-yl)ethoxy)phenyl)quinazolin-4(3H)-one | Active |
| 2-(3,5-dimethyl-4-(3-(pyrrolidin-1-yl)propoxy)phenyl)-5,7-dimethoxy-3-(3-(pyrrolidin-1-yl)propyl)quinazolin-4(3H)-one | Active |
| 2-(4-(2-(4-acetylpiperazin-1-yl)ethoxy)-3,5-dimethylphenyl)-5,7-dimethoxyquinazolin-4(3H)-one | Active |
| 2-(4-(2-(1H-imidazol-1-yl)ethoxy)-3,5-dimethylphenyl)-5,7-dimethoxyquinazolin-4(3H)-one | Active |
| 2-(3,5-dimethyl-4-(2-(pyrrolidin-1-yl)ethoxy)phenyl)-7-methoxyquinazolin-4(3H)-one | Active |
| 2-(3,5-dimethyl-4-(2-(4-methylpiperazin-1-yl)ethoxy)phenyl)-5,7-dimethoxyquinazolin-4(3H)-one | Active |
| 2-(3,5-dimethyl-4-(2-(piperidin-1-yl)ethoxy)phenyl)-5,7-dimethoxyquinazolin-4(3H)-one | Active |
| 5,7-dimethoxy-2-(3-methyl-4-(2-(pyrrolidin-1-yl)ethoxy)phenyl)quinazolin-4(3H)-one | Active |
| 3-(2-(4-(5,7-dimethoxy-4-oxo-3,4-dihydroquinazolin-2-yl)-2,6-dimethylphenoxy)ethyl)-1-isopropylimidazolidine-2,4-dione | Active |
| 2-(3,5-dimethyl-4-(3-(pyrrolidin-1-yl)propoxy)phenyl)-5,7-dimethoxyquinazolin-4(3H)-one | Active |
| 5,7-dimethoxy-2-(4-(2-(pyrrolidin-1-yl)ethoxy)phenyl)quinazolin-4(3H)-one | Active |
| 2-(3,5-dimethyl-4-(3-(pyrrolidin-1-yl)propyl)phenyl)-5,7-dimethoxyquinazolin-4(3H)-one | Active |
| 2-(3,5-dimethyl-4-(4-(pyrrolidin-1-yl)butoxy)phenyl)-5,7-dimethoxyquinazolin-4(3H)-one | Active |
| 2-(3,5-dimethyl-4-(2-(pyrrolidin-1-yl)ethoxy)phenyl)-8-methoxyquinazolin-4(3H)-one | Active |
| 3-(2-(4-(5,7-dimethoxy-4-oxo-3,4-dihydroquinazolin-2-yl)-2,6-dimethylphenoxy)ethyl)-5-phenylimidazolidine-2,4-dione | Active |
| 3-(4-(5,7-dimethoxy-4-oxo-3,4-dihydroquinazolin-2-yl)benzyl)imidazolidine-2,4-dione | Active |
| 2-(3,5-dimethyl-4-(2-(pyrrolidin-1-yl)ethoxy)phenyl)-6-methoxyquinazolin-4(3H)-one | Active |
| 2-(3,5-dimethyl-4-(2-(pyrrolidin-1-yl)ethoxy)phenyl)-5,7-dimethoxypyrido[2,3-d]pyrimidin-4(3H)-one | Active |
| 2-(3,5-dimethyl-4-(2-(pyrrolidin-1-yl)ethoxy)phenyl)-7-fluoro-5-(pyrrolidin-1-yl)quinazolin-4(3H)-one | Active |
| 5-chloro-2-(3,5-dimethyl-4-(2-(pyrrolidin-1-yl)ethoxy)phenyl)quinazolin-4(3H)-one | Active |
| 2-(4-(2-(azepan-1-yl)ethoxy)-3,5-dimethylphenyl)-5,7-dimethoxyquinazolin-4(3H)-one | Active |
| 2-(3,5-dimethyl-4-(2-(pyrrolidin-1-yl)ethoxy)phenyl)-5,7-difluoroquinazolin-4(3H)-one | Active |
| 2-(4-(2-(azetidin-1-yl)ethoxy)-3,5-dimethylphenyl)-5,7-dimethoxyquinazolin-4(3H)-one | Active |
| N-(1-(2-(4-(5,7-dimethoxy-4-oxo-3,4-dihydroquinazolin-2-yl)-2,6-dimethylphenoxy)ethyl)azetidin-3-yl)acetamide | Active |
| 2-(3,5-dimethyl-4-(2-(pyrrolidin-1-yl)ethoxy)phenyl)-5,7-diisopropoxyquinazolin-4(3H)-one | Active |
| 8-chloro-2-(3,5-dimethyl-4-(2-(pyrrolidin-1-yl)ethoxy)phenyl)quinazolin-4(3H)-one | Active |
| 2-(3,5-dimethyl-4-(2-(pyrrolidin-1-yl)ethoxy)phenyl)-5,7-dimethylquinazolin-4(3H)-one | Active |
| 2-(2-(4-(6,8-dimethoxy-1-oxo-1,2-dihydroisoquinolin-3-yl)-2,6-dimethylphenoxy)ethyl)isoindoline-1,3-dione | Active |
| 2-(3,5-dimethyl-4-(2-(pyrrolidin-1-yl)ethoxy)phenyl)-5,7-diisopropoxypyrido[2,3-d]pyrimidin-4(3H)-one | Active |
| 2-(2-(4-(5,7-dimethoxy-4-oxo-3,4-dihydroquinazolin-2-yl)-2,6-dimethylphenoxy)ethyl)isoindoline-1,3-dione | Active |

TABLE 2-continued

| Example | Inhibition of IL-6 expression |
|---|---|
| (S)-2-(3,5-dimethyl-4-((5-oxopyrrolidin-2-yl)methoxy)phenyl)-5,7-dimethoxyquinazolin-4(3H)-one | Active |
| 2-(4-((4-isopropylpiperazin-1-yl)methyl)phenyl)-5,7-dimethoxyquinazolin-4(3H)-one | Active |
| N-(1-(4-(5,7-dimethoxy-4-oxo-3,4-dihydroquinazolin-2-yl)benzyl)piperidin-4-yl)-N-isopropylacetamide | Active |
| 2-(4-((4-(isopropylamino)piperidin-1-yl)methyl)phenyl)-5,7-dimethoxyquinazolin-4(3H)-one | Active |
| 2-(4-((1H-tetrazol-5-yl)methyl)phenyl)-5,7-dimethoxyquinazolin-4(3H)-one | Active |
| 1-(2-(4-(5,7-dimethoxy-4-oxo-3,4-dihydroquinazolin-2-yl)-2,6-dimethylphenoxy)ethyl)pyrrolidine-2,5-dione | Active |
| 7-(2-(benzyloxy)ethoxy)-5-methoxy-2-(pyridin-4-yl)quinazolin-4(3H)-one | Active |
| 2-(2,6-dimethylpyridin-4-yl)-5,7-dimethoxyquinazolin-4(3H)-one | Active |
| 2-(2,6-dimethylpyridin-4-yl)-5-methoxy-7-(2-methoxyethoxy)quinazolin-4(3H)-one | Active |
| 2-(2,6-dimethylpyridin-4-yl)-5,7-bis(2-methoxyethoxy)quinazolin-4(3H)-one | Active |
| 2-(2,6-dimethylpyridin-4-yl)-7-methoxy-5-(2-(pyrrolidin-1-yl)ethoxy)quinazolin-4(3H)-one | Active |
| 2-(2,6-dimethylpyridin-4-yl)-6-((4-methylpiperazin-1-yl)methyl)quinazolin-4(3H)-one | Active |
| 2-(2,6-dimethylpyridin-4-yl)-5-methoxy-7-(2-phenoxyethoxy)quinazolin-4(3H)-one | Active |
| 2-(2,6-dimethylpyridin-4-yl)-7-methoxy-5-(2-phenoxyethoxy)quinazolin-4(3H)-one | Active |
| 2-(2,6-dimethylpyridin-4-yl)-7-methoxy-5-(2-methoxyethoxy)quinazolin-4(3H)-one | Active |
| 2-(2,6-dimethylpyridin-4-yl)-5-methoxy-7-(2-(pyrrolidin-1-yl)ethoxy)quinazolin-4(3H)-one | Active |
| 2-(2,6-dimethylpyridin-4-yl)-7-(2-isopropoxyethoxy)-5-methoxyquinazolin-4(3H)-one | Active |
| 2-(2,6-dimethylpyridin-4-yl)-5,7-bis(2-isopropoxyethoxy)quinazolin-4(3H)-one; | Active |
| 7-(2-(benzyloxy)ethoxy)-2-(2,6-dimethylpyridin-4-yl)-5-methoxyquinazolin-4(3H)-one | Active |
| 2-(2,6-dimethylpyridin-4-yl)-6-(2-morpholinoethyl)quinazolin-4(3H)-one | Active |
| 2-(2-methylpyridin-4-yl)-6-(morpholinomethyl)quinazolin-4(3H)-one | Active |
| 5-methoxy-7-(2-methoxyethoxy)-2-(2-methylpyridin-4-yl)quinazolin-4(3H)-one | Active |
| 2-(2,6-dimethylpyridin-4-yl)-6-(2-(pyrrolidin-1-yl)ethyl)quinazolin-4(3H)-one | Active |
| 2-(2,6-dimethylpyridin-4-yl)-7-(2-methoxyethoxy)-5-(2-(pyrrolidin-1-yl)ethoxy)quinazolin-4(3H)-one | Active |
| 2-(3,5-dimethoxyphenyl)-5,7-dimethoxyquinazolin-4(3H)-one | Active |
| 2-(3-(2-hydroxyethoxy)phenyl)-5,7-dimethoxyquinazolin-4(3H)-one | Active |
| 2-(3-(2-hydroxyethoxy)-5-methylphenyl)-5,7-dimethoxyquinazolin-4(3H)-one | Active |
| 5,7-dimethoxy-2-(3-methoxy-5-(2-(pyrrolidin-1-yl)ethoxy)phenyl)quinazolin-4(3H)-one | Active |
| N-(2-(3-(5,7-dimethoxy-4-oxo-3,4-dihydroquinazolin-2-yl)-5-methoxyphenoxy)ethyl)acetamide | Active |
| 2-(3,5-dimethoxyphenyl)-6-(pyridin-4-ylamino)quinazolin-4(3H)-one | Active |
| 5,7-dimethoxy-2-(3-methoxyphenyl)quinazolin-4(3H)-one | Active |

Example 128

Quantification of hVCAM mRNA

In this example, hIL-6 mRNA in tissue culture cells was quantitated to measure the transcriptional inhibition of hVCAM when treated with a compound of the invention.

Human umbilical vein endothelial cells (HUVECs) were plated in a 96-well plate ($4.0 \times 10^3$ cells/well) in 100 μL EGM media and incubated for 24 h prior to the addition of the compound of interest. The cells were pretreated for 1 h with the test compound prior to stimulation with tumor necrosis factor-α. The cells were incubated for an additional 24 h before the cells were harvested. At time of harvest, the spent media was removed from the HUVECs and rinsed in 200 μL PBS. Cell lysis solution (70 μL) was then added the cells in each well and incubated for ~5-10 min at room temperature, to allow for complete cell lysis and detachment. mRNA was then prepared using the "mRNA Catcher PLUS plate" (Invitrogen), according to the protocol supplied. After the last wash, as much wash buffer as possible was aspirated without allowing the wells to dry. Elution buffer (E3, 70 μL) was then added to each well. mRNA was then eluted by incubating the mRNA Catcher PLUS plate with elution buffer for 5 min at 68° C. and then immediately placing the plate on ice.

The eluted mRNA so isolated was then used in a one-step quantitative real-time PCR reaction, using components of the Ultra Sense Kit together with Applied Biosystems primer-probe mixes. Real-time PCR data was analyzed, normalizing the Ct values for hVCAM to an internal control, prior to determining the fold induction of each unknown sample, relative to the control.

In Table 3, an active compound is one that causes a ≥20% inhibition in VCAM-1 mRNA at a concentration less than or equal to 10 μM.

TABLE 3

| Example | Inhibition of VCAM-1 expression |
|---|---|
| 2-(4-(4-isopropylpiperazin-1-yl)phenyl)-5,7-dimethoxyquinazolin-4(3H)-one | Active |
| 2-(4-(4-acetylpiperazin-1-yl)phenyl)-5,7-dimethoxyquinazolin-4(3H)-one | Active |
| 5,7-dimethoxy-2-(4-(piperazin-1-yl)phenyl)quinazolin-4(3H)-one | Active |
| N-(1-(4-(5,7-dimethoxy-4-oxo-3,4-dihydroquinazolin-2-yl)phenyl)piperidin-4-yl)acetamide | Active |
| 2-(4-(4-hexanoylpiperazin-1-yl)phenyl)-5,7-dimethoxyquinazolin-4(3H)-one | Inactive |
| 2-(4-(4-isobutyrylpiperazin-1-yl)phenyl)-5,7-dimethoxyquinazolin-4(3H)-one | Active |
| 2-(4-(4-benzoylpiperazin-1-yl)phenyl)-5,7-dimethoxyquinazolin-4(3H)-one | Active |
| 2-(4-(4-(4-fluorobenzoyl)piperazin-1-yl)phenyl)-5,7-dimethoxyquinazolin-4(3H)-one | Active |
| N-(1-(4-(5,7-dimethoxy-4-oxo-3,4-dihydroquinazolin-2-yl)phenyl)piperidin-4-yl)benzamide | Active |
| 2-(4-(4-(5-chloro-1-methyl-1H-pyrazole-4-carbonyl)piperazin-1-yl)phenyl)-5,7-dimethoxyquinazolin-4(3H)-one | Active |
| 5,7-dimethoxy-2-(4-(4-(3,3,3-trifluoropropanoyl)piperazin-1-yl)phenyl)quinazolin-4(3H)-one | Active |
| 2-(4-(4-(2,5-dichlorothiophene-3-carbonyl)piperazin-1-yl)phenyl)-5,7-dimethoxyquinazolin-4(3H)-one | Active |
| 2-(4-(4-(cyclopropanecarbonyl)piperazin-1-yl)phenyl)-5,7-dimethoxyquinazolin-4(3H)-one | Active |
| 2-(4-(4-(2,2,2-trifluoroethyl)piperazin-1-yl)phenyl)quinazolin-4(3H)-one | Inactive |
| 2-(4-(4-butylpiperazin-1-yl)phenyl)-5,7-dimethoxyquinazolin-4(3H)-one | Active |
| 2-(4-(1,4-diazepan-1-yl)phenyl)-5,7-dimethoxyquinazolin-4(3H)-one | Active |
| 5,7-dimethoxy-2-(4-(4-methyl-1,4-diazepan-1-yl)phenyl)quinazolin-4(3H)-one | Active |
| N-(1-(4-(5,7-dimethoxy-4-oxo-3,4-dihydroquinazolin-2-yl)phenyl)piperidin-4-yl)-N-ethylacetamide | Active |
| 2-(4-((3R,5S)-4-acetyl-3,5-dimethylpiperazin-1-yl)phenyl)-5,7-dimethoxyquinazolin-4(3H)-one | Active |
| 2-(4-((3R,5S)-3,5-dimethylpiperazin-1-yl)phenyl)-5,7-dimethoxyquinazolin-4(3H)-one | Active |
| 2-(4-(4-acetyl-3-methylpiperazin-1-yl)phenyl)-5,7-dimethoxyquinazolin-4(3H)-one | Active |
| N-(1-(4-(5,7-dimethoxy-4-oxo-3,4-dihydroquinazolin-2-yl)phenyl)pyrrolidin-3-yl)acetamide | Active |
| 2-(4-(4-isopropylpiperazin-1-yl)phenyl)-8-methoxyquinazolin-4(3H)-one | Active |
| 2-(4-(4-(2-hydroxyethyl)piperazin-1-yl)phenyl)-5,7-dimethoxyquinazolin-4(3H)-one | Active |
| 2-(4-(dimethylamino)naphthalen-1-yl)-6,7-dimethoxyquinazolin-4(3H)-one | Active |
| 5,7-dimethoxy-2-(2-(pyrrolidin-1-ylmethyl)-1H-indol-5-yl)quinazolin-4(3H)-one | Active |
| 5,7-dimethoxy-2-(2-(2-(pyrrolidin-1-yl)ethyl)-1H-indol-5-yl)quinazolin-4(3H)-one | Active |
| 2-(2-((dimethylamino)methyl)-1H-indol-5-yl)-5,7-dimethoxyquinazolin-4(3H)-one | Active |
| 5,7-dimethoxy-2-(4-(pyridin-3-ylamino)phenyl)quinazolin-4(3H)-one | Active |
| 2-(3,5-dimethyl-4-(2-morpholinoethoxy)phenyl)-5,7-dimethoxyquinazolin-4(3H)-one | Active |
| 2-(3,5-dimethyl-4-(2-morpholinoethoxy)phenyl)quinazolin-4(3H)-one | Active |
| 7-(3,5-dimethyl-4-(2-morpholinoethoxy)phenyl)-2,4-dimethoxy-1,6-naphthyridin-5(6H)-one | Active |
| 2-(4-((4-ethylpiperazin-1-yl)methyl)phenyl)-5,7-dimethoxyquinazolin-4(3H)-one | Active |
| 2-(3,5-dimethyl-4-(2-(pyrrolidin-1-yl)ethoxy)phenyl)-5,7-dimethoxyquinazolin-4(3H)-one | Active |
| 2-(4-(2-(isoindolin-2-yl)ethoxy)-3,5-dimethylphenyl)-5,7-dimethoxyquinazolin-4(3H)-one | Active |
| 2-(3,5-dimethyl-4-(2-(pyrrolidin-1-yl)ethoxy)phenyl)-5-methoxyquinazolin-4(3H)-one | Active |
| 5,7-dichloro-2-(3,5-dimethyl-4-(2-(pyrrolidin-1-yl)ethoxy)phenyl)quinazolin-4(3H)-one | Active |
| 2-(4-(2-(4-acetylpiperazin-1-yl)ethoxy)-3,5-dimethylphenyl)-5,7-dimethoxyquinazolin-4(3H)-one | Active |
| 2-(4-(2-(1H-imidazol-1-yl)ethoxy)-3,5-dimethylphenyl)-5,7-dimethoxyquinazolin-4(3H)-one | Active |
| 2-(3,5-dimethyl-4-(2-(pyrrolidin-1-yl)ethoxy)phenyl)-7-methoxyquinazolin-4(3H)-one | Active |
| 2-(3,5-dimethyl-4-(2-(4-methylpiperazin-1-yl)ethoxy)phenyl)-5,7-dimethoxyquinazolin-4(3H)-one | Active |
| 2-(3,5-dimethyl-4-(2-(piperidin-1-yl)ethoxy)phenyl)-5,7-dimethoxyquinazolin-4(3H)-one | Active |
| 5,7-dimethoxy-2-(3-methyl-4-(2-(pyrrolidin-1-yl)ethoxy)phenyl)quinazolin-4(3H)-one | Active |

TABLE 3-continued

| Example | Inhibition of VCAM-1 expression |
|---|---|
| 3-(2-(4-(5,7-dimethoxy-4-oxo-3,4-dihydroquinazolin-2-yl)-2,6-dimethylphenoxy)ethyl)-1-isopropylimidazolidine-2,4-dione | Active |
| 2-(3,5-dimethyl-4-(3-(pyrrolidin-1-yl)propyl)phenyl)-5,7-dimethoxyquinazolin-4(3H)-one | Active |
| 2-(3,5-dimethyl-4-(4-(pyrrolidin-1-yl)butoxy)phenyl)-5,7-dimethoxyquinazolin-4(3H)-one | Active |
| 2-(3,5-dimethyl-4-(2-(pyrrolidin-1-yl)ethoxy)phenyl)-8-methoxyquinazolin-4(3H)-one | Active |
| 3-(2-(4-(5,7-dimethoxy-4-oxo-3,4-dihydroquinazolin-2-yl)-2,6-dimethylphenoxy)ethyl)-5-phenylimidazolidine-2,4-dione | Active |
| 3-(4-(5,7-dimethoxy-4-oxo-3,4-dihydroquinazolin-2-yl)benzyl)imidazolidine-2,4-dione | Active |
| 2-(3,5-dimethyl-4-(2-(pyrrolidin-1-yl)ethoxy)phenyl)-6-methoxyquinazolin-4(3H)-one | Active |
| 2-(3,5-dimethyl-4-(2-(pyrrolidin-1-yl)ethoxy)phenyl)-5,7-dimethoxypyrido[2,3-d]pyrimidin-4(3H)-one | Active |
| 2-(3,5-dimethyl-4-(2-(pyrrolidin-1-yl)ethoxy)phenyl)-7-fluoro-5-(pyrrolidin-1-yl)quinazolin-4(3H)-one | Active |
| 5-chloro-2-(3,5-dimethyl-4-(2-(pyrrolidin-1-yl)ethoxy)phenyl)quinazolin-4(3H)-one | Active |
| 2-(4-(2-(azepan-1-yl)ethoxy)-3,5-dimethylphenyl)-5,7-dimethoxyquinazolin-4(3H)-one | Active |
| 2-(3,5-dimethyl-4-(2-(pyrrolidin-1-yl)ethoxy)phenyl)-5,7-difluoroquinazolin-4(3H)-one | Active |
| 2-(2-(4-(5,7-dimethoxy-4-oxo-3,4-dihydroquinazolin-2-yl)-2,6-dimethylphenoxy)ethyl)isoindoline-1,3-dione | Active |
| (S)-2-(3,5-dimethyl-4-((5-oxopyrrolidin-2-yl)methoxy)phenyl)-5,7-dimethoxyquinazolin-4(3H)-one | Active |
| 1-(2-(4-(5,7-dimethoxy-4-oxo-3,4-dihydroquinazolin-2-yl)-2,6-dimethylphenoxy)ethyl)pyrrolidine-2,5-dione | Active |
| 7-(2-(benzyloxy)ethoxy)-5-methoxy-2-(pyridin-4-yl)quinazolin-4(3H)-one | Active |
| 2-(2,6-dimethylpyridin-4-yl)-5,7-bis(2-methoxyethoxy)quinazolin-4(3H)-one | Active |
| 2-(2,6-dimethylpyridin-4-yl)-7-methoxy-5-(2-(pyrrolidin-1-yl)ethoxy)quinazolin-4(3H)-one | Active |
| 2-(2,6-dimethylpyridin-4-yl)-5-methoxy-7-(2-phenoxyethoxy)quinazolin-4(3H)-one | Active |
| 2-(2,6-dimethylpyridin-4-yl)-7-methoxy-5-(2-phenoxyethoxy)quinazolin-4(3H)-one | Active |
| 2-(2,6-dimethylpyridin-4-yl)-7-methoxy-5-(2-methoxyethoxy)quinazolin-4(3H)-one | Inactive |
| 2-(2,6-dimethylpyridin-4-yl)-5-methoxy-7-(2-(pyrrolidin-1-yl)ethoxy)quinazolin-4(3H)-one | Inactive |
| 2-(2,6-dimethylpyridin-4-yl)-7-(2-isopropoxyethoxy)-5-methoxyquinazolin-4(3H)-one | Active |
| 2-(2,6-dimethylpyridin-4-yl)-5,7-bis(2-isopropoxyethoxy)quinazolin-4(3H)-one; | Active |
| 7-(2-(benzyloxy)ethoxy)-2-(2,6-dimethylpyridin-4-yl)-5-methoxyquinazolin-4(3H)-one | Active |
| 2-(2,6-dimethylpyridin-4-yl)-6-(2-morpholinoethyl)quinazolin-4(3H)-one | Inactive |
| 2-(2-methylpyridin-4-yl)-6-(morpholinomethyl)quinazolin-4(3H)-one | Inactive |
| 5-methoxy-7-(2-methoxyethoxy)-2-(2-methylpyridin-4-yl)quinazolin-4(3H)-one | Active |
| 2-(2,6-dimethylpyridin-4-yl)-6-(2-(pyrrolidin-1-yl)ethyl)quinazolin-4(3H)-one | Active |
| 2-(2,6-dimethylpyridin-4-yl)-7-(2-methoxyethoxy)-5-(2-(pyrrolidin-1-yl)ethoxy)quinazolin-4(3H)-one | Active |
| 2-(3,5-dimethoxyphenyl)-5,7-dimethoxyquinazolin-4(3H)-one | Active |
| 2-(3-(2-hydroxyethoxy)phenyl)-5,7-dimethoxyquinazolin-4(3H)-one | Active |
| 2-(3-(2-hydroxyethoxy)-5-methylphenyl)-5,7-dimethoxyquinazolin-4(3H)-one | Active |
| 5,7-dimethoxy-2-(3-methoxy-5-(2-(pyrrolidin-1-yl)ethoxy)phenyl)quinazolin-4(3H)-one | Active |
| N-(2-(3-(5,7-dimethoxy-4-oxo-3,4-dihydroquinazolin-2-yl)-5-methoxyphenoxy)ethyl)acetamide | Active |
| 2-(3,5-dimethoxyphenyl)-6-(pyridin-4-ylamino)quinazolin-4(3H)-one | Inactive |
| 5,7-dimethoxy-2-(3-methoxyphenyl)quinazolin-4(3H)-one | Active |

What is claimed is:

1. A method for treating non-cardiovascular inflammatory disorders mediated by VCAM-1 or IL-6, comprising administering a therapeutically effective amount of at least one compound of Formula III:

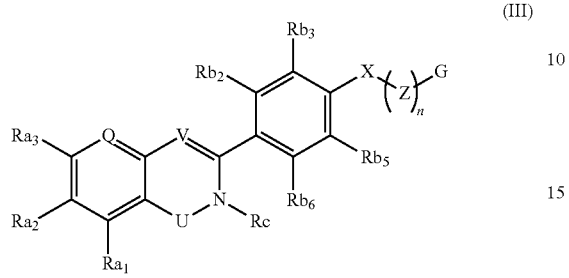

(III)

or a stereoisomer, tautomer, pharmaceutically acceptable salt, or hydrate thereof, wherein:

Q is $CR_{12}$;

V is nitrogen;

U is C=O;

X is selected from oxygen, sulfur, $SR_1$, nitrogen, and $CR_6R_7$;

Z is selected from unsubstituted $C_1$-$C_6$ alkyl and $C_1$-$C_6$ alkyl substituted with one or more groups selected from $C_1$-$C_3$ alkyl, $C_1$-$C_3$ alkoxy, cyclopropyl, hydroxyl, amino, and halogen;

n is 0, 1, 2, 3, 4, or 5;

G is selected from heterocycle, cycloalkyl, and aryl;

$R_1$ is selected from hydrogen and $C_1$-$C_6$ alkyl;

$R_6$, $R_7$, and $R_{12}$ are independently selected from hydrogen, $C_1$-$C_6$ alkyl, $C_3$-$C_6$ cycloalkyl, heterocycle, $C_1$-$C_6$ alkoxy, and halogen;

Rc is selected from hydrogen, $C_1$-$C_6$ alkyl, and $C_3$-$C_6$ cycloalkyl;

$Ra_1$, $Ra_2$, and $Ra_3$ are independently selected from hydrogen, $C_1$-$C_6$ alkyl, $C_1$-$C_6$ alkenyl, $C_1$-$C_6$ alkynyl, $C_1$-$C_6$ alkoxy, $C_3$-$C_6$ cycloalkyl, halogen, amino, amide, hydroxyl, and heterocycle, wherein $Ra_1$ and $Ra_2$ and/or $Ra_2$ and $Ra_3$ may be connected to form a cycloalkyl or a heterocycle;

$Rb_2$ and $Rb_6$ are independently selected from hydrogen, halogen, $C_1$-$C_6$ alkyl, $C_3$-$C_6$ cycloalkyl, $C_1$-$C_6$ alkenyl, hydroxyl, and amino; and $Rb_3$ and $Rb_5$ are independently selected from hydrogen, halogen, $C_1$-$C_6$ alkyl, $C_3$-$C_6$ cycloalkyl, $C_1$-$C_6$ alkoxy, hydroxyl, and amino, wherein $Rb_2$ and $Rb_3$ and/or $Rb_5$ and $Rb_6$ may be connected to form a cycloalkyl or a heterocycle;

provided that if $Ra_1$ and $Ra_3$ are OMe, and Q=CH, then

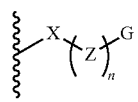

is not

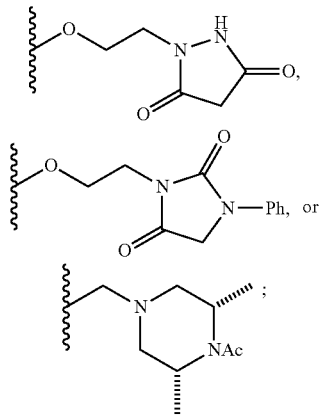

at least one of $Ra_1$, $Ra_2$, and $Ra_3$ is not hydrogen; and if $Ra_2$ or $Ra_3$ is chloro, then $Ra_1$ is not hydrogen.

2. The method according to claim 1, wherein

U is C=O;

Q is $CR_{12}$;

V is nitrogen;

Z is unsubstituted $C_1$-$C_6$ alkyl;

$R_{12}$ is selected from $C_1$-$C_6$ alkoxy and halogen;

Rc is selected from hydrogen and $C_1$-$C_6$ alkyl;

$Ra_2$ is selected from hydrogen and $C_1$-$C_6$ alkoxy;

$Ra_1$ and $Ra_3$ are independently selected from hydrogen, $C_1$-$C_6$ alkyl, $C_1$-$C_6$ alkoxy, halogen, and heterocycle;

$Rb_2$ and $Rb_6$ are both hydrogen;

$Rb_3$ and $Rb_5$ are independently selected from hydrogen and $C_1$-$C_6$ alkyl;

X is selected from oxygen and $CH_2$;

n is 0, 1, 2, 3, or 4; and

G is selected from heterocycle, cycloalkyl, and aryl.

3. The method according to claim 2, wherein

U is C=O;

Q is $CR_{12}$;

$R_{12}$ is selected from methoxy and chlorine;

Rc is selected from hydrogen and (pyrrolidin-1-yl)propyl;

$Ra_2$ is selected from hydrogen and methoxy;

$Ra_1$ and $Ra_3$ are independently selected from hydrogen, methyl, chlorine, fluorine, methoxy, isopropoxy, and pyrrolidin-1-yl;

$Rb_2$ and $Rb_6$ are both hydrogen;

$Rb_3$ and $Rb_5$ are independently selected from hydrogen and methyl; and

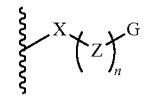

is selected from (N,N-dimethylpiperidine-1-carboxamide)-4-oxy, 1-acetylpiperidin-4-yloxy, 2-(isoindolin-2-yl)ethoxy, 2-(pyrrolidin-1-yl)ethoxy, 3-(pyrrolidin-1-yl)propoxy, 4-(pyrrolidin-1-yl)butoxy, (4-acetylpiperazin-1-yl)ethoxy, (1H-imidazol-1-yl) ethoxy, (4-methylpiperazin-1-yl)ethoxy, (piperidin-1-yl)ethoxy, (1-isopropylimidazolidine-2,4-dione)-3-ethoxy, (5-phenylimidazolidine-2,4-dione)-3-ethoxy, (imidazolidine-2,4-dione)-3-methyl, (2-azepan-1-yl) ethoxy, (2-azetidin-1-yl)ethoxy, N-(azetidin-3-yl)acetamide-1-ethoxy, (isoindoline-1,3-dione)-2-ethoxy, (5-oxopyrrolidin-2-yl)methoxy, (4-isopropylpiperazin-1-yl)methyl, N-isopropyl-N-(piperidin-4-methyl)acetamide-1-methyl, (4-(isopropylamino)piperidin-1-yl)methyl, (pyrrolidine-2,5-dione)ethoxy, and (1H-tetrazol-5-yl)methyl.

4. The method according to claim 1, comprising administering a therapeutically effective amount of at least one compound selected from:
2-(3,5-dimethyl-4-(2-morpholinoethoxy)phenyl)-5,7-dimethoxyquinazolin-4(3H)-one;
2-(3,5-dimethyl-4-(2-morpholinoethoxy)phenyl)quinazolin-4(3H)-one;
5,7-dimethoxy-2-(4-((4-methylpiperazin-1-yl)methyl) phenyl)quinazolin-4(3H)-one;
5,7-dimethoxy-2-(4-(morpholinomethyl)phenyl)quinazolin-4(3H)-one;
2-(4-((4-ethylpiperazin-1-yl)methyl)phenyl)-5,7-dimethoxyquinazolin-4(3H)-one;
2-(3,5-dimethyl-4-(2-(pyrrolidin-1-yl)ethoxy)phenyl)-5,7-dimethoxyquinazolin-4(3H)-one;
4-(4-(5,7-dimethoxy-4-oxo-3,4-dihydroquinazolin-2-yl) phenoxy)-N,N-dimethylpiperidine-1-carboxamide;
2-(4-(1-acetylpiperidin-4-yloxy)phenyl)-5,7-dimethoxyquinazolin-4(3H)-one;
2-(4-(2-(isoindolin-2-yl)ethoxy)-3,5-dimethylphenyl)-5,7-dimethoxyquinazolin-4(3H)-one;
2-(3,5-dimethyl-4-(2-(pyrrolidin-1-yl)ethoxy)phenyl)-5-methoxyquinazolin-4(3H)-one;
5,7-dichloro-2-(3,5-dimethyl-4-(2-(pyrrolidin-1-yl) ethoxy)phenyl)quinazolin-4(3H)-one;
2-(3,5-dimethyl-4-(3-(pyrrolidin-1-yl)propoxy)phenyl)-5,7-dimethoxy-3-(3-(pyrrolidin-1-yl)propyl)quinazolin-4(3H)-one;
2-(4-(2-(4-acetylpiperazin-1-yl)ethoxy)-3,5-dimethylphenyl)-5,7-dimethoxyquinazolin-4(3H)-one;
2-(4-(2-(1H-imidazol-1-yl)ethoxy)-3,5-dimethylphenyl)-5,7-dimethoxyquinazolin-4(3H)-one;
2-(3,5-dimethyl-4-(2-(pyrrolidin-1-yl)ethoxy)phenyl)-7-methoxyquinazolin-4(3H)-one;
2-(3,5-dimethyl-4-(2-(4-methylpiperazin-1-yl)ethoxy) phenyl)-5,7-dimethoxyquinazolin-4(3H)-one;
2-(3,5-dimethyl-4-(2-(piperidin-1-yl)ethoxy)phenyl)-5,7-dimethoxyquinazolin-4(3H)-one;
5,7-dimethoxy-2-(3-methyl-4-(2-(pyrrolidin-1-yl)ethoxy) phenyl)quinazolin-4(3H)-one;
3-(2-(4-(5,7-dimethoxy-4-oxo-3,4-dihydroquinazolin-2-yl)-2,6-dimethylphenoxy)ethyl)-1-isopropylimidazolidine-2,4-dione;
2-(3,5-dimethyl-4-(3-(pyrrolidin-1-yl)propoxy)phenyl)-5,7-dimethoxyquinazolin-4(3H)-one;
5,7-dimethoxy-2-(4-(2-(pyrrolidin-1-yl)ethoxy)phenyl) quinazolin-4(3H)-one;
2-(3,5-dimethyl-4-(3-(pyrrolidin-1-yl)propyl)phenyl)-5,7-dimethoxyquinazolin-4(3H)-one;
2-(3,5-dimethyl-4-(4-(pyrrolidin-1-yl)butoxy)phenyl)-5,7-dimethoxyquinazolin-4(3H)-one;
2-(3,5-dimethyl-4-(2-(pyrrolidin-1-yl)ethoxy)phenyl)-8-methoxyquinazolin-4(3H)-one;
3-(2-(4-(5,7-dimethoxy-4-oxo-3,4-dihydroquinazolin-2-yl)-2,6-dimethylphenoxy)ethyl)-5-phenylimidazolidine-2,4-dione;
3-(4-(5,7-dimethoxy-4-oxo-3,4-dihydroquinazolin-2-yl) benzyl)imidazolidine-2,4-dione;
2-(3,5-dimethyl-4-(2-(pyrrolidin-1-yl)ethoxy)phenyl)-6-methoxyquinazolin-4(3H)-one;
2-(3,5-dimethyl-4-(2-(pyrrolidin-1-yl)ethoxy)phenyl)-5,7-dimethoxypyrido[2,3-d]pyrimidin-4(3H)-one;
2-(3,5-dimethyl-4-(2-(pyrrolidin-1-yl)ethoxy)phenyl)-7-fluoro-5-(pyrrolidin-1-yl)quinazolin-4(3H)-one;
5-chloro-2-(3,5-dimethyl-4-(2-(pyrrolidin-1-yl)ethoxy) phenyl)quinazolin-4(3H)-one;
2-(4-(2-(azepan-1-yl)ethoxy)-3,5-dimethylphenyl)-5,7-dimethoxyquinazolin-4(3H)-one;
2-(3,5-dimethyl-4-(2-(pyrrolidin-1-yl)ethoxy)phenyl)-5,7-difluoroquinazolin-4(3H)-one;
2-(4-(2-(azetidin-1-yl)ethoxy)-3,5-dimethylphenyl)-5,7-dimethoxyquinazolin-4(3H)-one;
N-(1-(2-(4-(5,7-dimethoxy-4-oxo-3,4-dihydroquinazolin-2-yl)-2,6-dimethylphenoxy)ethyl)azetidin-3-yl)acetamide;
2-(3,5-dimethyl-4-(2-(pyrrolidin-1-yl)ethoxy)phenyl)-5,7-diisopropoxyquinazolin-4(3H)-one;
8-chloro-2-(3,5-dimethyl-4-(2-(pyrrolidin-1-yl)ethoxy) phenyl)quinazolin-4(3H)-one;
2-(3,5-dimethyl-4-(2-(pyrrolidin-1-yl)ethoxy)phenyl)-5,7-dimethylquinazolin-4(3H)-one;
2-(3,5-dimethyl-4-(2-(pyrrolidin-1-yl)ethoxy)phenyl)-5,7-diisopropoxypyrido[2,3-d]pyrimidin-4(3H)-one;
2-(2-(4-(5,7-dimethoxy-4-oxo-3,4-dihydroquinazolin-2-yl)-2,6-dimethylphenoxy)ethyl)isoindoline-1,3-dione;
(S)-2-(3,5-dimethyl-4-((5-oxopyrrolidin-2-yl)methoxy) phenyl)-5,7-dimethoxyquinazolin-4(3H)-one;
2-(4-((4-isopropylpiperazin-1-yl)methyl)phenyl)-5,7-dimethoxyquinazolin-4(3H)-one;
N-(1-(4-(5,7-dimethoxy-4-oxo-3,4-dihydroquinazolin-2-yl)benzyl)piperidin-4-yl)-N-isopropylacetamide;
2-(4-((4-(isopropylamino)piperidin-1-yl)methyl)phenyl)-5,7-dimethoxyquinazolin-4(3H)-one; and
2-(4-((1H-tetrazol-5-yl)methyl)phenyl)-5,7-dimethoxyquinazolin-4(3H)-one, or a pharmaceutically acceptable salt or hydrate thereof.

5. The method according to claim 1, wherein the therapeutically effective amount of the compound is administered with at least one pharmaceutically acceptable carrier in a pharmaceutically acceptable composition.

6. A compound of Formula III:

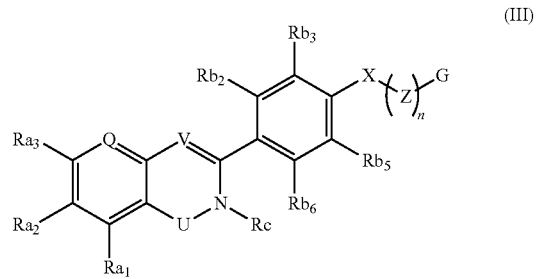

or a stereoisomer, tautomer, pharmaceutically acceptable salt, or hydrate thereof, wherein:

Q is CR$_{12}$;
V is nitrogen;
U is C=O;

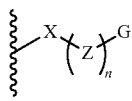

Is selected from (N,N-dimethylpiperidine-1-carboxamide)-4-oxy, 1-acetylpiperidin-4-yloxy, 2-(isoindolin-2-yl)ethoxy, (4-acetylpiperazin-1-yl)ethoxy, (1H-imidazol-1-yl)ethoxy, (piperidin-1-yl)ethoxy, (1-isopropylimidazolidine-2,4-dione)-3-ethoxy, (5-phenylimidazolidine-2,4-dione)-3-ethoxy, (imidazolidine-2,4-dione)-3-methyl, (2-azepan-1-yl)ethoxy, (2-azetidin-1-yl)ethoxy, N-(azetidin-3-yl)acetamide-1-ethoxy, (5-oxopyrrolidin-2-yl)methoxy, (4-isopropylpiperazin-1-yl)methyl, N-isopropyl-N-(piperidin-4-methyl)acetamide-1-methyl, (4-(isopropylamino)piperidin-1-yl)methyl, (pyrrolidine-2,5-dione)ethoxy, and (1H-tetrazol-5-yl)methyl;

R$_{12}$ is selected from hydrogen, C$_1$-C$_6$ alkyl, C$_3$-C$_6$ cycloalkyl, C$_1$-C$_6$ alkoxy, and halogen;

Rc is selected from hydrogen, C$_1$-C$_6$ alkyl, and C$_3$-C$_6$ cycloalkyl;

Ra$_1$, Ra$_2$, and Ra$_3$ are independently selected from hydrogen, C$_1$-C$_6$ alkyl, C$_1$-C$_6$ alkenyl, C$_1$-C$_6$ alkynyl, C$_1$-C$_6$ alkoxy, C$_3$-C$_6$ cycloalkyl, halogen, amino, amide, hydroxyl, and heterocycle, wherein Ra$_1$ and Ra$_2$ and/or Ra$_2$ and Ra$_3$ may be connected to form a cycloalkyl or a heterocycle;

Rb$_2$ and Rb$_6$ are independently selected from hydrogen, halogen, C$_1$-C$_6$ alkyl, C$_3$-C$_6$ cycloalkyl, C$_1$-C$_6$ alkenyl, hydroxyl, and amino; and Rb$_3$ and Rb$_5$ are independently selected from hydrogen, halogen, C$_1$-C$_6$ alkyl, C$_3$-C$_6$ cycloalkyl, C$_1$-C$_6$ alkoxy, hydroxyl, and amino, wherein Rb$_2$ and Rb$_3$ and/or Rb$_5$ and Rb$_6$ may be connected to form a cycloalkyl or a heterocycle;

provided that at least one of Ra$_1$, Ra$_2$, and Ra$_3$ is not hydrogen; and if Ra$_2$ or Ra$_3$ is chloro, then Ra$_1$ is not hydrogen.

7. The compound according to claim 6, wherein:
Q is CR$_{12}$;
V is nitrogen;
R$_{12}$ is selected from C$_1$-C$_6$ alkoxy and halogen;
Rc is selected from hydrogen and C$_1$-C$_6$ alkyl;
Ra$_2$ is selected from hydrogen and C$_1$-C$_6$ alkoxy;
Ra$_1$ and Ra$_3$ are independently selected from hydrogen, C$_1$-C$_6$ alkyl, C$_1$-C$_6$ alkoxy, halogen, and heterocycle;
Rb$_2$ and Rb$_6$ are both hydrogen;
Rb$_3$ and Rb$_5$ are independently selected from hydrogen and C$_1$-C$_6$ alkyl.

8. The compound according to claim 7, wherein:
Q is CR$_{12}$;
V is nitrogen;
R$_{12}$ is selected from methoxy and chlorine;
Rc is selected from hydrogen and (pyrrolidin-1-yl)propyl;
Ra$_2$ is selected from hydrogen and methoxy;
Ra$_1$ and Ra$_3$ are independently selected from hydrogen, methyl, chlorine, fluorine, methoxy, isopropoxy, and pyrrolidin-1-yl;
Rb$_2$ and Rb$_6$ are both hydrogen; and
Rb$_3$ and Rb$_5$ are independently selected from hydrogen and methyl.

9. A compound selected from:
4-(4-(5,7-dimethoxy-4-oxo-3,4-dihydroquinazolin-2-yl)phenoxy)-N,N-dimethylpiperidine-1-carboxamide;
2-(4-(1-acetylpiperidin-4-yloxy)phenyl)-5,7-dimethoxyquinazolin-4(3H)-one;
2-(4-(2-(isoindolin-2-yl)ethoxy)-3,5-dimethylphenyl)-5,7-dimethoxyquinazolin-4(3H)-one;
2-(3,5-dimethyl-4-(2-(pyrrolidin-1-yl)ethoxy)phenyl)-5-methoxyquinazolin-4(3H)-one;
5,7-dichloro-2-(3,5-dimethyl-4-(2-(pyrrolidin-1-yl)ethoxy)phenyl)quinazolin-4(3H)-one;
2-(3,5-dimethyl-4-(3-(pyrrolidin-1-yl)propoxy)phenyl)-5,7-dimethoxy-3-(3-(pyrrolidin-1-yl)propyl)quinazolin-4(3H)-one;
2-(4-(2-(4-acetylpiperazin-1-yl)ethoxy)-3,5-dimethylphenyl)-5,7-dimethoxyquinazolin-4(3H)-one;
2-(4-(2-(1H-imidazol-1-yl)ethoxy)-3,5-dimethylphenyl)-5,7-dimethoxyquinazolin-4(3H)-one;
2-(3,5-dimethyl-4-(2-(pyrrolidin-1-yl)ethoxy)phenyl)-7-methoxyquinazolin-4(3H)-one;
2-(3,5-dimethyl-4-(2-(4-methylpiperazin-1-yl)ethoxy)phenyl)-5,7-dimethoxyquinazolin-4(3H)-one;
2-(3,5-dimethyl-4-(2-(piperidin-1-yl)ethoxy)phenyl)-5,7-dimethoxyquinazolin-4(3H)-one;
5,7-dimethoxy-2-(3-methyl-4-(2-(pyrrolidin-1-yl)ethoxy)phenyl)quinazolin-4(3H)-one;
3-(2-(4-(5,7-dimethoxy-4-oxo-3,4-dihydroquinazolin-2-yl)-2,6-dimethylphenoxy)ethyl)-1-isopropylimidazolidine-2,4-dione;
5,7-dimethoxy-2-(4-(2-(pyrrolidin-1-yl)ethoxy)phenyl)quinazolin-4(3H)-one;
2-(3,5-dimethyl-4-(3-(pyrrolidin-1-yl)propyl)phenyl)-5,7-dimethoxyquinazolin-4(3H)-one;
2-(3,5-dimethyl-4-(2-(pyrrolidin-1-yl)ethoxy)phenyl)-8-methoxyquinazolin-4(3H)-one;
3-(2-(4-(5,7-dimethoxy-4-axo-3,4-dihydroquinazolin-2-yl)-2,6-dimethylphenoxy)ethyl)-5-phenylimidazolidine-2,4-dione;
3-(4-(5,7-dimethoxy-4-oxo-3,4-dihydroquinazolin-2-yl)benzyl)imidazolidine-2,4-dione;
2-(3,5-dimethyl-4-(2-(pyrrolidin-1-yl)ethoxy)phenyl)-6-methoxyquinazolin-4(3H)-one;
2-(3,5-dimethyl-4-(2-(pyrrolidin-1-yl)ethoxy)phenyl)-5,7-dimethoxypyrido[2,3-d]pyrimidin-4(3H)-one;
2-(3,5-dimethyl-4-(2-(pyrrolidin-1-yl)ethoxy)phenyl)-7-fluoro-5-(pyrrolidin-1-yl)quinazolin-4(3H)-one;
5-chloro-2-(3,5-dimethyl-4-(2-(pyrrolidin-1-yl)ethoxy)phenyl)quinazolin-4(3H)-one;
2-(4-(2-(azepan-1-yl)ethoxy)-3,5-dimethylphenyl)-5,7-dimethoxyquinazolin-4(3H)-one;
2-(3,5-dimethyl-4-(2-(pyrrolidin-1-yl)ethoxy)phenyl)-5,7-difluoroquinazolin-4(3H)-one;
2-(4-(2-(azetidin-1-yl)ethoxy)-3,5-dimethylphenyl)-5,7-dimethoxyquinazolin-4(3H)-one;
N-(1-(2-(4-(5,7-dimethoxy-4-oxo-3,4-dihydroquinazolin-2-yl)-2,6-dimethylphenoxy)ethyl)azetidin-3-yl)acetamide;
2-(3,5-dimethyl-4-(2-(pyrrolidin-1-yl)ethoxy)phenyl)-5,7-diisopropoxyquinazolin-4(3H)-one;
8-chloro-2-(3,5-dimethyl-4-(2-(pyrrolidin-1-yl)ethoxy)phenyl)quinazolin-4(3H)-one;
2-(3,5-dimethyl-4-(2-(pyrrolidin-1-yl)ethoxy)phenyl)-5,7-dimethylquinazolin-4(3H) one;
2-(3,5-dimethyl-4-(2-(pyrrolidin-1-yl)ethoxy)phenyl)-5,7-diisopropoxypyrido[2,3-d]pyrimidin-4(3H)-one;
(S)-2-(3,5-dimethyl-4-((5-oxopyrrolidin-2-yl)methoxy)phenyl)-5,7-dimethoxyquinazolin-4(3H)-one;

2-(4-((4-isopropylpiperazin-1-yl)methyl)phenyl)-5,7-dimethoxyquinazolin-4(3H)-one;

N-(1-(4-(5,7-dimethoxy-4-oxo-3,4-dihydroquinazolin-2-yl)benzyl)piperidin-4-yl)-N-isopropylacetamide;

2-(4-((4-(isopropylamino)piperidin-1-yl)methyl)phenyl)-5,7-dimethoxyquinazolin-4(3H)-one;

2-(4-((1 H-tetrazol-5-yl)methyl)phenyl)-5,7-dimethoxyquinazolin-4(3H)-one; and 1-(2-(4-(5,7-dimethoxy-4-oxo-3,4-dihydroquinazolin-2-yl)-2,6-dimethylphenoxy)ethyl)pyrrolidine-2,5-dione, and pharmaceutically acceptable salts and hydrates thereof.

10. A pharmaceutical composition comprising a compound according to claim 6 and a pharmaceutically acceptable carrier.

11. A method for reducing IL-6 and/or VCAM-1 in a subject, comprising administering a therapeutically effective amount of at least one compound according to any one of claim 6 to 10.

12. The method according to claim 11, wherein the subject is suffering from a disease characterized by elevated levels of IL-6 and/or VCAM-1, wherein the disease is selected from cardiovascular diseases, inflammatory diseases or related disease states, and cancer.

13. The method according to any one of claims 1 to 5, wherein the inflammatory disease is selected from rheumatoid arthritis, asthma, cystic fibrosis, post transplantation late and chronic solid organ rejection, systemic lupus erythematosus, ocular inflammation, uveitis, rhinitis, chronic obstructive pulmonary disease (COPD), glomerulonephritis, Grave's disease, gastrointestinal allergies, and conjunctivitis.

14. The method according to any one of claims 1 to 5 for treating cancer.

15. A pharmaceutical composition comprising a compound according to claim 9 and a pharmaceutically acceptable carrier.

16. A method for treating and/or reducing the risk of acquiring a disease mediated by IL-6 and/or VCAM-1 in a subject, comprising administering a therapeutically effective amount of at least one compound according to claim 9.

17. The method according to claim 16, wherein the disease mediated by IL-6 and/or VCAM-1 is a cardiovascular disease, an inflammatory disease or related disease state, or is a cancer.

18. The method according to claim 17, wherein the disease is selected from arthritis, rheumatoid arthritis, asthma, dermatitis, psoriasis, cystic fibrosis, post transplantation late and chronic solid organ rejection, multiple sclerosis, systemic lupus erythematosus, inflammatory bowel diseases, autoimmune diabetes, diabetic retinopathy, diabetic nephropathy, diabetic vasculopathy, ocular inflammation, uveitis, rhinitis, ischemia-reperfusion injury, chronic obstructive pulmonary disease (COPD), glomerulonephritis, Grave's disease, gastrointestinal allergies, and conjunctivitis.

19. The method according to claim 17, wherein the disease is selected from multiple myeloma, lymphoma, leukemia, solid tumors, prostate and bladder cancers, cardiac myxoma, tumor-induced cachexia, cancer-associated depression, cerebral edema secondary to brain tumors, hormone-independent prostate cancer, B cell lymphoma, AIDS-associated lymphoma, and metastatic renal cell carcinoma.

20. The method according to claim 14, wherein the cancer is selected from multiple myeloma, lymphoma, leukemia, solid tumors, prostate and bladder cancers, cardiac myxoma, tumor-induced cachexia, cancer-associated depression, cerebral edema secondary to brain tumors, hormone-independent prostate cancer, B cell lymphoma, AIDS-associated lymphoma, and metastatic renal cell carcinoma.

* * * * *

UNITED STATES PATENT AND TRADEMARK OFFICE
CERTIFICATE OF CORRECTION

PATENT NO. : 9,238,640 B2  Page 1 of 1
APPLICATION NO. : 13/257082
DATED : January 19, 2016
INVENTOR(S) : Henrik C. Hansen It is certified that error appears in the above-identified patent and that said Letters Patent is hereby corrected as shown below:

Claims

Claim 9, col. 173, line 7, "2-(4-((1I  H-tetrazol-5-yl)" should read -- 2-(4-((1H-tetrazol-5-yl) --.

Claim 11, col. 173, line 18, "any one of claim 6 to 10" should read -- any one of claims 6 to 10 --.

Signed and Sealed this
Twenty-sixth Day of April, 2016

Michelle K. Lee
*Director of the United States Patent and Trademark Office*